(12) United States Patent
Collinson et al.

(10) Patent No.: US 11,801,338 B2
(45) Date of Patent: *Oct. 31, 2023

(54) WOUND DRESSING AND METHOD OF TREATMENT

(71) Applicant: Smith & Nephew PLC, Watford (GB)

(72) Inventors: Sarah Jenny Collinson, Hull (GB); Philip Gowans, Doncaster (GB); Mark Russell, Roos (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/853,029

(22) Filed: Jun. 29, 2022

(65) Prior Publication Data

US 2022/0347018 A1 Nov. 3, 2022

Related U.S. Application Data

(63) Continuation of application No. 16/887,677, filed on May 29, 2020, which is a continuation of application (Continued)

(51) Int. Cl.
*A61M 1/00* (2006.01)
*A61F 13/02* (2006.01)
*A61F 13/00* (2006.01)

(52) U.S. Cl.
CPC ....... *A61M 1/915* (2021.05); *A61F 13/00012* (2013.01); *A61F 13/00017* (2013.01);
(Continued)

(58) Field of Classification Search
CPC .......... A61F 13/00042; A61F 13/00012; A61F 13/00017; A61F 13/00068; A61F 13/0206;
(Continued)

(56) References Cited

U.S. PATENT DOCUMENTS 2,331,271 A  10/1943 Gilchrist
2,727,382 A  12/1955 Karl et al.
(Continued)

FOREIGN PATENT DOCUMENTS

AU   674837 B2   1/1997
CN   1293953 A   5/2001
(Continued)

OTHER PUBLICATIONS

US 7,186,244 B1, 03/2007, Hunt et al. (withdrawn)
(Continued)

*Primary Examiner* — Jessica Arble
(74) *Attorney, Agent, or Firm* — Knobbe, Martens Olson & Bear, LLP

(57) ABSTRACT

Embodiments disclosed herein are directed to negative pressure treatment systems and wound dressing systems, apparatuses, and methods that may be used for the treatment of wounds. In particular, some embodiments are directed to improved wound dressings comprising an obscuring layer that may hide fluid contained therein. Some embodiments may further comprise one or more viewing windows disposed therethrough so as to enable monitoring or examination of fluids contained therein.

24 Claims, 98 Drawing Sheets

Related U.S. Application Data

No. 14/418,908, filed as application No. PCT/IB2013/002060 on Jul. 31, 2013, now Pat. No. 10,667,955.

(60) Provisional application No. 61/823,298, filed on May 14, 2013, provisional application No. 61/785,054, filed on Mar. 14, 2013, provisional application No. 61/753,878, filed on Jan. 17, 2013, provisional application No. 61/753,374, filed on Jan. 16, 2013, provisional application No. 61/678,569, filed on Aug. 1, 2012.

(52) U.S. Cl.
CPC .. *A61F 13/00042* (2013.01); *A61F 13/00068* (2013.01); *A61F 13/022* (2013.01); *A61F 13/0206* (2013.01); *A61F 13/0209* (2013.01); *A61F 13/0216* (2013.01); *A61F 13/0223* (2013.01); *A61F 13/0266* (2013.01); *A61M 1/90* (2021.05); *A61M 1/912* (2021.05); *A61F 13/00059* (2013.01); *A61F 2013/00153* (2013.01); *A61F 2013/00182* (2013.01); *A61F 2013/00289* (2013.01); *A61M 1/962* (2021.05); *A61M 1/982* (2021.05); *A61M 1/985* (2021.05)

(58) Field of Classification Search
CPC .............. A61F 13/0209; A61F 13/0216; A61F 13/022; A61F 13/0223; A61F 13/0266; A61F 13/00059; A61M 1/90
See application file for complete search history.

(56) References Cited

U.S. PATENT DOCUMENTS

| | | |
|---|---|---|
| 2,877,765 A | 3/1959 | John et al. |
| 2,889,039 A | 6/1959 | Peter et al. |
| 2,905,174 A | 9/1959 | Smith |
| 3,073,304 A | 1/1963 | Schaar |
| 3,285,245 A | 11/1966 | Eldredge et al. |
| 3,568,675 A | 3/1971 | Harvey |
| 3,687,136 A | 8/1972 | Carmody |
| 3,929,135 A | 12/1975 | Thompson |
| 3,943,734 A | 3/1976 | Fleissner |
| 3,964,039 A | 6/1976 | Craford et al. |
| 3,972,328 A | 8/1976 | Chen |
| 4,029,598 A | 6/1977 | Neisius et al. |
| 4,093,277 A | 6/1978 | Nolan et al. |
| 4,095,599 A | 6/1978 | Simonet-Haibe |
| 4,224,941 A | 9/1980 | Stivala |
| 4,541,426 A | 9/1985 | Webster |
| 4,605,399 A | 8/1986 | Weston et al. |
| 4,624,656 A | 11/1986 | Clark et al. |
| 4,681,562 A | 7/1987 | Beck et al. |
| 4,690,134 A | 9/1987 | Snyders |
| 4,699,134 A | 10/1987 | Samuelsen |
| 4,770,187 A | 9/1988 | Lash et al. |
| 4,798,603 A | 1/1989 | Meyer et al. |
| 4,813,942 A | 3/1989 | Alvarez |
| 4,834,735 A | 5/1989 | Alemany et al. |
| 4,846,164 A | 7/1989 | Martz |
| 4,886,697 A | 12/1989 | Perdelwitz, Jr. et al. |
| 4,921,492 A | 5/1990 | Schultz et al. |
| 4,928,680 A * | 5/1990 | Sandbank ............ A61F 13/023 602/57 |
| 4,968,181 A | 11/1990 | Goldman |
| 4,969,880 A | 11/1990 | Zamierowski |
| 4,973,325 A | 11/1990 | Sherrod et al. |
| 4,985,467 A | 1/1991 | Kelly et al. |
| 4,988,344 A | 1/1991 | Reising et al. |
| 4,988,345 A | 1/1991 | Reising |
| 5,000,172 A | 3/1991 | Ward |
| 5,000,741 A | 3/1991 | Kalt |
| 5,018,515 A | 5/1991 | Gilman |
| 5,021,050 A | 6/1991 | Iskra |
| 5,037,409 A | 8/1991 | Chen et al. |
| 5,056,510 A | 10/1991 | Gilman |
| 5,061,258 A | 10/1991 | Martz |
| 5,065,600 A | 11/1991 | Byles |
| 5,080,661 A | 1/1992 | Lavender et al. |
| 5,100,396 A | 3/1992 | Zamierowski |
| 5,106,629 A | 4/1992 | Cartmell et al. |
| 5,115,801 A | 5/1992 | Cartmell et al. |
| 5,124,197 A | 6/1992 | Bernardin et al. |
| 5,149,334 A | 9/1992 | Lahrman et al. |
| 5,151,091 A | 9/1992 | Glaug et al. |
| 5,152,757 A | 10/1992 | Eriksson |
| 5,160,328 A | 11/1992 | Cartmell et al. |
| 5,171,391 A | 12/1992 | Chmielewski et al. |
| 5,175,046 A | 12/1992 | Nguyen |
| 5,180,375 A | 1/1993 | Feibus |
| 5,181,905 A | 1/1993 | Flam |
| 5,197,945 A | 3/1993 | Cole et al. |
| 5,217,445 A | 6/1993 | Young et al. |
| 5,236,427 A | 8/1993 | Hamajima et al. |
| 5,238,732 A | 8/1993 | Krishnan |
| 5,242,435 A | 9/1993 | Murji et al. |
| 5,257,982 A | 11/1993 | Cohen et al. |
| 5,261,893 A | 11/1993 | Zamierowski |
| 5,264,218 A | 11/1993 | Rogozinski |
| 5,267,952 A | 12/1993 | Gardner |
| 5,271,987 A | 12/1993 | Iskra |
| 5,281,208 A | 1/1994 | Thompson et al. |
| 5,294,478 A | 3/1994 | Wanek et al. |
| 5,296,290 A | 3/1994 | Brassington |
| 5,314,743 A | 5/1994 | Meirowitz et al. |
| 5,318,554 A | 6/1994 | Young et al. |
| 5,330,456 A | 7/1994 | Robinson |
| 5,336,219 A | 8/1994 | Krantz |
| 5,342,336 A | 8/1994 | Meirowitz et al. |
| 5,348,547 A | 9/1994 | Payne et al. |
| 5,354,261 A | 10/1994 | Clark et al. |
| 5,356,405 A | 10/1994 | Thompson et al. |
| 5,358,492 A | 10/1994 | Feibus |
| 5,360,420 A | 11/1994 | Cook et al. |
| 5,364,381 A | 11/1994 | Soga et al. |
| 5,364,382 A | 11/1994 | Latimer et al. |
| 5,366,451 A | 11/1994 | Levesque |
| 5,368,909 A | 11/1994 | Langdon et al. |
| 5,368,926 A | 11/1994 | Thompson et al. |
| 5,374,260 A | 12/1994 | Lemay et al. |
| 5,380,294 A | 1/1995 | Persson |
| 5,382,245 A | 1/1995 | Thompson et al. |
| 5,387,208 A | 2/1995 | Ashton et al. |
| 5,397,316 A | 3/1995 | LaVon et al. |
| 5,401,267 A | 3/1995 | Couture-Dorschner et al. |
| 5,409,472 A | 4/1995 | Rawlings et al. |
| 5,425,725 A | 6/1995 | Tanzer et al. |
| 5,431,643 A | 7/1995 | Ouellette et al. |
| 5,447,492 A | 9/1995 | Cartmell et al. |
| 5,454,800 A | 10/1995 | Hirt et al. |
| 5,456,660 A | 10/1995 | Reich et al. |
| 5,465,735 A | 11/1995 | Patel |
| 5,470,326 A | 11/1995 | Dabi et al. |
| H1511 H | 12/1995 | Chappell et al. |
| 5,480,377 A | 1/1996 | Cartmell et al. |
| 5,486,167 A | 1/1996 | Dragoo et al. |
| 5,487,736 A | 1/1996 | Van Phan |
| 5,497,788 A | 3/1996 | Inman et al. |
| 5,500,270 A | 3/1996 | Langdon et al. |
| 5,501,661 A | 3/1996 | Cartmell et al. |
| 5,505,719 A | 4/1996 | Cohen et al. |
| 5,509,914 A | 4/1996 | Osborn, III |
| 5,514,120 A | 5/1996 | Johnston et al. |
| 5,520,629 A | 5/1996 | Heinecke et al. |
| 5,525,407 A | 6/1996 | Yang |
| 5,527,293 A | 6/1996 | Zamierowski |
| 5,536,264 A | 7/1996 | Hsueh et al. |
| 5,536,555 A | 7/1996 | Zelazoski et al. |
| 5,538,500 A | 7/1996 | Peterson |
| H1585 H | 8/1996 | Ahr |
| 5,545,155 A | 8/1996 | Hseih et al. |

(56) References Cited

U.S. PATENT DOCUMENTS

| | | |
|---|---|---|
| 5,549,584 A | 8/1996 | Gross |
| 5,549,589 A | 8/1996 | Horney et al. |
| 5,562,107 A | 10/1996 | Lavender et al. |
| 5,562,646 A | 10/1996 | Goldman et al. |
| 5,562,650 A | 10/1996 | Everett et al. |
| 5,579,765 A | 12/1996 | Cox et al. |
| 5,591,148 A | 1/1997 | McFall et al. |
| 5,591,149 A | 1/1997 | Cree et al. |
| 5,599,289 A | 2/1997 | Castellana |
| 5,603,707 A | 2/1997 | Trombetta et al. |
| 5,603,946 A | 2/1997 | Constantine |
| 5,605,165 A | 2/1997 | Sessions et al. |
| 5,609,588 A | 3/1997 | DiPalma et al. |
| 5,613,960 A | 3/1997 | Mizutani |
| 5,614,283 A | 3/1997 | Potnis et al. |
| 5,614,295 A | 3/1997 | Quincy, III et al. |
| 5,626,954 A | 5/1997 | Andersen et al. |
| 5,628,736 A | 5/1997 | Thompson |
| 5,632,731 A | 5/1997 | Patel |
| H1657 H | 6/1997 | Hammons et al. |
| 5,634,915 A | 6/1997 | Osterdahl |
| 5,636,643 A | 6/1997 | Argenta et al. |
| 5,637,080 A | 6/1997 | Geng |
| 5,643,189 A | 7/1997 | Masini |
| 5,643,238 A | 7/1997 | Baker |
| 5,645,081 A | 7/1997 | Argenta et al. |
| 5,648,142 A | 7/1997 | Phillips |
| 5,649,915 A | 7/1997 | Chauvette et al. |
| 5,649,916 A | 7/1997 | DiPalma et al. |
| 5,662,599 A | 9/1997 | Reich et al. |
| 5,665,082 A | 9/1997 | Boulanger |
| 5,669,895 A | 9/1997 | Murakami et al. |
| 5,675,079 A | 10/1997 | Gilman et al. |
| 5,678,564 A | 10/1997 | Lawrence et al. |
| 5,700,254 A | 12/1997 | McDowall et al. |
| 5,701,917 A | 12/1997 | Khouri |
| 5,702,356 A | 12/1997 | Hathman |
| 5,704,905 A | 1/1998 | Jensen et al. |
| 5,707,499 A | 1/1998 | Joshi et al. |
| 5,713,384 A | 2/1998 | Roach et al. |
| 5,713,842 A | 2/1998 | Kay |
| 5,716,703 A | 2/1998 | Payne |
| 5,728,084 A | 3/1998 | Palumbo et al. |
| 5,728,085 A | 3/1998 | Widlund et al. |
| 5,733,273 A | 3/1998 | Ahr |
| 5,735,145 A | 4/1998 | Pernick |
| 5,752,945 A | 5/1998 | Mosley et al. |
| 5,759,570 A | 6/1998 | Arnold |
| 5,762,641 A | 6/1998 | Bewick-Sonntag et al. |
| 5,788,684 A | 8/1998 | Abuto et al. |
| 5,795,439 A | 8/1998 | Euripides et al. |
| 5,795,584 A | 8/1998 | Totakura et al. |
| 5,801,107 A | 9/1998 | Everhart et al. |
| 5,804,021 A | 9/1998 | Abuto et al. |
| 5,810,798 A | 9/1998 | Finch et al. |
| 5,817,081 A | 10/1998 | LaVon et al. |
| 5,827,213 A | 10/1998 | Jensen |
| 5,827,254 A | 10/1998 | Trombetta et al. |
| 5,830,202 A | 11/1998 | Bogdanski et al. |
| 5,833,646 A | 11/1998 | Masini |
| 5,837,627 A | 11/1998 | Halabisky et al. |
| 5,840,052 A * | 11/1998 | Johns ............... A61F 13/023 602/54 |
| 5,843,025 A | 12/1998 | Shaari |
| 5,843,064 A | 12/1998 | Koczab |
| 5,852,126 A | 12/1998 | Barnard et al. |
| 5,855,572 A | 1/1999 | Schmidt |
| 5,865,822 A | 2/1999 | Hamajima et al. |
| 5,865,824 A | 2/1999 | Chen et al. |
| 5,868,724 A | 2/1999 | Dierckes, Jr. et al. |
| 5,873,867 A | 2/1999 | Coles et al. |
| 5,877,097 A | 3/1999 | West et al. |
| 5,891,120 A | 4/1999 | Chmielewski |
| 5,895,379 A | 4/1999 | Litchholt et al. |
| 5,897,541 A | 4/1999 | Uitenbroek et al. |
| 5,911,222 A | 6/1999 | Lawrence et al. |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,947,945 A | 9/1999 | Cree et al. |
| 5,951,535 A | 9/1999 | Fujiwara et al. |
| 5,960,795 A | 10/1999 | Schultz |
| 5,961,506 A | 10/1999 | Guidotti et al. |
| 5,968,027 A | 10/1999 | Cole et al. |
| 5,968,855 A | 10/1999 | Perdelwitz, Jr. et al. |
| 5,989,478 A | 11/1999 | Ouellette et al. |
| 6,008,429 A | 12/1999 | Ritger |
| 6,018,092 A * | 1/2000 | Dunshee ............... A61F 15/001 206/440 |
| 6,022,610 A | 2/2000 | Phan et al. |
| 6,037,518 A | 3/2000 | Guidotti et al. |
| 6,040,493 A | 3/2000 | Cooke et al. |
| 6,060,638 A | 5/2000 | Paul et al. |
| 6,068,620 A | 5/2000 | Chmielewski |
| 6,071,267 A | 6/2000 | Zamierowski |
| 6,075,177 A | 6/2000 | Bahia et al. |
| 6,077,526 A | 6/2000 | Scully et al. |
| 6,096,015 A | 8/2000 | Yeo et al. |
| 6,103,953 A | 8/2000 | Cree et al. |
| 6,103,954 A | 8/2000 | Grondin et al. |
| 6,107,539 A | 8/2000 | Palumbo et al. |
| 6,117,523 A | 9/2000 | Sugahara |
| 6,124,520 A | 9/2000 | Roberts |
| 6,124,521 A | 9/2000 | Roberts |
| 6,124,522 A * | 9/2000 | Schroeder ............... A61F 15/001 602/41 |
| 6,127,595 A | 10/2000 | Makoui et al. |
| 6,142,982 A | 11/2000 | Hunt et al. |
| 6,168,849 B1 | 1/2001 | Braverman et al. |
| 6,191,340 B1 | 2/2001 | Carlucci et al. |
| 6,206,865 B1 | 3/2001 | Chen et al. |
| 6,207,875 B1 | 3/2001 | Lindqvist et al. |
| 6,225,523 B1 | 5/2001 | Masini |
| 6,235,966 B1 | 5/2001 | Magnusson et al. |
| 6,241,697 B1 | 6/2001 | Augustine |
| 6,261,283 B1 | 7/2001 | Morgan et al. |
| 6,264,776 B1 | 7/2001 | DiPalma |
| 6,294,710 B1 | 9/2001 | Schmidt et al. |
| 6,297,422 B1 | 10/2001 | Hansen et al. |
| 6,297,423 B1 | 10/2001 | Schoenfeldt et al. |
| 6,312,416 B1 | 11/2001 | Brisebois et al. |
| 6,344,036 B1 | 2/2002 | Ivansson |
| 6,345,623 B1 | 2/2002 | Heaton et al. |
| 6,362,390 B1 | 3/2002 | Carlucci et al. |
| 6,369,292 B1 | 4/2002 | Strack et al. |
| 6,372,952 B1 | 4/2002 | Lash et al. |
| 6,398,767 B1 | 6/2002 | Fleischmann |
| 6,403,857 B1 | 6/2002 | Gross et al. |
| 6,447,799 B1 | 9/2002 | Ullman |
| 6,458,109 B1 | 10/2002 | Henley et al. |
| 6,461,339 B1 | 10/2002 | Sugahara |
| 6,468,295 B2 | 10/2002 | Augustine et al. |
| 6,478,781 B1 | 11/2002 | Urich et al. |
| 6,479,415 B1 | 11/2002 | Erspamer et al. |
| 6,482,491 B1 | 11/2002 | Samuelsen et al. |
| 6,497,688 B2 | 12/2002 | Lasko |
| 6,497,689 B1 | 12/2002 | Schmidt et al. |
| 6,506,175 B1 | 1/2003 | Goldstein |
| 6,506,960 B1 | 1/2003 | Young et al. |
| 6,521,813 B1 | 2/2003 | Chihani |
| 6,528,696 B1 | 3/2003 | Ireland |
| 6,534,149 B1 | 3/2003 | Daley et al. |
| D473,947 S | 4/2003 | Jacobson |
| 6,545,194 B1 | 4/2003 | Schmidt et al. |
| 6,551,295 B1 | 4/2003 | Schmidt et al. |
| 6,552,244 B1 | 4/2003 | Jacques et al. |
| 6,566,575 B1 | 5/2003 | Stickels et al. |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,586,653 B2 | 7/2003 | Graeme, III et al. |
| 6,599,262 B1 | 7/2003 | Masini |

(56) References Cited

U.S. PATENT DOCUMENTS

| | | | |
|---|---|---|---|
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,953 B1 | 9/2003 | Altura |
| 6,613,955 B1 | 9/2003 | Lindsay et al. |
| 6,626,891 B2 | 9/2003 | Ohmstede |
| 6,630,611 B1 | 10/2003 | Malowaniec |
| 6,648,862 B2 | 11/2003 | Watson |
| 6,664,439 B1 | 12/2003 | Arndt et al. |
| 6,683,229 B1 | 1/2004 | Ehrnsperger et al. |
| 6,685,681 B2 | 2/2004 | Lockwood et al. |
| 6,706,940 B2 | 3/2004 | Worthley |
| 6,719,742 B1 | 4/2004 | McCormack et al. |
| 6,727,403 B1 | 4/2004 | Ehrnsperger et al. |
| 6,752,794 B2 | 6/2004 | Lockwood et al. |
| 6,755,807 B2 | 6/2004 | Risk, Jr. et al. |
| 6,762,337 B2 | 7/2004 | Boukanov et al. |
| 6,764,459 B1 | 7/2004 | Donaldson |
| 6,764,462 B2 | 7/2004 | Risk, Jr. et al. |
| 6,767,334 B1 | 7/2004 | Randolph |
| 6,776,769 B2 | 8/2004 | Smith |
| 6,783,871 B1 | 8/2004 | Creagan et al. |
| 6,787,682 B2 | 9/2004 | Gilman |
| 6,800,074 B2 | 10/2004 | Henley et al. |
| 6,835,192 B1 | 12/2004 | Guidotti et al. |
| 6,838,589 B2 | 1/2005 | Liedtke et al. |
| 6,841,715 B2 | 1/2005 | Roberts |
| 6,855,135 B2 | 2/2005 | Lockwood et al. |
| 6,936,037 B2 | 8/2005 | Bubb et al. |
| 6,951,553 B2 | 10/2005 | Bubb et al. |
| 6,960,181 B2 | 11/2005 | Stevens |
| 6,979,324 B2 | 12/2005 | Bybordi et al. |
| D515,701 S | 2/2006 | Horhota et al. |
| 6,998,511 B2 | 2/2006 | Worthley |
| 7,004,915 B2 | 2/2006 | Boynton et al. |
| 7,022,113 B2 | 4/2006 | Lockwood et al. |
| 7,049,478 B1 | 5/2006 | Smith |
| D525,362 S | 7/2006 | Nielsen et al. |
| 7,070,584 B2 | 7/2006 | Johnson et al. |
| 7,108,683 B2 | 9/2006 | Zamierowski |
| 7,112,712 B1 | 9/2006 | Ancell |
| 7,118,545 B2 | 10/2006 | Boyde |
| 7,122,023 B1 | 10/2006 | Hinoki |
| 7,122,712 B2 | 10/2006 | Lutri et al. |
| D537,948 S | 3/2007 | Smith |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,267,681 B2 | 9/2007 | Dunshee |
| 7,279,612 B1 | 10/2007 | Heaton et al. |
| 7,294,751 B2 | 11/2007 | Propp et al. |
| 7,294,752 B1 | 11/2007 | Propp |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,429,689 B2 | 9/2008 | Chen et al. |
| 7,438,705 B2 | 10/2008 | Karpowicz et al. |
| 7,476,205 B2 | 1/2009 | Erdmann |
| 7,485,112 B2 | 2/2009 | Karpowicz et al. |
| 7,503,910 B2 | 3/2009 | Adahan |
| 7,511,187 B2 | 3/2009 | Kelly |
| 7,531,711 B2 | 5/2009 | Sigurjonsson et al. |
| 7,534,927 B2 | 5/2009 | Lockwood et al. |
| 7,553,306 B1 | 6/2009 | Hunt et al. |
| 7,563,940 B2 | 7/2009 | Kurata |
| 7,569,742 B2 | 8/2009 | Haggstrom et al. |
| 7,576,256 B2 | 8/2009 | Bjornberg et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,676,257 B2 | 3/2010 | Suryanarayanan et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,723,561 B2 | 5/2010 | Propp |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,794,438 B2 | 9/2010 | Henley et al. |
| D625,018 S | 10/2010 | Smith et al. |
| 7,811,269 B2 | 10/2010 | Boynton et al. |
| 7,812,212 B2 | 10/2010 | Propp et al. |
| 7,838,717 B2 | 11/2010 | Haggstrom et al. |
| 7,838,719 B2 | 11/2010 | Hilton, Jr. |
| 7,838,723 B1 | 11/2010 | Schmidt et al. |
| 7,846,141 B2 | 12/2010 | Weston |
| 7,862,718 B2 | 1/2011 | Doyen et al. |
| 7,880,050 B2 | 2/2011 | Robinson et al. |
| 7,880,051 B2 * | 2/2011 | Madsen ............ A61F 13/0226 602/41 |
| 7,884,258 B2 | 2/2011 | Boehringer et al. |
| 7,910,791 B2 | 3/2011 | Coffey |
| 7,922,703 B2 | 4/2011 | Riesinger |
| 7,935,066 B2 | 5/2011 | Shives et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,982,087 B2 | 7/2011 | Greener et al. |
| 7,988,673 B2 | 8/2011 | Wright et al. |
| 8,007,905 B2 | 8/2011 | Perez et al. |
| 8,021,347 B2 | 9/2011 | Vitaris et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,083,712 B2 | 12/2011 | Biggie et al. |
| 8,092,436 B2 | 1/2012 | Christensen |
| 8,118,794 B2 | 2/2012 | Weston |
| 8,129,580 B2 | 3/2012 | Wilkes et al. |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,152,785 B2 | 4/2012 | Vitaris |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,192,409 B2 | 6/2012 | Hardman et al. |
| 8,202,261 B2 | 6/2012 | Kazala, Jr. et al. |
| 8,207,392 B2 | 6/2012 | Haggstrom et al. |
| 8,212,101 B2 | 7/2012 | Propp |
| 8,241,261 B2 | 8/2012 | Randolph et al. |
| 8,246,606 B2 | 8/2012 | Stevenson et al. |
| 8,252,971 B2 | 8/2012 | Aali et al. |
| 8,267,908 B2 | 9/2012 | Coulthard |
| 8,282,611 B2 | 10/2012 | Weston |
| 8,298,200 B2 | 10/2012 | Vess et al. |
| 8,303,552 B2 | 11/2012 | Weston |
| 8,314,283 B2 | 11/2012 | Kingsford et al. |
| 8,328,858 B2 | 12/2012 | Barsky et al. |
| 8,376,972 B2 | 2/2013 | Fleischmann |
| 8,382,731 B2 | 2/2013 | Johannison |
| 8,403,899 B2 | 3/2013 | Sherman |
| 8,404,921 B2 | 3/2013 | Lee et al. |
| D679,402 S | 4/2013 | Conrad-Vlasak et al. |
| D679,819 S | 4/2013 | Peron |
| D679,820 S | 4/2013 | Peron |
| 8,409,170 B2 | 4/2013 | Locke et al. |
| 8,425,478 B2 | 4/2013 | Olson |
| 8,444,611 B2 | 5/2013 | Wilkes et al. |

(56) References Cited

U.S. PATENT DOCUMENTS

| | | |
|---|---|---|
| 8,444,612 B2 | 5/2013 | Patel et al. |
| 8,460,255 B2 | 6/2013 | Joshi et al. |
| 8,506,554 B2 | 8/2013 | Adahan |
| 8,535,296 B2 | 9/2013 | Blott et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,628,505 B2 | 1/2014 | Weston |
| 8,641,691 B2 | 2/2014 | Fink et al. |
| 8,663,198 B2 | 3/2014 | Buan et al. |
| 8,680,360 B2 | 3/2014 | Greener et al. |
| 8,715,256 B2 | 5/2014 | Greener |
| 8,734,410 B2 | 5/2014 | Hall et al. |
| 8,764,732 B2 | 7/2014 | Hartwell |
| 8,771,244 B2 | 7/2014 | Eckstein et al. |
| 8,784,392 B2 | 7/2014 | Vess et al. |
| 8,791,316 B2 | 7/2014 | Greener |
| 8,795,243 B2 | 8/2014 | Weston |
| 8,795,244 B2 | 8/2014 | Randolph et al. |
| 8,795,247 B2 | 8/2014 | Bennett et al. |
| 8,795,800 B2 | 8/2014 | Evans |
| 8,801,685 B2 | 8/2014 | Armstrong et al. |
| 8,808,274 B2 | 8/2014 | Hartwell |
| 8,814,842 B2 | 8/2014 | Coulthard et al. |
| D714,433 S | 9/2014 | Armstrong et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,905,985 B2 | 12/2014 | Allen et al. |
| 8,915,895 B2 | 12/2014 | Jaeb et al. |
| 8,916,742 B2 | 12/2014 | Smith |
| 8,951,235 B2 | 2/2015 | Allen et al. |
| 8,956,336 B2 | 2/2015 | Haggstrom et al. |
| 9,012,714 B2 | 4/2015 | Fleischmann |
| 9,017,302 B2 | 4/2015 | Vitaris et al. |
| 9,033,942 B2 | 5/2015 | Vess |
| 9,050,398 B2 | 6/2015 | Armstrong et al. |
| 9,061,095 B2 | 6/2015 | Adie et al. |
| 9,127,665 B2 | 9/2015 | Locke et al. |
| 9,168,330 B2 | 10/2015 | Joshi et al. |
| D746,435 S | 12/2015 | Armstrong et al. |
| 9,199,012 B2 | 12/2015 | Vitaris et al. |
| RE45,864 E | 1/2016 | Peron |
| 9,227,000 B2 | 1/2016 | Fink et al. |
| 9,254,353 B2 | 2/2016 | Locke et al. |
| 9,283,118 B2 | 3/2016 | Locke et al. |
| 9,302,033 B2 | 4/2016 | Riesinger |
| 9,327,065 B2 | 5/2016 | Albert et al. |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,446,178 B2 | 9/2016 | Blott et al. |
| 9,452,245 B2 | 9/2016 | Jaeb et al. |
| 9,452,248 B2 | 9/2016 | Blott et al. |
| 9,474,654 B2 | 10/2016 | Heagle et al. |
| 9,474,661 B2 | 10/2016 | Fouillet et al. |
| RE46,289 E | 1/2017 | Peron |
| 9,539,373 B2 | 1/2017 | Jones et al. |
| 9,629,986 B2 | 4/2017 | Patel et al. |
| 9,669,138 B2 | 6/2017 | Joshi et al. |
| 9,681,993 B2 | 6/2017 | Wu et al. |
| 9,795,725 B2 | 10/2017 | Joshi et al. |
| 9,808,561 B2 | 11/2017 | Adie et al. |
| 9,877,872 B2 | 1/2018 | Mumby et al. |
| 10,016,545 B2 | 7/2018 | Vitaris et al. |
| 10,046,096 B2 | 8/2018 | Askem et al. |
| 10,080,690 B2 | 9/2018 | Stevenson et al. |
| RE47,100 E | 10/2018 | Smith et al. |
| 11,083,628 B2 | 8/2021 | Greener et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0027302 A1 | 10/2001 | Glaug et al. |
| 2001/0027305 A1 | 10/2001 | Raidel et al. |
| 2001/0034499 A1 | 10/2001 | Sessions et al. |
| 2001/0044610 A1 | 11/2001 | Kim et al. |
| 2001/0051165 A1 | 12/2001 | Lenz et al. |
| 2001/0051178 A1 | 12/2001 | Blatchford et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0019602 A1 | 2/2002 | Geng |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035352 A1 | 3/2002 | Ronnberg et al. |
| 2002/0035354 A1 | 3/2002 | Mirle et al. |
| 2002/0052570 A1 | 5/2002 | Naimer |
| 2002/0062113 A1 | 5/2002 | Thomas et al. |
| 2002/0062114 A1 | 5/2002 | Murai et al. |
| 2002/0064639 A1 | 5/2002 | Rearick et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0123728 A1 | 9/2002 | Graef et al. |
| 2002/0133132 A1 | 9/2002 | Copat et al. |
| 2002/0150678 A1 | 10/2002 | Cramer et al. |
| 2002/0165509 A1 | 11/2002 | Baer et al. |
| 2002/0169405 A1 | 11/2002 | Roberts |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0009122 A1 | 1/2003 | Veras |
| 2003/0014025 A1 | 1/2003 | Allen et al. |
| 2003/0014786 P1 | 1/2003 | Meilland |
| 2003/0045707 A1 | 3/2003 | West et al. |
| 2003/0045825 A1 | 3/2003 | Etheredge, III |
| 2003/0050617 A1 | 3/2003 | Chen et al. |
| 2003/0069563 A1 | 4/2003 | Johnson |
| 2003/0070780 A1 | 4/2003 | Chen et al. |
| 2003/0073967 A1 | 4/2003 | Wahlstrom et al. |
| 2003/0088229 A1 | 5/2003 | Baker et al. |
| 2003/0088231 A1 | 5/2003 | Yoshimasa et al. |
| 2003/0093044 A1 | 5/2003 | Wahlstrom et al. |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0125646 A1 | 7/2003 | Whitlock |
| 2003/0134559 A1 | 7/2003 | Delzer et al. |
| 2003/0135174 A1 | 7/2003 | Benecke et al. |
| 2003/0135177 A1 | 7/2003 | Baker |
| 2003/0150551 A1 | 8/2003 | Baker |
| 2003/0157857 A1 | 8/2003 | Cook et al. |
| 2003/0171729 A1 | 9/2003 | Kaun et al. |
| 2003/0180341 A1 | 9/2003 | Gooch et al. |
| 2003/0199800 A1 | 10/2003 | Levin |
| 2003/0208175 A1 | 11/2003 | Gross et al. |
| 2003/0212357 A1 | 11/2003 | Pace |
| 2003/0212359 A1 | 11/2003 | Butler |
| 2003/0225383 A1 | 12/2003 | Glaug et al. |
| 2004/0015115 A1 | 1/2004 | Sinyagin |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024375 A1 | 2/2004 | Litvay |
| 2004/0030304 A1 | 2/2004 | Hunt et al. |
| 2004/0033750 A1 | 2/2004 | Everett et al. |
| 2004/0049146 A1 | 3/2004 | Kolte et al. |
| 2004/0054343 A1 | 3/2004 | Barnett et al. |
| 2004/0054344 A1 | 3/2004 | Roettger et al. |
| 2004/0064132 A1 | 4/2004 | Boehringer et al. |
| 2004/0065420 A1 | 4/2004 | Graef et al. |
| 2004/0078011 A1 | 4/2004 | Stevens |

(56) References Cited

U.S. PATENT DOCUMENTS

| | | |
|---|---|---|
| 2004/0078016 A1 | 4/2004 | Baker |
| 2004/0087884 A1 | 5/2004 | Haddock et al. |
| 2004/0087927 A1 | 5/2004 | Suzuki |
| 2004/0106888 A1 | 6/2004 | Lutri et al. |
| 2004/0111074 A1 | 6/2004 | Eliasson |
| 2004/0127839 A1 | 7/2004 | Sigurjonsson et al. |
| 2004/0127862 A1 | 7/2004 | Bubb et al. |
| 2004/0138602 A1 | 7/2004 | Rossen |
| 2004/0162512 A1 | 8/2004 | Liedtke et al. |
| 2004/0177935 A1 | 9/2004 | Hamed et al. |
| 2004/0181199 A1 | 9/2004 | Moberg-Alehammar et al. |
| 2004/0204696 A1 | 10/2004 | Chen |
| 2004/0230173 A1 | 11/2004 | Barge et al. |
| 2004/0230184 A1 | 11/2004 | Babusik et al. |
| 2004/0243042 A1 | 12/2004 | Lipman |
| 2004/0243080 A1 | 12/2004 | Baer |
| 2004/0243081 A1 | 12/2004 | Suzuki et al. |
| 2004/0253894 A1 | 12/2004 | Fell et al. |
| 2004/0254552 A1 | 12/2004 | Mangold |
| 2005/0008825 A1 | 1/2005 | Casey et al. |
| 2005/0013992 A1 | 1/2005 | Azad et al. |
| 2005/0015036 A1 | 1/2005 | Lutri et al. |
| 2005/0049566 A1 | 3/2005 | Vukos et al. |
| 2005/0079361 A1 | 4/2005 | Hamed et al. |
| 2005/0084641 A1 | 4/2005 | Downs et al. |
| 2005/0090860 A1 | 4/2005 | Paprocki |
| 2005/0096616 A1 | 5/2005 | Arora et al. |
| 2005/0101940 A1 | 5/2005 | Radl et al. |
| 2005/0112979 A1 | 5/2005 | Sawyer et al. |
| 2005/0119631 A1 | 6/2005 | Giloh et al. |
| 2005/0136773 A1 | 6/2005 | Yahiaoui et al. |
| 2005/0165371 A1 | 7/2005 | Giacometti |
| 2005/0209574 A1 | 9/2005 | Boehringer et al. |
| 2005/0215965 A1 | 9/2005 | Schmidt et al. |
| 2005/0215967 A1 | 9/2005 | Toro et al. |
| 2005/0222527 A1 | 10/2005 | Miller et al. |
| 2005/0222547 A1 | 10/2005 | Beruda et al. |
| 2005/0228353 A1 | 10/2005 | Thomas |
| 2005/0261649 A1 | 11/2005 | Cohen |
| 2005/0267429 A1 | 12/2005 | Cohen |
| 2005/0288691 A1 | 12/2005 | Leiboff |
| 2006/0003604 A1 | 1/2006 | Angerpointner |
| 2006/0009744 A1 | 1/2006 | Erdman et al. |
| 2006/0020234 A1 | 1/2006 | Chou et al. |
| 2006/0020250 A1 | 1/2006 | Chester et al. |
| 2006/0047257 A1 | 3/2006 | Raidel et al. |
| 2006/0058750 A1 | 3/2006 | Di Girolamo et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0100586 A1 | 5/2006 | Karpowicz et al. |
| 2006/0122548 A1 | 6/2006 | Abrams |
| 2006/0122572 A1 | 6/2006 | Suarez |
| 2006/0153904 A1 | 7/2006 | Smith et al. |
| 2006/0161122 A1 | 7/2006 | Erdman et al. |
| 2006/0178650 A1 | 8/2006 | Hakansson et al. |
| 2006/0184147 A1 | 8/2006 | Hamed |
| 2006/0184150 A1 | 8/2006 | Noel |
| 2006/0206047 A1 | 9/2006 | Lampe et al. |
| 2006/0206073 A1 | 9/2006 | Crane et al. |
| 2006/0206074 A1 | 9/2006 | Bernal et al. |
| 2006/0241542 A1 | 10/2006 | Gudnason et al. |
| 2006/0282028 A1 | 12/2006 | Howard et al. |
| 2007/0003604 A1 | 1/2007 | Jones |
| 2007/0055029 A1 | 3/2007 | Suzuki et al. |
| 2007/0055209 A1 | 3/2007 | Patel et al. |
| 2007/0060892 A1 | 3/2007 | Propp |
| 2007/0073200 A1 | 3/2007 | Hannigan et al. |
| 2007/0073254 A1 | 3/2007 | Ponomarenko et al. |
| 2007/0078467 A1 | 4/2007 | Mullen |
| 2007/0100308 A1 | 5/2007 | Miyairi |
| 2007/0142804 A1 | 6/2007 | Bernard |
| 2007/0156104 A1 | 7/2007 | Lockwood et al. |
| 2007/0167096 A1 | 7/2007 | Scott |
| 2007/0167884 A1 | 7/2007 | Mangrum et al. |
| 2007/0219497 A1 | 9/2007 | Johnson et al. |
| 2007/0220692 A1 | 9/2007 | Kusin |
| 2007/0224903 A1 | 9/2007 | Chakravarty et al. |
| 2007/0225663 A1 | 9/2007 | Watt et al. |
| 2007/0239232 A1 | 10/2007 | Kurtz et al. |
| 2007/0254550 A1 | 11/2007 | Hamed et al. |
| 2007/0270070 A1 | 11/2007 | Hamed |
| 2007/0282236 A1 | 12/2007 | LaGreca |
| 2007/0282310 A1 | 12/2007 | Bengtson et al. |
| 2008/0004581 A1 | 1/2008 | Babusik et al. |
| 2008/0015532 A1 | 1/2008 | Waksmundzki |
| 2008/0033325 A1 | 2/2008 | Van der Hulst |
| 2008/0058691 A1 | 3/2008 | Sorensen |
| 2008/0082075 A1 | 4/2008 | Morrell-Schwartz |
| 2008/0090050 A1 | 4/2008 | Seyler et al. |
| 2008/0113143 A1 | 5/2008 | Taylor |
| 2008/0114317 A1 | 5/2008 | Seyler |
| 2008/0119586 A1 | 5/2008 | Byerly et al. |
| 2008/0132821 A1 | 6/2008 | Propp et al. |
| 2008/0147024 A1 | 6/2008 | Potts et al. |
| 2008/0167592 A1 | 7/2008 | Greer |
| 2008/0172017 A1 | 7/2008 | Carlucci et al. |
| 2008/0243100 A1 | 10/2008 | Wu et al. |
| 2008/0255533 A1 | 10/2008 | Wu et al. |
| 2008/0275409 A1 | 11/2008 | Kane et al. |
| 2008/0306456 A1 | 12/2008 | Riesinger |
| 2008/0312621 A1 | 12/2008 | Hundorf et al. |
| 2008/0312622 A1 | 12/2008 | Hundorf et al. |
| 2009/0012483 A1 | 1/2009 | Blott et al. |
| 2009/0043268 A1 | 2/2009 | Eddy et al. |
| 2009/0062760 A1 | 3/2009 | Wright et al. |
| 2009/0076472 A1 | 3/2009 | Goldwasser et al. |
| 2009/0099519 A1 | 4/2009 | Kaplan |
| 2009/0105670 A1 | 4/2009 | Bentley et al. |
| 2009/0112175 A1 | 4/2009 | Bissah et al. |
| 2009/0125004 A1 | 5/2009 | Shen et al. |
| 2009/0131892 A1 | 5/2009 | Karpowicz et al. |
| 2009/0157016 A1 | 6/2009 | Adahan |
| 2009/0157024 A1 | 6/2009 | Song |
| 2009/0204087 A1 | 8/2009 | Herfert et al. |
| 2009/0216168 A1 | 8/2009 | Eckstein |
| 2009/0227935 A1 | 9/2009 | Zanella et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0240185 A1 | 9/2009 | Jaeb et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0299308 A1 | 12/2009 | Kazala, Jr. et al. |
| 2009/0299340 A1 | 12/2009 | Kazala, Jr. et al. |
| 2009/0326430 A1 | 12/2009 | Frederiksen et al. |
| 2010/0010461 A1 | 1/2010 | Herfert et al. |
| 2010/0030171 A1 | 2/2010 | Canada et al. |
| 2010/0036334 A1 | 2/2010 | Heagle et al. |
| 2010/0036342 A1 | 2/2010 | Carlucci et al. |
| 2010/0048072 A1 | 2/2010 | Kauschke et al. |
| 2010/0055158 A1 | 3/2010 | Vitaris et al. |
| 2010/0063484 A1 | 3/2010 | Heagle |
| 2010/0069850 A1 | 3/2010 | Fabo |
| 2010/0069858 A1 | 3/2010 | Olson |
| 2010/0084074 A1 | 4/2010 | McClernon et al. |
| 2010/0087767 A1 | 4/2010 | McNeil |
| 2010/0106113 A1 | 4/2010 | Heinecke |
| 2010/0106120 A1 | 4/2010 | Holm |
| 2010/0106121 A1 | 4/2010 | Holm |
| 2010/0121298 A1 | 5/2010 | Seyler et al. |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0137890 A1 | 6/2010 | Martinez et al. |
| 2010/0160877 A1* | 6/2010 | Kagan ............... A61F 13/0203 604/319 |
| 2010/0160901 A1 | 6/2010 | Hu et al. |
| 2010/0168695 A1 | 7/2010 | Robles et al. |
| 2010/0174250 A1 | 7/2010 | Hu et al. |

(56) References Cited

U.S. PATENT DOCUMENTS

| | | |
|---|---|---|
| 2010/0191207 A1 | 7/2010 | Oba et al. |
| 2010/0198127 A1 | 8/2010 | Addison |
| 2010/0217177 A1 | 8/2010 | Cali et al. |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0262091 A1 | 10/2010 | Larsson |
| 2010/0305526 A1 | 12/2010 | Robinson et al. |
| 2010/0310845 A1 | 12/2010 | Bond et al. |
| 2010/0312159 A1 | 12/2010 | Aali et al. |
| 2010/0318043 A1 | 12/2010 | Malhi et al. |
| 2010/0318047 A1 | 12/2010 | Ducker et al. |
| 2010/0318052 A1 | 12/2010 | Ha et al. |
| 2010/0324516 A1 | 12/2010 | Braga et al. |
| 2011/0004172 A1 | 1/2011 | Eckstein et al. |
| 2011/0021964 A1 | 1/2011 | Larsen et al. |
| 2011/0034892 A1 | 2/2011 | Buan |
| 2011/0052664 A1 | 3/2011 | Tennican et al. |
| 2011/0054422 A1 | 3/2011 | Locke et al. |
| 2011/0059329 A1 | 3/2011 | Dobrawa et al. |
| 2011/0060303 A1 | 3/2011 | Bissah et al. |
| 2011/0070391 A1 | 3/2011 | Cotton |
| 2011/0077605 A1 | 3/2011 | Karpowicz et al. |
| 2011/0092871 A1* | 4/2011 | Fabo ............... A61F 15/001 602/46 |
| 2011/0098621 A1 | 4/2011 | Fabo et al. |
| 2011/0112492 A1 | 5/2011 | Bharti et al. |
| 2011/0118683 A1 | 5/2011 | Weston |
| 2011/0125119 A1 | 5/2011 | Weismantel et al. |
| 2011/0130712 A1 | 6/2011 | Topaz |
| 2011/0137222 A1 | 6/2011 | Masini |
| 2011/0152813 A1 | 6/2011 | Ellingson |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0218509 A1 | 9/2011 | Dontas |
| 2011/0223413 A1 | 9/2011 | Herfert et al. |
| 2011/0224631 A1 | 9/2011 | Simmons et al. |
| 2011/0230849 A1* | 9/2011 | Coulthard ............ A61M 1/915 604/319 |
| 2011/0238026 A1 | 9/2011 | Zhang et al. |
| 2011/0245788 A1 | 10/2011 | Marquez Canada |
| 2011/0247636 A1 | 10/2011 | Pollack |
| 2011/0257572 A1 | 10/2011 | Locke et al. |
| 2011/0257611 A1 | 10/2011 | Locke et al. |
| 2011/0268932 A1 | 11/2011 | Catalan et al. |
| 2011/0313373 A1 | 12/2011 | Riesinger |
| 2011/0319801 A1 | 12/2011 | Ital et al. |
| 2012/0004632 A1 | 1/2012 | Zhang et al. |
| 2012/0041402 A1 | 2/2012 | Greener |
| 2012/0045639 A1 | 2/2012 | Whitmore et al. |
| 2012/0053547 A1 | 3/2012 | Schroeder et al. |
| 2012/0065664 A1 | 3/2012 | Avitable et al. |
| 2012/0071848 A1 | 3/2012 | Zhang et al. |
| 2012/0095380 A1 | 4/2012 | Gergely et al. |
| 2012/0095426 A1 | 4/2012 | Visscher et al. |
| 2012/0101465 A1 | 4/2012 | McGuire, Jr. |
| 2012/0123311 A1 | 5/2012 | Weidemann-Hendrickson et al. |
| 2012/0136326 A1 | 5/2012 | Croizat et al. |
| 2012/0136329 A1 | 5/2012 | Carney |
| 2012/0143158 A1 | 6/2012 | Yang et al. |
| 2012/0150078 A1 | 6/2012 | Chen et al. |
| 2012/0165765 A1 | 6/2012 | Barta et al. |
| 2012/0172778 A1 | 7/2012 | Rastegar et al. |
| 2012/0197229 A1 | 8/2012 | Buan et al. |
| 2012/0203145 A1 | 8/2012 | Nilsson |
| 2012/0203189 A1 | 8/2012 | Barta et al. |
| 2012/0220968 A1 | 8/2012 | Confalone et al. |
| 2012/0220973 A1 | 8/2012 | Chan et al. |
| 2012/0232502 A1 | 9/2012 | Lowing |
| 2012/0238932 A1 | 9/2012 | Atteia et al. |
| 2012/0302440 A1 | 11/2012 | Thelander et al. |
| 2012/0302976 A1 | 11/2012 | Locke et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330253 A1 | 12/2012 | Robinson et al. |
| 2013/0012902 A1 | 1/2013 | Rovaniemi |
| 2013/0052152 A1 | 2/2013 | Keplinger |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0150814 A1 | 6/2013 | Buan |
| 2013/0165878 A1 | 6/2013 | Heagle |
| 2013/0172835 A1 | 7/2013 | Braga et al. |
| 2013/0211349 A1 | 8/2013 | Stokes et al. |
| 2013/0245583 A1 | 9/2013 | Locke et al. |
| 2013/0253453 A1 | 9/2013 | Olson |
| 2013/0274688 A1 | 10/2013 | Weston |
| 2013/0296762 A1 | 11/2013 | Toth |
| 2013/0310781 A1 | 11/2013 | Phillips et al. |
| 2014/0010673 A1 | 1/2014 | Locke et al. |
| 2014/0114268 A1 | 4/2014 | Auguste et al. |
| 2014/0127148 A1 | 5/2014 | Derain |
| 2014/0200533 A1 | 7/2014 | Whyte et al. |
| 2014/0228791 A1 | 8/2014 | Hartwell |
| 2014/0236109 A1 | 8/2014 | Greener |
| 2014/0249493 A1 | 9/2014 | Hartwell |
| 2014/0316359 A1 | 10/2014 | Collinson et al. |
| 2014/0343520 A1 | 11/2014 | Bennett et al. |
| 2014/0350496 A1 | 11/2014 | Riesinger |
| 2015/0032035 A1 | 1/2015 | Banwell et al. |
| 2015/0057625 A1 | 2/2015 | Coulthard |
| 2015/0065965 A1 | 3/2015 | Haggstrom et al. |
| 2015/0141941 A1 | 5/2015 | Allen et al. |
| 2015/0159066 A1 | 6/2015 | Hartwell et al. |
| 2015/0182677 A1 | 7/2015 | Collinson et al. |
| 2015/0190286 A1 | 7/2015 | Allen et al. |
| 2015/0209492 A1 | 7/2015 | Blott et al. |
| 2015/0335798 A1 | 11/2015 | De Samber et al. |
| 2016/0000610 A1 | 1/2016 | Riesinger |
| 2016/0000611 A1 | 1/2016 | Niederauer et al. |
| 2016/0081859 A1 | 3/2016 | Hartwell |
| 2016/0144084 A1 | 5/2016 | Collinson et al. |
| 2016/0317357 A1 | 11/2016 | Vitaris et al. |
| 2017/0007748 A1 | 1/2017 | Locke et al. |
| 2017/0128642 A1 | 5/2017 | Buan |
| 2017/0181896 A1 | 6/2017 | Hartwell |
| 2017/0181897 A1 | 6/2017 | Hartwell |
| 2019/0110932 A1 | 4/2019 | Mumby et al. |
| 2020/0360189 A1 | 11/2020 | Allen et al. |
| 2021/0052431 A1 | 2/2021 | Lattimore et al. |
| 2021/0353472 A1 | 11/2021 | Allen et al. |

FOREIGN PATENT DOCUMENTS

| | | |
|---|---|---|
| CN | 2676918 Y | 2/2005 |
| CN | 2843399 Y | 12/2006 |
| CN | 201139694 Y | 10/2008 |
| CN | 201375590 Y | 1/2010 |
| CN | 201418816 Y | 3/2010 |
| CN | 102274574 A | 12/2011 |
| CN | 202263100 U | 6/2012 |
| DE | 3443101 A1 | 5/1986 |
| DE | 4030465 A1 | 4/1992 |
| DE | 9017289 U1 | 4/1992 |
| DE | 19844355 A1 | 4/2000 |
| DE | 202004017052 U1 | 6/2005 |
| EP | 0053936 A2 | 6/1982 |
| EP | 0257916 A1 | 3/1988 |
| EP | 0340018 A2 | 11/1989 |
| EP | 0541251 A1 | 5/1993 |
| EP | 0392640 B1 | 6/1995 |
| EP | 0441418 B1 | 7/1995 |
| EP | 0549781 B1 | 9/1996 |
| EP | 0748894 A2 | 12/1996 |
| EP | 0599871 B1 | 4/1997 |
| EP | 0768071 A1 | 4/1997 |
| EP | 0853950 A1 | 7/1998 |

(56) References Cited

FOREIGN PATENT DOCUMENTS

| | | | |
|---|---|---|---|
| EP | 0777504 B1 | 10/1998 |
| EP | 0875224 A1 | 11/1998 |
| EP | 0941726 A1 | 9/1999 |
| EP | 1013290 A1 | 6/2000 |
| EP | 1048278 A2 | 11/2000 |
| EP | 1066809 A2 | 1/2001 |
| EP | 1139951 A2 | 10/2001 |
| EP | 1169071 A1 | 1/2002 |
| EP | 1312328 A2 | 5/2003 |
| EP | 1353001 A1 | 10/2003 |
| EP | 1452156 A1 | 9/2004 |
| EP | 0630629 B1 | 11/2004 |
| EP | 0982015 B1 | 8/2006 |
| EP | 1905465 B1 | 1/2010 |
| EP | 2161011 A1 | 3/2010 |
| EP | 2259767 A2 | 12/2010 |
| EP | 2263627 A2 | 12/2010 |
| EP | 2319550 A1 | 5/2011 |
| EP | 1578477 B1 | 9/2011 |
| EP | 2366721 A1 | 9/2011 |
| EP | 2529766 A3 | 12/2012 |
| EP | 2529767 A2 | 12/2012 |
| EP | 2413858 B1 | 1/2013 |
| EP | 2545946 A3 | 3/2013 |
| EP | 2477674 B1 | 7/2013 |
| EP | 2628500 B1 | 5/2014 |
| EP | 2051675 B1 | 6/2014 |
| EP | 2349154 B1 | 8/2014 |
| EP | 2269603 B1 | 5/2015 |
| EP | 2879636 B1 | 3/2017 |
| FR | 1163907 A | 10/1958 |
| GB | 1255395 A | 12/1971 |
| GB | 2099306 A | 12/1982 |
| GB | 2331937 A | 6/1999 |
| GB | 2336546 A | 10/1999 |
| GB | 2307180 B | 6/2000 |
| GB | 2344531 B | 7/2000 |
| GB | 2355228 A | 4/2001 |
| GB | 2389794 A | 12/2003 |
| GB | 2435422 A | 8/2007 |
| GB | 2435423 A | 8/2007 |
| GB | 2468905 A | 9/2010 |
| GB | 2489947 A | 10/2012 |
| JP | S5230463 U | 3/1977 |
| JP | H02131432 U | 11/1990 |
| JP | H0788131 A | 4/1995 |
| JP | 2006025918 A | 2/2006 |
| JP | 2008073187 A | 4/2008 |
| JP | 2008183244 A | 8/2008 |
| JP | 2012016476 A | 1/2012 |
| RU | 62504 U1 | 4/2007 |
| RU | 2432177 C1 | 10/2011 |
| WO | WO-8300742 A1 | 3/1983 |
| WO | WO-9111161 A1 | 8/1991 |
| WO | WO-9111162 A1 | 8/1991 |
| WO | WO-9216245 A1 | 10/1992 |
| WO | WO-9301778 A1 | 2/1993 |
| WO | WO-9301779 A1 | 2/1993 |
| WO | WO-9301780 A1 | 2/1993 |
| WO | WO-9301781 A1 | 2/1993 |
| WO | WO-9309745 A1 | 5/1993 |
| WO | WO-9311726 A1 | 6/1993 |
| WO | WO-9423677 A2 | 10/1994 |
| WO | WO-9504511 A1 | 2/1995 |
| WO | WO-9513042 A1 | 5/1995 |
| WO | WO-9513776 A1 | 5/1995 |
| WO | WO-9513779 A1 | 5/1995 |
| WO | WO-9514451 A1 | 6/1995 |
| WO | WO-9516424 A1 | 6/1995 |
| WO | WO-9525492 A1 | 9/1995 |
| WO | WO-9607783 A1 | 3/1996 |
| WO | WO-9621410 A1 | 7/1996 |
| WO | WO-9711658 A1 | 4/1997 |
| WO | WO-9714384 A1 | 4/1997 |
| WO | WO-9741816 A1 | 11/1997 |
| WO | WO-9820916 A1 | 5/1998 |
| WO | WO-9822279 A1 | 5/1998 |
| WO | WO-9904830 A1 | 2/1999 |
| WO | WO-9939671 A1 | 8/1999 |
| WO | WO-9945876 A1 | 9/1999 |
| WO | WO-9945878 A1 | 9/1999 |
| WO | WO-9956687 A1 | 11/1999 |
| WO | WO-9963922 A1 | 12/1999 |
| WO | WO-0000016 A1 | 1/2000 |
| WO | WO-0000127 A1 | 1/2000 |
| WO | WO-0000129 A1 | 1/2000 |
| WO | WO-0000130 A1 | 1/2000 |
| WO | WO-0000131 A1 | 1/2000 |
| WO | WO-0007653 A1 | 2/2000 |
| WO | WO-0040190 A1 | 7/2000 |
| WO | WO-0042957 A1 | 7/2000 |
| WO | WO-0059438 A1 | 10/2000 |
| WO | WO-0154743 A1 | 8/2001 |
| WO | WO-0172251 A1 | 10/2001 |
| WO | WO-0190465 A2 | 11/2001 |
| WO | WO-0217840 A1 | 3/2002 |
| WO | WO-0224132 A2 | 3/2002 |
| WO | WO-0226180 A1 | 4/2002 |
| WO | WO-0238096 A2 | 5/2002 |
| WO | WO-02076379 A2 | 10/2002 |
| WO | WO-03051409 A1 | 6/2003 |
| WO | WO-03073971 A2 | 9/2003 |
| WO | WO-03086232 A2 | 10/2003 |
| WO | WO-2004043321 A1 | 5/2004 |
| WO | WO-2004073566 A1 | 9/2004 |
| WO | WO-2004098474 A1 | 11/2004 |
| WO | WO-2005016179 A2 | 2/2005 |
| WO | WO-2005046760 A1 | 5/2005 |
| WO | WO-2005061025 A1 | 7/2005 |
| WO | WO-2005105174 A1 | 11/2005 |
| WO | WO-2005105180 A1 | 11/2005 |
| WO | WO-2006105305 A1 | 10/2006 |
| WO | WO-2006114637 A2 | 11/2006 |
| WO | WO-2007006306 A1 | 1/2007 |
| WO | WO-2007016590 A2 | 2/2007 |
| WO | WO-2007019038 A2 | 2/2007 |
| WO | WO-2007035038 A1 | 3/2007 |
| WO | WO-2007040606 A2 | 4/2007 |
| WO | WO-2007066699 A1 | 6/2007 |
| WO | WO-2007077214 A1 | 7/2007 |
| WO | WO-2007077216 A1 | 7/2007 |
| WO | WO-2007085396 A1 | 8/2007 |
| WO | WO-2007092397 A2 | 8/2007 |
| WO | WO-2007095180 A2 | 8/2007 |
| WO | WO-2007106590 A2 | 9/2007 |
| WO | WO-2007106591 A2 | 9/2007 |
| WO | WO-2007113597 A2 | 10/2007 |
| WO | WO-2007116347 A2 | 10/2007 |
| WO | WO-2008008032 A1 | 1/2008 |
| WO | WO-2008012278 A1 | 1/2008 |
| WO | WO-2008027449 A2 | 3/2008 |
| WO | WO-2008043067 A2 | 4/2008 |
| WO | WO-2008049277 A1 | 5/2008 |
| WO | WO-2008100437 A1 | 8/2008 |
| WO | WO-2008100440 A1 | 8/2008 |
| WO | WO-2008100446 A2 | 8/2008 |
| WO | WO-2008131895 A1 | 11/2008 |
| WO | WO-2008135997 A2 | 11/2008 |
| WO | WO-2008141470 A1 | 11/2008 |
| WO | WO-2009002260 A1 | 12/2008 |
| WO | WO-2009021523 A1 | 2/2009 |
| WO | WO-2009066104 A2 | 5/2009 |
| WO | WO-2009068665 A1 | 6/2009 |
| WO | WO-2009086580 A1 | 7/2009 |
| WO | WO-2009088925 A1 | 7/2009 |
| WO | WO-2009111655 A2 | 9/2009 |
| WO | WO-2009114760 A1 | 9/2009 |
| WO | WO-2009135171 A2 | 11/2009 |
| WO | WO-2009137194 A2 | 11/2009 |
| WO | WO-2009140376 A1 | 11/2009 |
| WO | WO-2009145894 A1 | 12/2009 |
| WO | WO-2009146441 A1 | 12/2009 |
| WO | WO-2009147402 A2 | 12/2009 |
| WO | WO-2009152021 A2 | 12/2009 |

(56) References Cited

FOREIGN PATENT DOCUMENTS

| | | |
|---|---|---|
| WO | WO-2009156949 A2 | 12/2009 |
| WO | WO-2009158129 A1 | 12/2009 |
| WO | WO-2010010398 A1 | 1/2010 |
| WO | WO-2010014177 A2 | 2/2010 |
| WO | WO-2010016791 A1 | 2/2010 |
| WO | WO-2010017437 A1 | 2/2010 |
| WO | WO-2010032951 A2 | 3/2010 |
| WO | WO-2010033271 A1 | 3/2010 |
| WO | WO-2010033272 A1 | 3/2010 |
| WO | WO-2010033574 A1 | 3/2010 |
| WO | WO-2010033769 A1 | 3/2010 |
| WO | WO-2010048480 A1 | 4/2010 |
| WO | WO-2010059712 A2 | 5/2010 |
| WO | WO-2010078166 A2 | 7/2010 |
| WO | WO-2010082872 A1 | 7/2010 |
| WO | WO-2010089448 A1 | 8/2010 |
| WO | WO-2010122665 A1 | 10/2010 |
| WO | WO-2010139926 A1 | 12/2010 |
| WO | WO-2011023650 A1 | 3/2011 |
| WO | WO-2011034789 A1 | 3/2011 |
| WO | WO-2011040970 A1 | 4/2011 |
| WO | WO-2011049562 A1 | 4/2011 |
| WO | WO-2011058311 A1 | 5/2011 |
| WO | WO-2011080427 A1 | 7/2011 |
| WO | WO-2011100851 A1 | 8/2011 |
| WO | WO-2011112794 A1 | 9/2011 |
| WO | WO-2011112870 A1 | 9/2011 |
| WO | WO-2011113728 A1 | 9/2011 |
| WO | WO-2011115908 A1 | 9/2011 |
| WO | WO-2011128651 A1 | 10/2011 |
| WO | WO-2011135284 A1 | 11/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2011152368 A1 | 12/2011 |
| WO | WO-2012009370 A2 | 1/2012 |
| WO | WO-2012035787 A1 | 3/2012 |
| WO | WO-2012069793 A1 | 5/2012 |
| WO | WO-2012069794 A1 | 5/2012 |
| WO | WO-2012074512 A1 | 6/2012 |
| WO | WO-2012142002 A1 | 10/2012 |
| WO | WO-2012143665 A1 | 10/2012 |
| WO | WO-2012146656 A1 | 11/2012 |
| WO | WO-2012150235 A1 | 11/2012 |
| WO | WO-2012168298 A1 | 12/2012 |
| WO | WO-2012174672 A1 | 12/2012 |
| WO | WO-2013013938 A1 | 1/2013 |
| WO | WO-2013014317 A1 | 1/2013 |
| WO | WO-2013016239 A1 | 1/2013 |
| WO | WO-2013019438 A1 | 2/2013 |
| WO | WO-2013029652 A1 | 3/2013 |
| WO | WO-2013043972 A1 | 3/2013 |
| WO | WO-2013060732 A1 | 5/2013 |
| WO | WO-2013076450 A1 | 5/2013 |
| WO | WO-2013090810 A1 | 6/2013 |
| WO | WO-2013110008 A1 | 7/2013 |
| WO | WO-2013123005 A1 | 8/2013 |
| WO | WO-2013136181 A2 | 9/2013 |
| WO | WO-2014016759 A1 | 1/2014 |
| WO | WO-2014020440 A1 | 2/2014 |
| WO | WO-2014020443 A2 | 2/2014 |
| WO | WO-2014066057 A1 | 5/2014 |
| WO | WO-2014043238 A3 | 9/2014 |
| WO | WO-2014158526 A1 | 10/2014 |
| WO | WO-2015022340 A1 | 2/2015 |
| ZA | 9605526 B | 2/1997 |

OTHER PUBLICATIONS

Wikipedia, "Parallel (geometry)," retrieved from https://en.wikipedia.org/w/index.php?title=Parallel_(geometry)oldid=1080576469, last edited on Apr. 2, 2022, 9 pages.

Advantec MFS, Inc., "Membrane Filters" (catalog), retrieved from http://www.advantecmfs.com/catalog/filt/membrane.pdf, on Jan. 29, 2016, Copyright 2001-2011, 17 pages.
Annex to the Communication for European Patent No. EP2879636, dated Jan. 22, 2020, 4 pages.
Annex to the Communication for European Patent No. EP2879636, dated Oct. 28, 2019, 13 pages.
Annex to the Communication, the Opposition of European Patent No. 2879636, dated Jan. 21, 2019, 22 pages.
Application Data Sheet for U.S. Appl. No. 61/785,054—Appendix A, filed Feb. 18, 2020, in the Opposition of European Patent No. EP2879636, *Dr. H. Ulrich Dorries* vs. *Smith & Nephew PLC*, 6 pages.
Assignment Agreement—Appendix C, filed Feb. 18, 2020, in the Opposition of European Patent No. EP2879636, *Dr. H. Ulrich Dorries* vs. *Smith & Nephew PLC*, 3 pages.
Assignment Agreement from Inventors to T.J. Smith & Nephew Limited—Exhibit BB01 A, filed Mar. 13, 2020, in the Opposition of European Patent No. EP2879636, *Pajaro Limited* vs. *Smith & Nephew PLC*, 12 pages.
Assignment Agreement transferring Rights to Smith & Nephew PLC, Exhibit BB01B, filed Mar. 13, 2020, in the Opposition of European Patent No. EP2879636, *Pajaro Limited* vs. *Smith & Nephew PLC*, 3 pages.
Boards of Appeal for the decision T 0101/17 Datasheet, dated Jan. 29, 2020, 17 pages.<gdiv class="ginger-extension-definitionpopup" style="left: 283.881px; top: 17.6px; z-index: 2147483646; display: none;"><gdiv class="ginger-dp"> <gdiv class="ginger-dp-content"> <gdiv class="ginger-dp-title"><gspan id="dp-title">December</gspan></gdiv> <gdiv class="ginger-dp-description" id="dp-description">the last (12th) month of the year</gdiv> <gdiv class="ginger-dp-more">More <gspan>(Definitions, Synonyms, Translation)</gspan></gdiv>.</gdiv></gdiv></gdiv>.
Boards of Appeal for the decision T 0892/08 Datasheet, dated Sep. 15, 2010, 20 pages.
Boards of Appeal for the decision T 1482/17 Datasheet, dated Sep. 18, 2020, 39 pages.
Boards of Appeal for the decision T 1848/12 Datasheet, dated Dec. 16, 2016, 41 pages.<gdiv class="ginger-extension-definitionpopup" style="left: 267.956px; top: 17.6px; z-index: 2147483646; display: none;"><gdiv class="ginger-dp"> <gdiv class="ginger-dp-content"> <gdiv class="ginger-dp-title"<>gspan id="dp-title">September</gspan></gdiv> <gdiv class="ginger-dp-description" id="dp-description">the month following August and preceding October</gdiv> <gdiv class="ginger-dp-more">More <gspan>(Definitions, Synonyms, Translation)</gspanx/gdiv>.</gdiv></gdiv></gdiv>.
Brief Communication—Letter from the Opponent for HGF European Patent No. EP2879636, mailed on Oct. 2, 2019, 7 pages.
Brief Communication of Oral proceedings—Letter from the Opponent Bird & Bird for the Opposition of European Patent No. 2879636, dated Feb. 26, 2021, 18 pages.
Brief Communication of Oral proceedings—Letter from the Opponent Wallinger Ricker Schlotter Tostmann for the Opposition of European Patent No. 2879636, dated Mar. 1, 2021, 25 pages.
Declaration of Nadeem Bridi submitted in the Opposition against EP2395957, dated Jan. 25, 2017, 1 page.
Emerging Technologies, "Chem-Posite™ 11C-450," Technical Data, the superabsorbent source (publication date unknown), 1 page.
Feature Analysis of Claim 1 of EP2879636, Exhibit D2 in Opposition European Patent No. 2879636, 1 page.
Grounds of Appeal—Opposition by KCI Licensing for European Patent No. 2879636, dated Feb. 11, 2022, 26 pages.
HGF's Written Submission in Preparation for the Oral Proceedings, re the Opposition of European Patent No. 2879636, dated Feb. 26, 2021, 3 pages.
HGF's Written Submission in Preparation for the Oral Proceedings, re the Opposition of European Patent No. EP2879636, dated Mar. 13, 2020, 17 pages.
Information about the Result of Oral Proceedings for the Opposition of European Patent No. 2879636, dated Apr. 26, 2021, 4 pages.
Information about the Result of Oral Proceedings, re the Opposition of European Patent No. EP2879636, dated Oct. 8, 2019, 1 page.

(56) References Cited

OTHER PUBLICATIONS

Interlocutory decision in Opposition proceedings (Art. 101(3)(a) and 106(2) EPC) for European patent No. 2879636, mailed on Jun. 1, 2021, 186 pages.
International Preliminary Report on Patentability for Application No. PCT/IB2013/002060, dated Feb. 12, 2015, 11 pages.
International Preliminary Report on Patentability for Application No. PCT/IB2013/002102, dated Feb. 12, 2015, 14 pages.
International Search Report and Written Opinion for Application No. PCT/IB2013/002060, dated Jan. 10, 2014, 18 pages.
International Search Report and Written Opinion for Application No. PCT/IB2013/002102, dated Jan. 22, 2014, 20 pages.
Invitation to Pay and Partial Search Report for Application No. PCT/IB2013/002060, dated Nov. 25, 2013, 7 pages.
Invitation to Pay and Partial Search Report for Application No. PCT/IB2013/002102, dated Nov. 21, 2013, 8 pages.
KCI, Inc., "V.A.C. Therapy Safety Information," leaflet, 2008, 4 pages.
KCI Licensing Inc, "Prevena™ Incision Management System—Clinician Guide—Instructions for Use," 390061 Rev D, Jan. 2010, 10 pages.
KCI Licensing Inc, "Prevena™ Incision Management System—Clinician Guide—Instructions for Use," 390153-WEB Rev B, Jan. 2010, 12 pages.
KCI Licensing, "PREVENA™ Incision Management System—Patient Guide", 390064 Rev D, Jan. 2010, 4 pages.
KCI Licensing, "PREVENA™ Incision Management System—Patient Guide," 390152-WEB C, Jan. 2011, 6 pages.
KCI Licensing, Prevena™ Incision Management System, Jun. 22, 2010, in 2 pages.
KCI's Written Submission in Preparation for the Oral Proceedings, the Opposition of European Patent No. 2879636, mailed on Sep. 26, 2019, 6 pages.
KCI's Written Submission in Preparation for the Oral Proceedings, the Opposition of European Patent No. 2879636, mailed on Aug. 7, 2019, 8 pages.
KCI's Written Submission in Preparation for the Oral Proceedings for European Patent No. EP 2879636, mailed on Mar. 11, 2020, 7 pages.
Kendall ULTEC Hydrocolloid Dressing (4×4"), Product Ordering Page, web page downloaded on Jul. 13, 2014, 1 page.
Letter accompanying subsequently filed items on behalf of the opponent Wallinger Ricker Schlotter Tostmann for the Opposition of European Patent No. 2879636, dated Jun. 25, 2021, 5 pages.
Letter regarding the Opposition Procedure for European Patent No. EP 2879636, mailed on Jan. 3, 2020, 4 pages.
Letter regarding the Opposition Procedure, in Reply to the Patentee's Auxiliary Requests of the European Patent No. 2879636, mailed on Sep. 11, 2018, 225 pages.
Letter relating to the Appeal Procedure for the Opposition of the European Patent No. 2879636, mailed on Nov. 29, 2021, 39 pages.
Merriam-Webster, "Gauze," Retrieved from https://www.merriam-webster.com/dictionary/gauze on Oct. 22, 2019, 9 pages.
Notice In response to Proprietor's submissions of Mar. 13, 2020 and in preparation of oral proceedings for European Patent No. 2879636, mailed on May 27, 2020, 9 pages.
Notice of Opposition—Facts and Arguments for the European Patent No. 2879636, mailed on Dec. 22, 2017, including cited references D1—EP2879636B1, D2—Feature analysis of claim of the opposed patent, D3—U.S. Pat. No. 7,976,519, D4—US20100305526, D5—EP2361641, D5a—WO009111657, D6—WO2011028407, D7—WO2011087871, D8—U.S. Pat. No. 5,591,149, D9—WO2011135284, D10—US20120095380, D11—US20110282309, D12—US20080172017, 698 pages.
Notice of Opposition—Statement of Facts and Evidence for the European Patent No. 2879636, mailed on Dec. 12, 2017, including cited references D1—U.S. Pat. No. 6,071,267, D2—WO2007041642, D3—EP2345438, D4—WO02043634, D5—US20070265586, D6—US20120095380, D7—US20080172017 and relied upon documents for background 01—Extract from Wikipedia Capillary Action, 02—Extract from the Concise Oxford English Dictionary, 03—Extract from Wikipedia Fluid, and 04—Extract from Wikipedia Rayon, 292 pages.
Notice of Opposition against a European Patent No. 2879636, mailed on Dec. 15, 2017, including cited references D1—US20110282309, D2—WO2009066106, D3a—EP2571467 (published as WO2011144888), D3b—WO2011135284, D4—WO2009111657, D5—US20070265586, D6—US20110004172, D7—U.S. Pat. No. 7,976,519, D8—US20100305526, D9—US20120095380, D10—WO99063922, D11—U.S. Pat. No. 5,360,420, D12—US20040019338, 473 pages.
Opponent Dorries' Written Submission in Preparation for the Oral Proceedings, re the Opposition of European Patent No. EP2879636, dated Aug. 2, 2019, 25 pages.
Opponent Dorries' Written Submission in Preparation for the Oral Proceedings, re the Opposition of European Patent No. EP2879636, dated Feb. 18, 2020, 29 pages.
Pajaro's Written Submission in Preparation for the Oral Proceedings, re the Opposition of European Patent No. EP2879636, dated Aug. 7, 2019, 36 pages.
Pajaro's Written Submission in Preparation for the Oral Proceedings, the Opposition of European Patent No. EP2879636, mailed on Jan. 22, 2020, 2 pages.
Pajaro's Written Submissions in Preparation for the Oral Proceedings, re the Opposition of European Patent No. EP2879636, filed Jan. 24, 2020, 33 pages.
PCT Application form of WO2014020440A1 (PCT Application No. PCT/IB2013/002060)—Exhibit BB01-D1, filed Jan. 24, 2020, in the Opposition of European Patent No. EP2879636, *Pajaro Limited* vs. *Smith & Nephew PLC*, 11 pages.
PCT Request of PCT Application No. PCT/IB2013/002060—Appendix B, filed Feb. 18, 2020, in the Opposition of European Patent No. EP2879636, *Dr. H. Ulrich Dorries* vs. *Smith & Nephew PLC*, 11 pages.
"Pico Application," YouTube video, retrieved from URL: https://www.youtube.com/watch?v=yCifiV6RRDw, Jun. 6, 2012, 2 pages.
Protz K., "Modern Wound Dressings Support the Healing Process," Wound care: Indications and Application, Geriatrie Journal, Apr. 2005, pp. 3333-3339 (17 pages with English translation).
Provision of the Minutes for European Patent No. EP2879636, mailed on Oct. 24, 2019, 9 pages.
Reply of the Patent Proprietor to the Notice of the Opposition, the Opposition of European Patent No. 2879636, mailed on Jul. 20, 2018, 143 pages.
Reply to Appeal by Simmons & Simmons for European Patent No. 2879636, mailed on Feb. 18, 2022, 3 pages.
Reply to Appeal for European Patent No. 2879636, *Pajaro Limited* Vs *Smith & Nephew PLC*, mailed on Apr. 7, 2022, 17 pages.
Reply to Appeal for European Patent No. 2879636, *Pajaro Limited* Vs *Smith & Nephew PLC*, mailed on Feb. 21, 2022, 30 pages.
Smith & Nephew, "PICO Single Use Negative Pressure Wound Therapy System," Spiral Booklet, Mar. 2011, 7 pages.
Smith & Nephew, Allevyn Gentle Border Multisite, Jun. 2011, 2 pages.
Smith and Nephew Inc., "Allevyn Wound Dressings Pamphlet," 2008, 2 pages.
Smith and Nephew Medical Ltd., "Reach for the Right Dressing. Reach for Allevyn," Allevyn Educational Booklet, Apr. 2014, 2 pages.
SNaP, "SNaP® BLUE Foam Dressing," Color Brochure (L22162 rev. 130429), Jun. 2013, 2 pages.
SNaP, "SNaP®—Product Overview," Wound Care System, Captured on Wayback Machine on Nov. 17, 2011, 2 pages.
Statement of Grounds of Appeal by opponent, re the Opposition of European Patent No. 2879636, mailed on Oct. 8, 2021, 31 pages.
Statement of Grounds of Appeal by proprietor, re the Opposition of European Patent No. 2879636, mailed on Oct. 8, 2021, 10 pages.
Statement of Grounds of Appeal by opponent, re the Opposition of European Patent No. 2879636, mailed on Oct. 4, 2021, 35 pages.
Summons to Attend Oral Proceedings pursuant to Rule 115(1) for European Patent No. 2879636 mailed on Sep. 17, 2020, 22 pages.
U.S. Appl. No. 61/650,904—priority application of WO2013175306A1—Exhibit D22-P1, filed Jan. 24, 2020, in the

(56) References Cited

OTHER PUBLICATIONS

Opposition of European Patent No. EP2879636, *Pajaro Limited* vs. *Smith & Nephew PLC*, 42 pages.
U.S. Appl. No. 61/678,569—first priority application of WO2014020440A1—Exhibit BB01-P1, filed Jan. 24, 2020, in the Opposition of European Patent No. EP2879636, *Pajaro Limited* vs. *Smith & Nephew PLC*, 132 pages.
U.S. Appl. No. 61/753,374, second priority application of WO2014020440A1, Exhibit BB01-P2, filed Jan. 24, 2020, in the Opposition of European Patent No. EP2879636, *Pajaro Limited* vs. *Smith & Nephew PLC*, 263 pages.
U.S. Appl. No. 61/753,878, third priority application of WO2014020440A1, Exhibit BB01-P3, filed Jan. 24, 2020, in the Opposition of European Patent No. EP2879636, *Pajaro Limited* vs. *Smith & Nephew PLC*, 277 pages.
U.S. Appl. No. 61/785,054, fourth priority application of WO2014020440A1, Exhibit BB01-P4, filed Jan. 24, 2020, in the Opposition of European Patent No. EP2879636, *Pajaro Limited* vs. *Smith & Nephew PLC*, 310 pages.
U.S. Appl. No. 61/785,927 priority application of WO 2013175306A1, Exhibit D22-P2, filed Jan. 24, 2020, in the Opposition of European Patent No. EP 2879636, *Pajaro Limited* vs. *Smith & Nephew PLC*, 215 pages.
U.S. Appl. No. 61/823,298, fifth priority application of WO 2014020440A1, Exhibit BB01-P5, filed Jan. 24, 2020, in the Opposition of European Patent No. EP 2879636, *Pajaro Limited* vs. *Smith & Nephew PLC*, 170 pages.
U.S. Assignment History Reel No. 030899, frames 0098-0111, Exhibit BB02, filed Jan. 24, 2020, in the Opposition of European Patent No. EP 2 879 636, *Pajaro Limited* vs. *Smith & Nephew PLC*, 14 pages.
U.S. Assignment History Reel No. 030899, frames 0158-0161, Exhibit BB03, filed Jan. 24, 2020, in the Opposition of European Patent No. EP2879636, *Pajaro Limited* vs. *Smith & Nephew PLC*, 4 pages.
Wikipedia, "Gauze," Retrieved from https://en.wikipedia.org/wiki/Gauze on Oct. 22, 2019, 3 pages.
WO2014020440A1 (PCT Application No. PCT/IB2013/002060), published Feb. 6, 2014, by Smith & Nephew PLC, Exhibit BB01, filed Jan. 24, 2020, in the Opposition of European Patent No. EP2879636, *Pajaro Limited* vs. *Smith & Nephew PLC*, 191 pages.
Written Submission in Preparation for the Oral Proceedings, Opposition of European Patent No. EP2879636, mailed Oct. 2, 2019, 18 pages.
Written Submission in Preparation for the Oral Proceedings, Opposition of European Patent No. EP2879636, mailed Oct. 4, 2019, 107 pages.
Written Submission in Preparation for the Oral Proceedings, Opposition of European Patent No. EP2879636, mailed Aug. 8, 2019, 192 pages.

\* cited by examiner

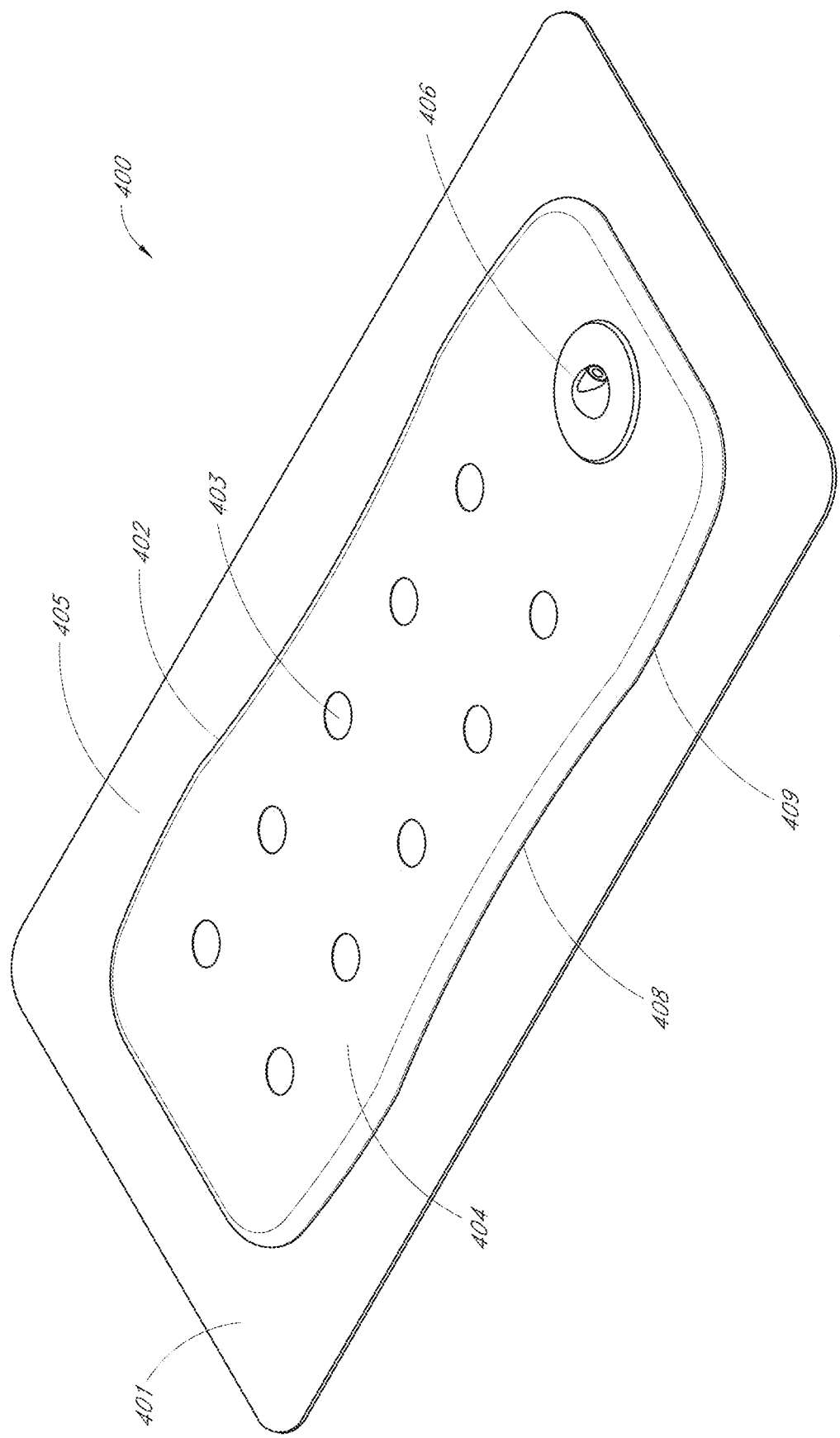

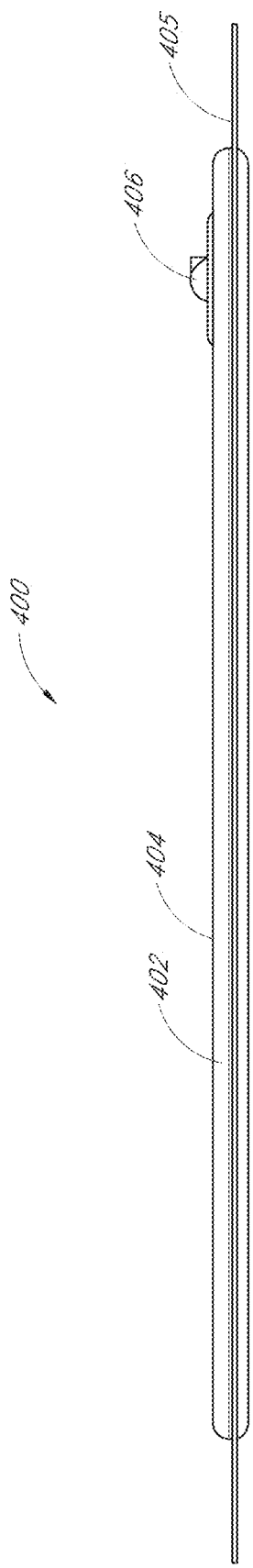

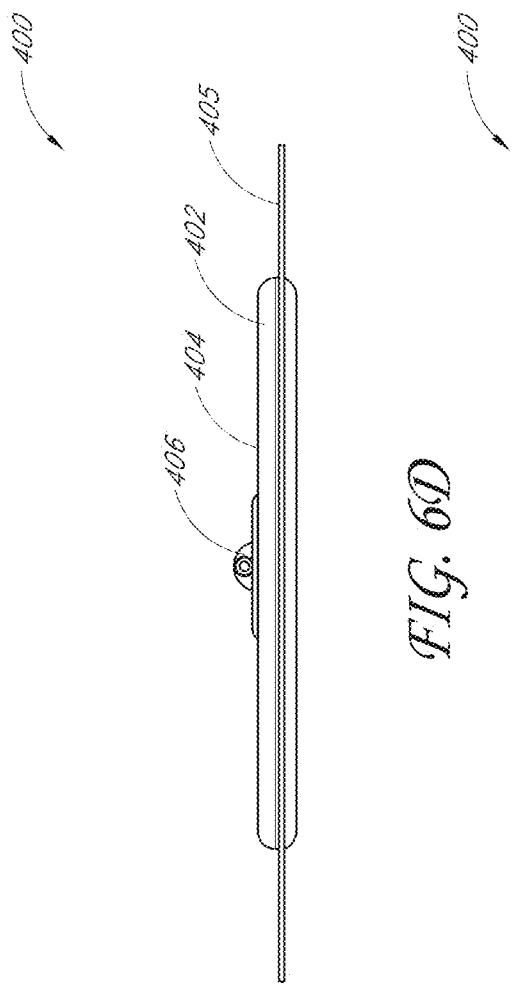

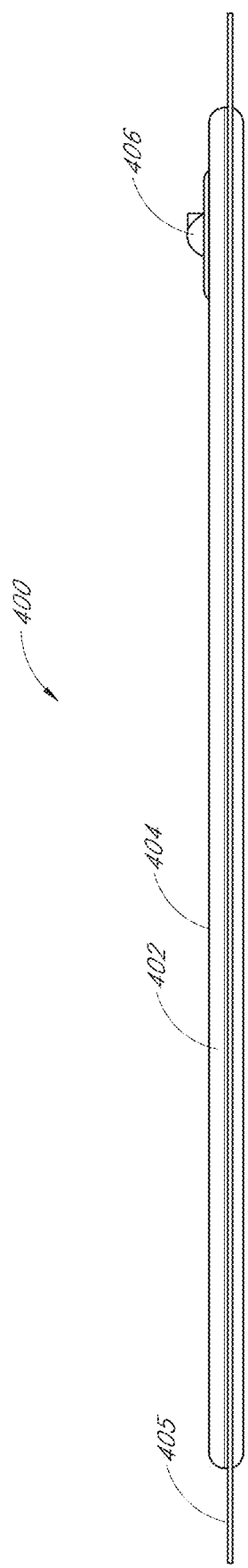

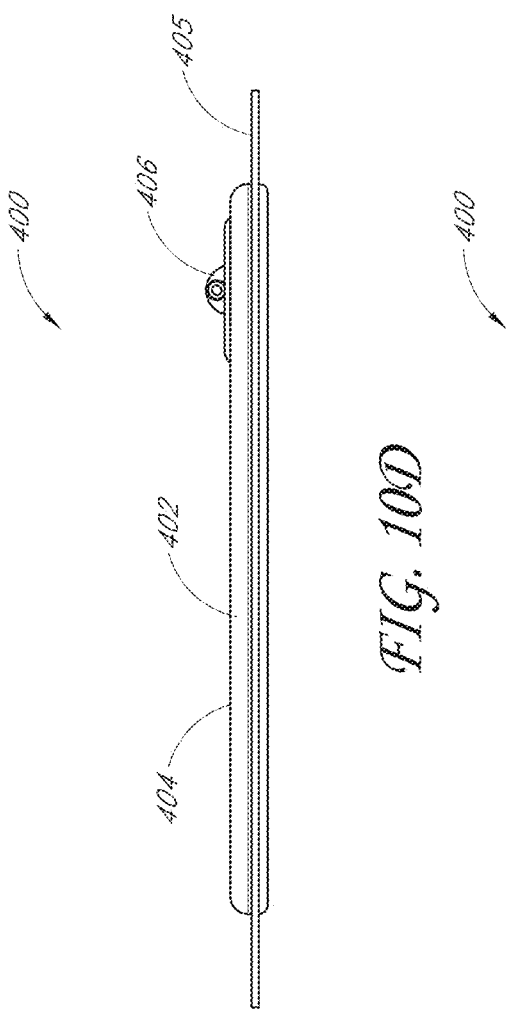
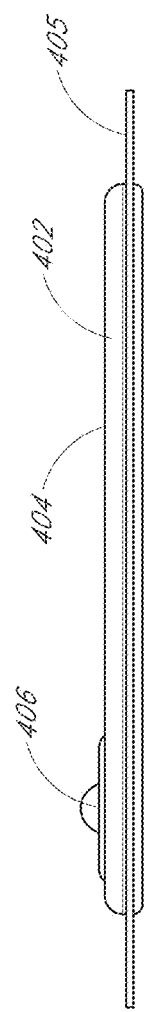
FIG. 10D
FIG. 10E

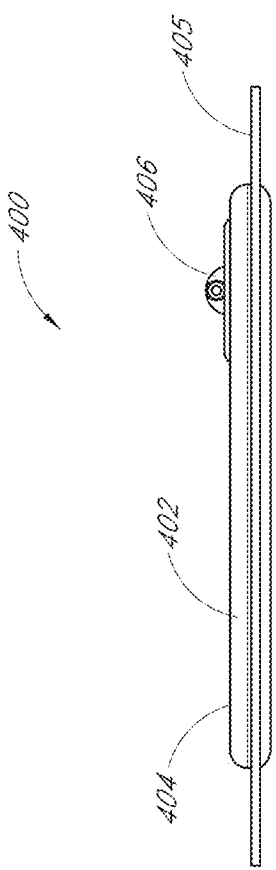
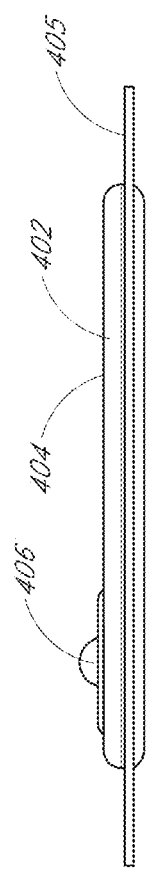
FIG. 11D
FIG. 11E

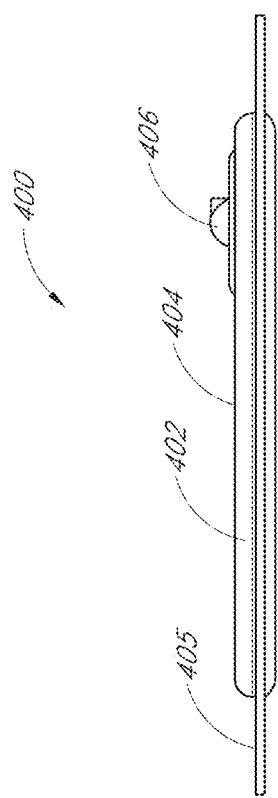

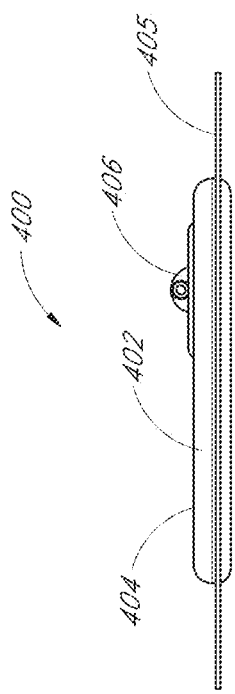
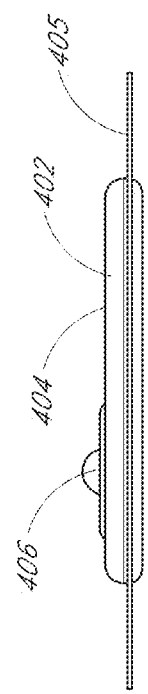
FIG. 12D
FIG. 12E

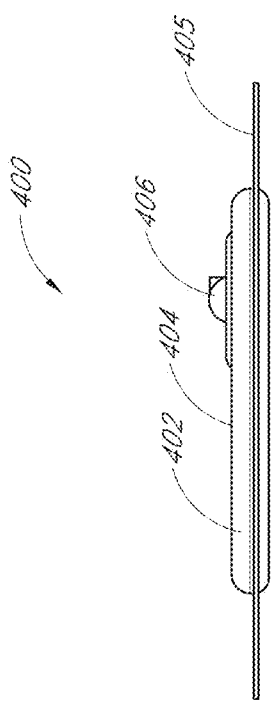

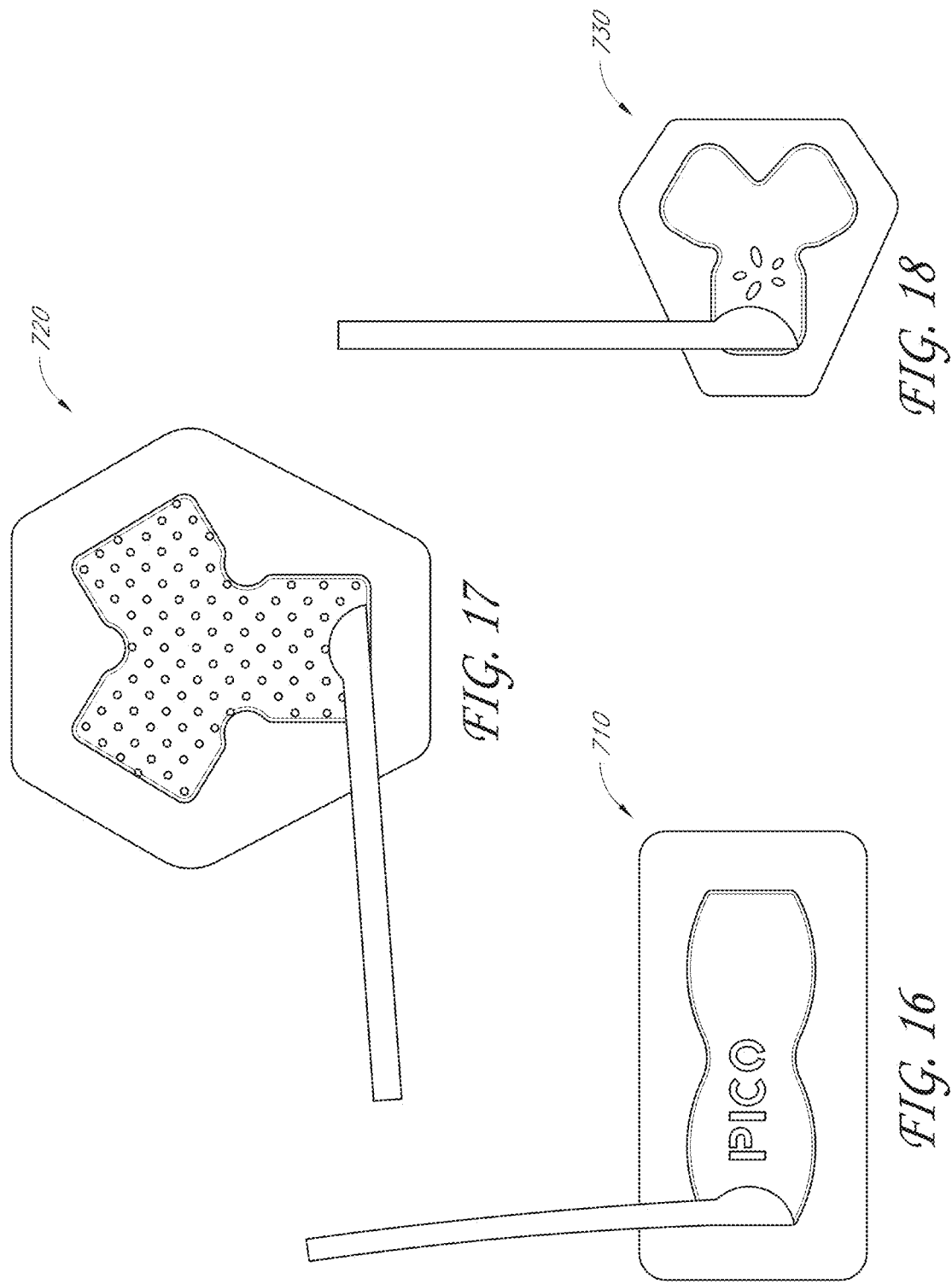

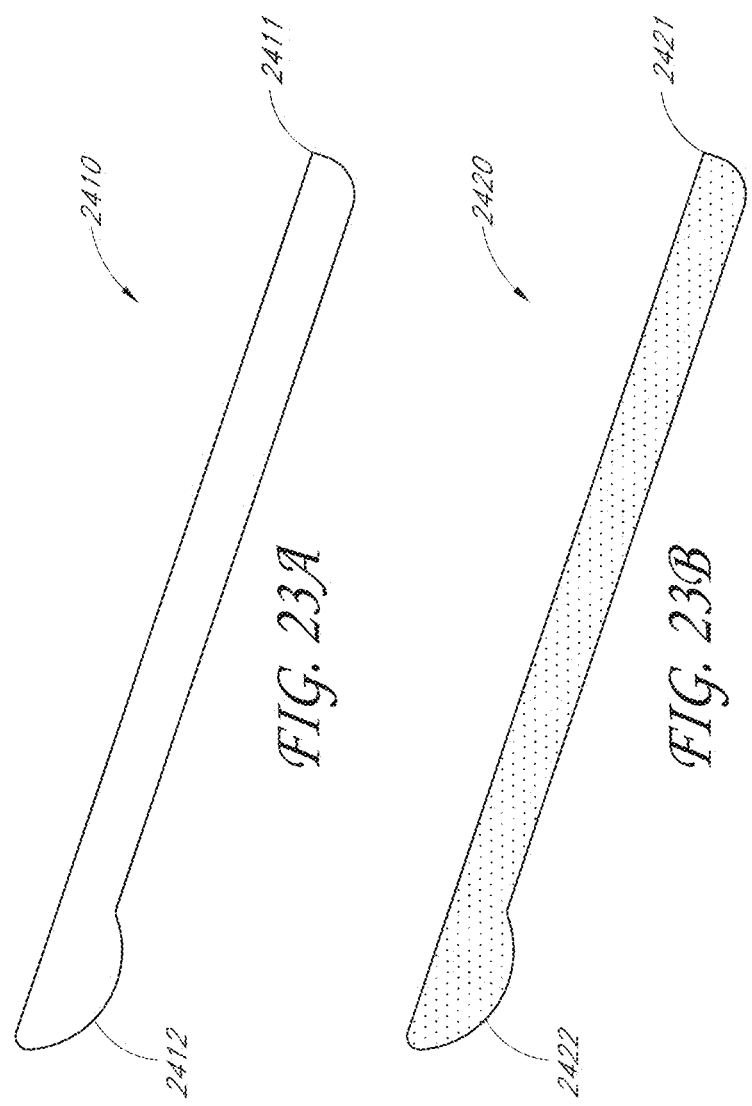

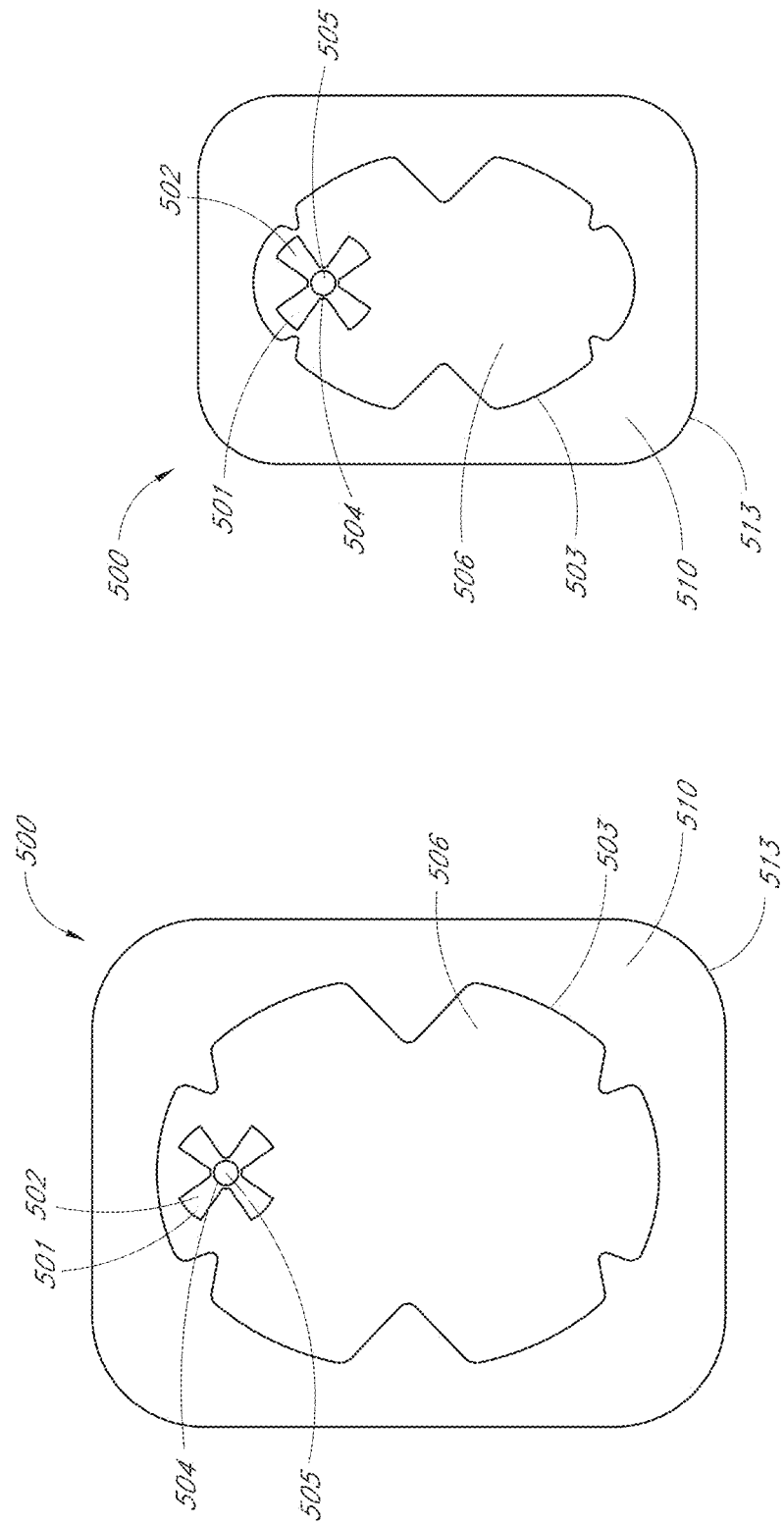

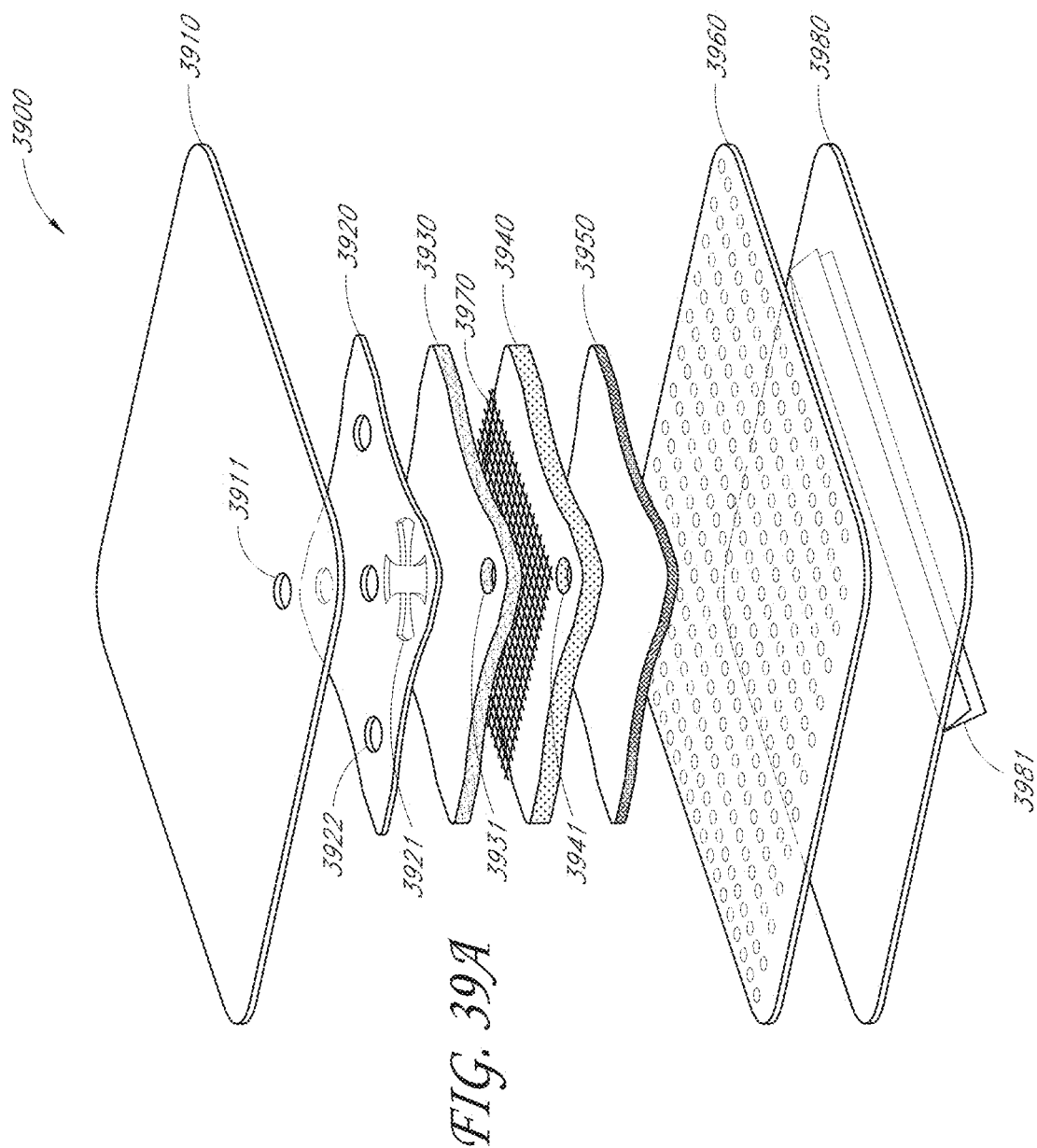

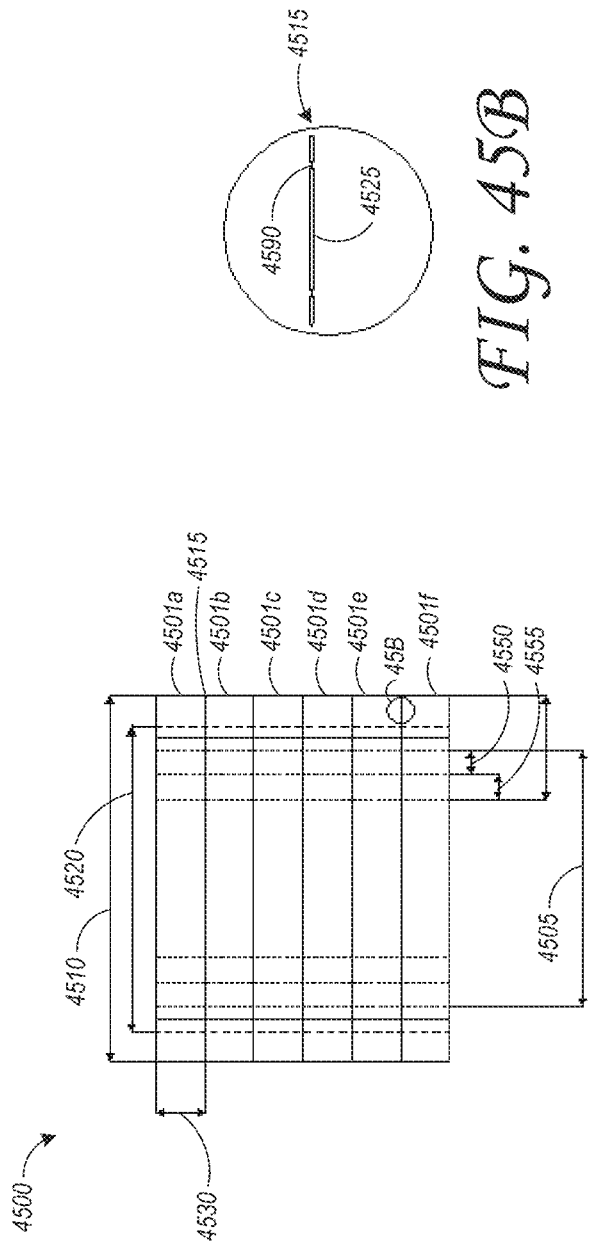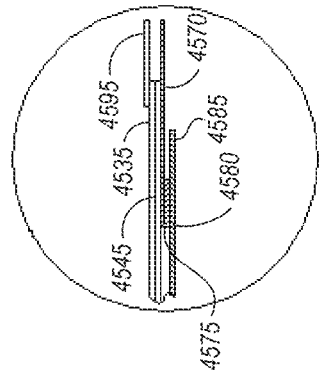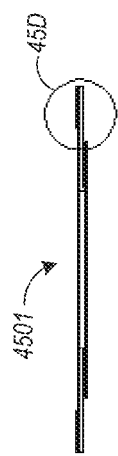

WOUND DRESSING AND METHOD OF TREATMENT

CROSS-REFERENCE TO RELATED APPLICATIONS

This application is a continuation of U.S. application Ser. No. 16/887,677, filed May 29, 2020, which is a continuation of U.S. application Ser. No. 14/418,908, filed on Jan. 30, 2015 and now issued as U.S. Pat. No. 10,667,955, which is a national stage application of International Patent Application No. PCT/IB2013/002060, filed on Jul. 31, 2013, which claims the benefit of U.S. Provisional Application Ser. No. 61/678,569, filed Aug. 1, 2012, titled "WOUND DRESSING AND METHOD OF TREATMENT," U.S. Provisional Application Ser. No. 61/753,374, filed Jan. 16, 2013, titled "WOUND DRESSING AND METHOD OF TREATMENT," U.S. Provisional Application Ser. No. 61/753,878, filed Jan. 17, 2013, titled "WOUND DRESSING AND METHOD OF TREATMENT," U.S. Provisional Application Ser. No. 61/785,054, filed Mar. 14, 2013, titled "WOUND DRESSING AND METHOD OF TREATMENT," and U.S. Provisional Application Ser. No. 61/823,298, filed May 14, 2013, titled "WOUND DRESSING AND METHOD OF TREATMENT," the entireties of each of which are hereby incorporated by reference.

BACKGROUND OF THE INVENTION

Field of the Invention

Embodiments described herein relate to apparatuses, systems, and methods the treatment of wounds, for example using dressings in combination with negative pressure wound therapy.

DESCRIPTION OF THE RELATED ART

Prior art dressings for use in negative pressure have been difficult to apply, particularly around curved or non-flat body surfaces. Further, when used, wound exudate may soak into the dressing, which some patients may find aesthetically unpleasing and difficult to address in social situations.

SUMMARY OF THE INVENTION

Accordingly, certain embodiments disclosed herein relate to improved wound dressing that exhibit enhanced conformability and aesthetic presentation. Also disclosed are improved methods of use and systems for use of the same, preferably in conjunction with negative pressure wound therapy.

In one embodiment, a wound dressing comprises:
an acquisition distribution layer;
an absorbent layer over the acquisition distribution layer; and
a backing layer above the absorbent layer.

In some embodiments, the wound dressing may further comprise a fluidic connector configured to connect the backing layer to a source of negative pressure. The fluidic connector may be positioned over an opening in the backing layer.

The acquisition distribution layer may be configured to horizontally wick fluid as the fluid is absorbed upward through the wound dressing. In some embodiments, the acquisition distribution layer may comprise a mix of cellulosic fibers and composite fibers, the composite fibers comprising a PET core and a PE outer layer. The acquisition distribution layer may comprise a plurality of fibers, and a majority of the fiber volume may extend horizontally, or substantially or generally horizontally. The acquisition distribution layer may comprise a plurality of fibers, and approximately 80% to approximately 90% of the fiber volume may extend horizontally, or substantially or generally horizontally. The acquisition distribution layer may comprise a plurality of fibers, and all or substantially all of the fiber volume may extend horizontally, or substantially or generally horizontally extending fibers. The acquisition distribution layer may comprise a plurality of fibers, and a majority of the fibers may span a distance perpendicular to the thickness of the acquisition distribution layer that is greater than the thickness of the acquisition distribution layer. The wound dressing may be configured such that a ratio of an amount of fluid wicking laterally across the acquisition distribution layer to an amount of fluid wicking vertically through the acquisition distribution layer when under negative pressure is about 2:1 or more.

In some embodiments, the absorbent layer and acquisition distribution layer may be bonded together by one or more of adhesive, stitching, or heat bonding. The absorbent layer may comprise a fibrous network and superabsorbing particles within the fibrous network. The wound dressing may further comprise a wound contact layer below the acquisition distribution layer. The wound dressing may further comprise a transmission layer between the wound contact layer and the acquisition distribution layer.

The transmission layer may be configured to vertically wick fluid. The transmission layer may comprise a top fabric layer, a bottom fabric layer, and a plurality of filaments extending generally perpendicularly between said top fabric layer and said bottom fabric layer. In some embodiments, a majority of filaments, by volume, may extend vertically, or substantially or generally vertically. In another embodiment, approximately 80% to approximately 90% of the filaments, by volume, may extend vertically, or substantially or generally vertically. In yet another embodiment, all or substantially all of the filaments, by volume, may extend vertically, or substantially or generally vertically. In some embodiments, a majority of filaments may extend upward from the bottom fabric layer and/or downward from the top fabric layer and may extend over a length more than half the distance between the top and bottom fabric layers. A majority of filaments may span a distance that is greater in a direction perpendicular to the top and bottom fabric layers than in a direction parallel to the top and bottom fabric layers. A ratio of an amount of fluid wicking vertically through the transmission layer to an amount of fluid wicking laterally across the transmission layer when under negative pressure may be, in some embodiments, about 2:1 or more.

In some embodiments, the acquisition distribution layer may comprise viscose, polyester, polypropylene, cellulose, polyethylene or a combination of some or all of these materials. The absorbent layer may comprise between 30% and 40% cellulose matrix and 60% and 70% superabsorbing polymers. The absorbent layer may comprise a mix of cellulosic fibers and composite fibers, and the composite fibers may comprise a PET core and a PE outer layer. The absorbent layer may comprise a plurality of layers. The plurality of layers of the absorbent layer may comprise a textured layer configured to laterally spread absorbed fluid, an absorption layer configured to draw fluid upward into an interior of the absorbent layer, a storage layer configured to absorb the fluid, and a liquid distribution layer configured to apply a reverse suction effect to the storage layer. The absorbent layer may further comprise a tissue dispersant layer.

The backing layer may be transparent or translucent, and the wound dressing may further comprise an obscuring layer between the absorbent layer and the backing layer. The wound dressing may comprise one or more viewing windows in the obscuring layer. At least the obscuring layer may be shaped with a narrowed central portion along its length. The obscuring layer may comprise two rows of three viewing windows. The obscuring layer may comprise one row of three viewing windows. The obscuring layer may comprise one row of eight viewing windows. The obscuring layer may comprise two rows of five viewing windows. The obscuring layer may comprise one row of five viewing windows. At least the obscuring layer may be shaped with a narrowed central portion along both its width and its length. The obscuring layer may comprise a 3×3 array of viewing windows. The obscuring layer may comprise a quincunx array of viewing windows. At least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected.

In one embodiment, a wound treatment apparatus for treatment of a wound site comprises:
a wound dressing comprising:
an absorbent layer configured to retain fluid,
a backing layer above the absorbent layer, and
an obscuring layer configured to at least partly visually obscure fluid within the absorbent layer; and
a fluidic connector configured to transmit negative pressure from a negative pressure source to the wound dressing for the application of topical negative pressure at the wound site.

In some embodiments, the obscuring layer is above or below the backing layer. The obscuring layer may be configured to at least partially visually obscure fluid contained within the absorbent layer. The obscuring layer may comprise at least one viewing window configured to allow a visual determination of the saturation level of the absorbent layer. The at least one viewing window may comprise at least one aperture made through the obscuring layer. The at least one viewing window may comprise at least one uncolored region of the obscuring layer. The viewing window may comprise an array of dots. The array of dots may be distributed in a straight line of dots, the straight line of dots being positioned on a center line along a length of the absorbent layer. The straight line of dots may comprise an array of three dots. The straight line of dots may comprise an array of five dots. The straight line of dots may comprise an array of eight dots. The array of dots may be distributed in two straight lines of dots, the two straight lines of dots positioned to be an equal distance from a center line along a length of the absorbent layer, the two straight lines of dots having an equal number of dots. The two straight lines of dots may comprise an array of three dots. The two straight lines of dots may comprise an array of five dots. The array of dots may be distributed regularly over the obscuring layer to enable assessment of wound exudate spread. The viewing window may be selected from the group consisting of a graphical element or a typographical element. The obscuring layer may comprise an auxiliary compound, wherein the auxiliary compound may comprise activated charcoal configured to absorb odors and configured to color or tint the obscuring layer. The fluidic connector may comprise an obscuring element configured to substantially visually obscure wound exudate.

Some embodiments may further comprise an acquisition distribution layer between the wound contact layer and the absorbent material. The absorbent layer may comprise cellulose fibers and between 40% and 80% (or between about 40% and about 80%) superabsorbent particles. The obscuring layer, in a dry state, may be configured to yield a CIE y value of 0.4 or less and a CIE x value of 0.5 or less on a CIE x, y chromaticity diagram. The obscuring layer, in a dry state, may have a color of Bg, gB, B, pB, bP, P, rP, pPk, RP, O, rO, or yO on a CIE x, y chromaticity diagram. In some embodiments, the wound dressing further comprises an orifice in the backing layer, the orifice configured to communicate negative pressure to the wound site. The obscuring layer may comprise at least one orifice viewing window configured to be positioned adjacent to the orifice in the backing layer, the orifice viewing window configured to allow a visual determination of the saturation level of the absorbent layer adjacent to the orifice. The orifice viewing window may be cross-shaped. The wound dressing may comprise a first length corresponding to a first edge of a wound dressing and a first width corresponding to a second edge of the wound dressing, a first x axis runs along the first width and a first y axis runs along the first length, wherein the first x axis and the first y axis are in a perpendicular alignment. The viewing window may comprise a first arm and a second arm, the first arm of the viewing window define a second length and the second arm defines a second width, a second x axis runs along the second width and a second y axis runs along the second length, wherein the second x axis and the second y axis are in a perpendicular alignment. The second x axis and second y axis of the viewing window is offset from the first x axis and the first y axis of the absorbent layer. The second x axis and second y axis of the viewing window may be aligned with the first x axis and the first y axis of the absorbent layer. The cross-shaped viewing window may comprise flared ends. The fluidic connector may be configured to transmit air. The fluidic connector may comprise a filter, the filter configured to block fluid transport past itself. The fluidic connector may comprise a secondary air leak channel, the secondary air leak channel configured to allow a flow of ambient air to the wound site. The secondary air leak channel may comprise a filter. The fluidic connector may comprise a soft fluidic connector. The soft fluidic connector may comprise a three dimensional fabric. In some embodiments, the three dimensional fabric is configured to transmit therapeutic levels of negative pressure while an external pressure up to 2 kg/cm$^2$ is applied thereto. The soft fluidic connector may be configured to be connected to a tube in fluid communication with the vacuum source. The soft fluidic connector may be configured to be connected directly to the vacuum source. The soft fluidic connector may comprise an enlarged distal end, the enlarged distal end configured to be connected to the wound dressing. The apparatus may further comprise a tube connected to the fluidic connector. The apparatus may further comprise a pump in fluid communication with the fluidic connector. In some embodiments, the absorbent layer comprises two or more lobes. The absorbent layer may further comprise a tissue dispersant layer.

In another embodiment, a wound treatment apparatus for treatment of a wound site comprises:
- a wound dressing configured to be positioned over a wound site, the wound dressing comprising:
  - a backing layer having an upper surface and a lower surface and defining a perimeter configured to be positioned over skin surrounding the wound site, the backing layer including an opening;
  - a wound contact layer adhered to the lower surface of the backing layer, the wound contact layer comprising an adhesive on a lower surface thereof;
  - an absorbent material positioned between the backing layer and the wound contact layer, wherein the absorbent material comprises a vertical hole positioned below the opening in the backing layer;
  - an obscuring layer positioned at least partially over the absorbent material, wherein the obscuring layer comprises a vertical hole positioned between the opening in the backing layer and the vertical hole in the absorbent material;
  - one or more viewing windows extending through the obscuring layer configured to allow visualization of wound exudate in the absorbent material; and
  - a port positioned over the opening in the backing layer configured to transmit negative pressure through the port for the application of topical negative pressure at the wound site.

In some embodiments, the backing layer is transparent or translucent. The backing layer may define a perimeter with a rectangular or a square shape. The wound contact layer may be adhered to the lower surface of the backing layer along the perimeter of the backing layer. The hole in the obscuring layer may have a different diameter than the hole in the absorbent material or the opening in the backing layer. The one or more viewing windows may be arranged in a repeating pattern across the obscuring layer. The one or more viewing windows may have a circular shape. Some embodiments may further comprise an acquisition distribution layer between the wound contact layer and the absorbent material. The absorbent layer may comprise cellulose fibers and between 40% and 800% (or between about 40% and about 80%) superabsorbent particles. The obscuring layer, in a dry state, may be configured to yield a color of Bg, gB, B, pB, bP, P, rP, pPk, RP, O, rO, or yO on the CIE x, y chromaticity diagram.

Some embodiments further comprise a transmission layer between the absorbent material and the wound contact layer. In some embodiments, the apparatus further comprises a hydrophobic filter positioned in or below the port. The absorbent material may have a longitudinal length and a transverse width, wherein the length is greater than the width, and wherein the width of the absorbent material narrows in a central portion along the longitudinal length of the absorbent material. The obscuring layer may have substantially the same perimeter shape as the absorbent material. The apparatus may further comprise a pump In another embodiment, a wound treatment apparatus for treatment of a wound site comprises:
- a wound dressing configured to be conformable to a nonplanar wound comprising:
  - an absorbent layer comprising a contoured shape, the contoured shape comprising a substantially rectangular body with a waisted portion, and
  - a backing layer above the absorbent layer; and
- a fluidic connector configured to transmit negative pressure from a negative pressure source to the wound dressing for the application of topical negative pressure at a wound site.

Some embodiments may further comprise a wound contact layer. The backing layer may be rectangular. In some embodiments, the negative pressure source is a pump. In some embodiments, the wound dressing has a longer axis and a shorter axis, and wherein the waisted portion configured to be on the longer axis. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots. The fluidic connector may be located along a side or corner of the rectangular body. Some embodiments may further comprise an acquisition distribution layer between the wound contact layer and the absorbent material. The absorbent layer may comprise cellulose fibers and 40%-80% (or about 40% to about 80%) superabsorbent particles. The obscuring layer, in a dry state, may be configured to yield a color of Bg, gB, B, pB, bP, P, rP, pPk, RP, O, rO, or yO on the CIE x, y chromaticity diagram. The absorbent layer may further comprise a tissue dispersant layer.

In yet another embodiment, an apparatus for dressing a wound for the application of topical negative pressure at a wound site, comprises:
- an absorbent layer having one or more slits extending at least partially across the width of the absorbent layer; and
- a backing layer above the absorbent layer, the backing layer having an orifice for communicating negative pressure to the wound site, wherein the orifice is positioned over a portion of the absorbent layer having no slits.

In some embodiments, the one or more slits comprise one or more concentric arcs.

In another embodiment, a wound treatment apparatus comprises:
- a wound dressing configured to be conformable to a nonplanar wound comprising:
  - an absorbent layer above the contact layer, the absorbent layer comprising a contoured shape, the contoured shape comprising two or more lobes, and
  - a backing layer above the absorbent layer.

In some embodiments, the wound treatment apparatus comprises a pump. The wound dressing may comprise a fluidic connector configured to transmit negative pressure from a pump to the wound dressing for the application of topical negative pressure at a wound site. The wound dressing may also comprise a wound-facing contact layer. The contoured shape may comprise three lobes. The contoured shape may comprise four lobes. The two or more lobes may comprise rounded projections. The apparatus may comprise two or more lobes flared lobes. The contoured shape may be oval-shaped. The contoured shape may comprise six lobes. The apparatus may further comprise an obscuring layer disposed so as to obscure the absorbent layer. The apparatus may further comprise an obscuring layer configured to at least partly visually obscure fluid within the absorbent layer. The obscuring layer may comprise at least one viewing window configured to allow a visual determination of the saturation level of the absorbent layer. The viewing window may comprise an array of dots.

In yet another embodiment, an apparatus for dressing a wound for the application of topical negative pressure at a wound site, comprises:

an absorbent layer configured to retain fluid, a backing layer above the absorbent layer, and an obscuring layer configured to at least partly visually obscure fluid within the absorbent layer, wherein the obscuring layer, in a dry state, is configured to yield a color of Bg, gB, B, pB, bP, P, rP, pPk, RP, O, rO, or yO on the CIE x, y chromaticity diagram.

Some embodiments may further comprise one or more viewing windows in the backing layer. At least the obscuring layer may be shaped with a narrowed central portion along its length. The obscuring layer may comprise a 3×3 array of viewing window or a quincunx array of viewing windows. In some embodiments, at least the obscuring layer may comprise a six-lobed shape. The absorbent layer and acquisition distribution layer may be substantially the same shape as the obscuring layer. The obscuring layer may further comprise a cross or maltese cross shaped hole over which a fluidic connector for transmitting negative pressure may be connected. The apparatus may further comprise a fluidic connector configured to connect the backing layer to a source of negative pressure. The absorbent layer may further comprise a tissue dispersant layer.

In some embodiments, a negative pressure wound therapy kit is provided comprising:

a wound dressing; and a sheet comprising a plurality of sealing strips and a plurality of perforations configured to facilitate separation of the sealing strips from the sheet.

The wound dressing may be any of the dressings described herein. In some embodiments, the kit may further comprise a fluidic connector attached to the wound dressing. The sheet comprising a plurality of sealing strips may comprise an adhesive film and at least one protective layer over an adhesive surface of the adhesive film. The at least one sealing strip may further comprise a carrier layer configured to be releasably attached to a non-adhesive surface of the adhesive film. The carrier layer may comprise at least one tab. The at least one protective layer may comprise a central protective layer and two outer protective layers . . .

BRIEF DESCRIPTION OF THE DRAWINGS

FIGS. 5A-F-9A-F illustrate a perspective view, a top view, a bottom view, a front view, a back view, and a side view, respectively, of embodiments of a wound dressing including an obscuring layer and viewing windows;

FIGS. 10A-F illustrate a perspective view, a top view, a bottom view, a front view, a back view, and a side view, respectively, of embodiments of a wound dressing including an obscuring layer and viewing windows.

FIGS. 11A-F-12A-F illustrate a perspective view, a top view, a bottom view, a front view, a back view, and a side view, respectively, of embodiments of a wound dressing including an obscuring layer and viewing windows;

FIG. 16 illustrates an embodiment of a dressing comprising a viewing window in the shape of a trademarked brand name;

FIG. 17 illustrates a top view of an embodiment of a three-lobe configuration of a wound dressing and a dot pattern of viewing windows;

FIG. 18 illustrates a top view of an embodiment of a three-lobe configuration of a wound dressing and viewing windows in the shape of a logo;

FIG. 23A-B illustrate embodiments of white and colored fluidic connectors, respectively;

FIGS. 33A-B illustrate embodiments of an oval-shaped wound dressing comprising an obscuring layer and an orifice viewing window;

FIG. 39A illustrates an exploded view of another embodiment of a wound dressing;

FIGS. 45A-D illustrate one embodiment of a sealing strip assembly which may be used with a dressing and/or fluidic connector.

DETAILED DESCRIPTION OF THE PREFERRED EMBODIMENTS

Figure 1:
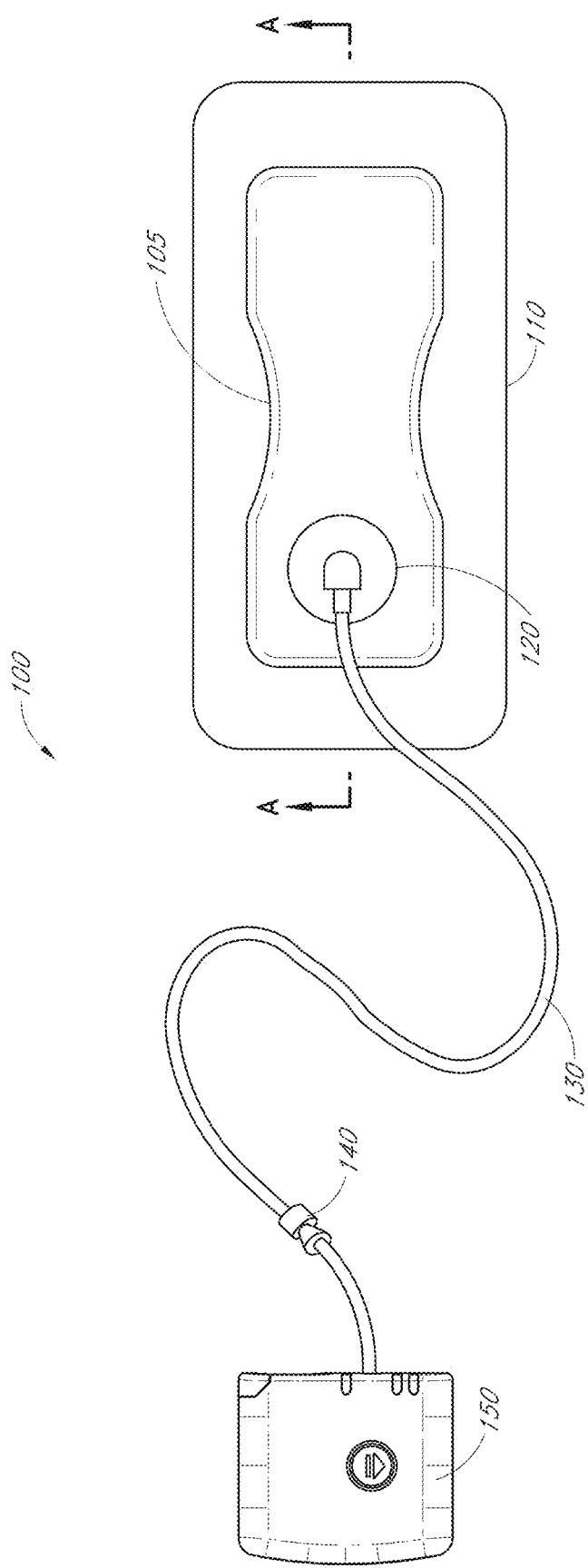
FIG. 1 illustrates an embodiment of a wound treatment system.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in U.S. Provisional Application Ser. No. 61/650,904, filed May 23, 2012, titled "APPARATUSES AND METHODS FOR NEGATIVE PRESSURE WOUND THERAPY," International Application No. PCT/IB2013/001469, filed May 22, 2013, titled "APPARATUSES AND METHODS FOR NEGATIVE PRESSURE WOUND THERAPY," U.S. Provisional Application Ser. No. 61/678,569, filed Aug. 1, 2012, titled "WOUND DRESSING AND METHOD OF TREATMENT," U.S. Provisional Application Ser. No. 61/753,374, filed Jan. 16, 2013, titled "WOUND DRESSING AND METHOD OF TREATMENT," U.S. Provisional Application Ser. No. 61/753,878, filed Jan. 17, 2013, titled "WOUND DRESSING AND METHOD OF TREATMENT," U.S. Provisional Application Ser. No. 61/785,054, filed Mar. 14, 2013, titled "WOUND DRESSING AND METHOD OF TREATMENT," and U.S. Provisional Application Ser. No. 61/823,298, filed May 14, 2013, titled "WOUND DRESSING AND METHOD OF TREATMENT," which are hereby incorporated by reference into this present application in their entireties. Embodiments of the wound dressings, wound treatment apparatuses and methods described herein may also be used in combination or in addition to those described in application Ser. No. 13/092,042, filed Apr. 21, 2011, published as US2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

FIG. 1 illustrates an embodiment of a TNP wound treatment system 100 comprising a wound dressing 110 in combination with a pump 150. As stated above, the wound dressing 110 can be any wound dressing embodiment disclosed herein including without limitation dressing embodiment or have any combination of features of any number of wound dressing embodiments disclosed herein. Here, the dressing 110 may be placed over a wound as described previously, and a conduit 130 may then be connected to the port 120, although in some embodiments the dressing 101 may be provided with at least a portion of the conduit 130 preattached to the port 120. Preferably, the dressing 110 is provided as a single article with all wound dressing elements (including the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes.

Figure 2A:
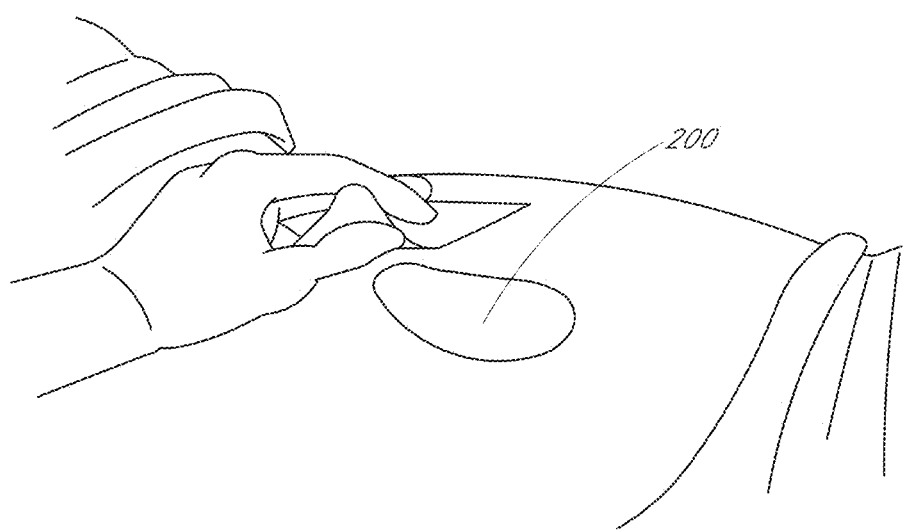
FIGS. 2A-D illustrate the use and application of an embodiment of a wound treatment system onto a patient.

FIGS. 2A-D illustrate the use of an embodiment of a TNP wound treatment system being used to treat a wound site on a patient. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound.

Figure 2B:
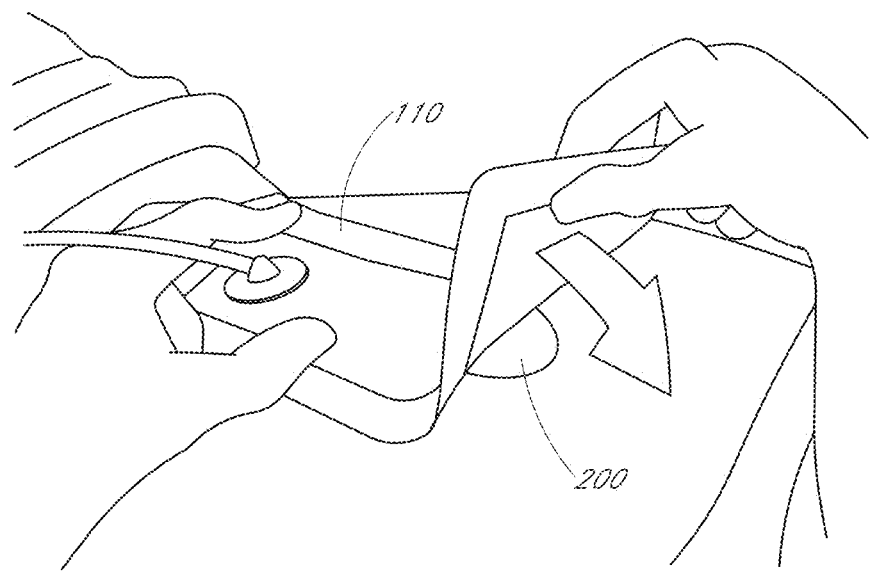

After the skin surrounding the wound site 200 is dry, and with reference now to FIG. 2B, the wound dressing 110 may be positioned and placed over the wound site 200. Preferably, the wound dressing 110 is placed with the wound contact layer 2102 over and/or in contact with the wound site 200. In some embodiments, an adhesive layer is provided on the lower surface 2101 of the wound contact layer 2102, which may in some cases be protected by an optional release layer to be removed prior to placement of the wound dressing 110 over the wound site 200. Preferably, the dressing 110 is positioned such that the port 2150 is in a raised position with respect to the remainder of the dressing 110 so as to avoid fluid pooling around the port. In some embodiments, the dressing 110 is positioned so that the port 2150 is not directly overlying the wound, and is level with or at a higher point than the wound. To help ensure adequate sealing for TNP, the edges of the dressing 110 are preferably smoothed over to avoid creases or folds.

Figure 2C:
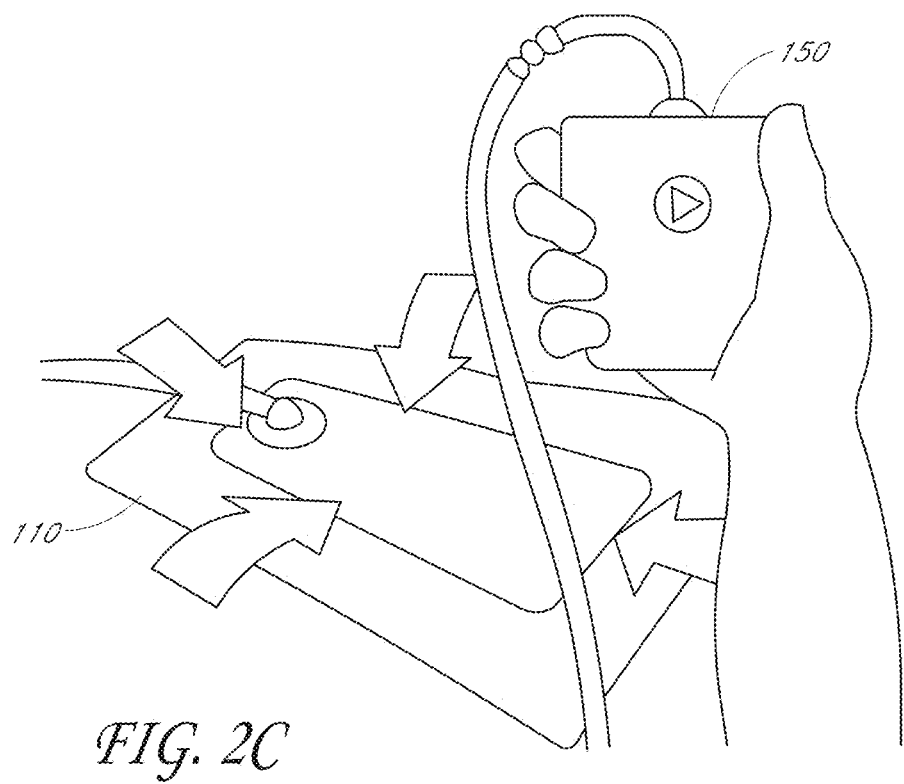

With reference now to FIG. 2C, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150. Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Figure 2D:
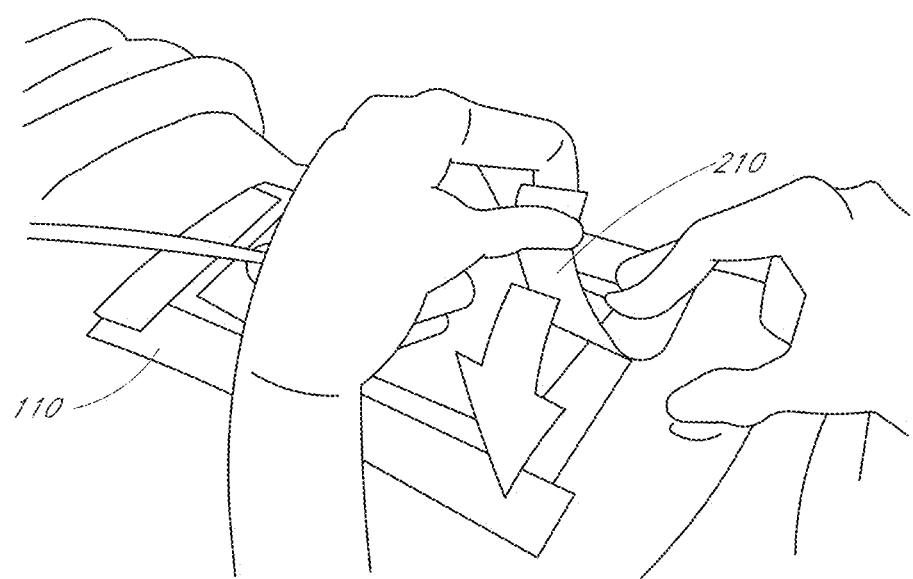

Turning to FIG. 2D, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

Figure 3A:
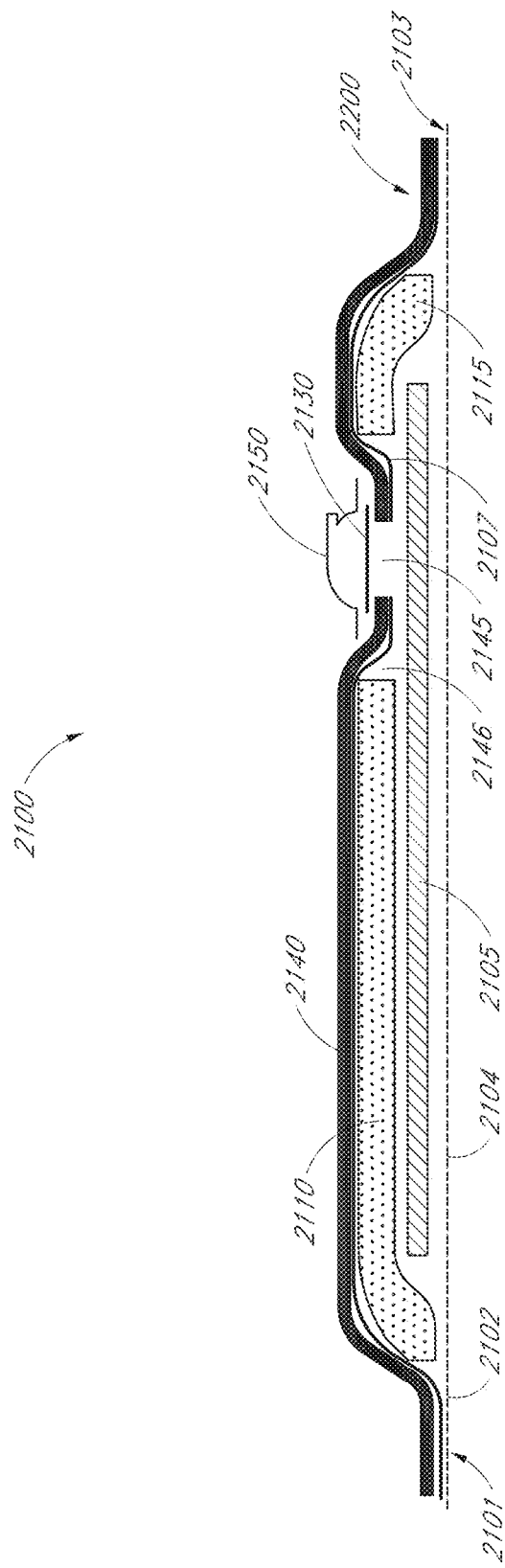
FIG. 3A illustrates an embodiment of a wound dressing in cross-section.
Figure 3B:
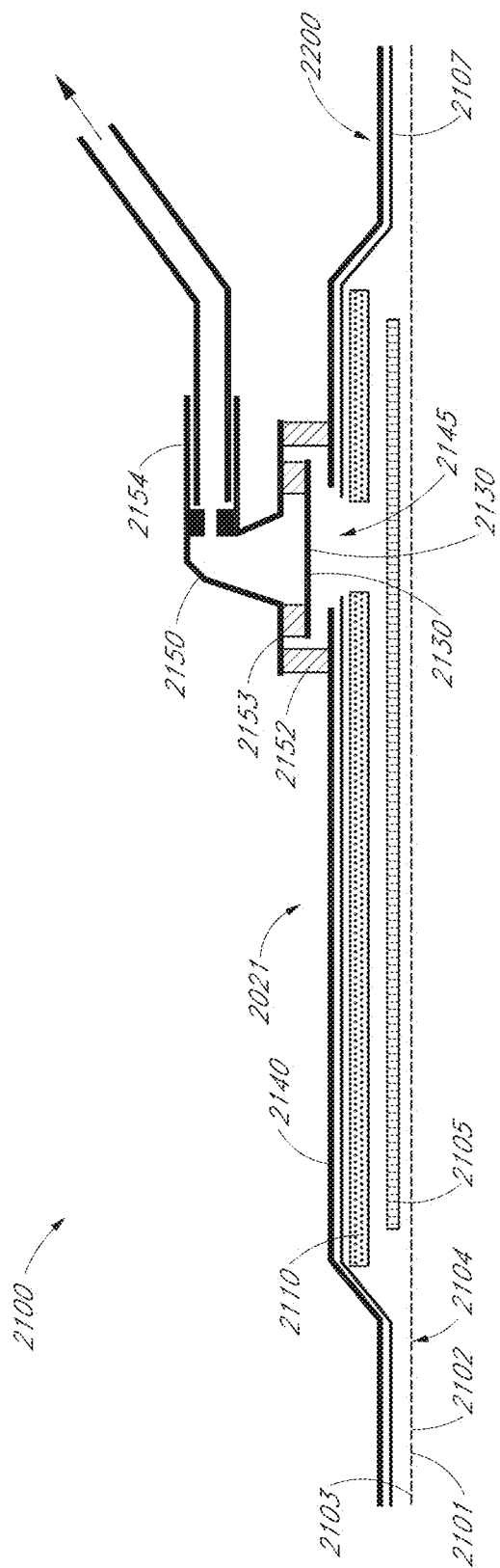
FIG. 3B illustrates another embodiment of a wound dressing in cross-section.
Figure 3C:
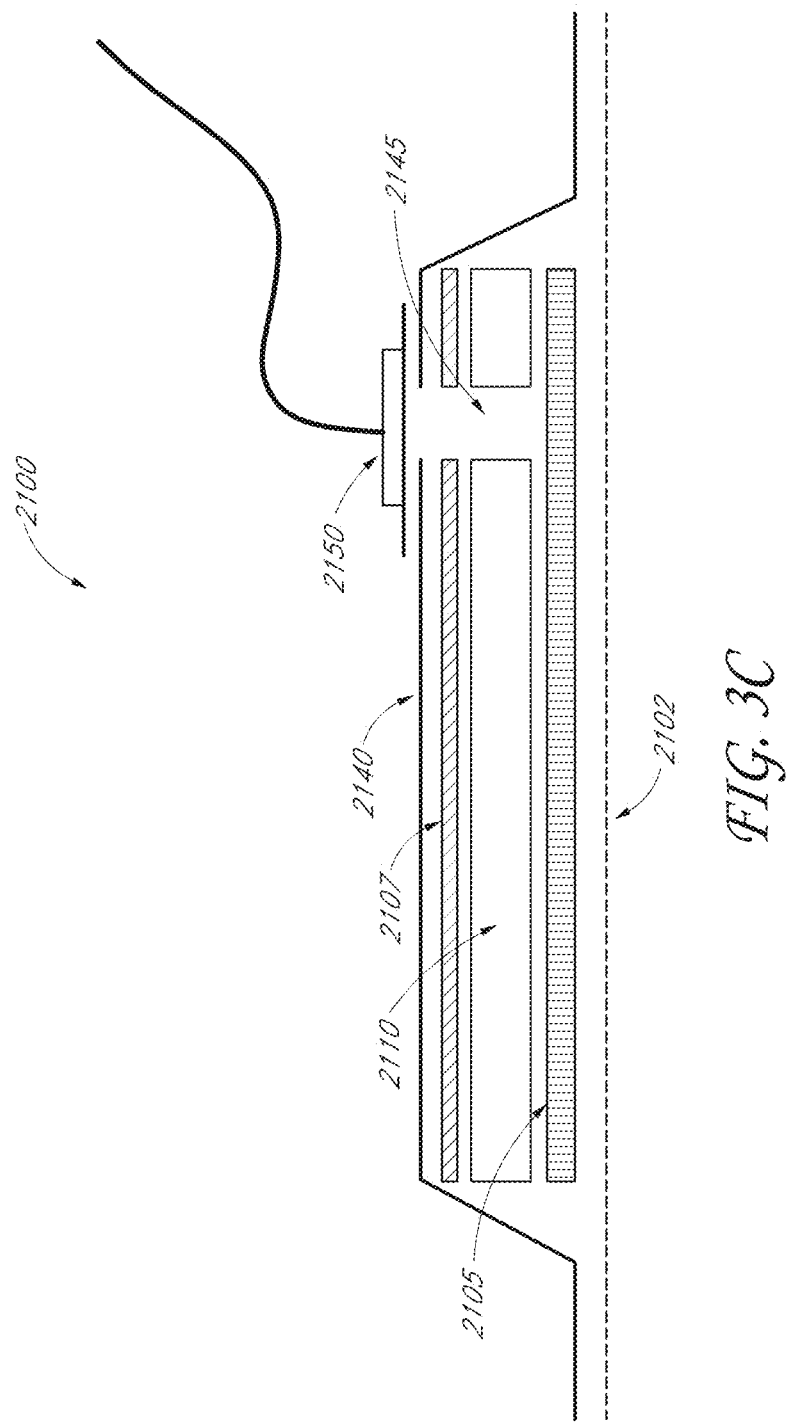
FIG. 3C illustrates another embodiment of a wound dressing in cross-section.

FIGS. 3A-C illustrate cross-sections through a wound dressing 2100 similar to the wound dressing of FIG. 1 according to an embodiment of the disclosure. A view from above the wound dressing 2100 is illustrated in FIG. 1 with the line A-A indicating the location of the cross-section shown in FIGS. 3A and 3B. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, both of which are described in greater detail below. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 2105 and an absorbent layer 2110.

As illustrated in FIGS. 3A-C, a lower surface 2101 of the wound dressing 2100 may be provided with an optional wound contact layer 2102. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer 2102 has a lower surface 2101 and an upper surface 2103. The perforations 2104 preferably comprise through holes in the wound contact layer 2102 which enable fluid to flow through the layer 2102. The wound contact layer 2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 2102 may help maintain the integrity of the entire dressing 2100 while also creating an air tight seal around the absorbent pad in order to maintain negative pressure at the wound.

Some embodiments of the wound contact layer 2102 may also act as a carrier for an optional lower and upper adhesive layer (not shown). For example, a lower pressure sensitive adhesive may be provided on the lower surface 2101 of the wound dressing 2100 whilst an upper pressure sensitive adhesive layer may be provided on the upper surface 2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure. The layer 2105 may be formed of a material having a three dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIGS. 3A-C, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Additionally, the obscuring layer 2107 can be positioned adjacent to the backing layer 2140, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an airlaid, thermally-bonded composite.

An orifice 2145 is preferably provided in the backing layer 2140 to allow a negative pressure to be applied to the dressing 2100. A suction port 2150 is preferably attached or sealed to the top of the backing layer 2140 over an orifice 2145 made into the dressing 2100, and communicates negative pressure through the orifice 2145. A length of tubing 2220 may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material, for example using the embodiments described below in FIGS. 23A-B.

Preferably the absorbent layer 2110 and the obscuring layer 2107 include at least one through hole 2146 located so as to underlie the port 2150. The through hole 2146, while illustrated here as being larger than the hole through the obscuring layer 2107 and backing layer 2140, may in some embodiments be bigger or smaller than either. Of course, the respective holes through these various layers 2107, 2140, and 2110 may be of different sizes with respect to each other. As illustrated in FIGS. 3A-C a single through hole can be used to produce an opening underlying the port 2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the superabsorbent layer may provide a fluid flow pathway which remains unblocked in particular when the absorbent layer 2100 is near saturation.

The aperture or through-hole 2146 is preferably provided in the absorbent layer 2110 and the obscuring layer 2107 beneath the orifice 2145 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2145 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane film and an adhesive pattern spread onto the film. The polyurethane film is preferably moisture vapor permeable and may be manufactured from a material that has an increased water transmission rate when wet.

The absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

As shown in FIG. 3A, one embodiment of the wound dressing 2100 comprises an aperture 2146 in the absorbent layer 2110 situated underneath the port 2150. In use, for example when negative pressure is applied to the dressing 2100, a wound facing portion of the port 150 may thus come into contact with the transmission layer 2105, which can thus aid in transmitting negative pressure to the wound site even when the absorbent layer 2110 is filled with wound fluids. Some embodiments may have the backing layer 2140 be at least partly adhered to the transmission layer 2105. In some embodiments, the aperture 2146 is at least 1-2 mm larger than the diameter of the wound facing portion of the port 2150, or the orifice 2145.

A filter element 2130 that is impermeable to liquids, but permeable to gases is provided to act as a liquid barrier, and to ensure that no liquids are able to escape from the wound dressing. The filter element may also function as a bacterial barrier. Typically the pore size is 0.2 μm. Suitable materials for the filter material of the filter element 2130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer 2140 over the orifice 2145. For example, the filter element 2130 may be molded into the port 2150, or may be adhered to both the top of the backing layer 2140 and bottom of the port 2150 using an adhesive such as, but not limited to, a UV cured adhesive.

In FIG. 3B, an embodiment of the wound dressing 2100 is illustrated which comprises spacer elements 2152, 2153 in conjunction with the port 2150 and the filter 2130. With the addition of such spacer elements 2152, 2153, the port 2150 and filter 2130 may be supported out of direct contact with the absorbent layer 2110 and/or the transmission layer 2105. The absorbent layer 2110 may also act as an additional spacer element to keep the filter 2130 from contacting the transmission layer 2105. Accordingly, with such a configuration contact of the filter 2130 with the transmission layer 2105 and wound fluids during use may thus be minimized. As contrasted with the embodiment illustrated in FIG. 3A, the aperture 2146 through the absorbent layer 2110 and the obscuring layer 2107 may not necessarily need to be as large or larger than the port 2150, and would thus only need to be large enough such that an air path can be maintained from the port to the transmission layer 2105 when the absorbent layer 2110 is saturated with wound fluids.

With reference now to FIG. 3C, which shares many of the elements illustrated in FIGS. 3A-C, the embodiment illustrated here comprises the backing layer 2140, masking layer 2107, and absorbent layer 2110, all of which have a cut or opening made therethrough which communicate directly to the transmission layer 2105 so as to form the orifice 2145. The suction port 2150 is preferably situated above it and communicates with the orifice 2145.

In particular for embodiments with a single port 2150 and through hole, it may be preferable for the port 2150 and through hole to be located in an off-center position as illustrated in FIGS. 3A-C and in FIG. 1. Such a location may permit the dressing 2100 to be positioned onto a patient such that the port 2150 is raised in relation to the remainder of the dressing 2100. So positioned, the port 2150 and the filter 2130 may be less likely to come into contact with wound fluids that could prematurely occlude the filter 2130 so as to impair the transmission of negative pressure to the wound site.

Figure 4A:
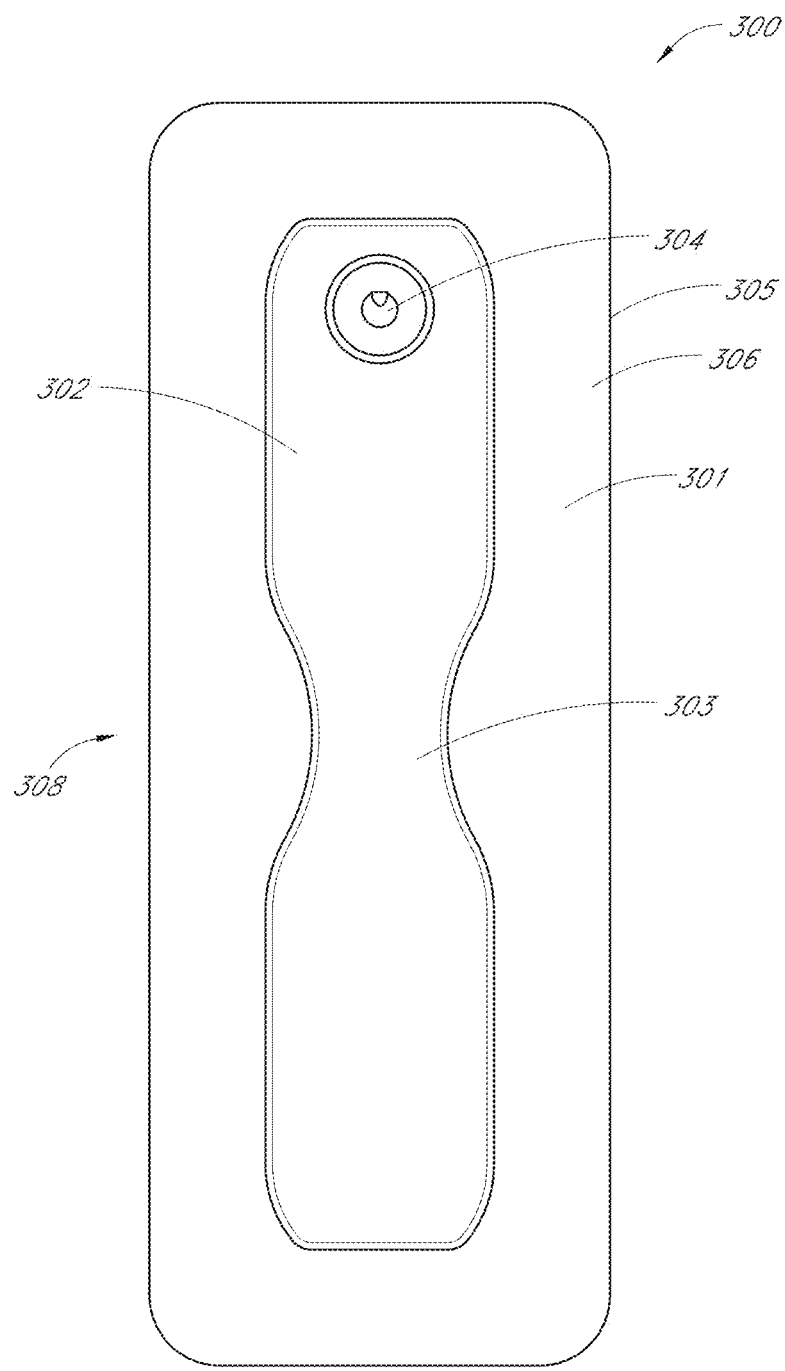
FIGS. 4A-C illustrate a top view of an embodiment of a wound dressing with a narrow central portion.
Figure 4B:
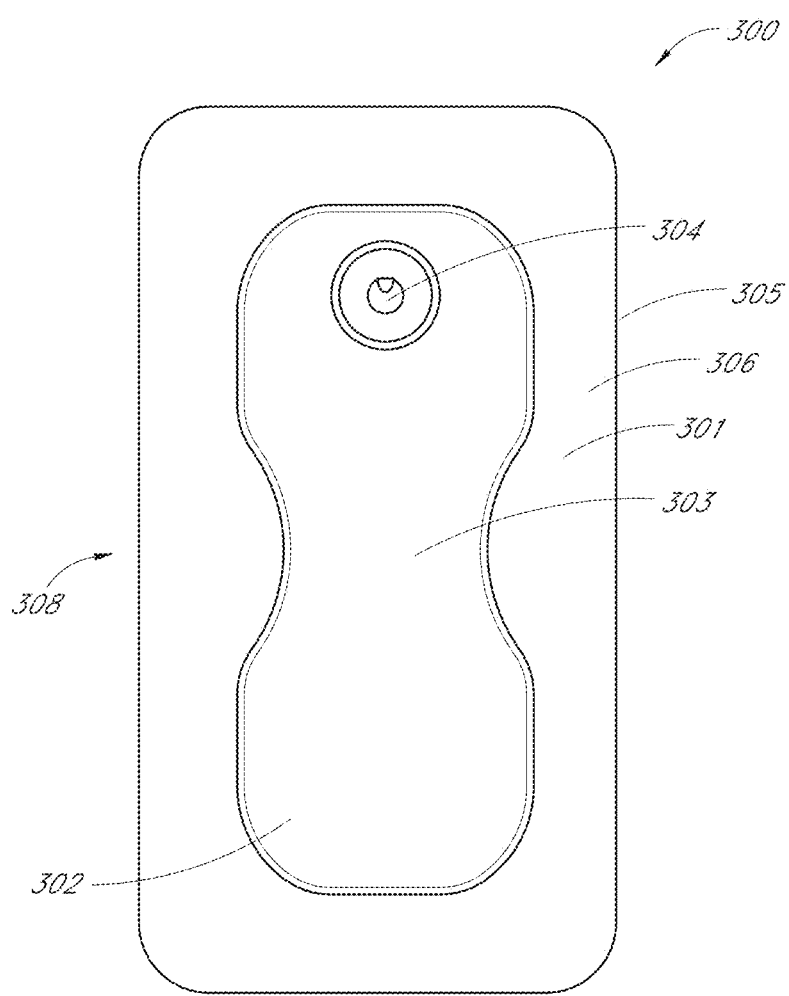
Figure 4C:
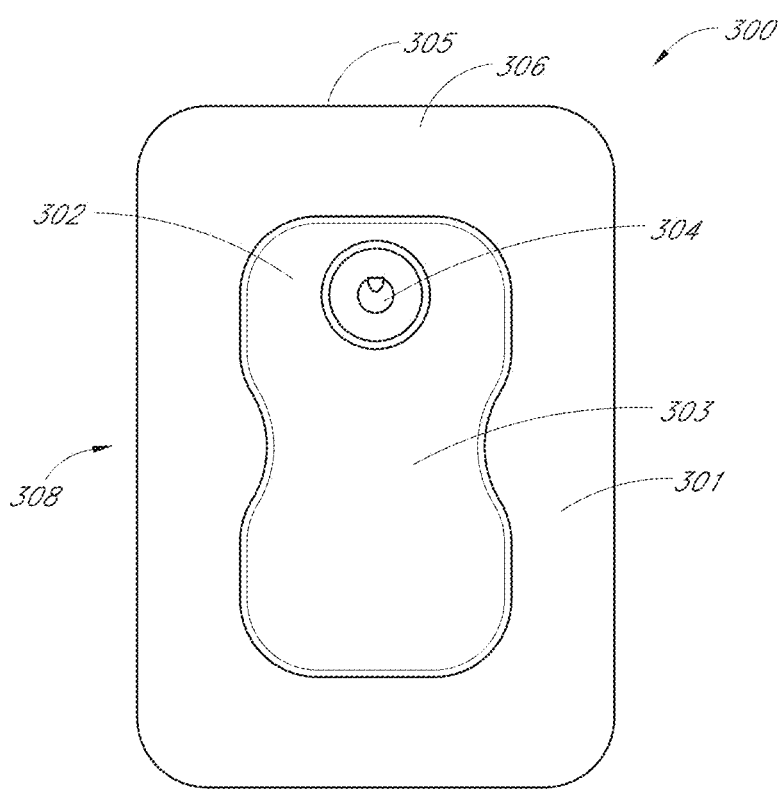

FIGS. 4A-C illustrate embodiments of wound dressings 300 similar to the embodiments described above and provided with a narrowed central portion in various lengths and widths. FIG. 4A illustrates an embodiment of a wound dressing 300 with a narrowed central portion or a waisted middle portion. The wound dressing 300 has a backing layer 301. The backing layer 301 can have a rectangular or square shaped perimeter and can be a transparent or translucent material. The backing layer 301 can have a lower surface 305 and an upper surface 306. The lower surface of the backing layer 301 can be configured to be placed on the skin surface surrounding the wound site as discussed previously with reference to FIGS. 3A-C. Additionally, the lower surface 305 can have a wound contact layer. The wound contact layer can have all the features and embodiments described herein, including without limitation wound dressing embodiments described in reference to FIGS. 3A-C. The wound contact layer can be adhered to the perimeter of the lower surface 305 of the backing layer 301. The wound contact layer can comprise an adhesive or any other method of attachment that allows attachment of the wound dressing to the skin surface as previously described.

In some embodiments, the wound dressing 300 can have a port 304 offset from the center of the dressing as described previously. The port 304 can be a domed port or a soft fluidic connector (described in detail below). Although the port 304 can be placed in a central location on the dressing, it is preferably offset from the center of the dressing to a particular side or edge. As such, the orientation of the port 304, when placed on the body, may thus permit the port 304 to be situated in an elevated position, thereby increasing the amount of time that the dressing 300 may be used before coming into contact with fluids. Although other orientations may be used, and may occur in practice (e.g., when the patient shifts positions), placing the port 304 at a lower position may cause the filter proximate the port (not illustrated here) to become saturated, which may cause the dressing to need changing even though there may still remain some absorptive capacity within the absorbent layer. Preferably, the port 304 has an orifice for the connection of a tube or conduit thereto; this orifice may be angled away from the center of the dressing 300 so as to permit the tube or conduit to extend away from the dressing 300. In some preferred embodiments, the port 304 comprises an orifice that permits the tube or conduit inserted therein to be approximately parallel to the top surface of the backing layer 301.

In various embodiments, the wound dressing 300 can have an absorbent material 302. The absorbent material 302 can be accompanied by the additional components within the wound dressing as described with reference to the wound dressing cross-section in FIG. 3A-B, such as a transmission layer and a masking or obscuring layer (not shown).

In some embodiments, the wound dressing 300 can have an absorbent material 302 with a central portion 308. The absorbent material 302 can have a longitudinal length and a transverse width. In some embodiments, the longitudinal length is greater than the transverse width. In some embodiments, the longitudinal length and the transverse width are of equal size. In various embodiments, the absorbent material 302 can have a contoured shape with a substantially rectangular body.

The central portion 308 of the absorbent material 302 may comprise a waisted portion 303. The waisted portion 303 can be defined by the transverse width of the absorbent material 302 narrowing at the central portion 308 of the longitudinal length. For example, in some embodiments, the waisted portion 303 can be a narrow width at the central portion 308 of the absorbent material 302, as illustrated in FIGS. 4A-C. Additional embodiments of the waisted portion 303 are possible including those described herein. Further, the shape of the accompanying components within the wound dressing as described with reference to FIGS. 3A-C can be formed to the same contoured shape of the absorbent material including the waisted portion.

The waisted portion 303 can increase the flexibility of the wound dressing and can allow enhanced compatibility of the wound dressing to the patient's body. For example, the narrow central region may allow for improved contact and adhesion of the wound dressing to the skin surface when the wound dressing is used on non-planar surfaces and/or wrapped around an arm or leg. Further, the narrow central portion provides increased compatibility with the patient's body and patient movement.

As in FIGS. 15A-B, embodiments of wound dressings may comprise various configurations of slits (described in detail below) so as to further enhance conformability of the dressing in non-planar wounds. Also, as described below, the absorbent layers may be colored or obscured with an obscuring layer, and optionally provided with one or more viewing windows. The domed ports may also be replaced with one or more fluidic connectors of the type described below in FIGS. 23A-B. Further, the wound dressing 300 can comprise all designs or embodiments herein described or have any combination of features of any number of wound dressing embodiments disclosed herein.

FIG. 4B illustrates an embodiment of a wound dressing 300 with a waisted portion. A wound dressing 300 as illustrated in FIG. 4B can have the features and embodiments as described above with reference to FIG. 4A. However, FIG. 4B illustrates an embodiment with a shorter longitudinal length with respect to the transverse width. FIG. 4C illustrates an additional embodiment of a wound dressing 300 with a waisted portion. As illustrated in FIG. 4C, the wound dressing can have a longitudinal length and a transverse width that are not substantially different in size, as opposed to a longitudinal length that is substantially longer than the transverse width of the wound dressing as shown in the embodiments illustrated in FIGS. 4A and 4B. The embodiments of a wound dressing illustrated in FIGS. 4B and 4C can include all features and embodiments described herein for wound dressings including those embodiments of the waisted portion 303 described with reference to FIG. 4A.

FIGS. 5A-F, 6A-F, 7A-F, 8A-F, 9A-F, 10A-F, 11A-F, 12A-F, and 24 illustrate additional embodiments of wound dressings. In these embodiments, a waisted portion 408 is located inwardly with reference to an edge 409 of the absorbent layer 402. Preferably, the contour of the absorbent layer 402 is curved from the edge 409 to the waisted portion 408, so as to form a smooth contour.

Figure 5B:
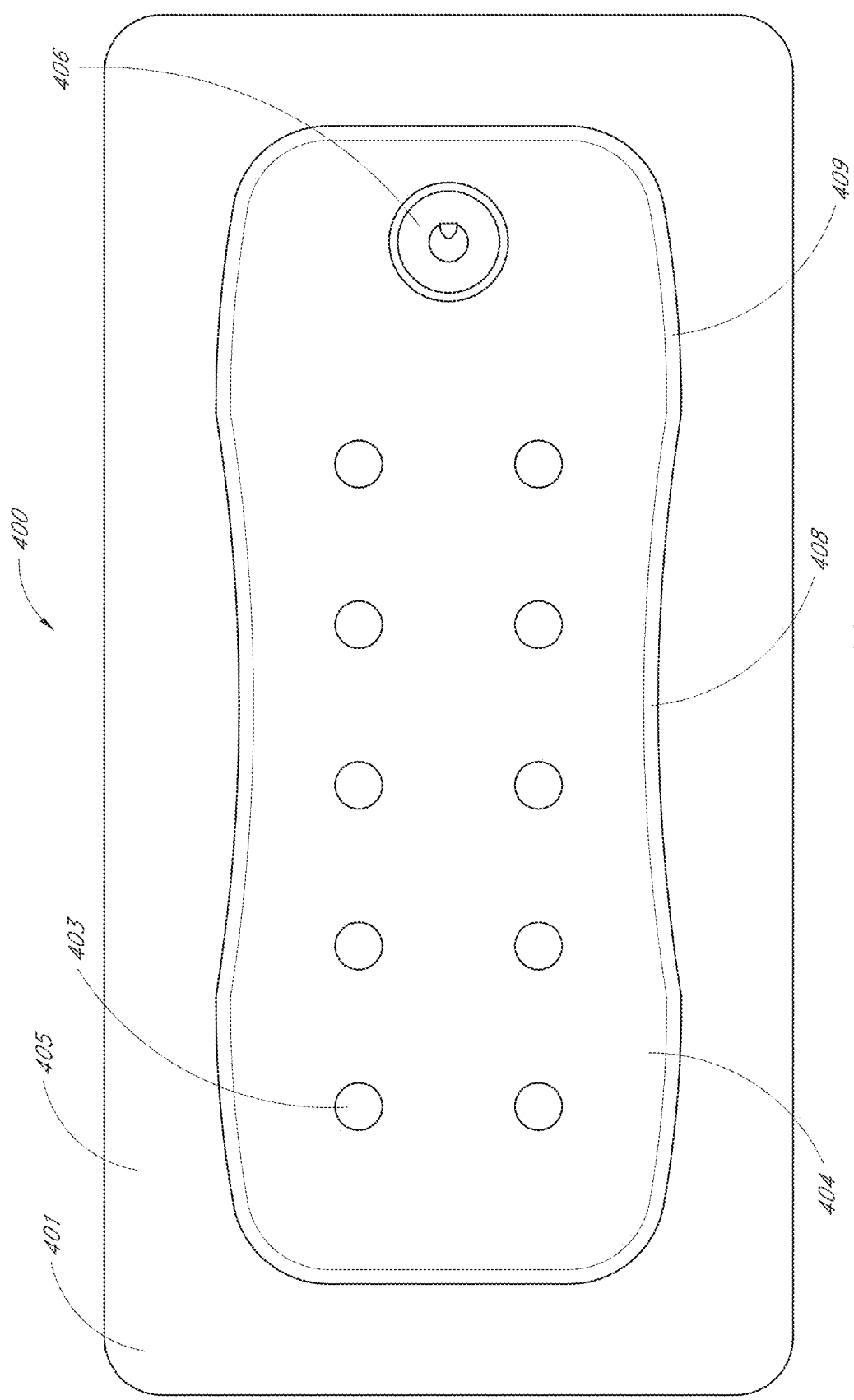

FIGS. 5A-F illustrate multiple views of an embodiment of a wound dressing with a waisted portion, obscuring layer, and viewing windows. FIG. 5A illustrates a perspective view of an embodiment of a wound dressing 400. The wound dressing 400 preferably comprises a port 406. The port 406 is preferably configured to be in fluid communication with a pump as described with reference to FIG. 1, and may include a tube or conduit pre-attached to the port. Alternatively, negative pressure can be supplied to the wound dressing through other suitable fluidic connectors, including but not limited to the fluidic connectors of the type described below in FIGS. 23A-B.

The wound dressing 400 can be constructed similar to the embodiments of FIGS. 3A and 3B above, and may comprise an absorbent material 402 underneath or within a backing layer 405. Optionally, a wound contact layer and a transmission layer may also be provided as part of the wound dressing 400 as described above. The absorbent material 402 can contain a narrowed central or waisted portion 408, as described previously to increase flexibility and conformability of the wound dressing to the skin surface. The backing layer 405 may have a border region 401 that extends beyond the periphery of the absorbent material 402. The backing layer 405 may be a translucent or transparent backing layer, such that the border region 401 created from the backing layer 405 can be translucent or transparent. The area of the border region 401 of the backing layer 405 can be approximately equal around the perimeter of the entire dressing with the exception of the narrowed central portion, where the area of the border region is larger. One will recognize that the size of the border region 401 will depend on the full dimensions of the dressing and any other design choices.

As illustrated in FIG. 5A, provided at least at the top of or over the absorbent layer 402 and under the backing layer 405 may be an obscuring layer 404 that optionally has one or more viewing windows 403. The obscuring layer 404 may partially or completely obscure contents (such as fluids) contained within the wound dressing 400 and/or the absorbent material (i.e., within the absorbent material 402 or under the backing layer 405). The obscuring layer may be a colored portion of the absorbent material, or may be a separate layer that covers the absorbent material. In some embodiments, the absorbent material 402 may be hidden (partially or completely), colored, or tinted, via the obscuring layer 404, so as to provide cosmetic and/or aesthetic enhancements, in a similar manner to what is described above. The obscuring layer is preferably provided between the topmost backing layer 405 and the absorbent material 402, although other configurations are possible. The cross-sectional view in FIGS. 3A and B illustrates this arrangement with respect to the masking or obscuring layer 2107. Other layers and other wound dressing components can be incorporated into the dressing as herein described.

The obscuring layer 404 can be positioned at least partially over the absorbent material 402. In some embodiments, the obscuring layer 404 can be positioned adjacent to the backing layer, or can be positioned adjacent to any other dressing layer desired. In some embodiments, the obscuring layer 404 can be adhered to or integrally formed with the backing layer and/or the absorbent material.

As illustrated in FIG. 5A, the obscuring layer 404 can have substantially the same perimeter shape and size as the absorbent material 402. The obscuring layer 404 and absorbent material 402 can be of equal size so that the entirety of the absorbent material 402 can be obscured by the obscuring layer 404. The obscuring layer 404 may allow for obscuring of wound exudate, blood, or other matter released from a wound. Further, the obscuring layer 404 can be completely or partially opaque having cut-out viewing windows or perforations.

In some embodiments, the obscuring layer 404 can help to reduce the unsightly appearance of a dressing during use, by using materials that impart partial obscuring or masking of the dressing surface. The obscuring layer 404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer 402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound.

Additionally, FIG. 5A illustrates an embodiment of the wound dressing including one or more viewing windows 403. The one or more viewing windows 403 preferably extend through the obscuring layer 404. These viewing windows 403 may allow visualization by a clinician or patient of the wound exudate in the absorbent material below the obscuring layer. FIG. 5A illustrates an array of dots (e.g., in one or more parallel rows) that can serve as viewing windows 403 in the obscuring layer 404 of the wound dressing. In a preferred embodiment, two or more viewing windows 403 may be parallel with one or more sides of the dressing 400. In some embodiments, the one or more viewing windows may measure between 0.1 mm and 20 mm, preferably 0.4 mm to 10 mm, and even more preferably, 1 mm to 4 mm.

The viewing windows 403 may be cut through the obscuring layer 404 or may be part of an uncolored area of the obscuring layer 404 and therefore may allow visualization of the absorbent material 402. The one or more viewing windows 403 can be arranged in a repeating pattern across the obscuring layer 404 or can be arranged at random across the obscuring layer. Additionally, the one or more viewing windows can be a circular shape or dots. Preferably, the one or more viewing windows 403 are configured so as to permit not only the degree of saturation, but also the progression or spread of fluid toward the fluid port 406, as in some embodiments, dressing performance may be adversely affected when the level of fluid has saturated the fluid proximate the port 406. In some embodiments, a "starburst" array of viewing windows 403 emanating around the port 406 may be suitable to show this progression, although of course other configurations are possible.

In FIG. 5A, the viewing windows 403 correspond to the area of the absorbent material 402 that is not covered by the obscuring layer 404. As such, the absorbent material 402 is directly adjacent the backing layer 405 in this area. Since the obscuring layer 404 acts as a partial obscuring layer, the viewing windows 403 may be used by a clinician or other trained user to assess the spread of wound exudate throughout the dressing. In some embodiments, the viewing windows 403 can comprise an array of dots or crescent shaped cut-outs. For example, an array of dots as viewing windows 403 are illustrated in FIGS. 5A-F, 6A-F, 7A-F, 8A-F, 9A-F, 10A-F, 11A-F, and 12A-F in which the array of dots are arranged in an 5×2, 3×2, 8×1, 5×1, 3×1, 3×3, 3×3, and quincunx array respectively. Additionally, in some embodiments, the dot pattern can be distributed evenly throughout the obscuring layer and across the entire or substantially the entire surface of the obscuring layer. In some embodiments, the viewing windows 403 may be distributed randomly throughout the obscuring layer. Preferably, the area of the obscuring layer 404 uncovered by the one or more viewing windows 403 is balanced to as to minimize the appearance of exudate while permitting the inspection of the dressing 400 and/or absorbent material 402. In some embodiments, the area exposed by the one or more viewing windows 403 does not exceed 20% of the area of the obscuring layer 404, preferably 10%, and even more preferably 5%.

The viewing windows 403 may take several configurations, as will be discussed in relation to FIGS. 16-18. In FIG. 17, the viewing windows 403 may comprise an array of regularly spaced uncolored dots (holes) made into the obscuring layer 404. While the dots illustrated here are in a particular pattern, the dots may be arranged in different configurations, or at random. The viewing windows 403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer 402 may therefore present a more discreet external appearance so as to reduce patient embarrassment and visibility and thereby enhance patient comfort. In some configurations, the one or more viewing windows 403 may be used to provide a numerical assessment of the degree of saturation of the dressing 400. This may be done electronically (e.g., via a digital photograph assessment), or manually. For example, the degree of saturation may be monitored by counting the number of viewing windows 403 which may be obscured or tinted by exudate or other wound fluids.

In some embodiments, the absorbent layer 402 or the obscuring layer 404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows 403 may be monitored electronically, and may be used in conjunction with a computer program or system to alert a patient or physician to the saturation level of the dressing 400.

FIG. 16 illustrates an embodiment of a dressing containing a viewing window in the shape of a trademarked brand name ("PICO"). FIG. 18 illustrates an embodiment of a dressing comprising a viewing window in the shape of a logo, here, the Smith & Nephew logo. Of course, many other configurations are possible, including other graphics, texts, or designs. The graphical or textual elements present in the viewing window may also be, for example, instructional in nature.

In other alternatives, instructions may be given to change the wound dressing when the exudate reaches a predetermined distance from the edge of the wound dressing, such as 5 mm from the wound dressing edge or 7 mm from the wound dressing edge, etc. Alternatively a 'traffic light' system may be implemented whereby an electronic indicator shows green, amber or red light to indicate the spread of exudate in the wound dressing. Alternatively or additionally, another suitable indicator may be used for indicating the spread of exudate over the dressing.

Figure 5C:
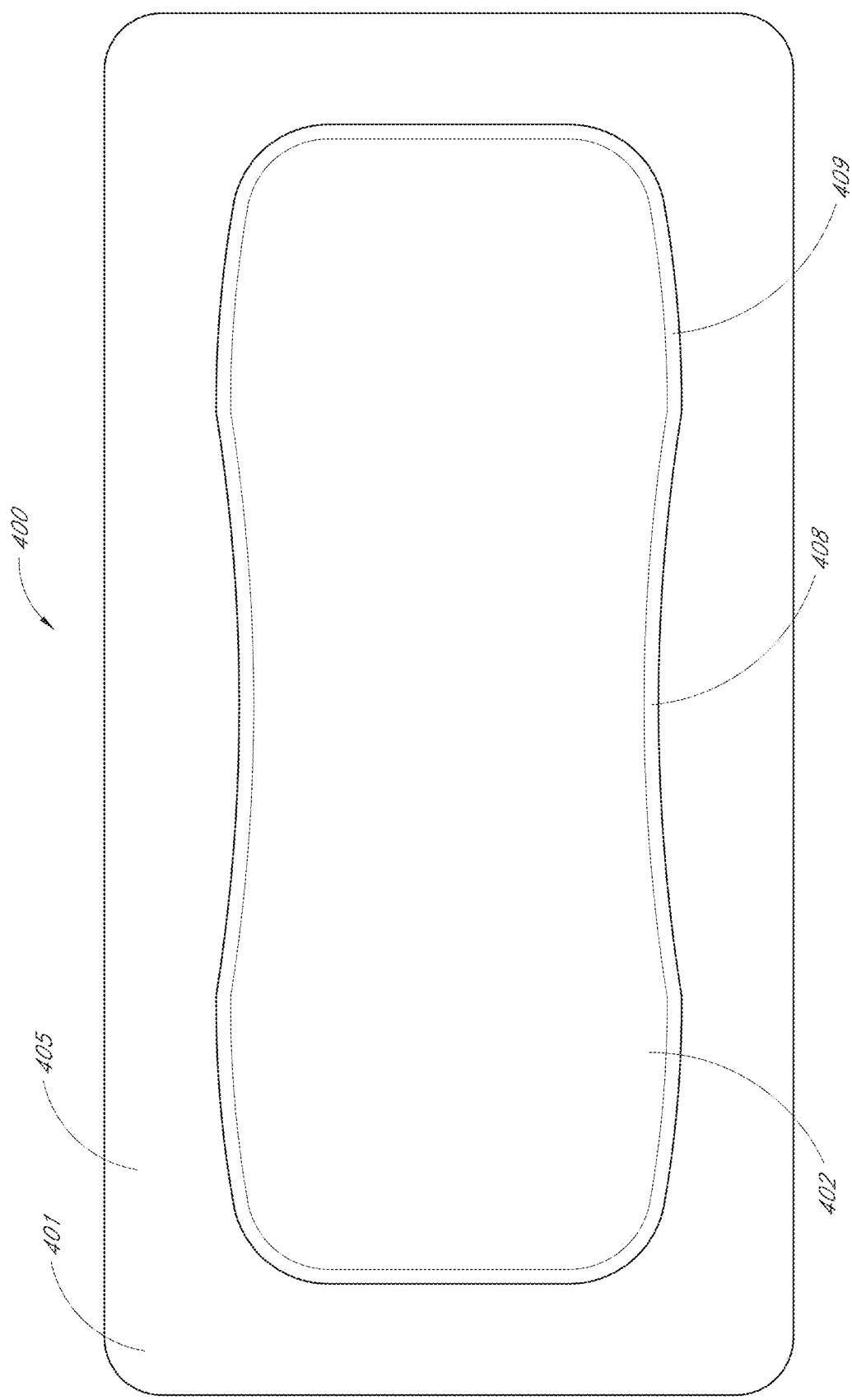
Figures 5D, 5E:
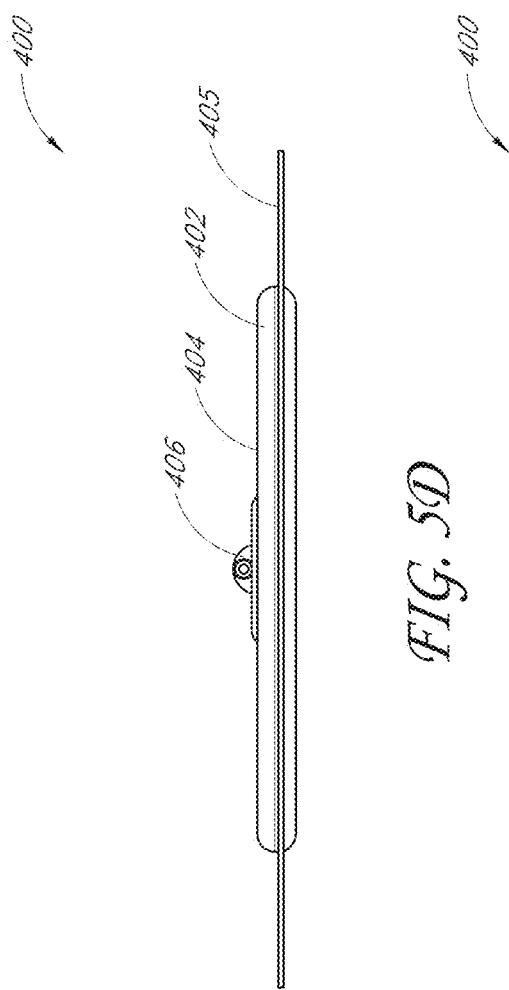
Figure 6A:
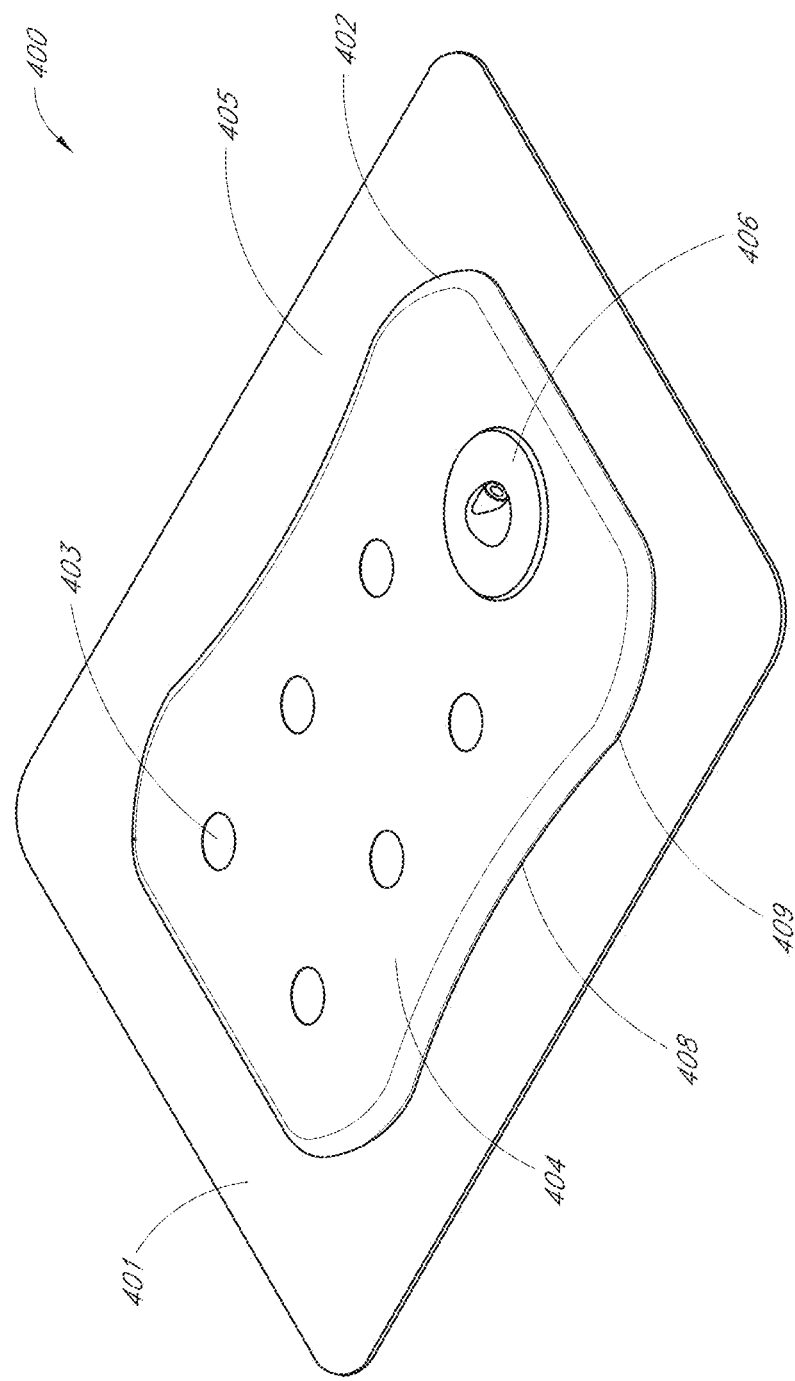
Figure 6B:
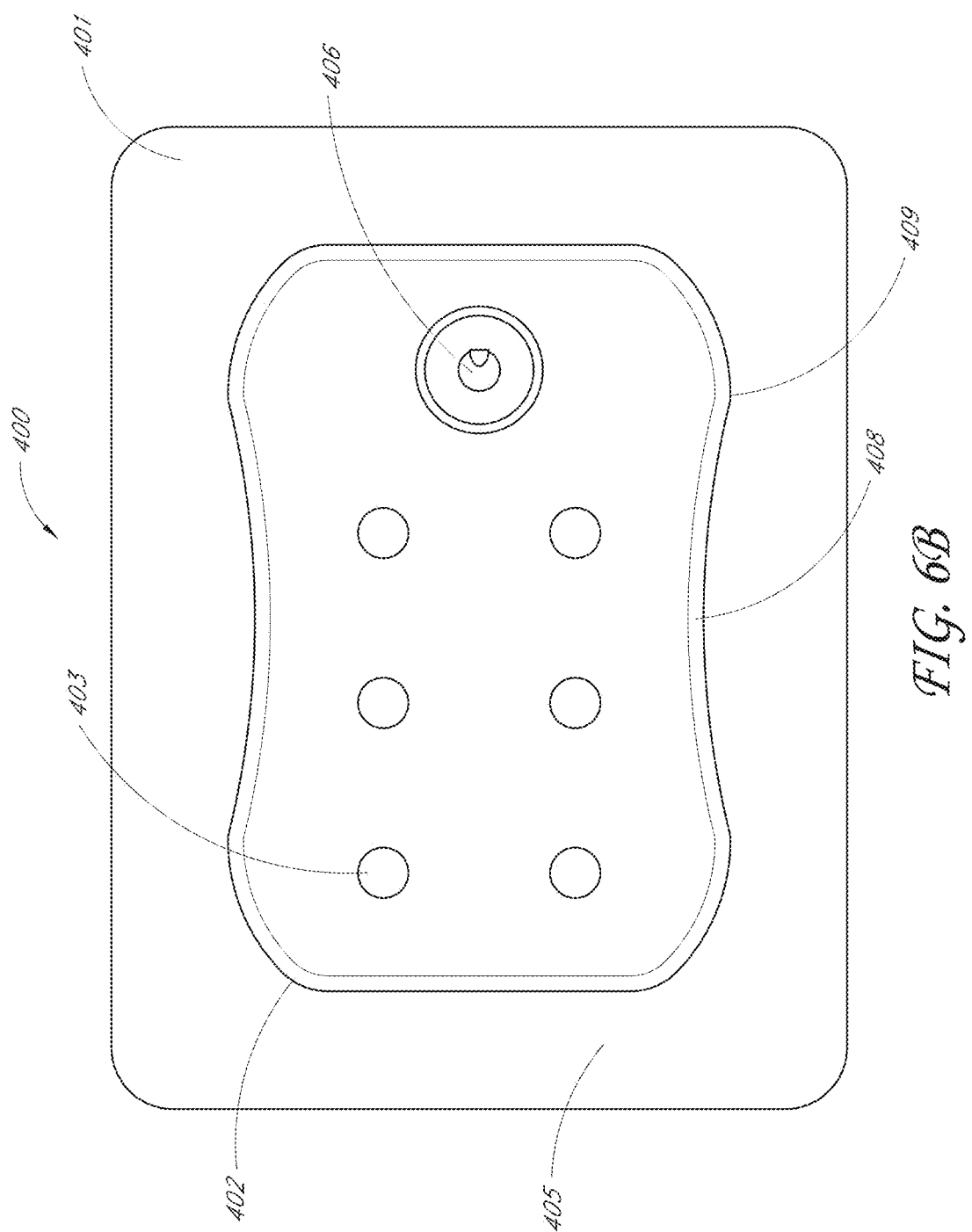
Figure 6C:
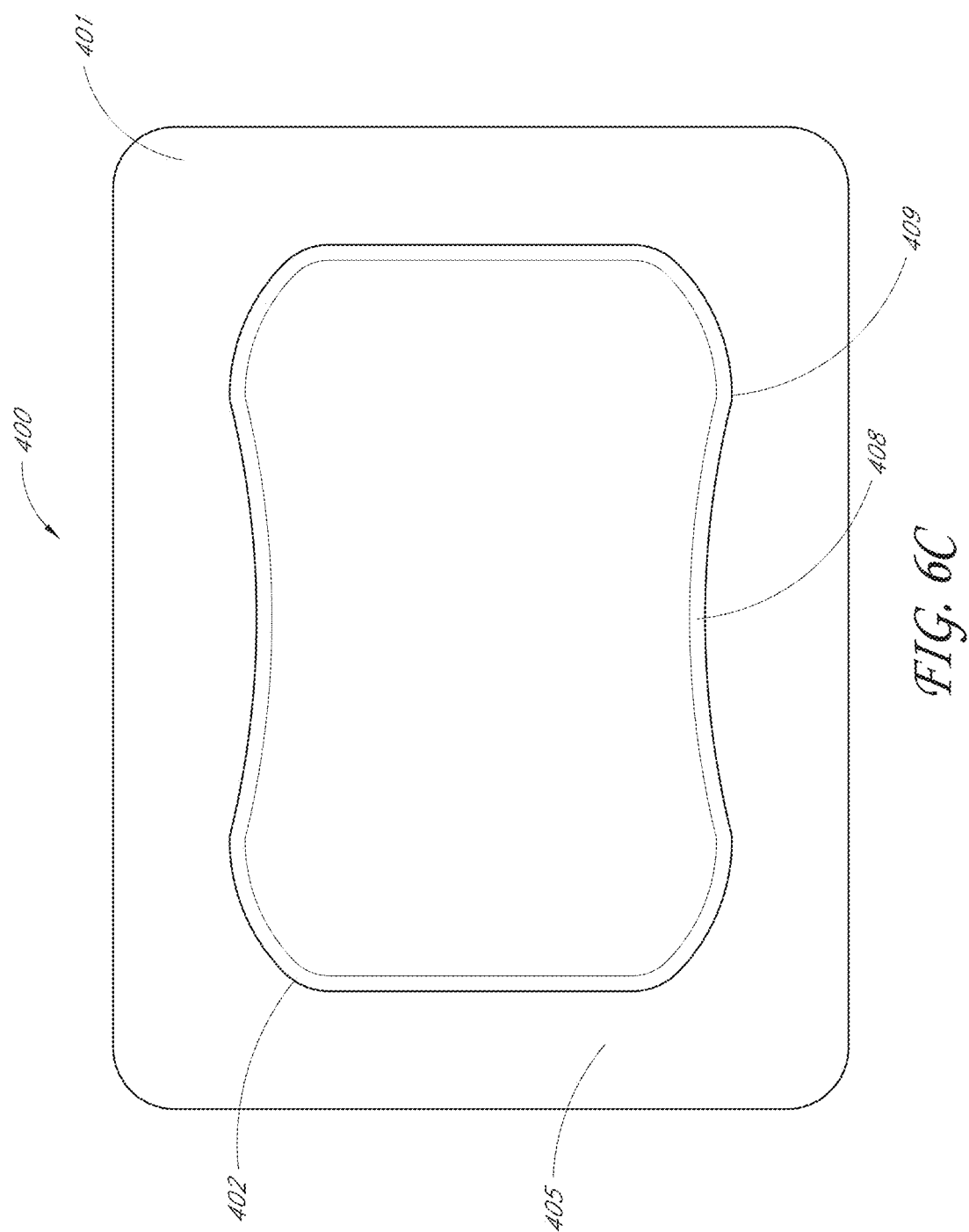
Figure 6F:
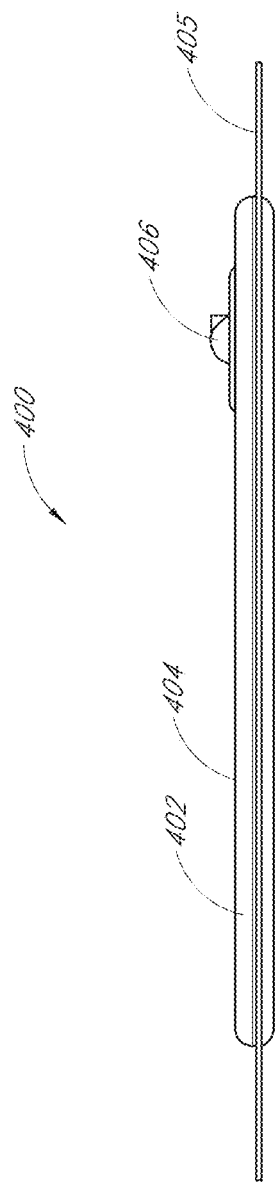
Figure 7A:
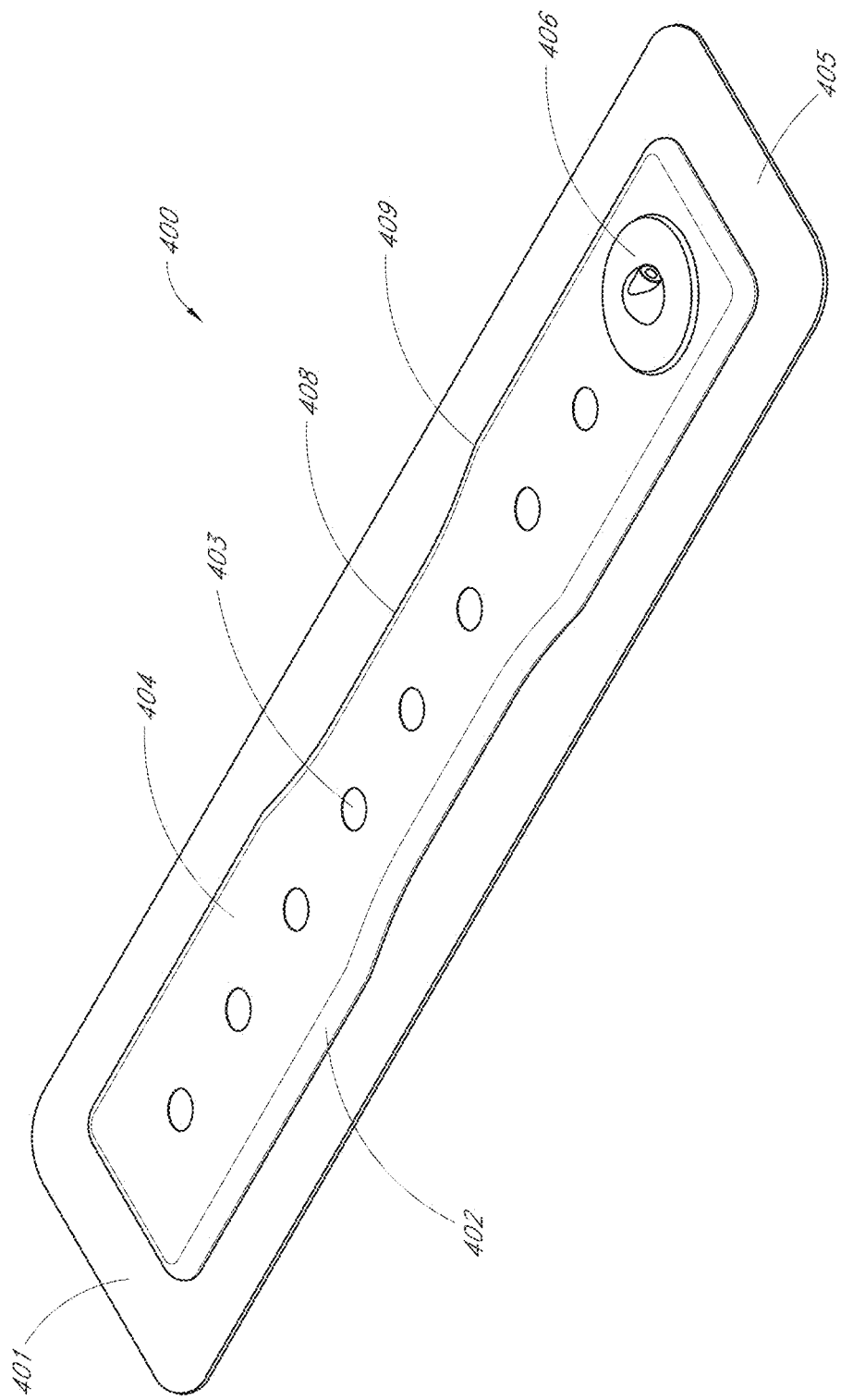
Figure 7B:
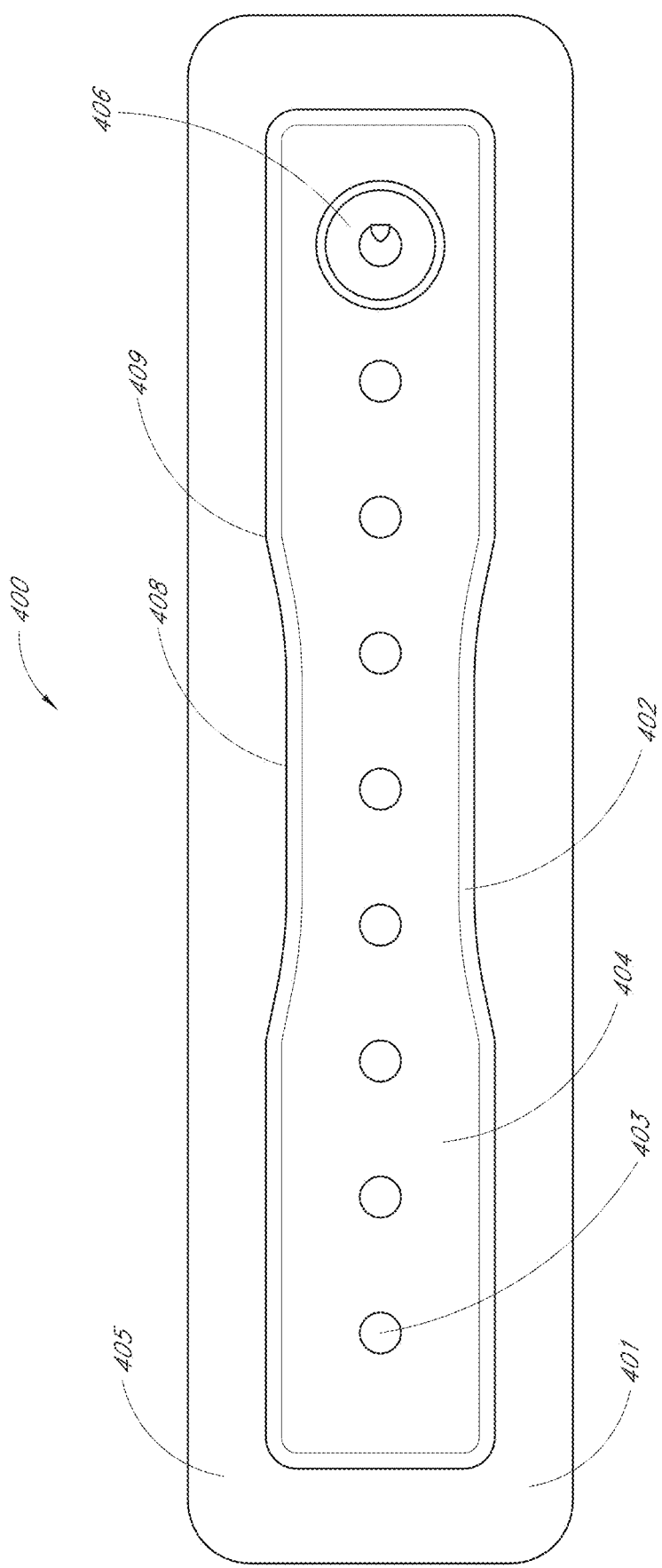
Figure 7C:
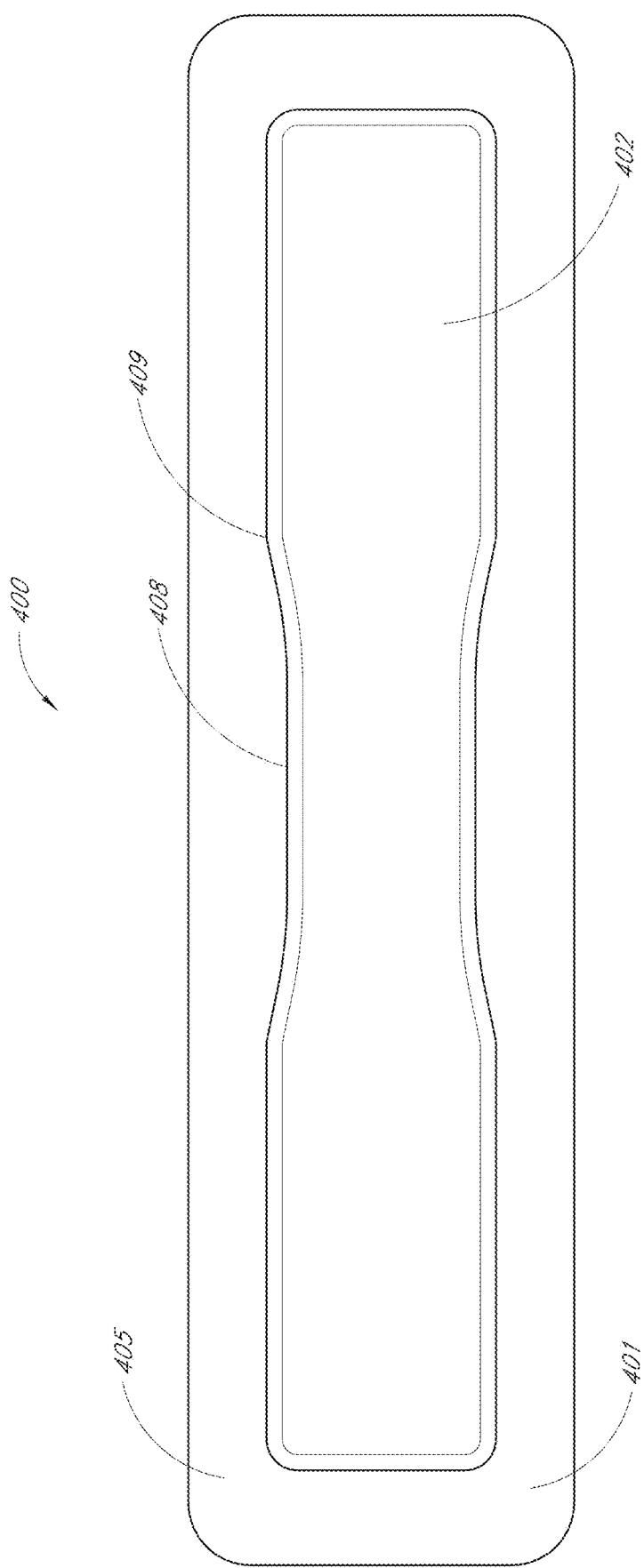
Figures 7D, 7E:
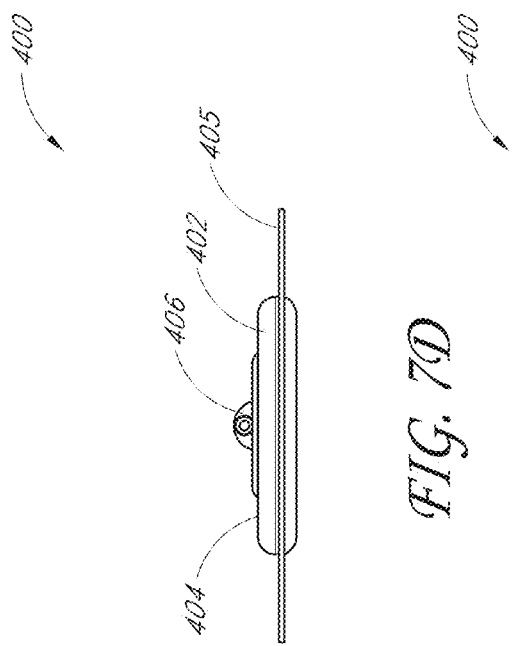
Figure 8A:
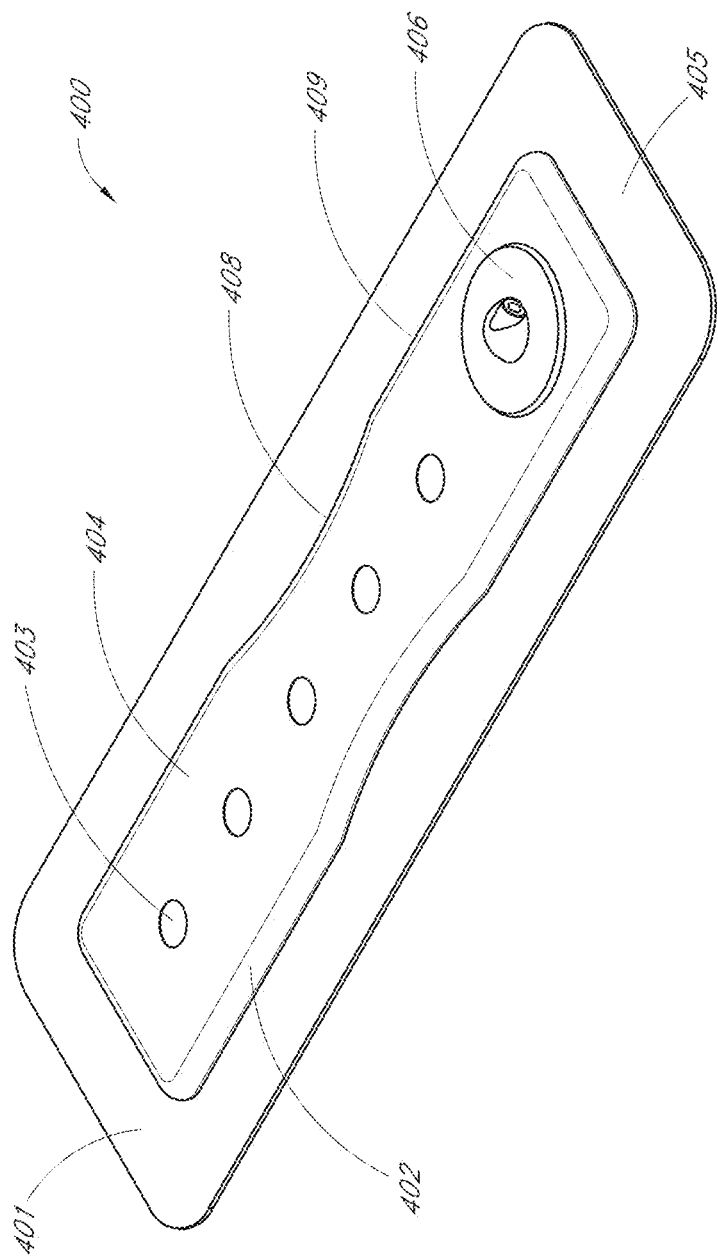
Figure 8B:
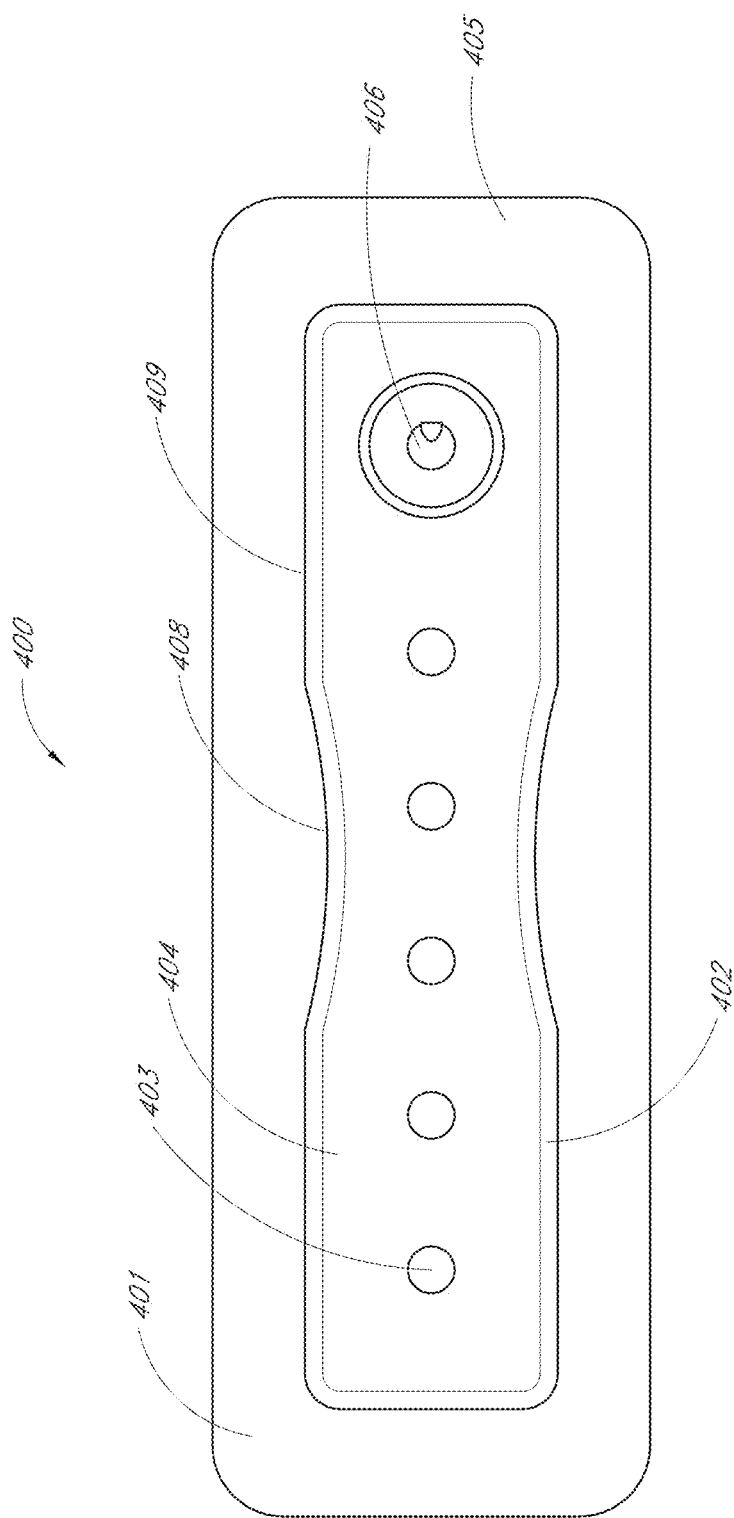
Figure 8C:
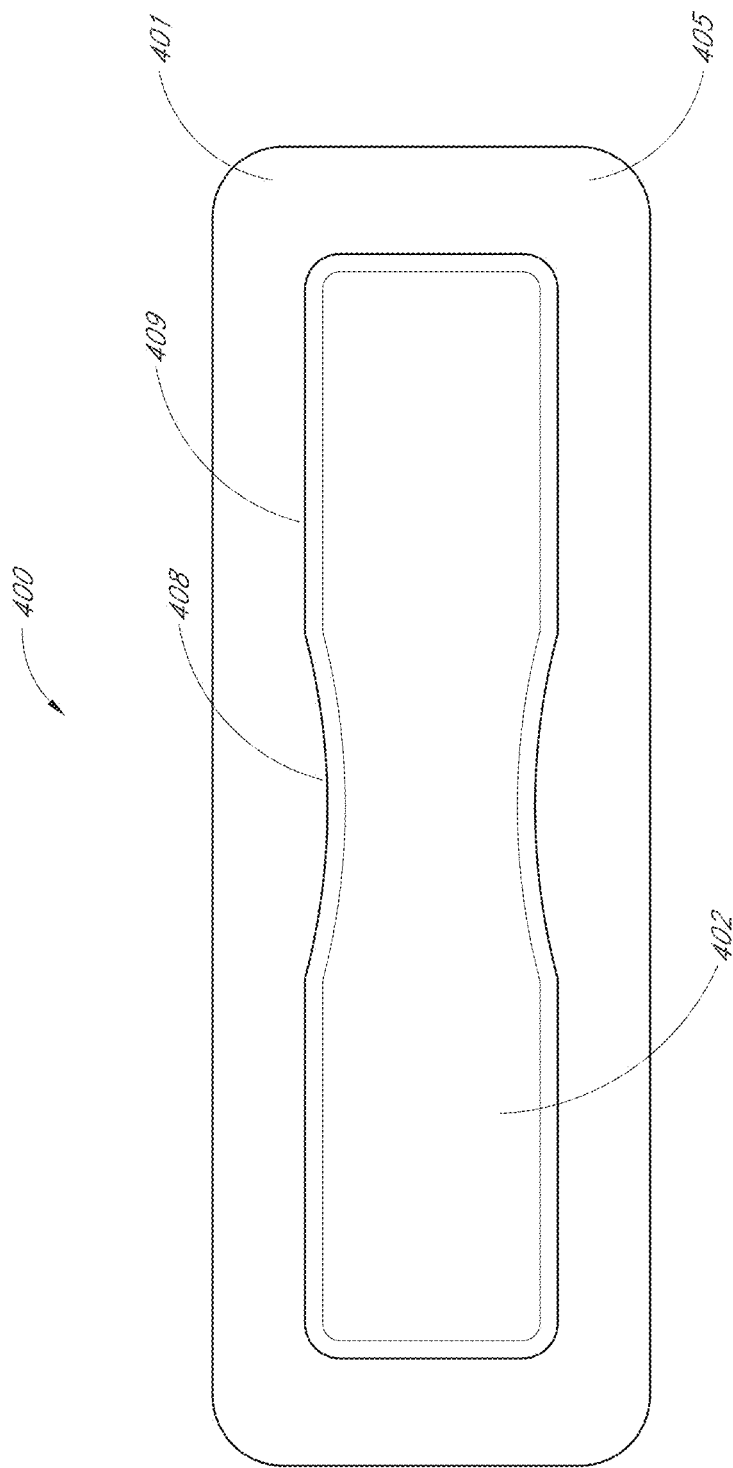
Figures 8D, 8E:
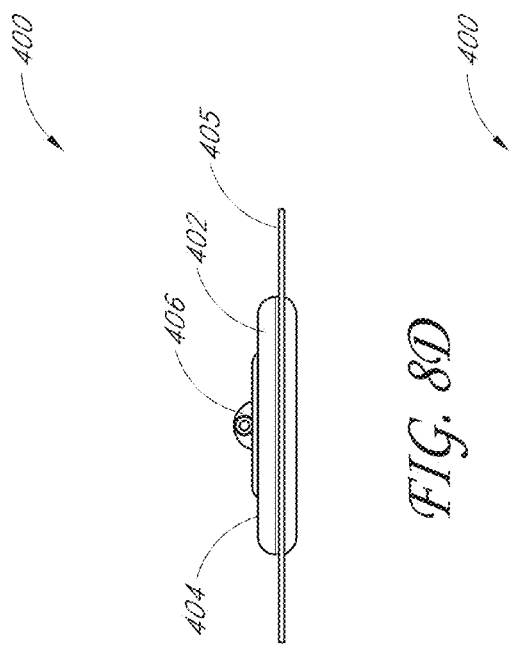
Figure 8F:
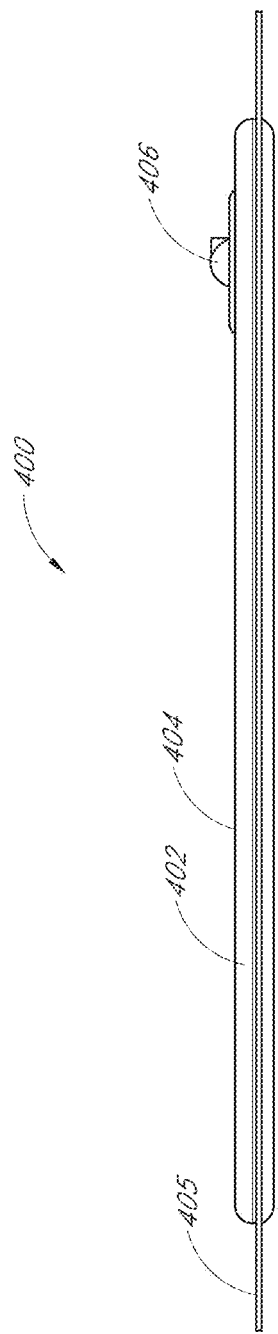
Figure 9A:
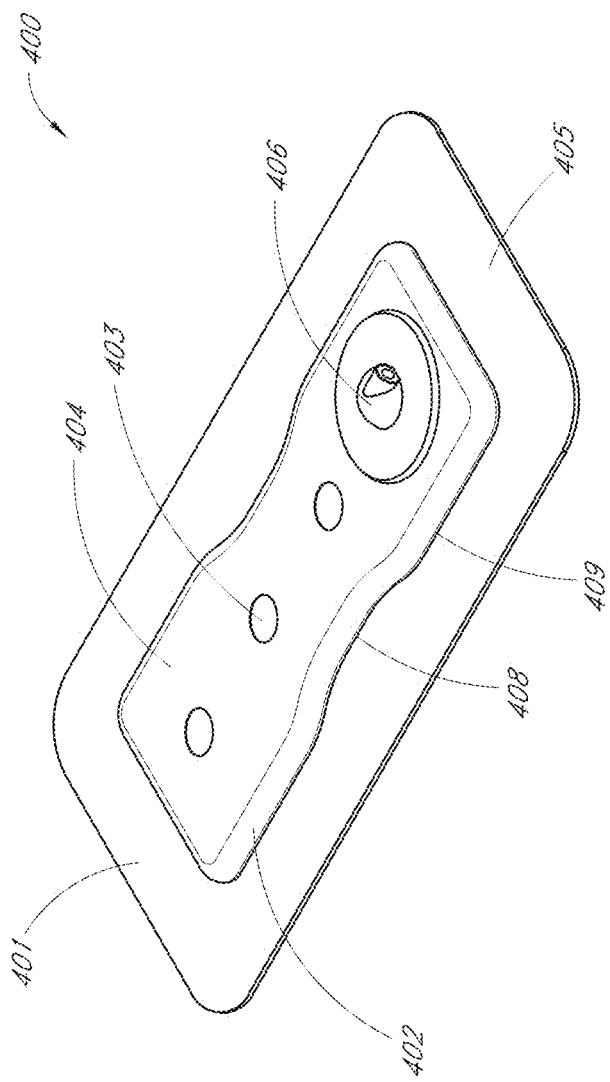
Figure 9B:
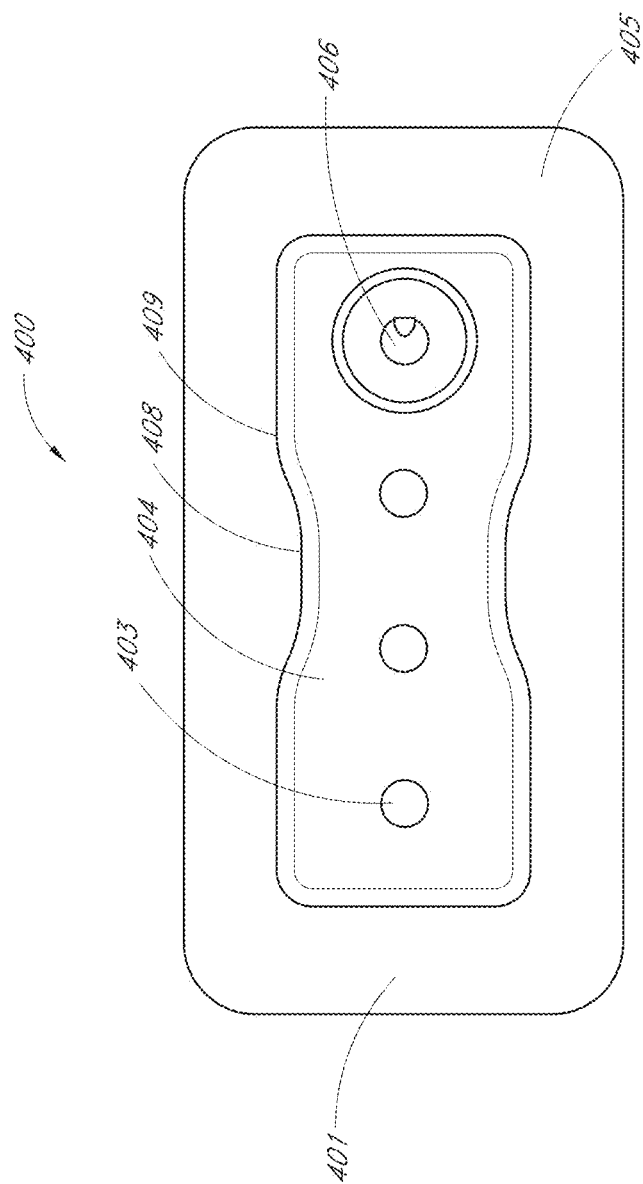
Figure 9C:
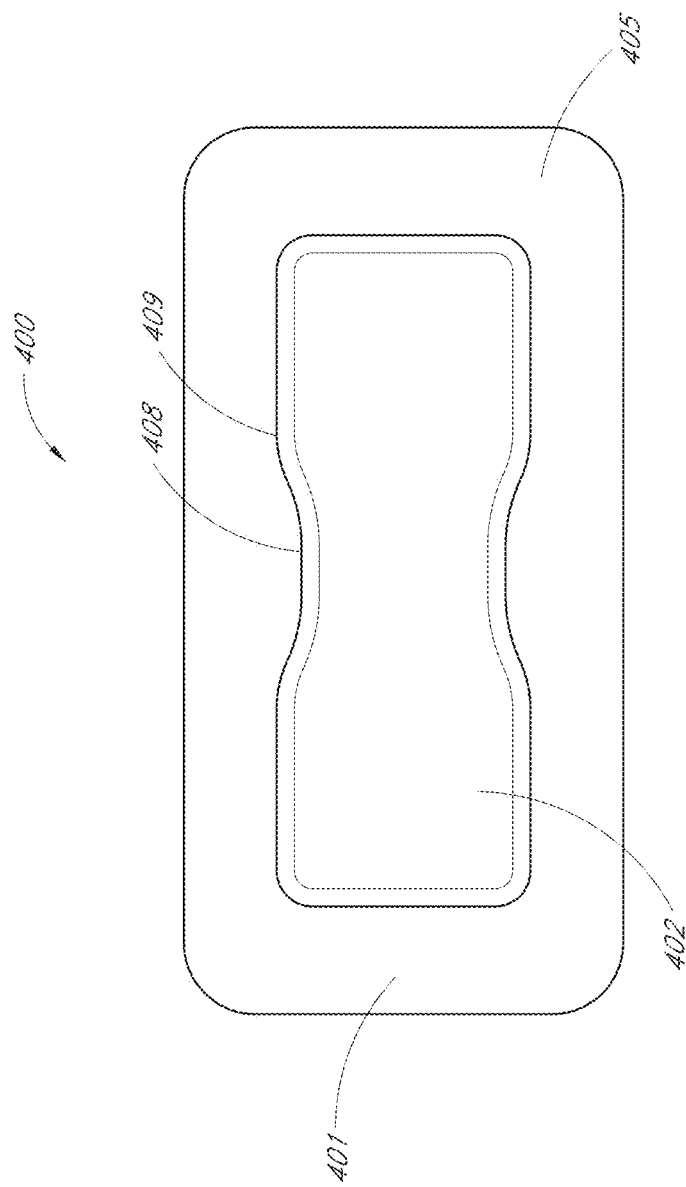
Figures 9D, 9E:
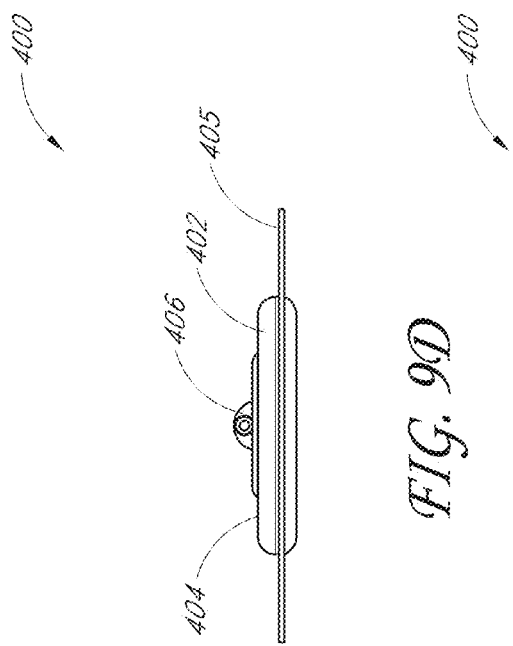
Figure 9F:
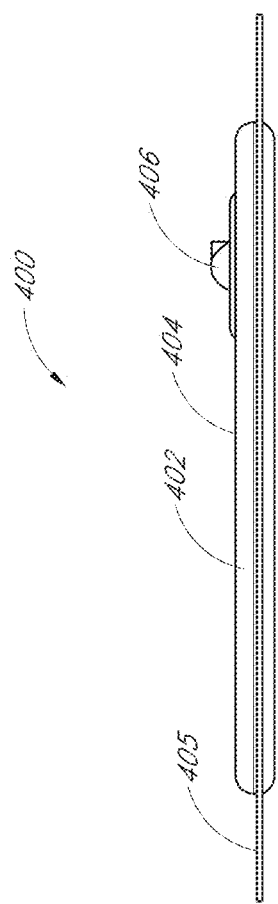

FIGS. 5A-F illustrate multiple views of the wound dressing 400. FIG. 5A illustrates a perspective view of a wound dressing with the dimensions of 300 mm×150 mm. FIGS. 5B and 5C illustrate a top view and bottom view of the embodiment of a wound dressing described in FIG. 5A. FIGS. 5D and 5E illustrate a front and back view respectively of the wound dressing 400 described in FIG. 5A. FIG. 5F illustrates a side view of the wound dressing as described in FIG. 5A.

Embodiments of the wound dressings described herein may be arranged such that each embodiment may have enhanced compatibility with body movement. This can be achieved by using a different shape for different wound types or areas of the body. Wound dressing embodiments can be of any suitable shape or form or size as illustrated in FIGS. 5A-F, 6A-F, 7A-F, 8A-F, 9A-F, 10A-F, 11A-F, 12A-F, and 24A-F. The overall dimensions of the dressings as illustrated in FIGS. 5A-F, 6A-F, 7A-F, 8A-F, 9A-F, 10A-F, 11A-F, 12A-F may be, for example but without limitation, 300 mm×150 mm, 200 mm×150 mm, 400 mm×100 mm, 300 mm×100 mm, 200 mm×100 mm, 250 mm×250 mm, 200 mm×200 mm, and 150 mm×150 mm, respectively, although any total size may be used, and the size may be determined to match particular wound sizes. The oval-shaped dressing in FIGS. 24A-F may, in some embodiments, measure 190 mm×230 mm, or 145.5 mm×190 mm. Again, it will be understood that the embodiments described in the foregoing are simply illustrative embodiments illustrating possible sizes, dimensions, and configurations of wound dressings, and that other configurations are possible.

As noted above, the preceding embodiments illustrated in FIGS. 5A-F, 6A-F, 7A-F, 8A-F, 9A-F, 10A-F, 11A-F and 12A-F may comprise a waisted portion 408 located inwardly with reference to an edge 409 of the absorbent layer 402. The contour of the absorbent layer to the waisted portion 408 is preferably rounded and smooth. In the embodiments of FIGS. 5A-F, 6A-F, 7A-F, 8A-F, and 9A-F, the inward distance between the edge 409 and the waisted portion 408 may range from 1 mm, 5 mm, 10 mm, 15 mm, 20 mm, and 30 mm. Preferably, the inward distance is 10 mm. In the embodiments of FIGS. 10A-F, 11A-F, and 12A-F the inward distance between the edge 409 and the waisted portion 408 may range from 5 mm, 10 mm, 20 mm, 30 mm, 40 mm, 45 mm, 50 mm, 60 mm, and 75 mm. FIGS. 6A-F illustrate a perspective view, a top view, a bottom view, a front view, a back view, and a side view, respectively, of an embodiment of a wound dressing 400. In some embodiments, the dressing may measure 200 mm×150 mm. The wound dressing 400 of FIGS. 6A-F can have a similar configuration and components as described above for FIGS. 5A-F, except the embodiments of FIG. 6A-F are of a smaller size. Additionally, in contrast to the embodiment of FIGS. 5A-F which comprises a 5×2 configuration of an array of dots viewing windows, the embodiment of FIGS. 6A-F comprises a viewing window configuration comprising a 3×2 array of dots.

FIGS. 7A-F illustrate a perspective view, a top view, a bottom view, a front view, a back view, and a side view, respectively, of an embodiment of a wound dressing 400. In some embodiments, the dressing may measure 400 mm×100 mm. The wound dressing 400 of FIGS. 7A-F can have a similar configuration and components as described above for FIGS. 5A-F, except the embodiments of FIG. 7A-F are of a different size. Additionally, in contrast to the embodiment of FIGS. 5A-F, the embodiment of FIGS. 7A-F comprises a viewing window configuration comprising an 8×1 array of dots.

FIGS. 8A-F illustrate a perspective view, a top view, a bottom view, a front view, a back view, and a side view, respectively, of an embodiment of a wound dressing 400. In some embodiments, the dressing may measure 300 mm×100 mm. The wound dressing 400 of FIGS. 8A-F can have a similar configuration and components as described above for FIGS. 5A-F, except the embodiments of FIG. 8A-F are of a different size. Additionally, in contrast to the embodiment of FIGS. 5A-F, the embodiment of FIGS. 8A-F comprises a viewing window configuration comprising a 5×1 array of dots.

FIGS. 9A-F illustrate a perspective view, a top view, a bottom view, a front view, a back view, and a side view, respectively, of an embodiment of a wound dressing 400. In some embodiments, the dressing may measure 200 mm×100 mm. The wound dressing 400 of FIGS. 9A-F can have a similar configuration and components as described above for FIGS. 5A-F, except the embodiments of FIG. 9A-F are of a different size. Additionally, in contrast to the embodiment of FIGS. 5A-F, the embodiment of FIGS. 9A-F comprises a viewing window configuration comprising a 3×1 array of dots.

FIGS. 12A-F illustrate a perspective view, a top view, a bottom view, a front view, a back view, and a side view, respectively, of an embodiment of a wound dressing 400. In some embodiments, the dressing may measure 150 mm×150 mm. The wound dressing 400 of FIGS. 12A-F can have a similar configuration and components as described above for FIGS. 5A-F, except the embodiments of FIG. 9A-F are of a different size. Additionally, in contrast to the embodiment of FIGS. 5A-F, the embodiment of FIGS. 12A-F comprises a viewing window configuration comprising a quincunx array of dots. The quincunx array of dots configuration consists of five dots arranged in a cross, with four of the dots forming a square or rectangle where one dot is positioned at each of the four corners of the square or rectangle shaped wound dressing and a fifth dot in the center. However, one corner of the wound dressing preferably has the fluidic connector or port 406 in place of a dot in the quincunx dot array.

Figure 10A:
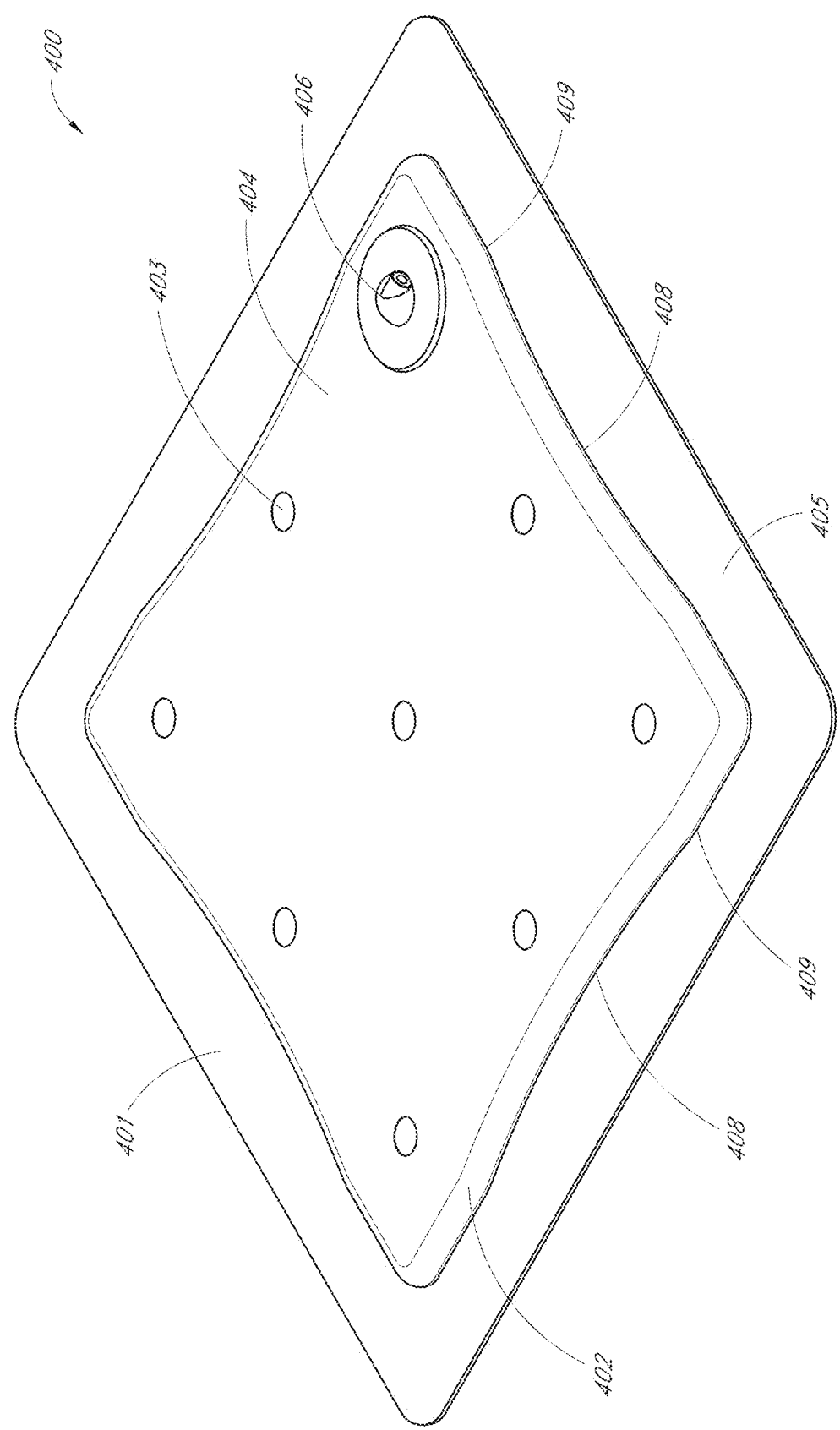
Figure 10B:
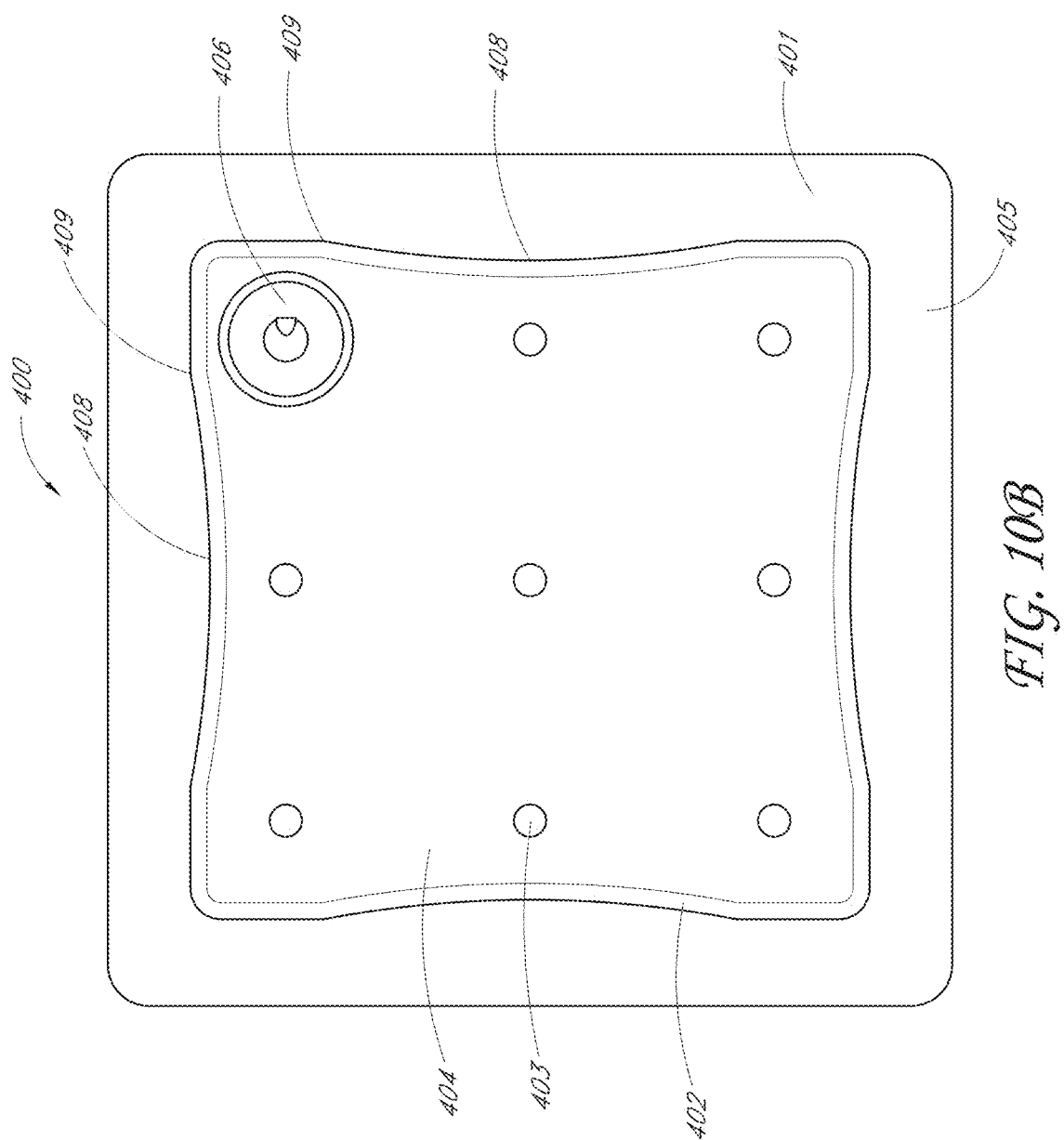
Figure 10C:
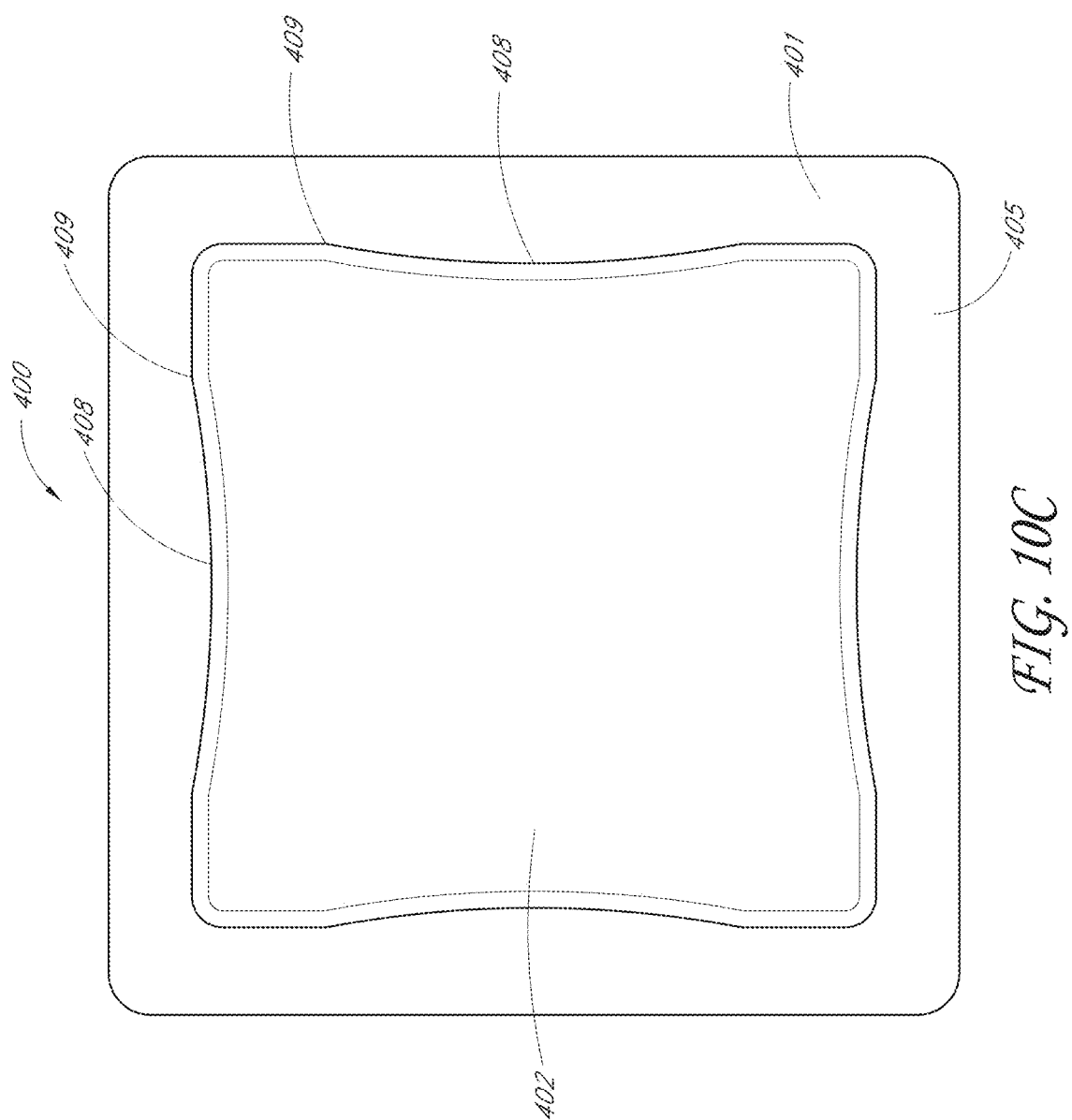
Figure 10F:
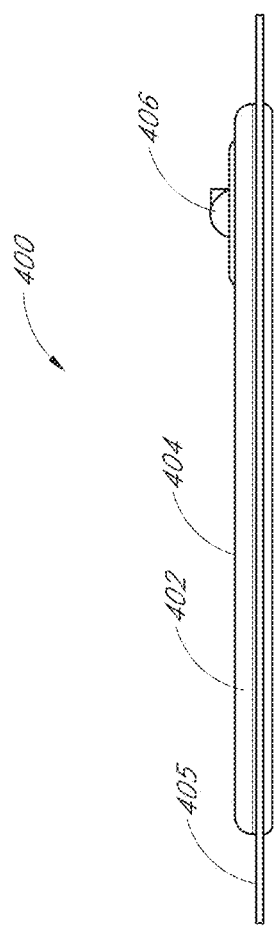
Figure 10G:
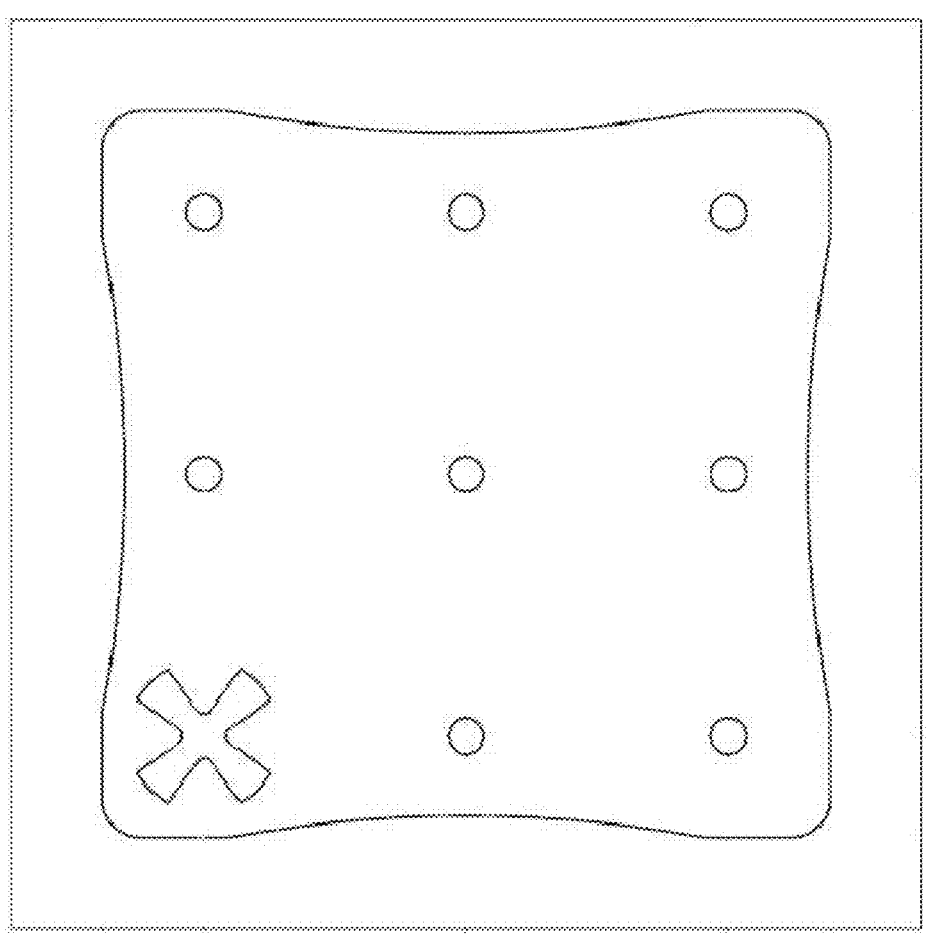
FIG. 10G illustrates a top view of the wound dressing of FIGS. 10A-F with a maltese cross shaped viewing window in the obscuring layer.
Figure 11A:
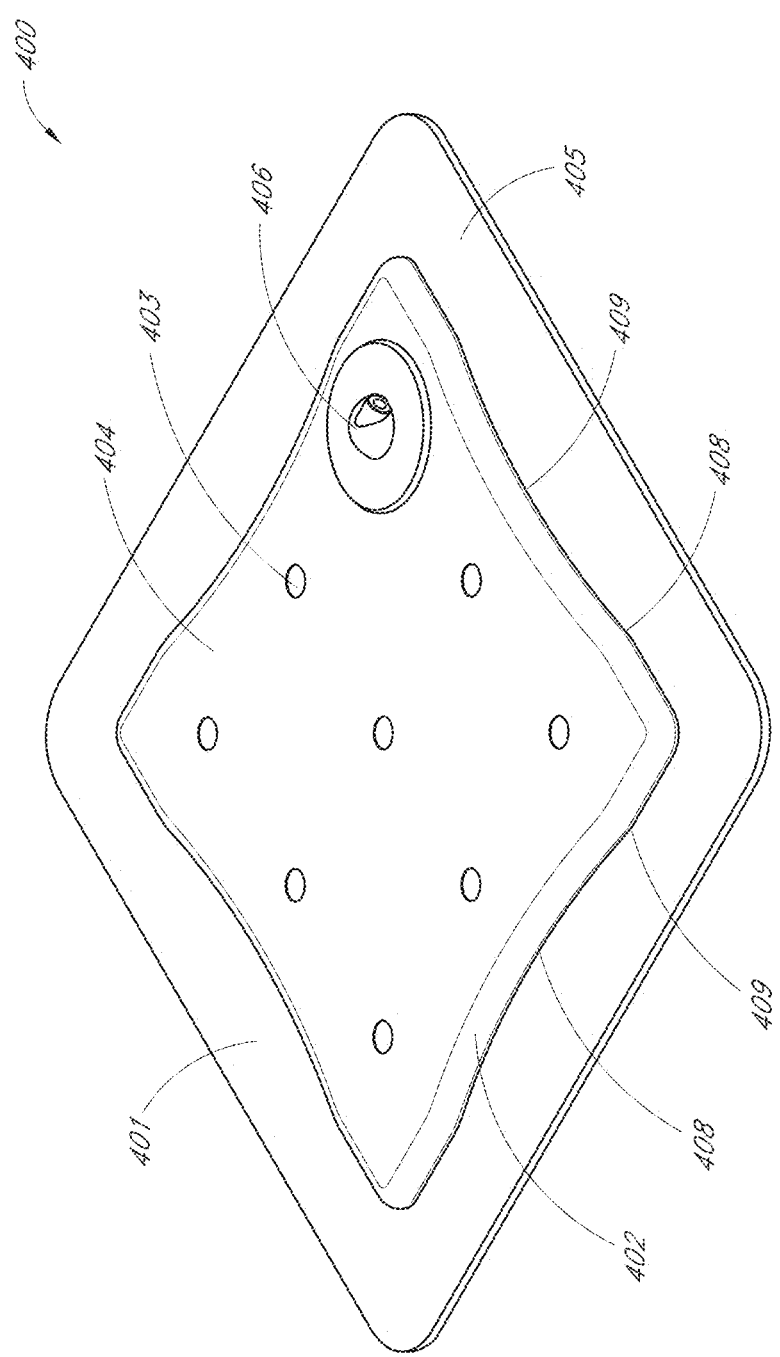
Figure 11B:
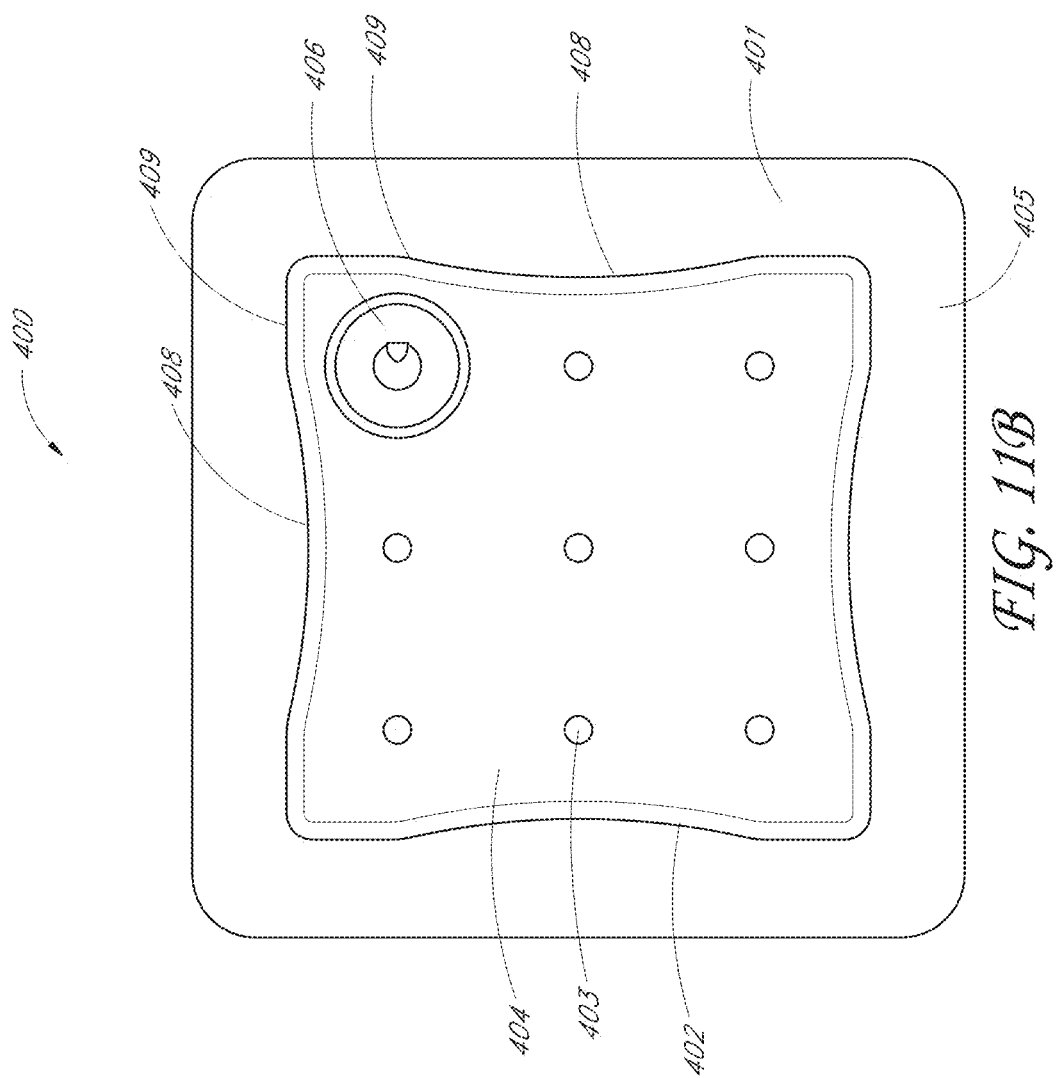
Figure 11C:
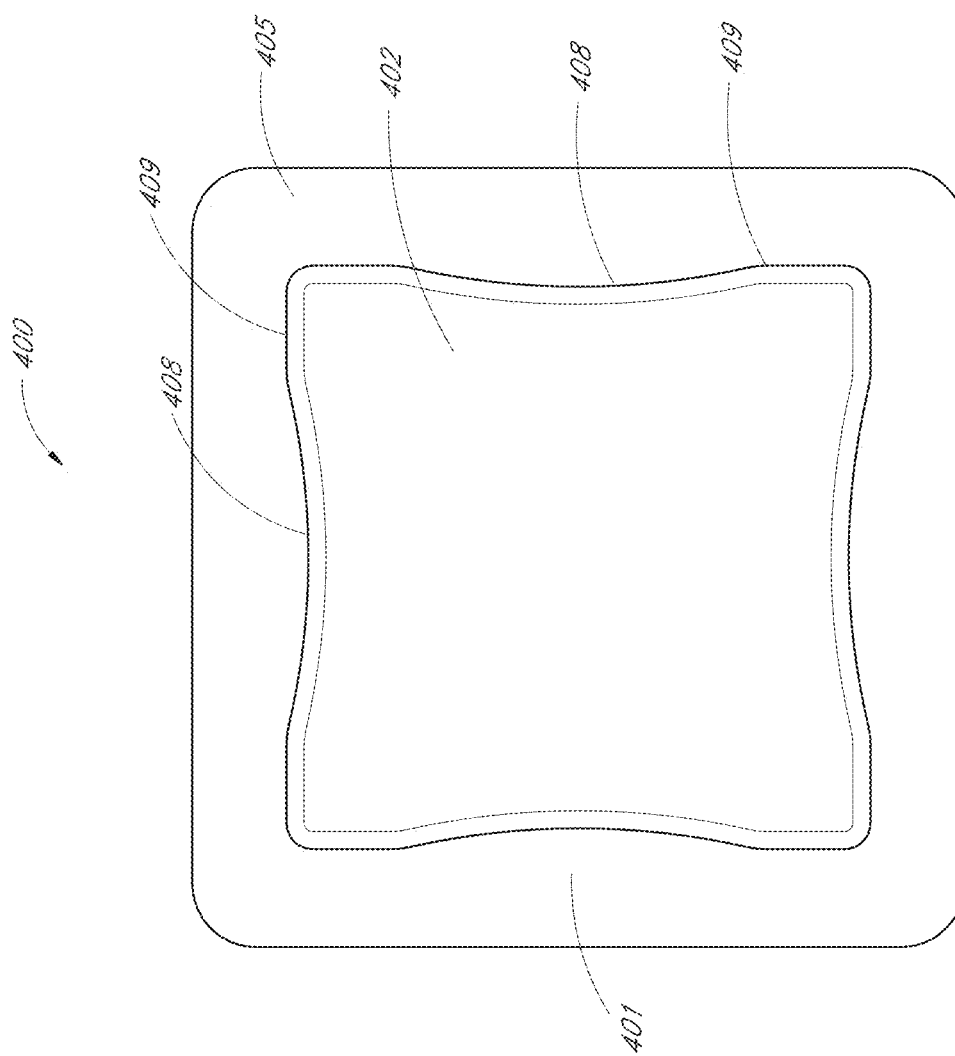
Figure 12A:
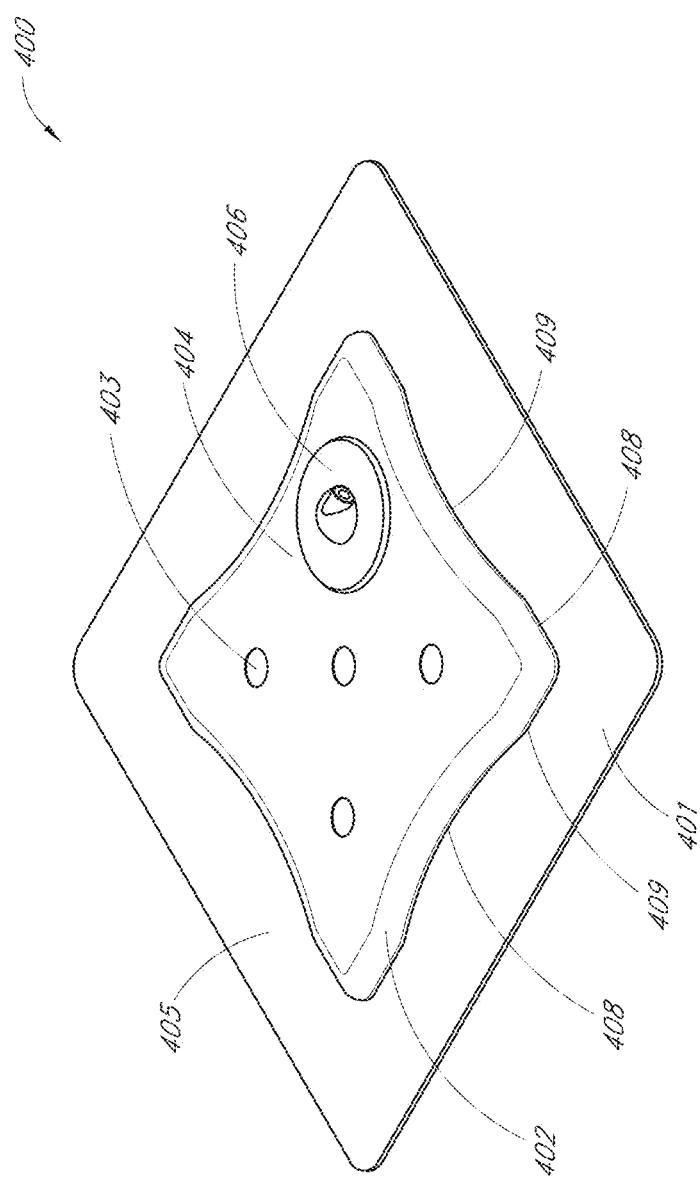
Figure 12B:
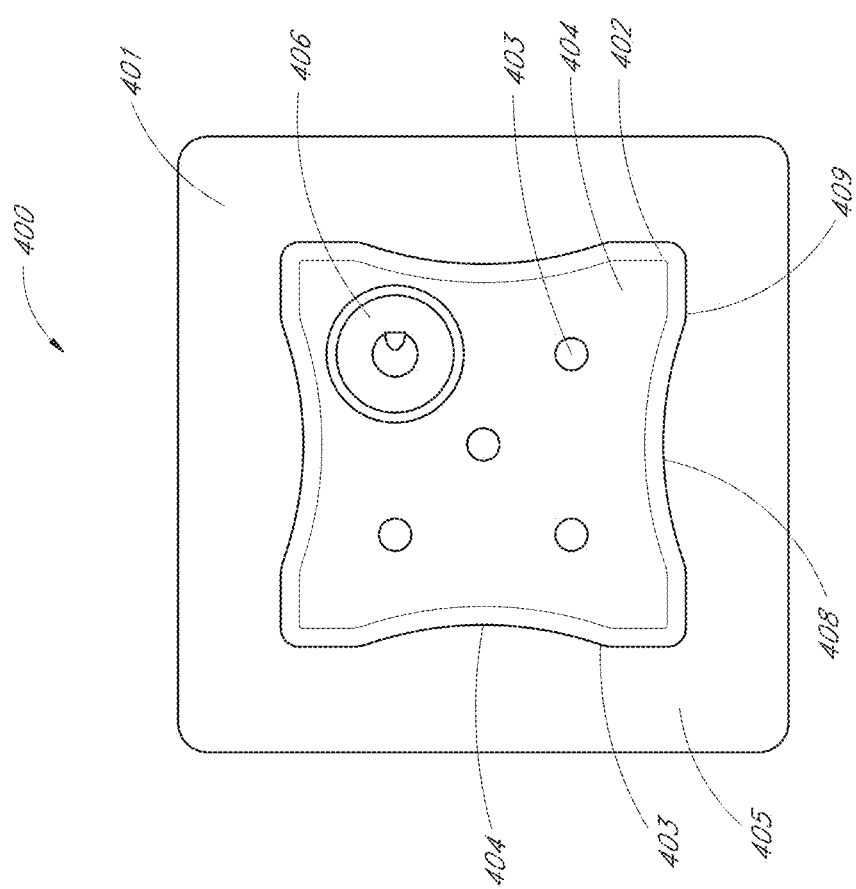
Figure 12C:
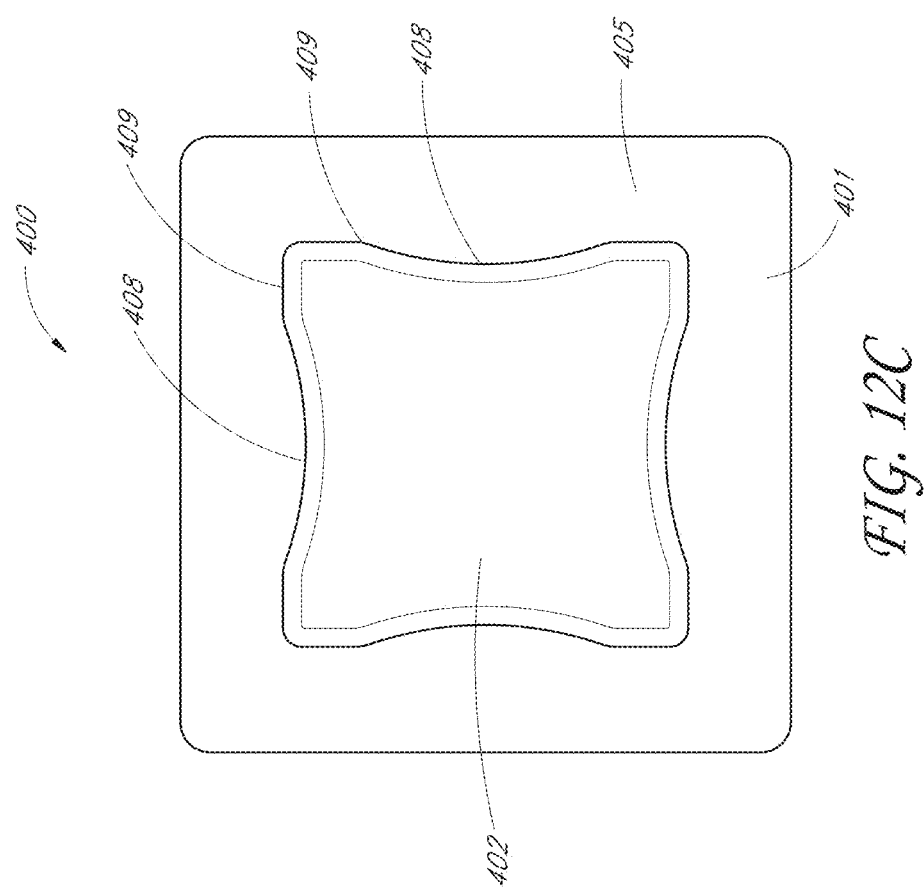

FIGS. 10A-F illustrate a perspective view, a top view, a bottom view, a front view, a back view, and a side view, respectively, of an embodiment of a wound dressing 400. In some embodiments, the dressing may measure 250 mm×250 mm. The wound dressing 400 of FIGS. 10A-F can have a similar configuration and components as described above for FIGS. 5A-F, except the embodiments of FIG. 10A-F are of a different size. Additionally, in contrast to the embodiment of FIGS. 5A-F, the embodiment of FIGS. 10A-F comprises a viewing window configuration comprising a 3×3 array of dots with an absent dot at a corner position of the wound dressing and in its place is a domed port or a fluidic connector 406 completing the 3×3 array. FIG. 10G illustrates a top view of the wound dressing 400 of FIGS. 10A-F (without showing a port or fluidic connector or an opening in the backing layer) with a cross shaped opening (for example a maltese cross) in the obscuring layer, described further below. A port or fluidic connector may be secured over the maltese cross shaped viewing window and over an opening in the backing layer for transmission of negative pressure to the wound dressing. An outer perimeter of the maltese cross may extend beyond an outer perimeter of the port so that the arms of the cross shaped opening forms viewing windows through the obscuring layer (see, for example, FIGS. 37A and 37C). The cross shaped opening in the obscuring layer may be provided in any of the wound dressings described in this specification. As illustrated in FIG. 10G, the cross in one embodiment may have 4 arms that extend at 45 degree angles relative to the sides of the backing layer, but in other embodiments may be at different angles or may have 2 opposite arms parallel to one side of the backing layer, with the other 2 opposite arms perpendicular thereto.

FIGS. 11A-F illustrate a perspective view, a top view, a bottom view, a front view, a back view, and a side view, respectively, of an embodiment of a wound dressing 400. In some embodiments, the dressing may measure 200 mm×200 mm. The wound dressing 400 of FIGS. 11A-F can have a similar configuration and components as described above for FIGS. 5A-F, except the embodiments of FIGS. 11A-F are of a different size. Additionally, in contrast to the embodiment of FIGS. 5A-F, the embodiment of FIGS. 11A-F comprises a viewing window configuration comprising a 3×3 array of dots with an absent dot at a corner position of the wound dressing and in its place is a domed port or a fluidic connector completing the 3×3 array.

The additional sizes and shapes illustrated in FIGS. 5A-F, 6A-F, 7A-F, 8A-F, 9A-F, 10A-F, 11A-F, 12A-F, and 24 may incorporate the waisted portion 408, obscuring layer 404, viewing windows 403, and other components and embodiments described herein.

Figures 13A, 13B:
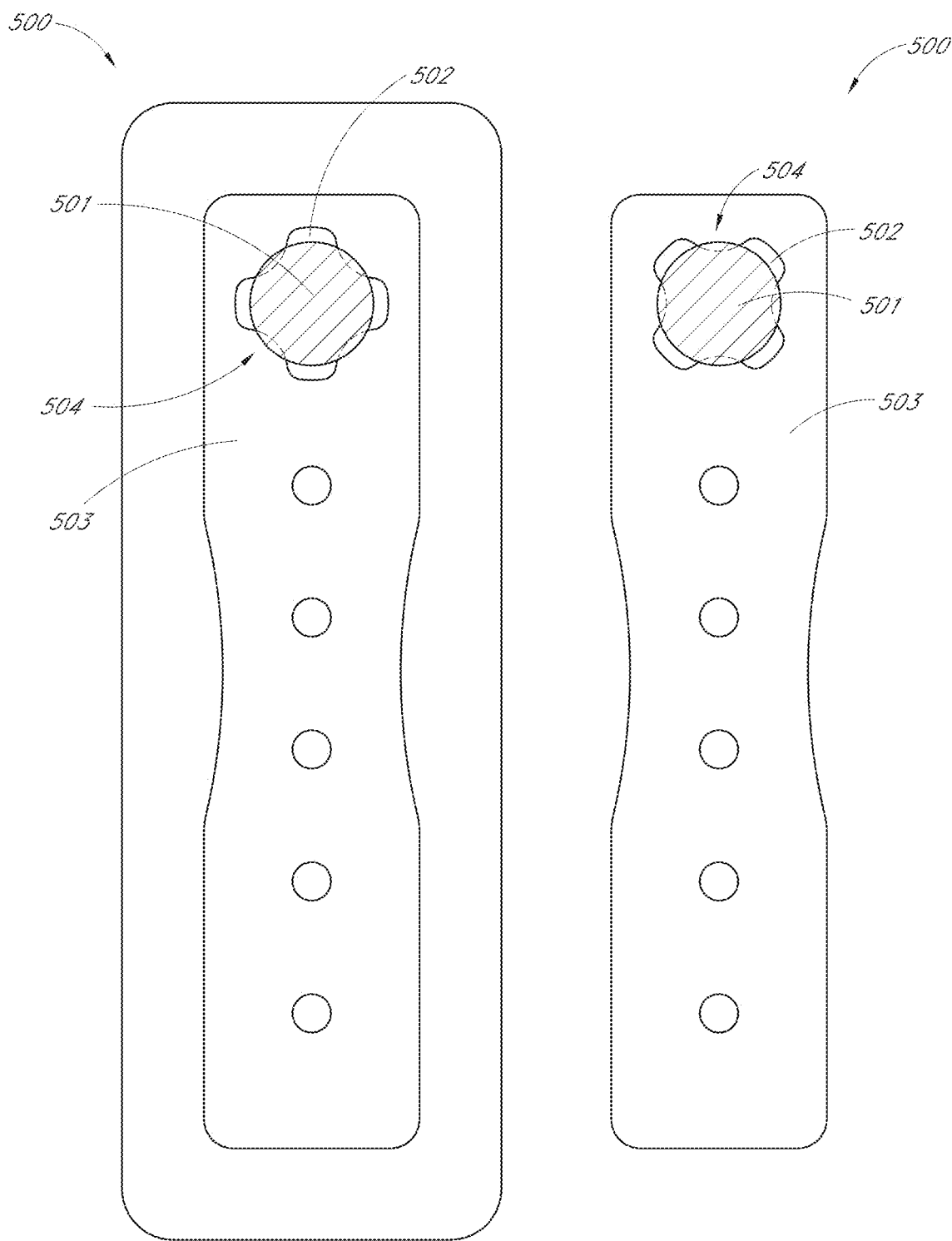
FIGS. 13A-B and 14 illustrate a top view of an embodiment of a wound dressing including a cross-shaped viewing window.
Figure 14:
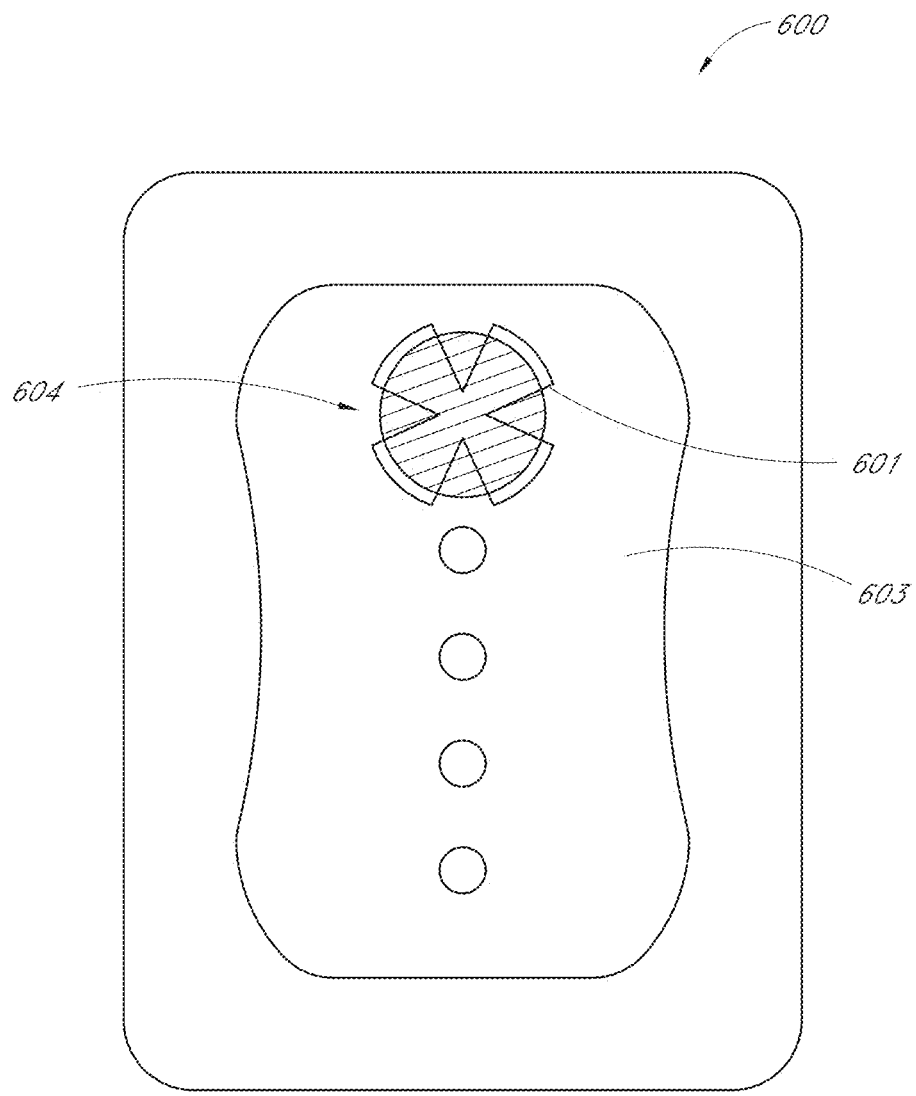

FIGS. 13A, 13B, and 14 illustrate embodiments of a dressing 500 comprising one or more orifice viewing windows 502 at, near, or adjacent to the port. The orifice viewing windows 502 can be provided at, near, adjacent to the port 504 in the backing layer for viewing of the absorbent material 503 present in proximity to the port 504. The orifice viewing windows 502 can have the same structure and/or function as the viewing windows herein described. In some embodiments, the orifice viewing window 502 can be formed from a cross-shaped or Maltese-cross-shaped aperture or cut-out 501 in the obscuring layer. The arms of the cross-shaped cut-out 501 can be aligned with the longitudinal length and transverse width of the absorbent material 503 as shown in FIG. 13A. Alternatively, the arms of the cross-shaped cut-out 501 can be offset from the longitudinal length and transverse width of the absorbent material, at an angle, for example, a 45° angle, as illustrated in FIG. 13B. The arms of the cross-shaped cut-out may span a larger dimension than a hole in the absorbent material below the cut-out 501. For example, the arms may span a dimension of about 25 mm, while the through-hole in the absorbent material may have a diameter of 10 mm.

Additionally, FIG. 14 illustrates an embodiment of a wound dressing 600 in which the arms of the cross-shaped aperture can have flared edges 601. The orifice viewing windows 502 at, near, or adjacent to the port 604 may be used to indicate that fluid is approaching the port 604 or that the dressing 600 is otherwise becoming saturated. This can assist the clinician or patient in maintaining the wound dressing and determining when to change the dressing, because once fluid contacts the center of the port, such fluid contact may at least partially occlude the hydrophobic filter that may be contained therein so as to interrupt or at least partially block the application of negative pressure. The orifice viewing windows 502 can be used with the fluidic connector as well as the domed port or any other suitable connector.

Figure 15A:
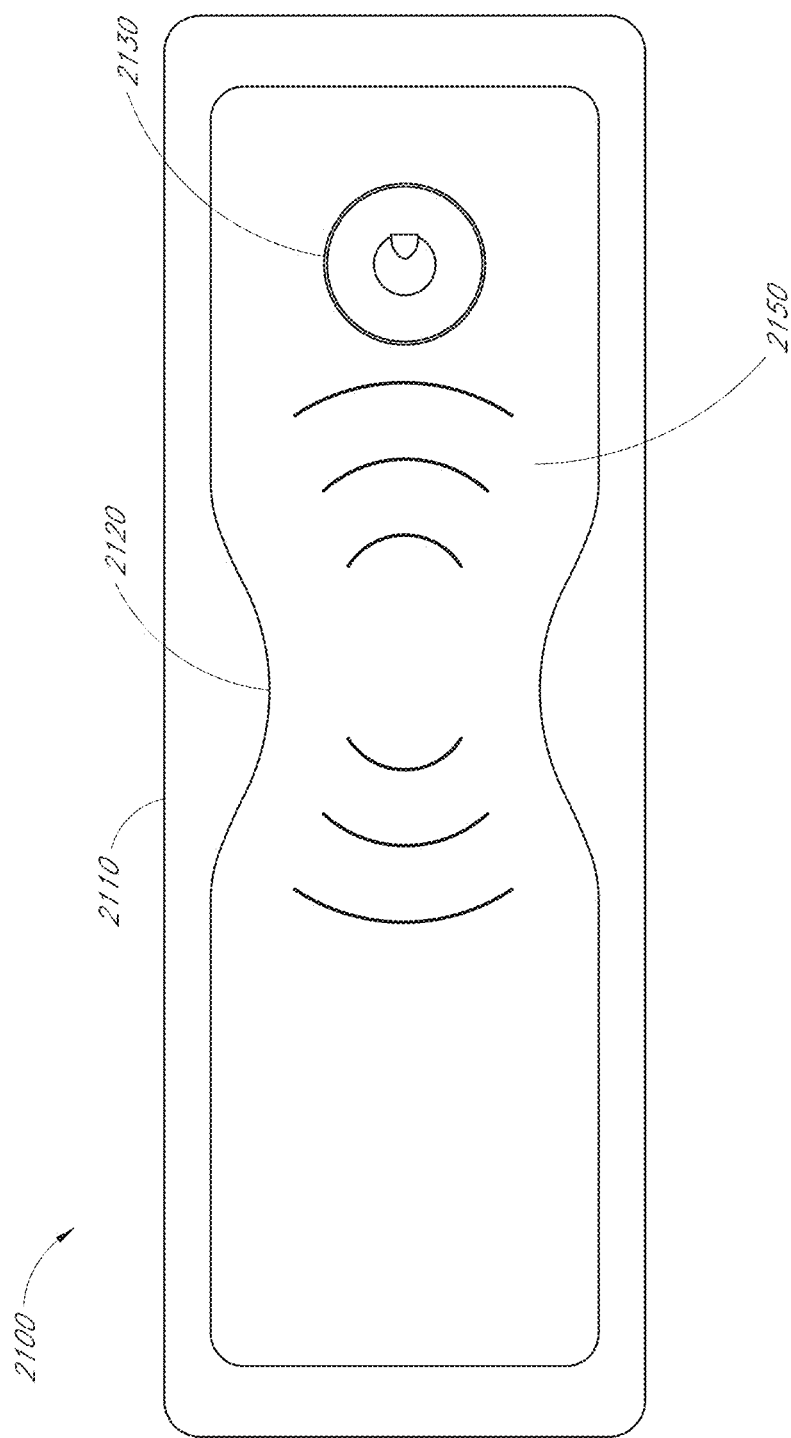
FIGS. 15A-B illustrate a top view of an embodiment of a wound dressing including slits in the wound dressing.

As with FIGS. 15A and 158, the wound dressing may also be provided with one or more slits 2150 to aid the dressing in conforming to a non-planar area. FIG. 15A illustrates an embodiment of a wound dressing 2100 with a narrowed central portion or waisted portion 2120 and concentric slits 2150. This embodiment may be useful for the treatment of wounds on non-planar surfaces or otherwise contoured wounds, including, for example, feet, knees, sacral regions, or other such areas. In some embodiments, the wound dressing 2100 may provide for one or more slits 2150 cut into the dressing, preferably into the absorbent layer, that may enhance the conformability of the dressing. In this embodiment, the slits 2150 are cut in concentric ovoid arcs, although other configurations (as discussed below) are possible. Preferably, the area under the port 2130 or fluidic connector disposed at the top of the device is free from the slits 2150, as this may interfere with fluid transfer from the dressing. In some embodiments, the slits 2150 may be formed as part of, in addition to, or instead of baffles that may be present within the absorbent layer so as to may aid in distribution of wound exudate. In these embodiments, and with all other embodiments described herein, although a domed connector is shown attached to the dressing, this may be interchanged with any other suitable connector, including for example embodiments of the fluidic connectors described in FIGS. 23A and 23B (as described below).

Figure 15B:
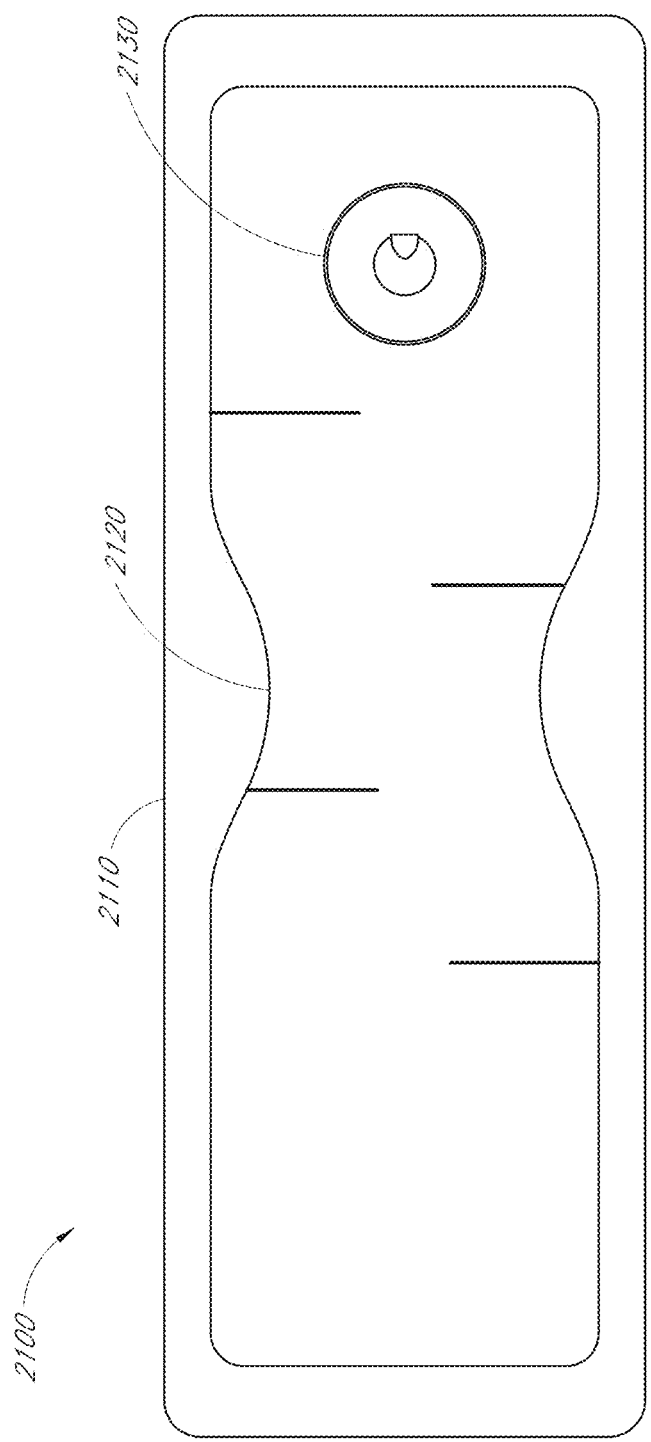

FIG. 15B illustrates an embodiment of a wound dressing 2100 with a narrow central portion 2120. Here, however, one or more slits 2150 extending across the width of the dressing may be present. Preferably, these slits 2150 do not extend entirely across the width of the dressing, in order to promote fluid transfer within the absorbent layer. The slits 2150 may enhance conformability of the dressing, possibly in conjunction with the waisted configuration of the dressing, when applied to a non-planar or contoured wound area. For example, such a dressing 2100 may be useful when applied so as to wrap around an arm or a leg.

FIGS. 23A and 23B illustrate embodiments of white and black (or colored) fluidic connectors 2410, 2420, respectively, that may be used to connect an embodiment of a wound dressing described herein to a source of negative pressure. In some embodiments, the domed port used in other embodiments discussed herein (e.g., as illustrated above in FIG. 1) may be replaced by the fluidic connector 2410, 2420, for example as illustrated in FIGS. 16-19. The fluidic connector 2410, 2420 may be flexible and/or enhance the comfort of the patient. The fluidic connector 2410, 2420 preferably comprises a fluidic connector body configured to transmit fluid through itself, including, for example, negative pressure and/or wound exudate. The fluidic connector body is preferably encapsulated within one or more layers of fluid-impermeable material. In some embodiments, the fluid-impermeable material is heat-sealed together to enclose the fluid connector body.

With reference now to FIG. 23A, the body of the fluidic connector 2410 is preferably be constructed from a material configured to transmit fluids therethrough, including fabrics such as 3D fabric. In some embodiments, the thickness of the fluidic connector body may measure between 0.5 to 4 mm, preferably 0.7 to 3 mm, and even more preferably between 1 and 2 mm; in a preferred embodiment the fluid connector body is 1.5 mm thick. Suitable materials that may be used for the fluidic connector body, including the 3D fabric, are disclosed in U.S. application Ser. No. 13/381,885, filed Dec. 30, 2011, published as US2012/0116334, titled "APPARATUSES AND METHODS FOR NEGATIVE PRESSURE WOUND THERAPY," and which is hereby incorporated by reference in its entirety. Use of the 3D fabric in the fluidic connector body may help alleviate fluid blockage when the connector is kinked, and may further provide for a soft fluidic connector that alleviates contact pressure onto a patient, for example when the patient's weight is pressed against the fluidic connector. This may enhance patient comfort and reduce the likelihood of pressure ulcers.

Testing of various weights in various configurations on embodiments of fluidic connectors comprising a 3D fabric was completed. The testing included weights above those believed to be likely to be encountered by a patient, as maximal pressure on a heel for a patient using dressings was found to be 1.3 kg/cm$^2$ in some studies. Preferably, embodiments of the fluidic connectors described herein, especially when comprising 3D fabric, can transmit therapeutic levels of negative pressure (i.e., in an amount sufficient to heal a wound) while a weight is pressed down thereupon. For example, embodiments are preferably able to transmit therapeutic levels of negative pressure while an external pressure applied on the dressing and/or 3D fabric of up to 1 kg/cm$^2$, preferably up to 2 kg/cm$^2$, and even more preferably up to 4 kg/cm$^2$. Certain embodiments, as described below, have been tested as being capable of transmitting therapeutic levels of negative pressure while an external pressure applied on the dressing and/or 3D fabric is above 6 kg/cm$^2$.

In the testing, a 400 ml wound cavity was used, and pressure was measured both at the wound and at the pump. Embodiments of a fluidic connector comprising 3D fabric were tested when laid flat with a weight placed thereupon. Testing indicated that when no pressure was applied to the fluidic connector, the pressure differential between the pressure at the pump and at the cavity was approximately 2 mmHg. Various different weights were applied, ranging between 2 and 12 kg/cm$^2$, in 2 kg increments, and the resulting pressure difference was approximately linear, with the pressure difference at 12 kg/cm$^2$ being calculated at 33 mmHg, while the pressure difference at 2 kg/cm$^2$ being only 16 mmHg. The relation between the pressure difference in mmHg was found to equal approximately 4.5 times the applied load in kg/cm$^2$. Testing also indicated that the relative pressure difference between the pressure at the pump and the pressure at the wound after five minutes was less than 10 mmHg when measured at the pump for loads under 4 kg/cm$^2$, and under 20 mmHg when measured at the wound for loads under 4 kg/cm$^2$.

Testing was also performed with a weight laid on an embodiment of a fluidic connector, while being bent at a 90° angle. Various different weights were applied, ranging between 2 and 12 kg/cm$^2$, in 2 kg increments, and the resulting pressure difference was approximately linear, with the pressure difference at 12 kg/cm$^2$ being calculated at 51 mmHg, while the pressure difference at 2 kg/cm$^2$ being 17 mmHg. The relation between the pressure difference in mmHg was found to equal approximately 8 times the applied load in kg/cm$^2$. Testing also indicated that the relative pressure difference between the pressure at the pump and the pressure at the wound after five minutes was approximately 20 mmHg when measured at the pump for loads under 4 kg/cm², and under 30 mmHg when measured at the wound for loads under 4 kg/cm².

Further testing was performed with a weight laid on an embodiment of a fluidic connector, while being bent at a 180° angle (i.e., folded over itself). Various different weights were applied, ranging between 2 and 12 kg/cm², in 2 kg increments, and the resulting pressure difference was approximately linear, with the pressure difference at 12 kg/cm² being calculated at 76 mmHg, while the pressure difference at 2 kg/cm² being 25 mmHg. The relation between the pressure difference in mmHg was found to equal approximately 10.7 times the applied load in kg/cm². Testing also indicated that the relative pressure difference between the pressure at the pump and the pressure at the wound after five minutes was approximately 20 mmHg when measured at the pump for loads under 4 kg/cm², and under 30 mmHg when measured at the wound for loads under 4 kg/cm.

Testing was also performed on different widths and thicknesses of 3D fabric that may be used in embodiments of fluidic connectors described herein. In a particular example, the maximum negative pressure that could be applied using 3D fabric measuring 1, 1.25, 1.5, 1.75, and 2 cm in width was found to be between 85 and 92 mmHg, respectively. Upon application of an applied load of 1 kg/cm², however, the maximum negative pressure applied for a 1cm-width embodiment dropped to 75 mmHg, while the 1.25 and 1.5 cm-width embodiments were essentially unchanged, exhibiting pressures between 85 and 90 mmHg. Application of a 1 kg/cm² weight made the 1 cm-width embodiment maximum negative pressure drop to about 73 mmHg, while the 1.25 cm-width embodiment dropped to about 84 mmHg. The 1.5 cm-width embodiment showed a minimal maximum negative pressure change down to approximately 86 mmHg. As tested, the greatest increases in flow rate (as evidenced by the maximal negative pressures applied) were greatest when increasing the width of the 3D fabric from 1 cm to 1.25 cm, and stabilized above 1.5 cm. Similarly, increasing the width of the 3D fabric (i.e., above 1 cm) was found to slightly reduce the amount of time required to pump a wound cavity down to a target negative pressure.

Further testing with single and double layers of Baltex 3540 3D fabric, either single or double thickness, indicated that while the maximum negative pressure applied using a single thickness fabric dropped from about 88 mmHg with no applied weight to about 73 mmHg with a 2 kg/cm² weight. However, a double thickness fabric showed minimal change in the maximum amount of negative pressure applied, dropping from 90 mmHg with no weight applied to about 87 mmHg with an applied load of 2 kg/cm².

Depending on the particular application, using wider and/or thicker 3D fabric may permit improved air flow, together with greater pressure and kink resistance in some context; this may be useful especially if higher absolute negative pressure need to be applied to the wound. However, the greater kink and pressure resistance may need to be balanced with other concerns such as perceived bulk and size of the fluidic connector, aesthetics, and comfort, which may require use of a thinner 3D fabric.

In some embodiments, the proximal end 2411 of the fluidic connector 2410 is configured to be connected to a tube or other conduit that is in fluid communication with a source of negative pressure via the fluid connector body, although some embodiments may provide for the fluidic connector 2410 to be directly connectable to a source of negative pressure without needing a conventional tube. The distal end 2412 of the fluidic connector 2410 may be enlarged, and is configured to be attached and/or adhered to a dressing, for example via an aperture in the backing layer of the dressing and/or in the fluidic connector 2410, so that the fluid connector body is in fluid communication therewith.

In one configuration and as illustrated in FIG. 23A, the distal end 2412 of the fluidic connector 2410 may be convex on one side and flat on the opposite side. As illustrated in FIGS. 16-18 below, the flat side may be aligned with the edge of the absorbent layer with the convex side extending over the aperture in the backing layer. The fluidic connector 2410 may be provided preattached to the dressing portion, or may be provided in an unattached format so as to be connectable to the dressing portion by the patient or caregiver. The enlarged distal end 2412 may aid in providing a larger area capable of transmitting negative pressure to the dressing, although the distal end may be provided without any enlargement. Although preferred embodiments of the fluidic connector 2410 are used in dressings that contain substantially all wound exudate within the absorbent material, such that the fluidic connector transmits essentially only air, some embodiments of the fluidic connector may be configured so as to transfer exudate in addition to air. In embodiments of the fluidic connector that are configured to transfer essentially only air (while wound exudate remains substantially within the absorbent material), the distal end of the fluidic connector is preferably provided with a filter configured to block fluid transport beyond itself, such as a hydrophobic filter. An example of such a configuration is described in International Application No. PCT/IB2013/001469, filed May 22, 2013, titled "APPARATUSES AND METHODS FOR NEGATIVE PRESSURE WOUND THERAPY," and which is hereby incorporated into this present application in its entirety.

In embodiments of the fluidic connector that are configured to transfer exudate in addition to air, the fluidic connector may be provided with a secondary air leak channel configured to provide a flow of ambient air to the wound site. Preferably, the secondary air leak channel is provided with a filter to prevent contamination of the wound.

Turning now to FIG. 23B, this figure shows an embodiment similar to FIG. 23A, but where the fluidic connector 2420 may appear colored, for example as a result of an obscuring layer similar to that previously described. In some embodiments, obscuring coloration may be provided by dyeing the material used in the fluidic connector 2420, for example the 3D fabric that may be used therein. In some embodiments, the obscuring layer may be placed above the 3D fabric, either above or below the fluid-impermeable material. In some embodiments, the encapsulating fluid-impermeable material may be colored or tinted. Coloring the fluidic connector 2420 (e.g., via the obscuring layer) may enhance the aesthetic appeal of the device, help in disguising or making the device less obtrusive (in particular when the fluidic connector is visible to others), and, when the fluidic connector is used to transfer exudates away from the wound, may hide the presence of the exudates therein.

In some embodiments, the fluidic connector body may be colored as a result of an auxiliary compound such as activated charcoal. Further, some embodiments may provide for text or images to be printed thereon, for example for instructional or advertising purposes. Such improvements may enhance patient comfort and minimize embarrassment, thereby increasing patient compliance and satisfaction with the device. The obscuring layer in the fluidic connector can have all features described with reference to the obscuring layer of the wound dressing as herein described.

FIG. 17 illustrates an embodiment of a wound dressing 720 that comprises a hexagonal backing layer and a three-lobed configuration for the absorbent material and the obscuring layer. This wound dressing 720, as with several other embodiments described herein, may be advantageously applied to wounds or areas surrounding wounds that are located in non-planar areas. The embodiment illustrated here may be particularly advantageous when applied to protruding body portions, for example elbows and heels.

FIG. 18 illustrates a wound dressing 730 with a three-lobed configuration similar in some respects to the embodiment illustrated in FIG. 17. Here, however, the dressing is smaller and comprises more rounded projections. FIGS. 16-18 illustrate a fluidic connector 721, 731 similar to those described in FIGS. 23A and 23B attached to the device, with the flat end aligned with the edge of the absorbent material and the convex end extending over an aperture in the backing layer. This fluidic connector may enhance comfort and prevent pressure ulcers or other complications that may result from extended pressure of a conventional tube onto the wound or skin surrounding the wound (as described above). Of course, different connectors may be used, such as the domed port illustrated in FIG. 1.

Figure 20:
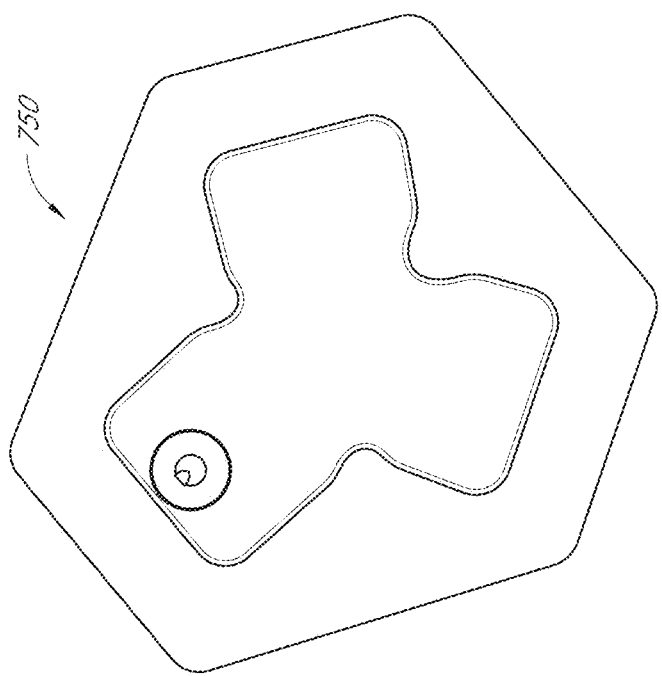
FIG. 20 illustrates a top view of an embodiment of a three-lobe wound dressing with flared ends on each lobe.
Figure 19:
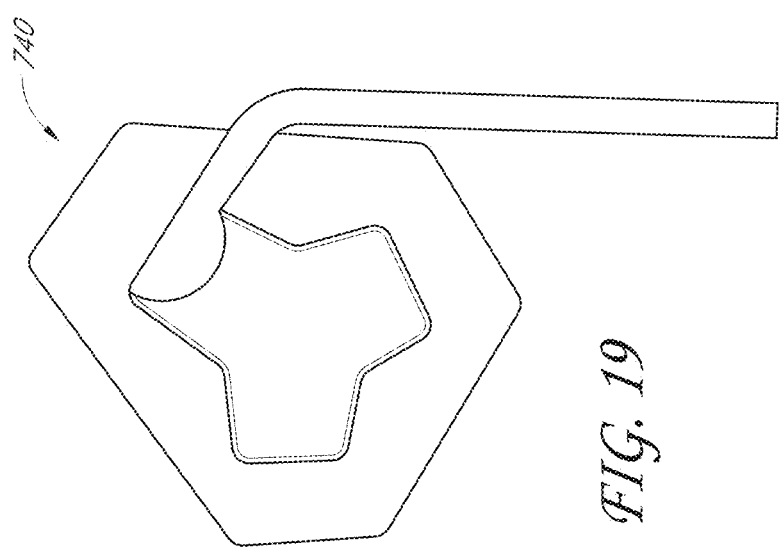
FIG. 19 illustrates a top view of an embodiment of a three-lobe wound dressing.

FIGS. 19-20 also illustrate additional embodiments of wound dressings 740, 750 with three-lobed configurations for the absorbent material and a hexagonal backing layer. The wound dressing 750 illustrated in FIG. 20 is larger where the lobes of the absorbent material comprises flared ends, while the wound dressing 740 illustrated in FIG. 19 is smaller and the absorbent material does not have flared ends. All suitable fluidic connectors or conduits may be used, and the domed port connector of FIG. 20 may be used in place of the fluidic connector of FIG. 19, and vice versa. As with the preceding embodiments, the absorbent layers may be colored or obscured, and one or more slits may be formed onto the absorbent layers to enhance conformability to non-planar surfaces. It will be appreciated that in the embodiments of FIGS. 17-20, the number of lobes may be varied, and the backing layer can have other shapes, and is not limited to being hexagonal.

Figure 21A:
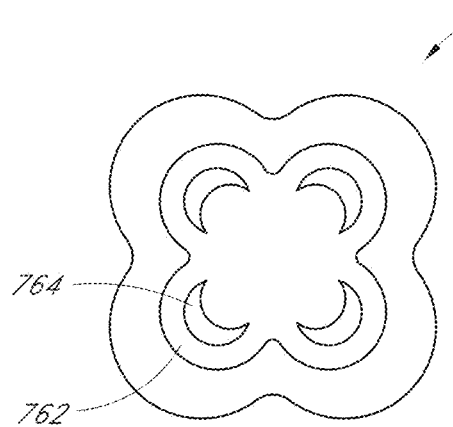
FIG. 21A illustrates a top view of an embodiment of a four-lobe wound dressing with crescent shaped cut-outs as viewing windows.
Figure 21B:
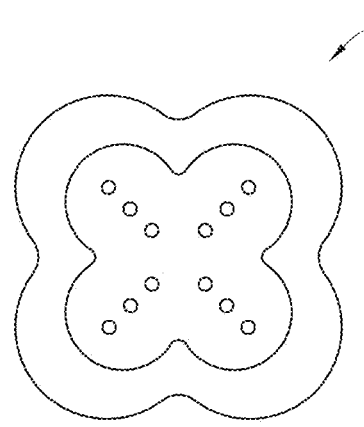
FIG. 21B illustrates a top view of an embodiment of a four-lobe wound dressing with an array of dots at viewing windows.
Figure 21C:
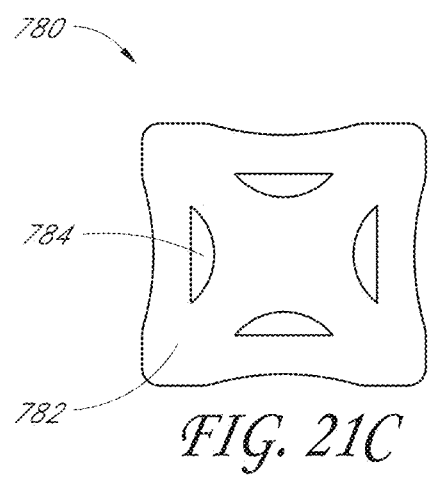
FIG. 21C illustrates a top view of an embodiment of a four-lobe wound dressing with viewing windows.

Additionally, FIGS. 21A-C and 22 illustrate embodiments of a wound dressing 760, 770, 780, 790 that comprises a four-lobed configuration. Although these embodiments are illustrated without a port or fluidic connector attached thereto, it will of course be understood that such ports and fluidic connectors are envisioned and may be attached in a similar fashion as described previously herein. FIGS. 21A-C comprise embodiments of a four-lobed wound dressing comprising an obscuring layer and viewing windows extending through the obscuring layer. The viewing windows can be used as discussed above for visualization of wound exudate in the absorbent layer. Examples of such viewing windows are illustrated in FIGS. 21A and 21B. The dressing 760 shown in FIG. 21A includes an obscuring layer 762 and crescent-shaped viewing windows 764 provided in the obscuring layer to extend through the obscuring layer allowing visibility of the dressing therebelow. The dressing 770 of FIG. 21B includes an obscuring layer 772 and a number of holes 774 therethrough acting as viewing windows for viewing the state of the dressing therebelow. FIG. 21C shows another dressing 780 including an obscuring layer 782 with viewing windows 784. With the dressings 760, 770, 780 the progress of exudate spread over the dressing and towards the edge of the dressing can be monitored.

Figure 22:
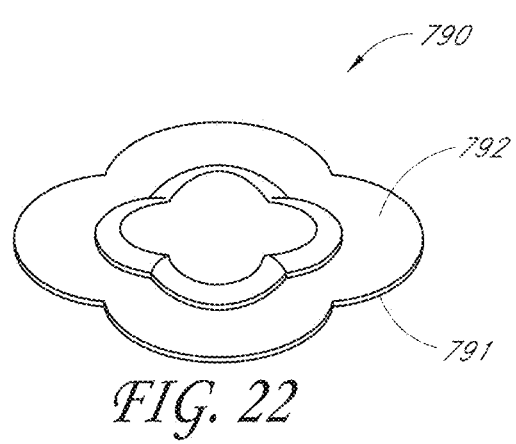
FIG. 22 illustrates a perspective view of an embodiment of a four-lobe wound dressing.

FIG. 22 illustrates a perspective view of an embodiment of a wound dressing 790 according to an embodiment of the four-lobe configuration. FIG. 22 shows a possible four-lobe configuration of a dressing, useful for enhanced compatibility with body movement, where each layer is shaped to reduce the incident angle of the pad edge, and to provide somewhat independently moving sub-sections of the dressing. The dressing border, including the wound contact layer 791 and the backing layer 792 can also comprise slits, provided to further enhance the conformability on application by allowing the borders to overlap if needed. The wound dressing with a four-lobe configuration, as well as other configurations, are described in detail in International Application PCT/GB2012/000587, titled "WOUND DRESSING AND METHOD OF TREATMENT" and filed on Jul. 12, 2012. which is incorporated by reference herein.

Additionally, FIGS. 24A-F illustrate an embodiment of a wound dressing 2300 with an oval shaped absorbent layer 2308 having multiple lobes 2301. FIGS. 24A-F illustrate, respectively, perspective, top, bottom, left, right, and side views of an embodiment of the dressing 2300. In some embodiments, the absorbent layer 2308 can have six lobes. Preferably, two or more lobes 2301 (e.g., six lobes) are provided on the wound dressing 2300; the lobes 2301, and specifically, the gaps between the lobes 2301, aid the wound dressing 2300 in conforming to nonplanar wounds. For example, it may be advantageous to use the dressing 2300 to conform around joints such as elbows and knees.

Figure 24A:
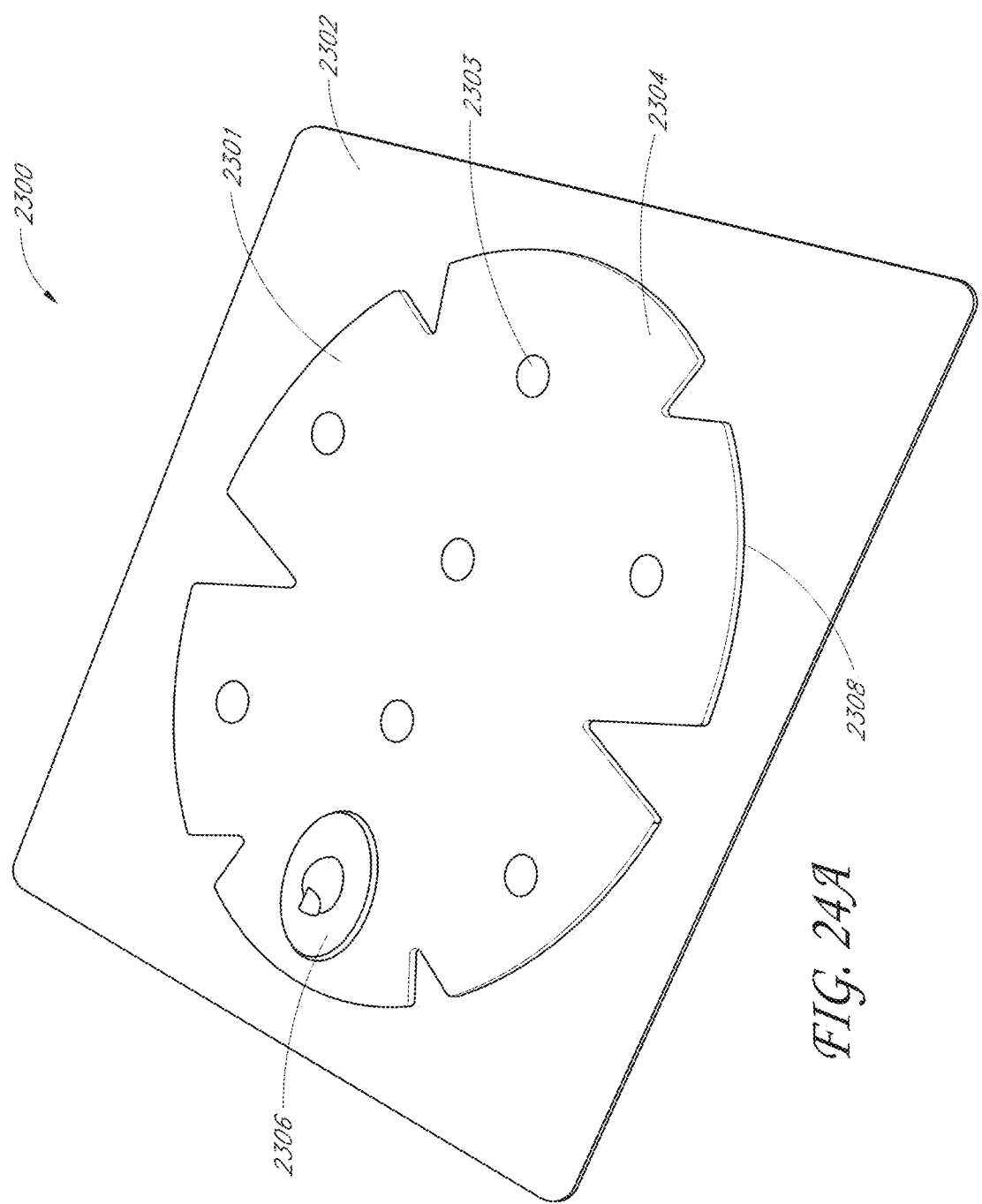
FIGS. 24A-F illustrate a perspective view, a top view, a bottom view, a front view, a back view, and a side view, respectively, of an embodiment of an oval-shaped wound dressing.
Figure 24B:
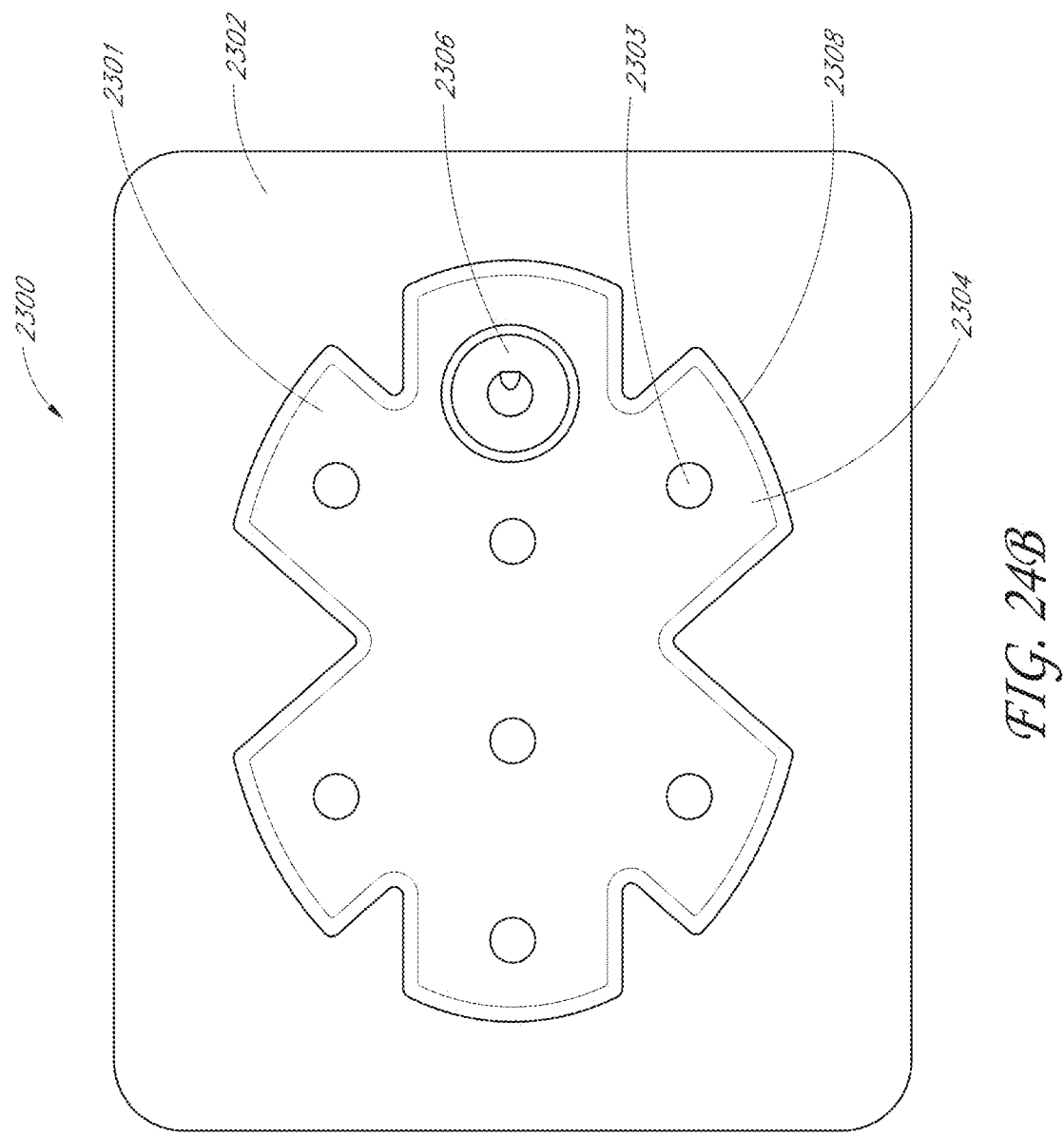
Figure 24C:
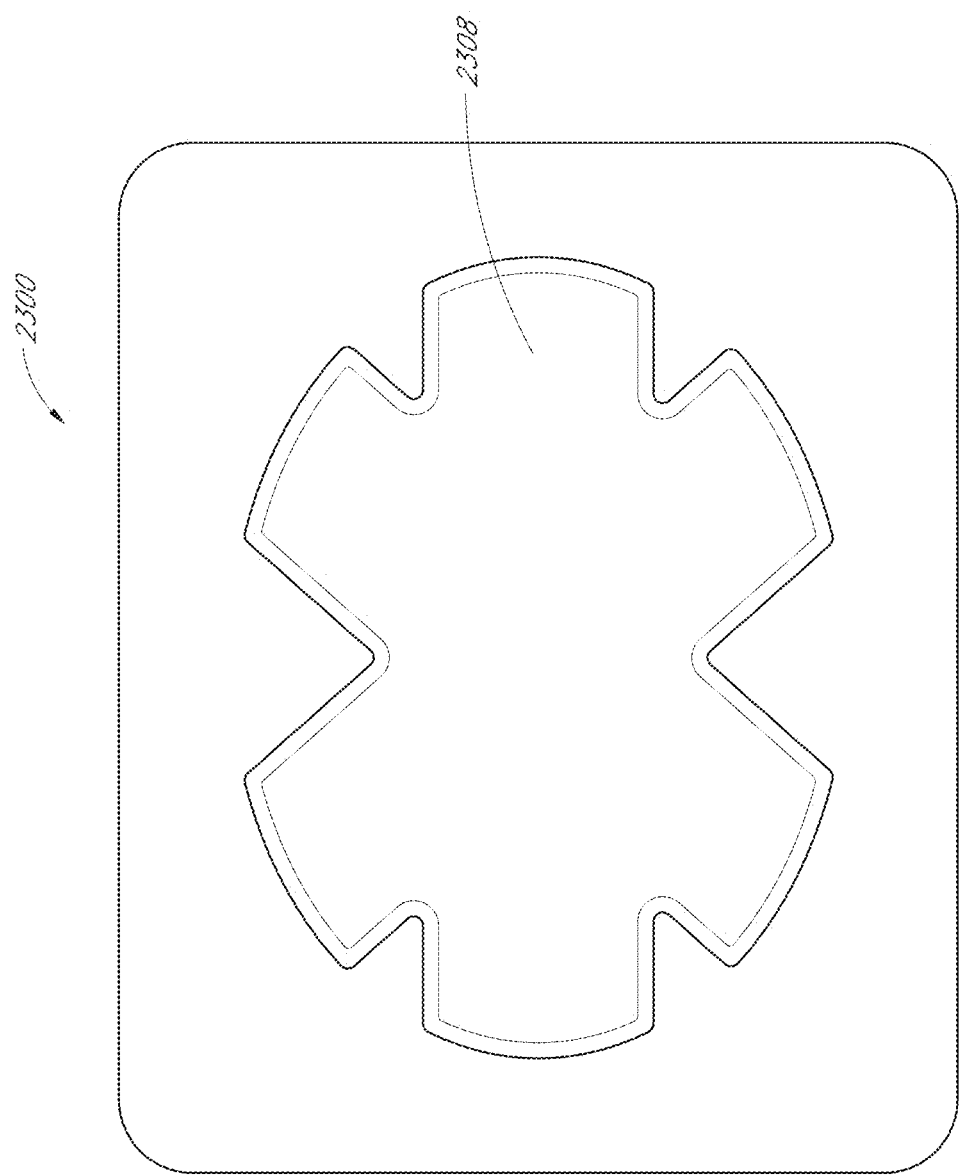
Figure 24D:
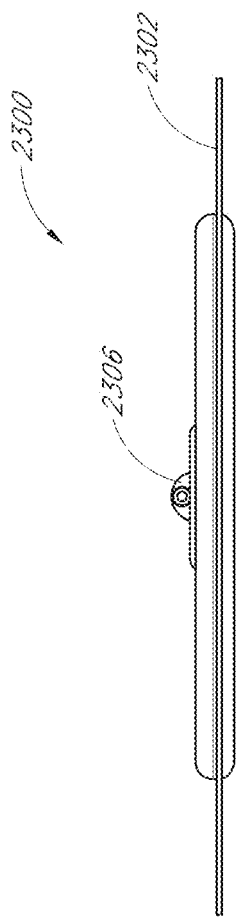
Figure 24E:
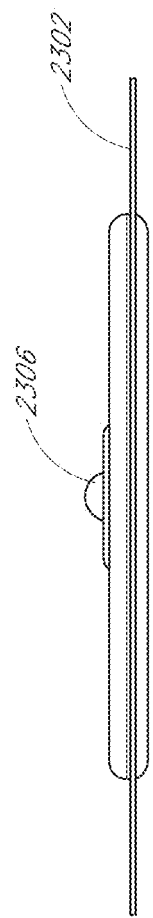
Figure 24F:
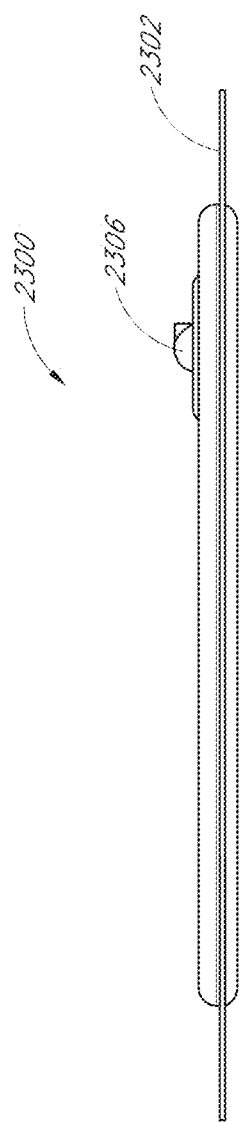

The dressing 2300 can have a rectangular or square shaped backing layer 2302, and in some embodiments, the overall dressing 2300 may measure 190 mm×230 mm, or 145.5 mm×190 mm. Preferably, a fluidic connector such as a port 2306 is attached to the dressing 2300, although it will of be recognized that the fluidic connector of FIGS. 23A-B may be used instead or in addition. Additionally, in some embodiments, the dressing 2300 can have an obscuring layer 2304 with a similar perimeter shape as the absorbent layer and one or more viewing windows 2303 similar to that described for other embodiments herein. FIG. 24A illustrates a perspective view of the dressing 2300, while FIG. 24B illustrates a top view, 24C a bottom view, and 24D-F represent views of the four sides of the dressing 2300.

Figure 24G:
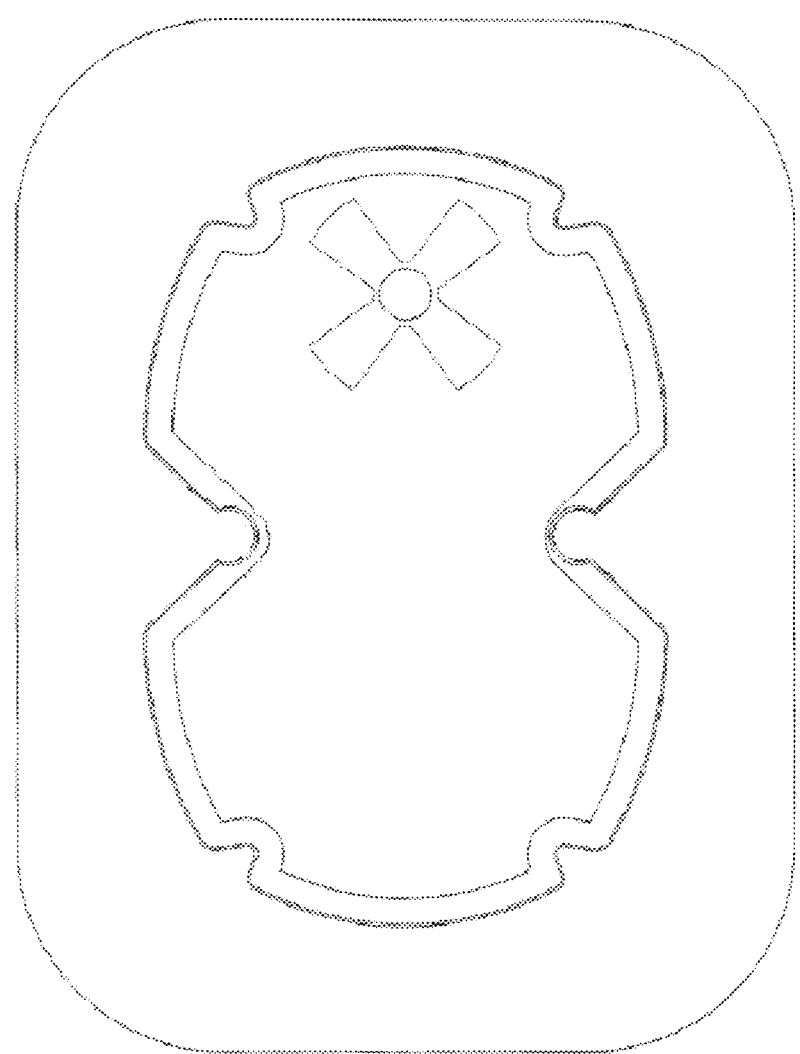
FIG. 24G illustrates a top view of an alternate embodiment of the wound dressing of FIGS. 24A-F.

FIG. 24G illustrates a top view of an alternate embodiment of the wound dressing of FIGS. 24A-F. The dressing may have circular cutouts in a central waisted portion, which may be located along a midline of the dressing transverse to a longitudinal axis of the dressing. Such cutouts may be, in some embodiments, 10 mm, or approximately 10 mm, in diameter, or may be in the range of 5 mm to 25 mm, or approximately 5 mm to approximately 25 mm, in diameter. As illustrated, the circular cutouts are symmetrically arranged on opposite sides of a longitudinal midline of the dressing, and may form an arc of greater than 180 degrees, preferably between 180 and 270 (or about 180 to 270) degrees. The dressing embodiment is illustrated with a cross-shaped viewing window in the obscuring layer and a hole in the backing layer at the middle of the cross-shaped viewing window, which may be positioned so as to underlie a port sealed to the dressing. The outer perimeter of the cross-shaped viewing window may extend beyond the outer perimeter of an attached port to provide a visual indication of the level of saturation of the absorbent layer underlying the port. Though illustrated without additional viewing windows, the obscuring layer in the dressing may be provided with one or more additional viewing windows, for example in a 1×3 array, a 2×3 array, or any other configuration suitable for providing a visual indication of the spread of exudate through the absorbent layer of the dressing.

Figure 25A:
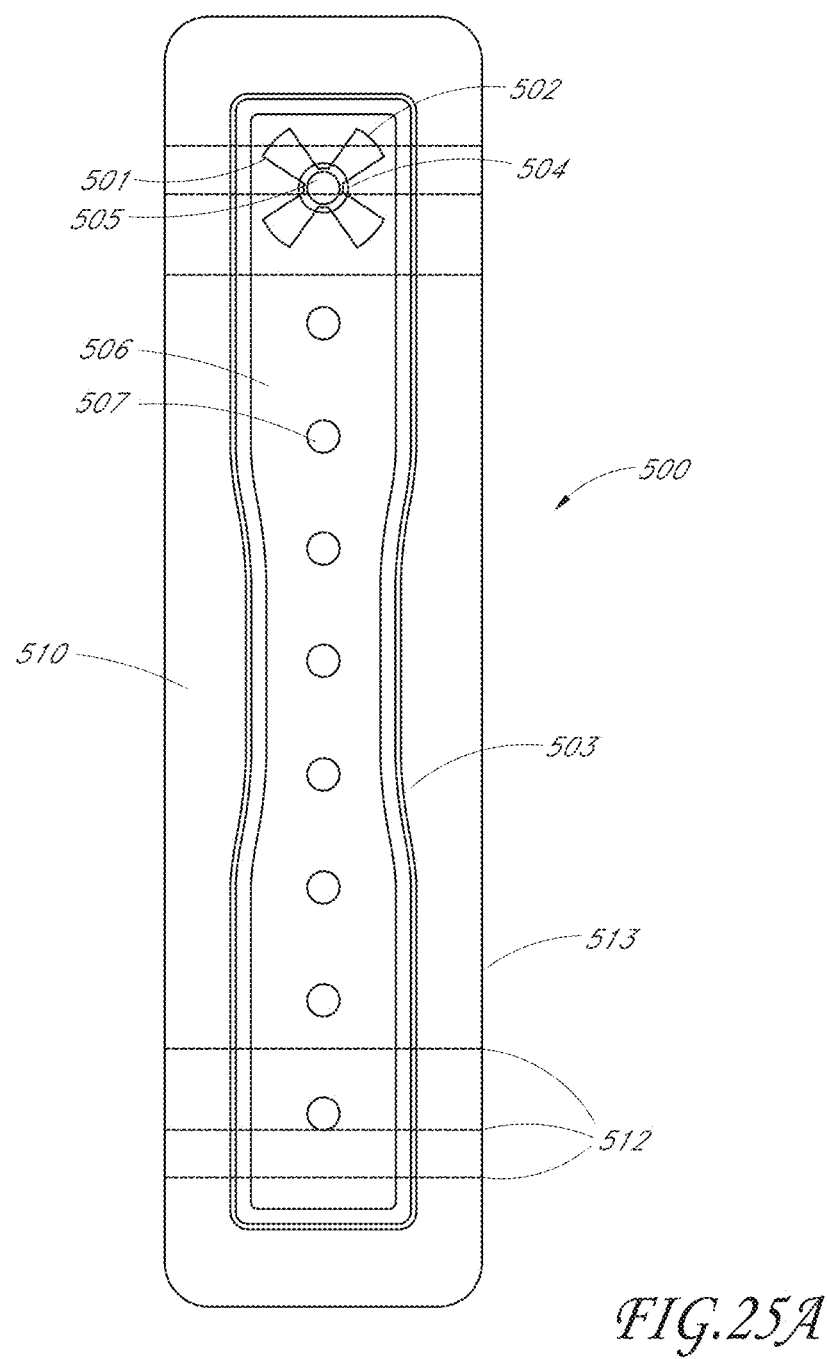
FIGS. 25A-32B illustrate embodiments of a wound dressing including an obscuring layer and viewing windows including an orifice viewing window.
Figure 25B:
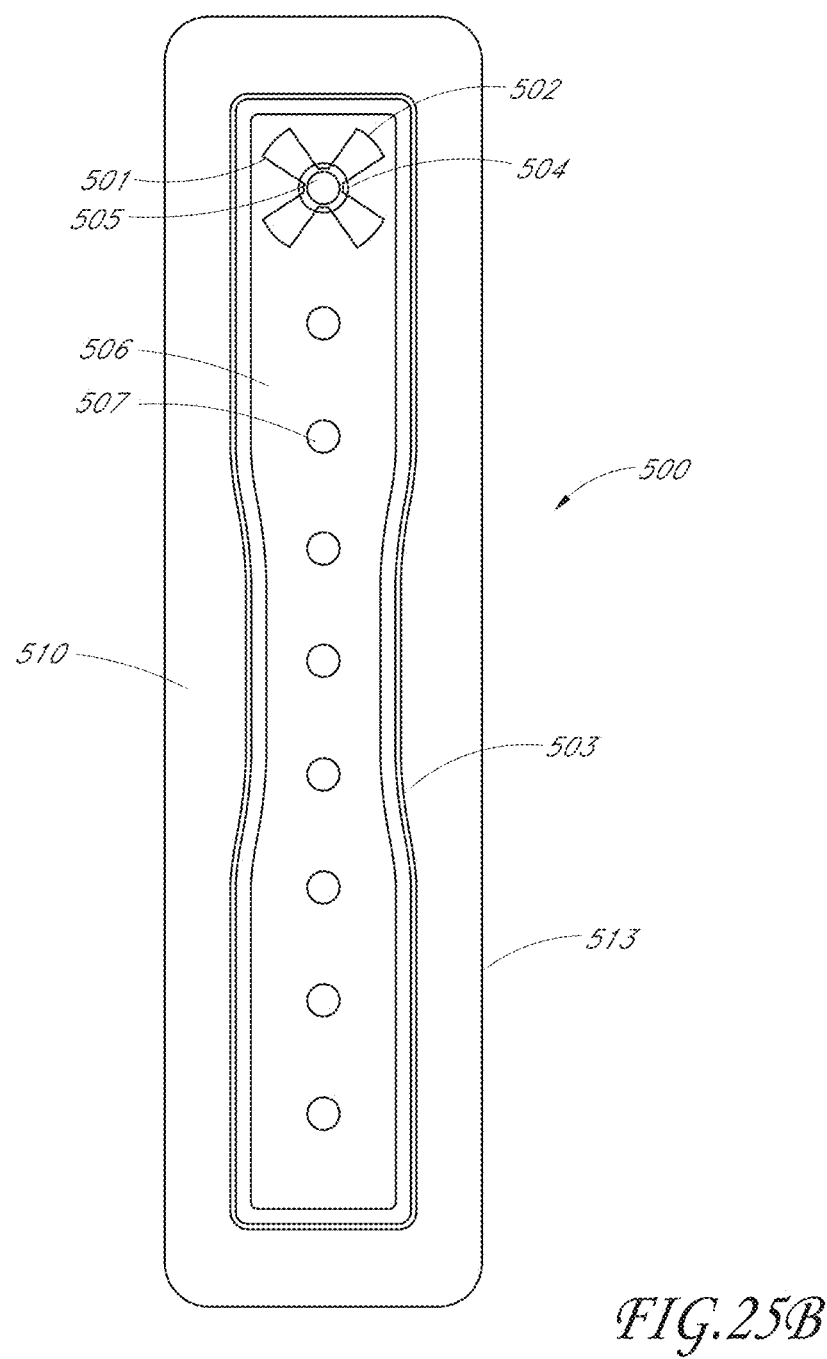

FIGS. 25A-B illustrate an embodiment similar in shape and overall configuration to the embodiments illustrated above in FIGS. 7A-F. Here, however, the dressing 500 comprises an orifice viewing window 502 similar to that described in relation to FIGS. 13A-B and 14. The orifice viewing window 502 is preferably formed from a cross-shaped or Maltese-cross shaped aperture or cutout 501 in the obscuring layer 506. The backing layer 510 provided over the obscuring layer preferably has an orifice 504 located at the center of the orifice viewing window 502. Reference number 504 can also be considered to designate a port that may be provided in or over the backing layer 510 to provide a connection to a source of negative pressure, for example, a port provided over the orifice in the backing layer as described above. A smaller orifice 505 may be located in the absorbent layer 503 that is provided below the obscuring layer 506. The dressing 500 may comprise one or more viewing windows 507; here, eight viewing windows 507 are provided in a linear arrangement. The bottom side of the dressing 500 optionally comprises a layer of adhesive, over which a release layer 513 may be placed. Dashed lines 512 illustrated in FIG. 25A illustrate possible locations where breaks in the release liner 513 may be provided.

In a preferred embodiment, the dressing 500 illustrated here has a longitudinal length of approximately 400 mm, and a transverse width of approximately 100 mm. The central axis of each arm of the cutout 501 of the orifice viewing window 502 is preferably offset from the longitudinal length and transverse width of the absorbent material, at an angle, for example, a 45° angle, as illustrated. The spacing between each arm of the cutout 501 may be, as illustrated here, 72°, although it will of course be recognized that other angles and configurations are possible. Dashed lines 512 illustrated in FIG. 25A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on the transverse midline of the dressing 500, and situated approximately 52-55 mm from the top edge of the dressing 500. Although the location may be changed, it may be preferable to locate the port 504 near or along a side, edge, or corner of the dressing 500, which is then preferably elevated with respect to the remainder of the dressing. This configuration may extend the life of the dressing, as fluid would be slower in saturating the absorbent layer below or near the orifice or port 504.

Figure 26A:
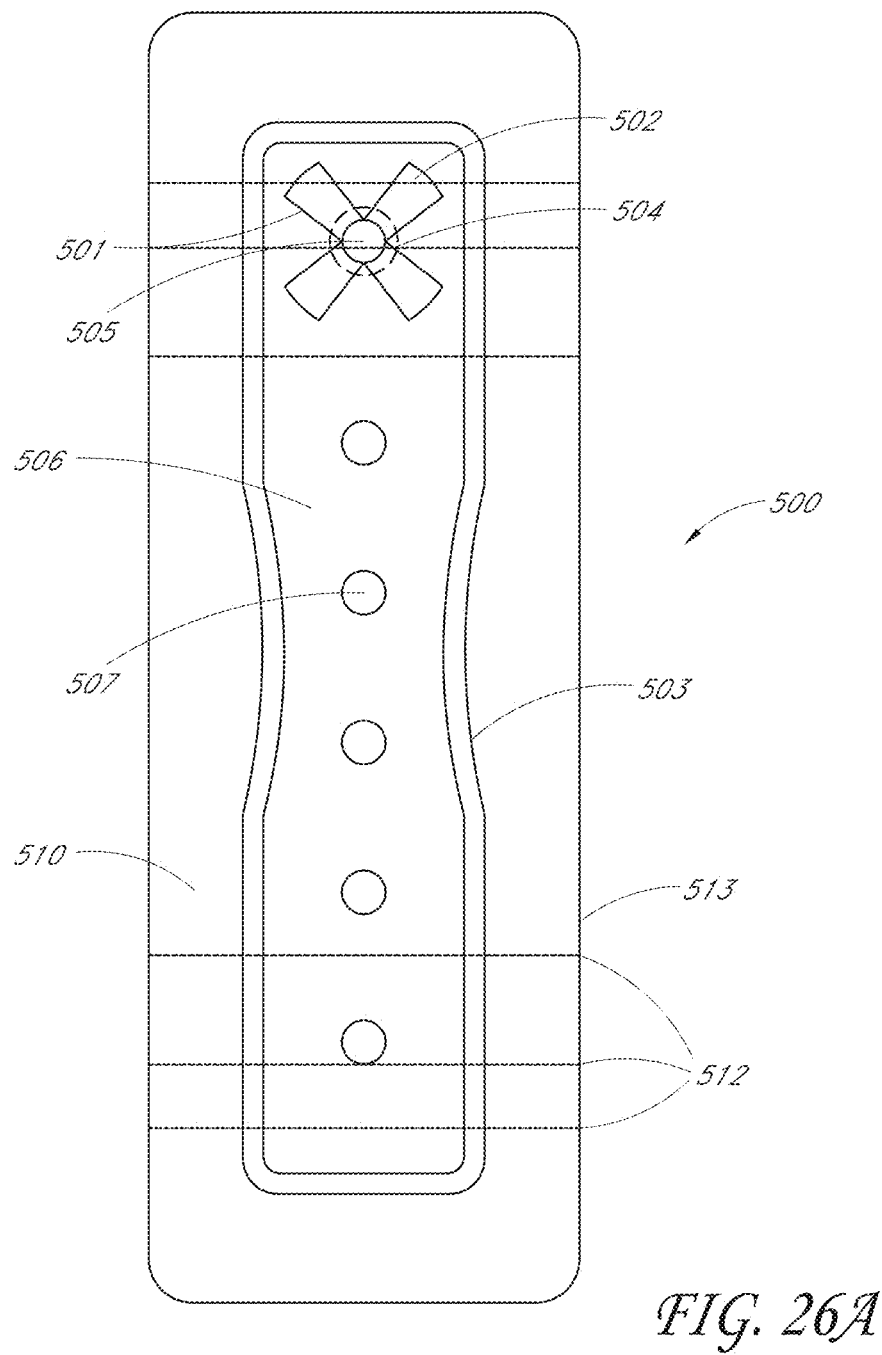
Figure 26B:
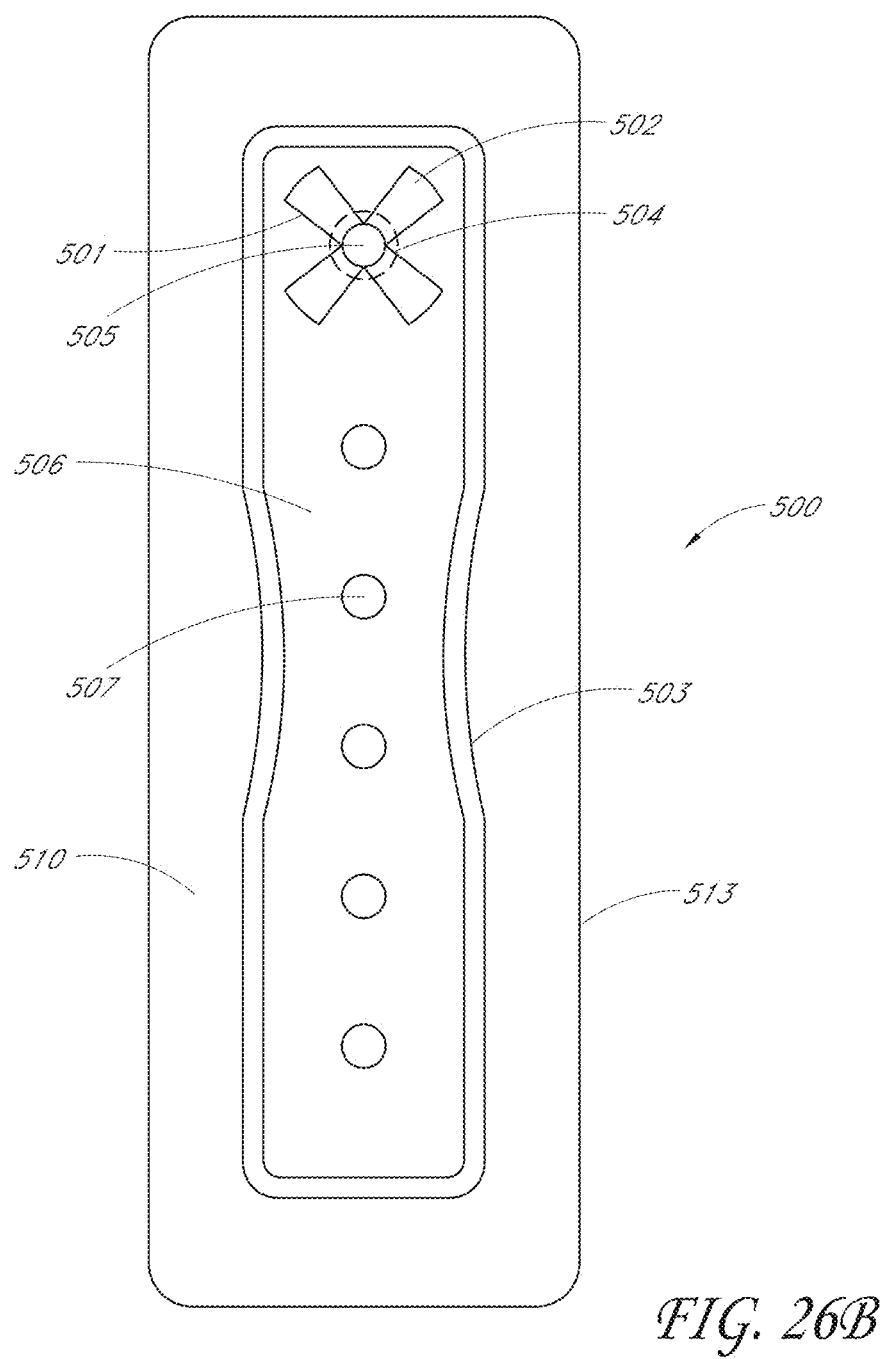

FIGS. 26A-B illustrate an embodiment similar in shape and overall configuration to the embodiments illustrated above in FIGS. 8A-F. Here, however, the dressing 500 comprises an orifice viewing window 502 and cutout 501, with for example five linearly arranged viewing windows 507, among other parts, that are similar to that described above in relation to FIGS. 25A-B. In a preferred embodiment, the dressing 500 illustrated here has a longitudinal length of approximately 300 mm, and a transverse width of approximately 100 mm. The spacing between each arm of the cutout 501 may be, as illustrated here, 72°, although it will of course be recognized that other angles and configurations are possible. Dashed lines 512 illustrated in FIG. 26A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on the transverse midline of the dressing 500, and situated approximately 52-55 mm from the top edge of the dressing 500.

Figure 27A:
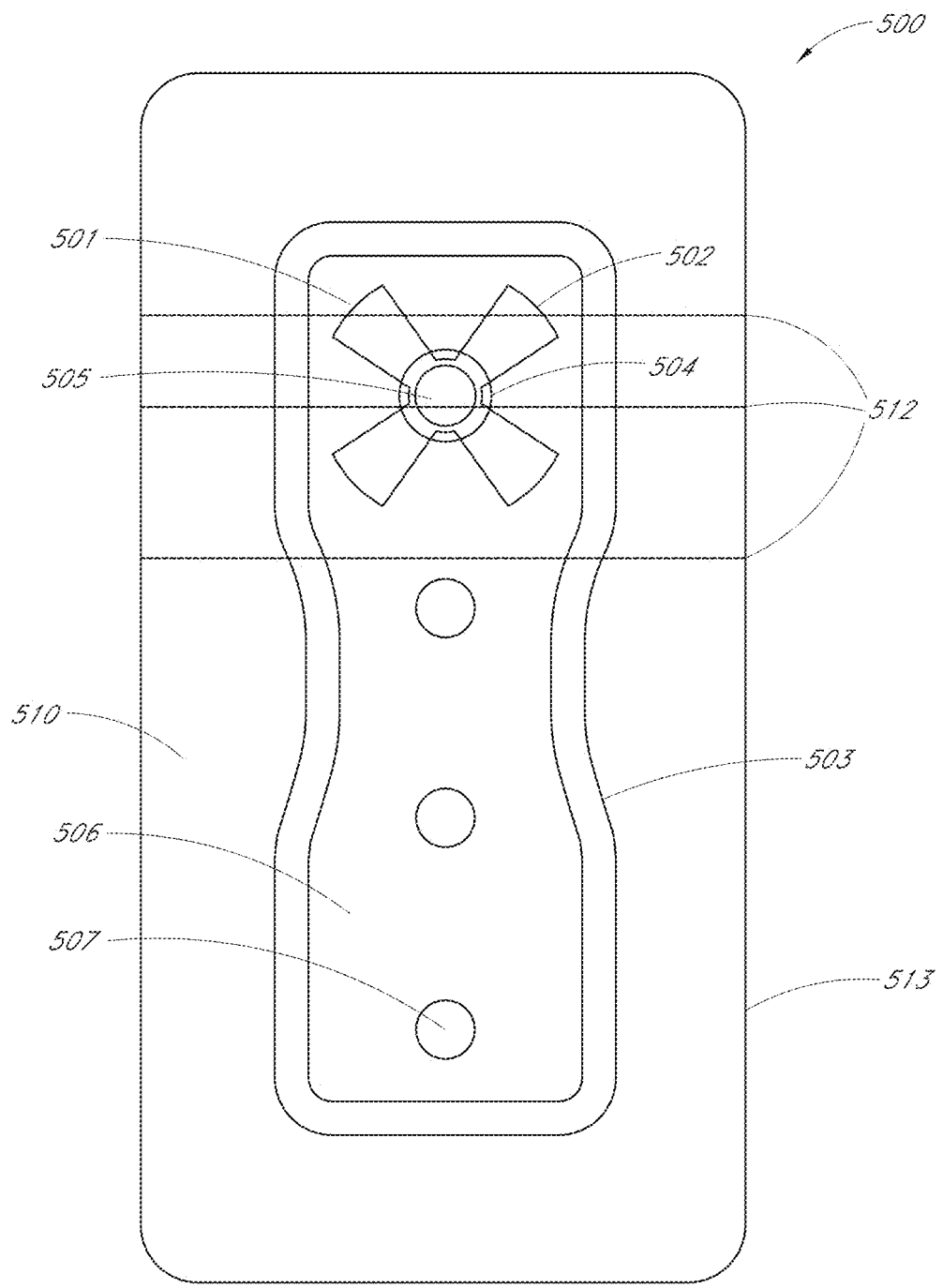
Figure 27B:
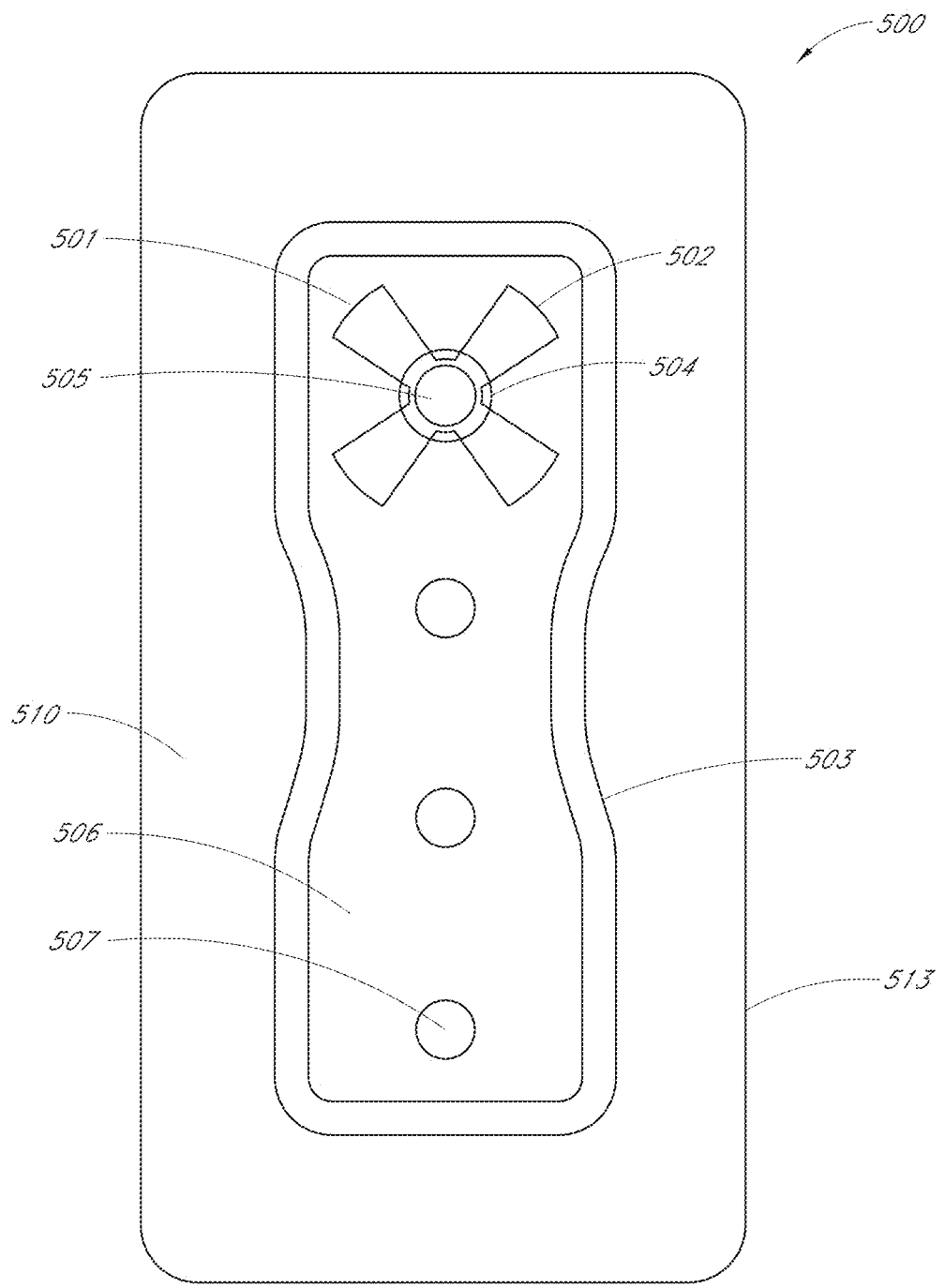

FIGS. 27A-B illustrate an embodiment similar in shape and overall configuration to the embodiments illustrated above in FIGS. 9A-F. Here, however, the dressing 500 comprises an orifice viewing window 502 and cutout 501, with for example three linearly arranged viewing windows 507, among other parts, that are similar to that described above in relation to FIGS. 25A-B. In a preferred embodiment, the dressing 500 illustrated here has a longitudinal length of approximately 200 mm, and a transverse width of approximately 100 mm. The spacing between each arm of the cutout 501 may be, as illustrated here, 72°, although it will of course be recognized that other angles and configurations are possible. Dashed lines 512 illustrated in FIG. 27A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on the transverse midline of the dressing 500, and situated approximately 52-55 mm from the top edge of the dressing 500.

Figure 28A:
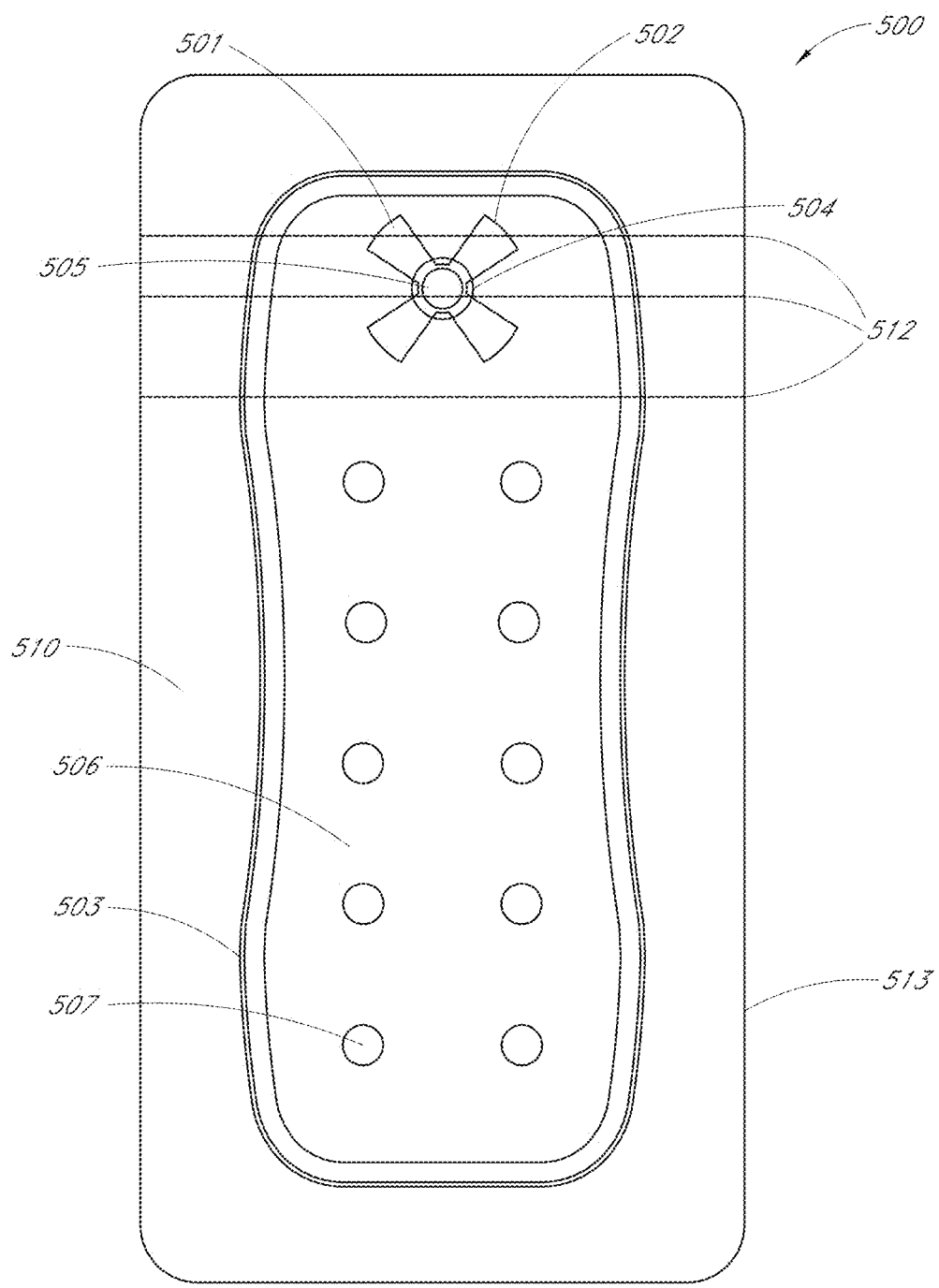
Figure 28B:
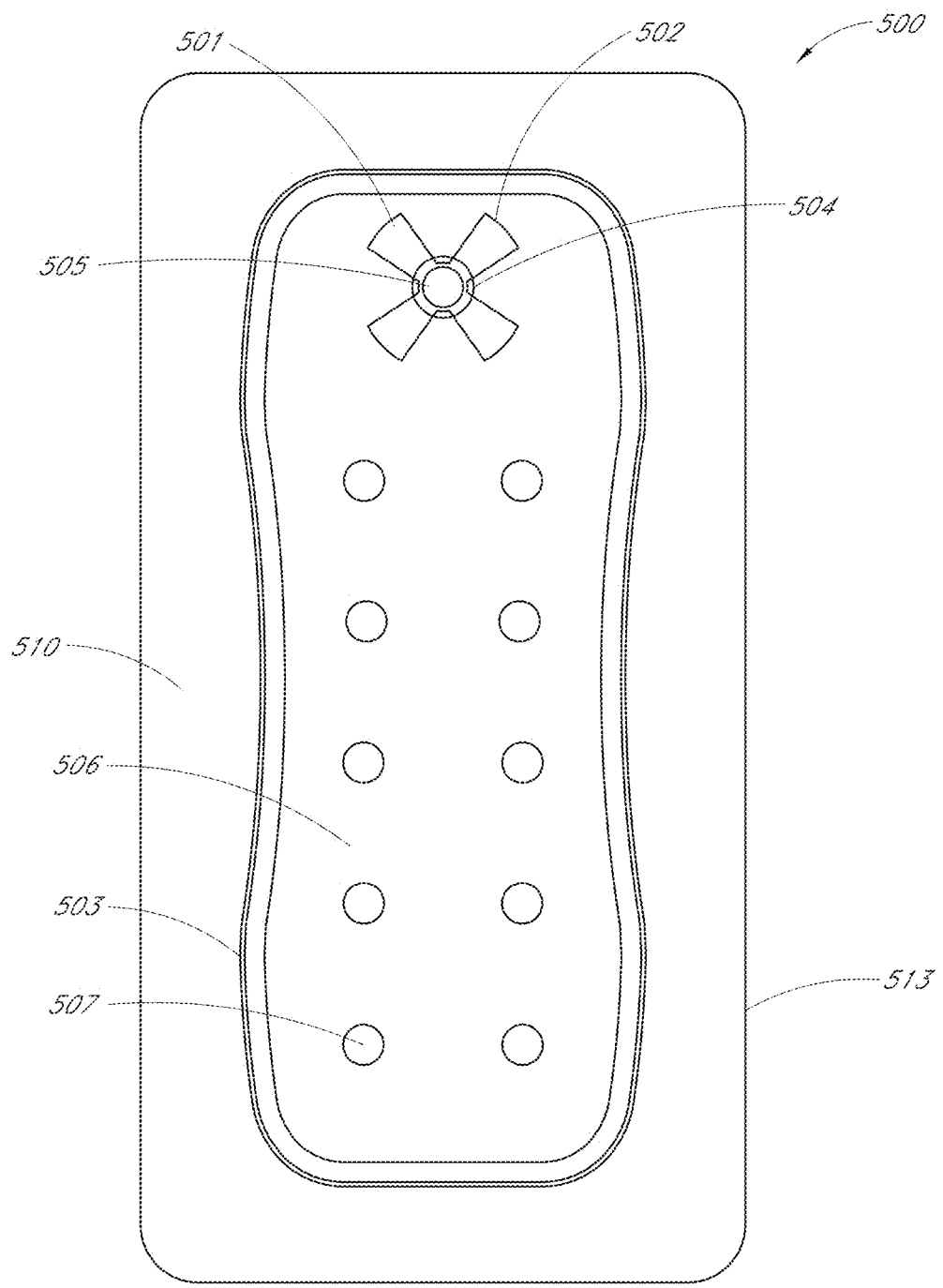

FIGS. 28A-B illustrate an embodiment similar in shape and overall configuration to the embodiments illustrated above in FIGS. 5A-F. Here, however, the dressing 500 comprises an orifice viewing window 502 and cutout 501, with for example two rows of five linearly arranged viewing windows 507, among other parts, that are similar to that described above in relation to FIGS. 25A-B. In a preferred embodiment, the dressing 500 illustrated here has a longitudinal length of approximately 300 mm, and a transverse width of approximately 150 mm. The spacing between each arm of the cutout 501 may be, as illustrated here, 72°, although it will of course be recognized that other angles and configurations are possible. Dashed lines 512 illustrated in FIG. 28A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on the transverse midline of the dressing 500, and situated approximately 52-55 mm from the top edge of the dressing 500.

Figure 29A:
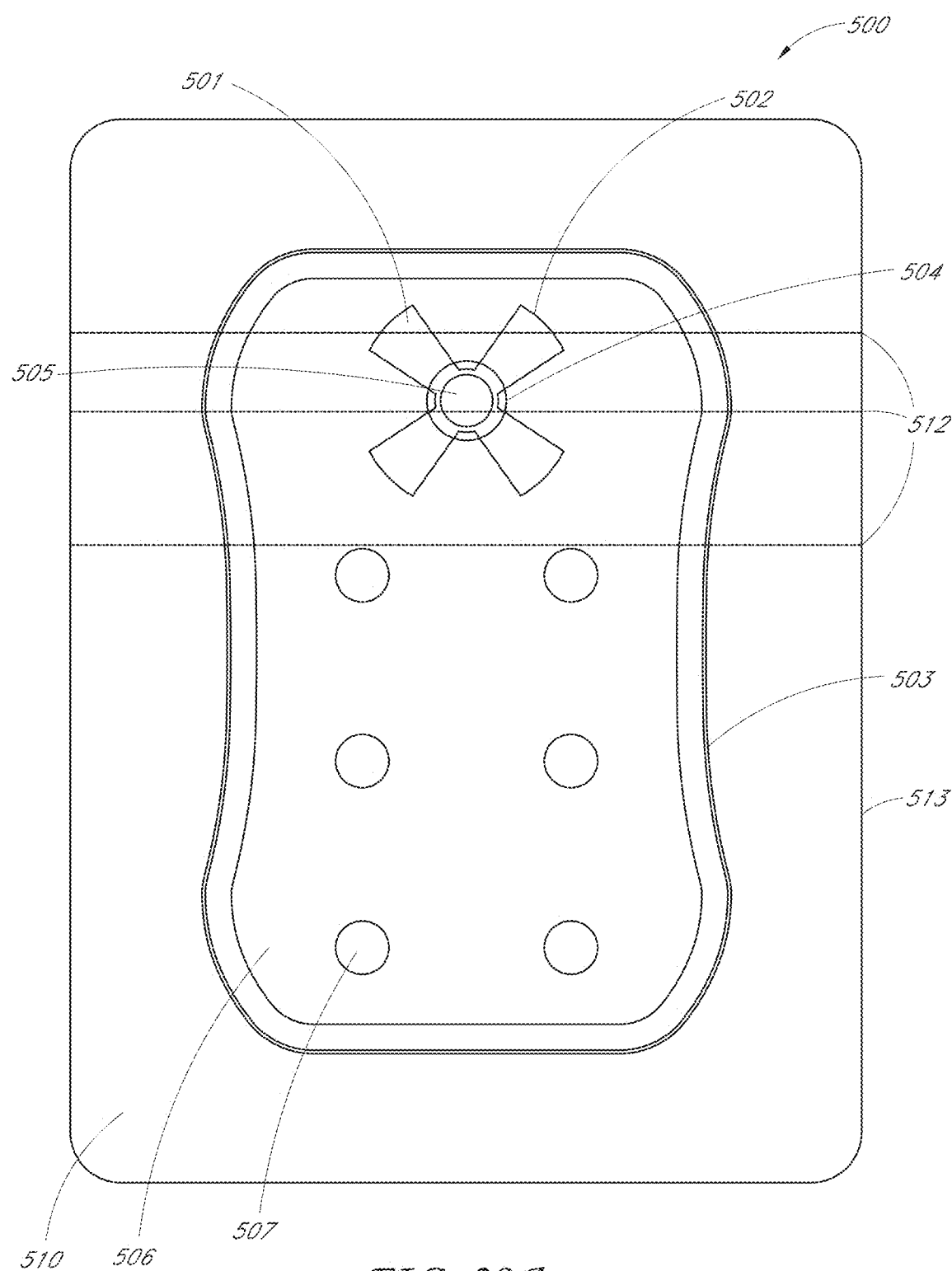
Figure 29B:
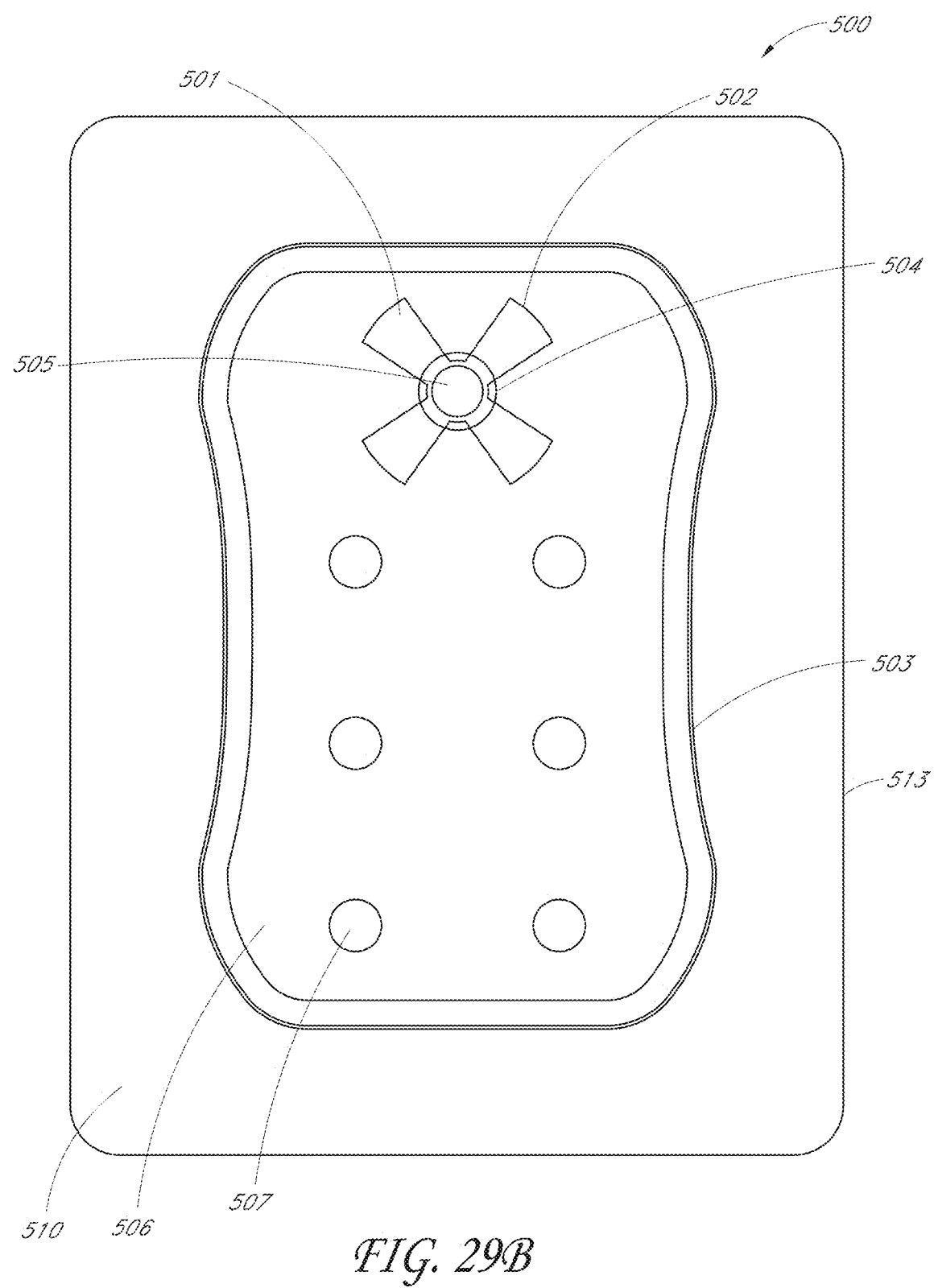

FIGS. 29A-B illustrate an embodiment similar in shape and overall configuration to the embodiments illustrated above in FIGS. 6A-F. Here, however, the dressing 500 comprises an orifice viewing window 502 and cutout 501, with for example two rows of three linearly arranged viewing windows 507, among other parts, that are similar to that described above in relation to FIGS. 25A-B. In a preferred embodiment, the dressing 500 illustrated here has a longitudinal length of approximately 300 mm, and a transverse width of approximately 100 mm. The spacing between each arm of the cutout 501 may be, as illustrated here, 72°, although it will of course be recognized that other angles and configurations are possible. Dashed lines 512 illustrated in FIG. 29A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on the transverse midline of the dressing 500, and situated approximately 52-55 mm from the top edge of the dressing 500.

Figure 30A:
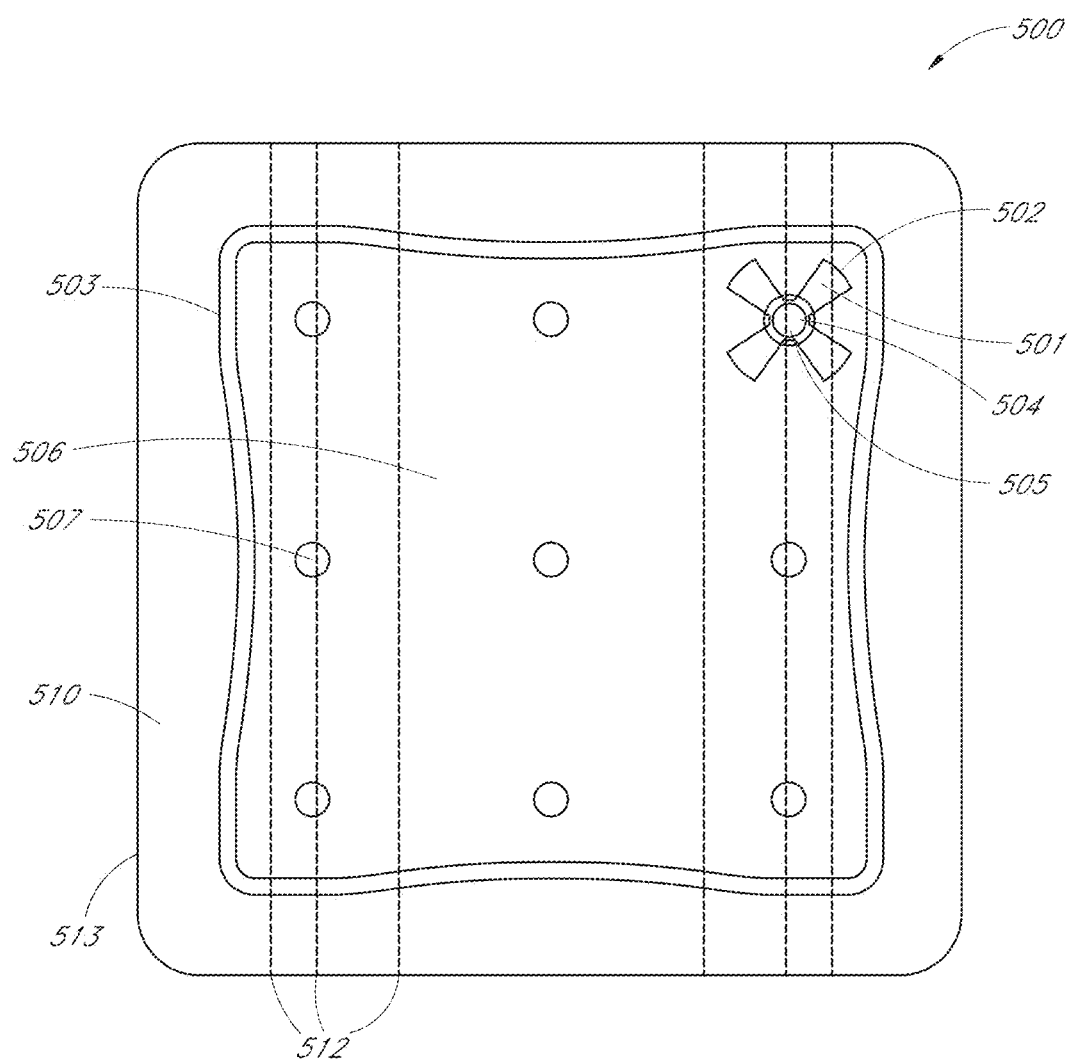
Figure 30B:
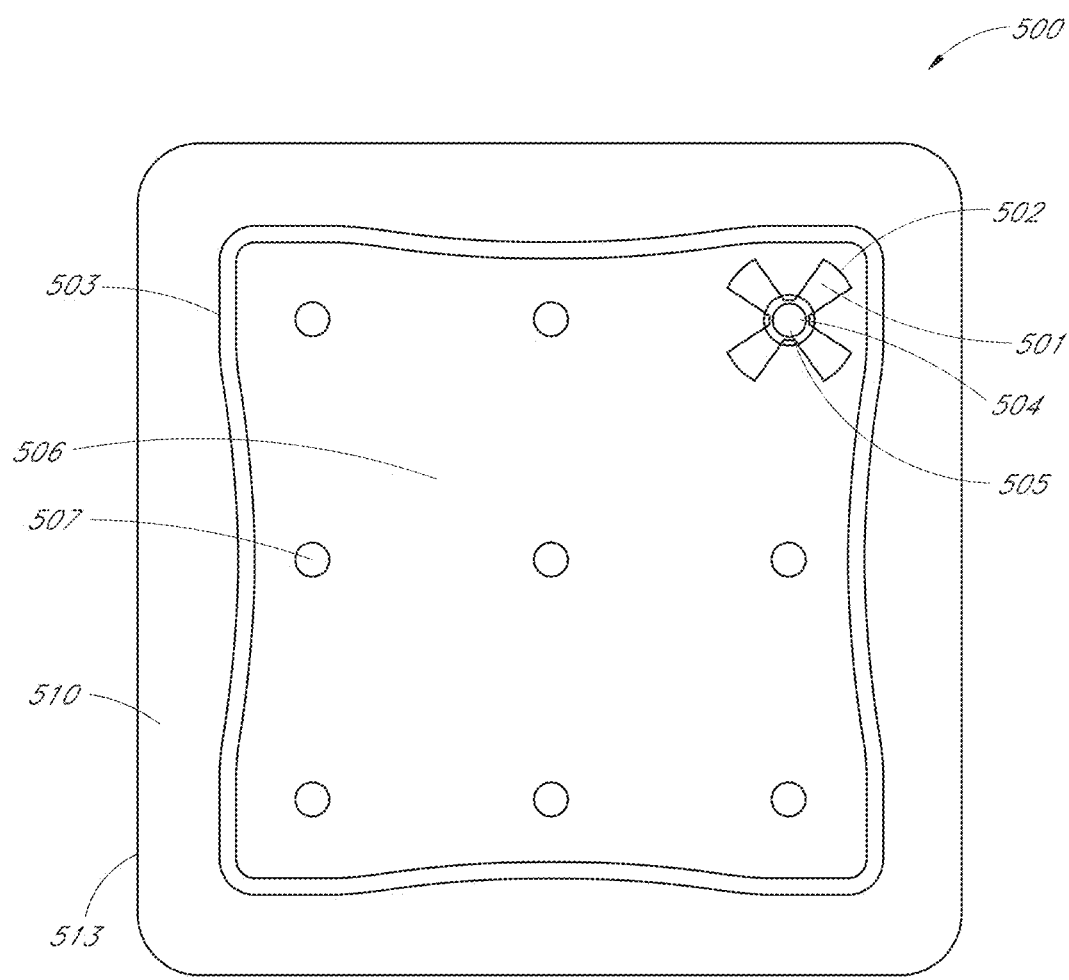

FIGS. 30A-B illustrate an embodiment similar in shape and overall configuration to the embodiments illustrated above in FIGS. 10A-F. Here, however, the dressing 500 comprises an orifice viewing window 502 and cutout 501, with a 3×3 array of viewing windows absent a viewing window at a corner position of the wound dressing, among other parts, that are similar to that described above in relation to FIGS. 25A-B but located in a corner of the dressing 500. In a preferred embodiment, the dressing 500 illustrated here is approximately square, with each side measuring approximately 250 mm. The spacing between each arm of the cutout 501 may be, as illustrated here, 72°, although it will of course be recognized that other angles and configurations are possible. Dashed lines 512 illustrated in FIG. 30A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on a corner of the dressing 500, and situated approximately 52-55 mm from the top edge of the dressing 500.

Figure 31A:
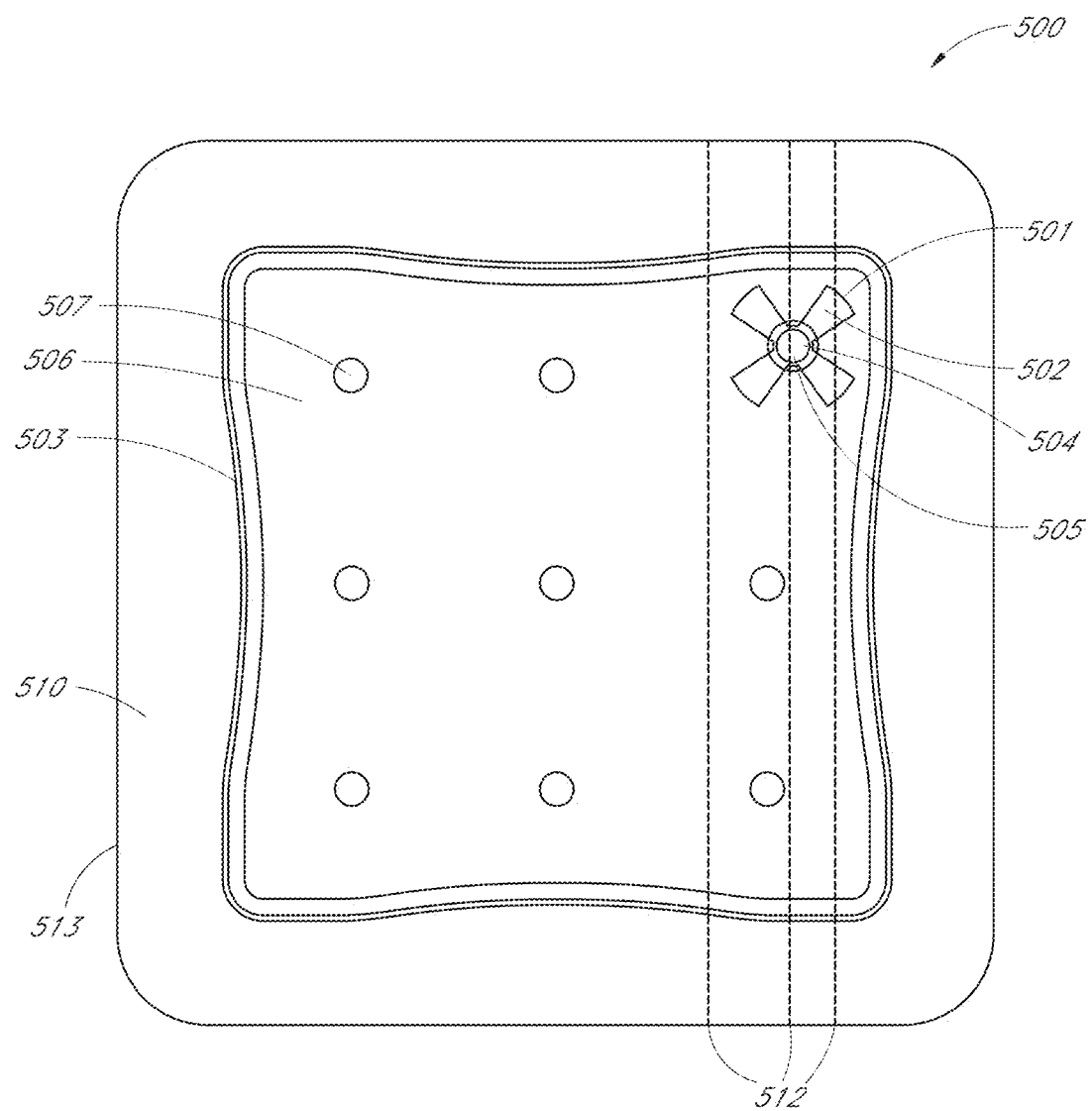
Figure 31B:
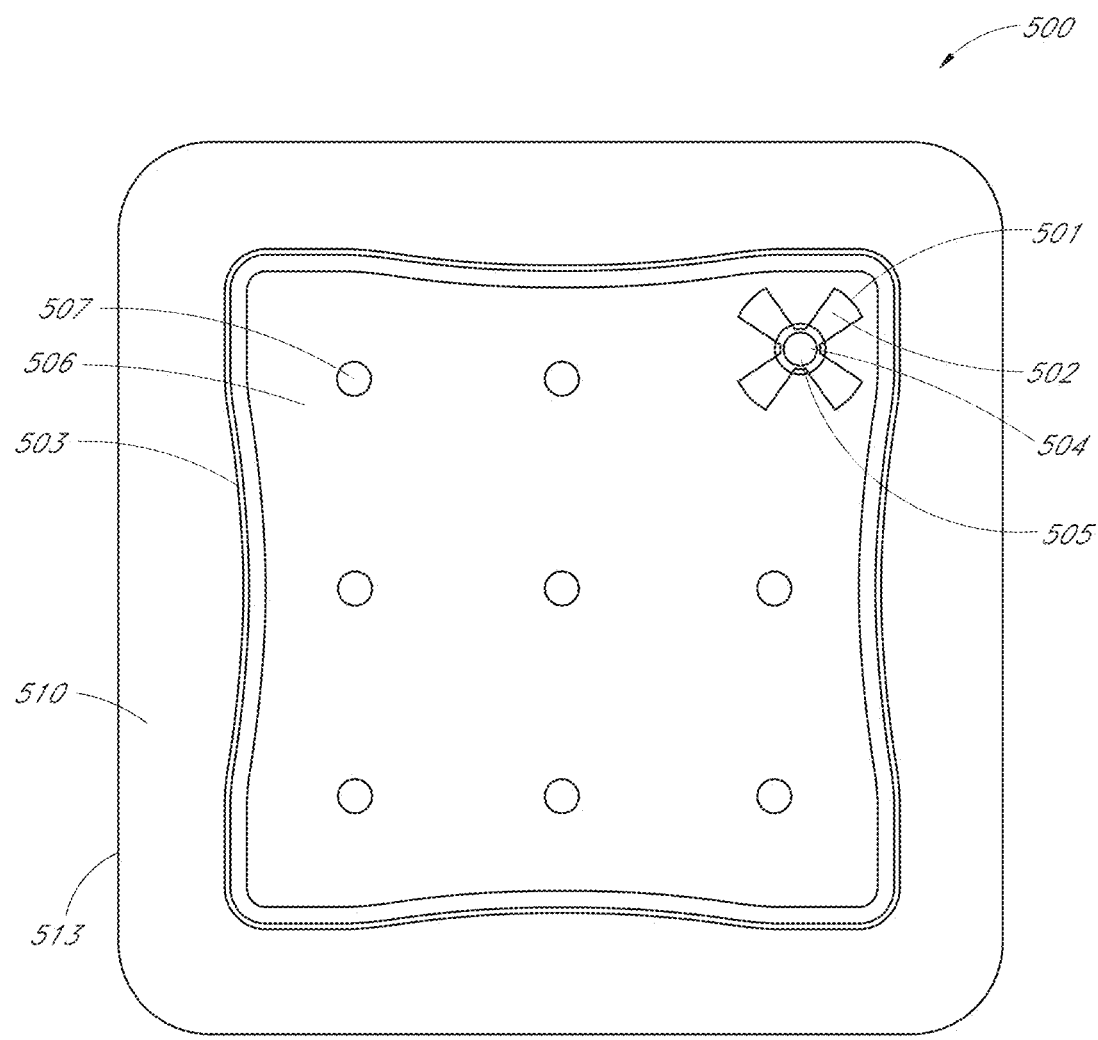

FIGS. 31A-B illustrate an embodiment similar in shape and overall configuration to the embodiments illustrated above in FIGS. 11A-F. Here, however, the dressing 500 comprises an orifice viewing window 502 and cutout 501, with a 3×3 array of viewing windows absent a viewing window at a corner position of the wound dressing, among other parts, that are similar to that described above in relation to FIGS. 25A-B but located in a corner of the dressing 500. In a preferred embodiment, the dressing 500 illustrated here is approximately square, with each side measuring approximately 200 mm. The spacing between each arm of the cutout 501 may be, as illustrated here, 72°, although it will of course be recognized that other angles and configurations are possible. Dashed lines 512 illustrated in FIG. 31A, indicating possible locations where breaks in the release liner 513 may be provided, can be located, for example, at 80 mm, 40±4 mm, and 25±4 mm from each of the top and bottom edges of the dressing 500. As illustrated, the orifice or port 504 (and cutout 501) are preferably centered on a corner of the dressing 500, and situated approximately 52-55 mm from the top edge of the dressing 500.

Figure 32A:
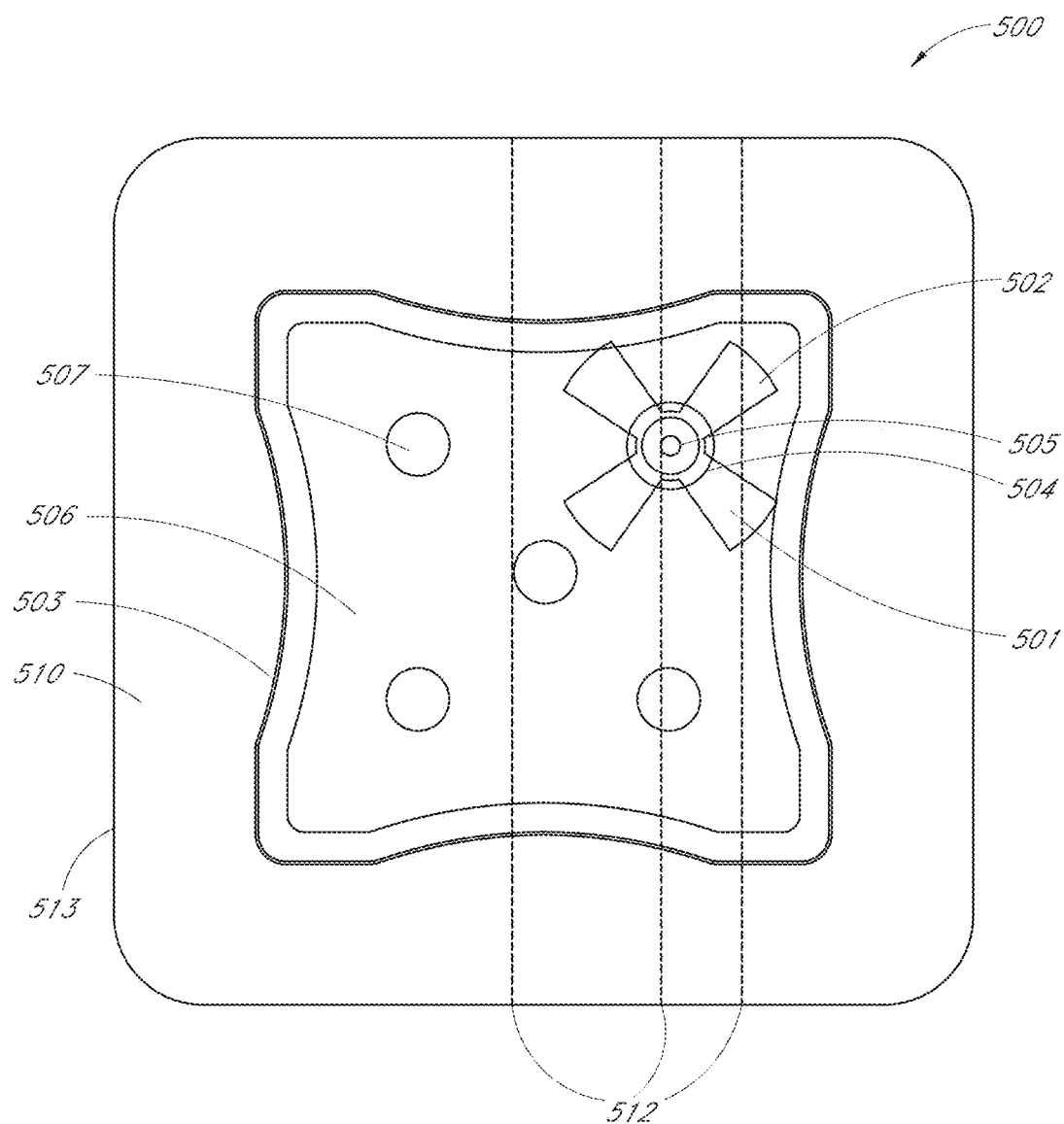
Figure 32B:
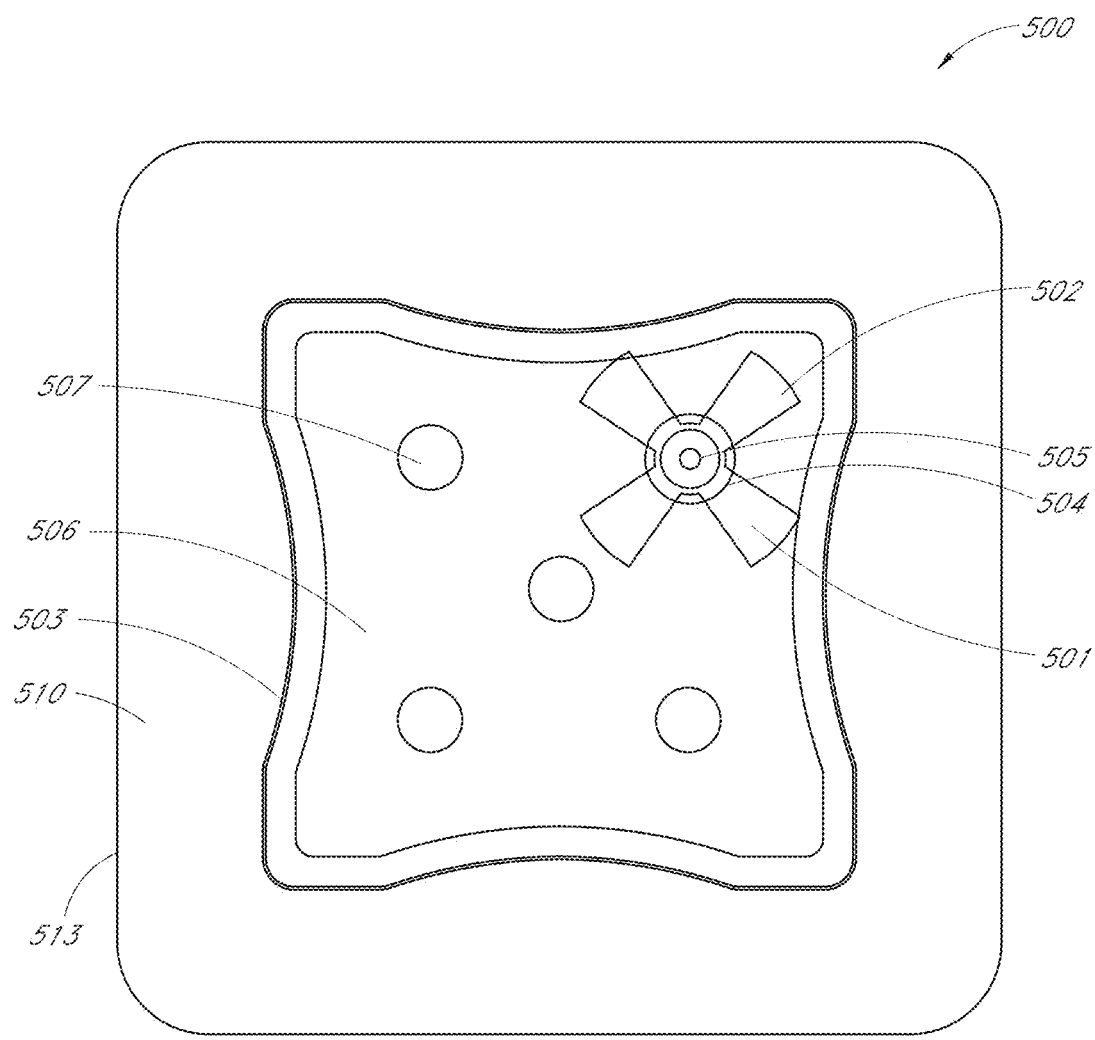

FIGS. 32A-B illustrate an embodiment similar in shape and overall configuration to the embodiments illustrated above in FIGS. 12A-F. Here, however, the dressing 500 comprises an orifice viewing window 502 and cutout 501, with a quincunx array of viewing windows absent a viewing window at a corner position of the wound dressing, among other parts, that are similar to that described above in relation to FIGS. 25A-B but located in a corner of the dressing 500. In a preferred embodiment, the dressing 500 illustrated here is approximately square, with each side measuring approximately 150 mm. The spacing between each arm of the cutout 501 may be, as illustrated here, 72°, although it will of course be recognized that other angles and configurations are possible. Dashed lines 512 of FIG. 32A, indicating possible locations where breaks in the release liner 513 may be provided, can be located, for example, at 80 mm, 40±4 mm, and 25±4 mm from each of the top and bottom edges of the dressing 500. As illustrated, the port 504 (and cutout 501) are preferably centered on a corner of the dressing 500, and situated approximately 52-55 mm from the top edge of the dressing 500.

FIG. 33A-B illustrates an embodiment somewhat similar in shape and overall configuration to the embodiments illustrated above in FIGS. 24A-F. Here, however, the oval-shaped dressing 500 comprises an orifice viewing window 502 and cutout 501, among other parts, that are similar to that described above in relation to FIG. 25. Viewing windows are not shown, but may be provided as in one embodiment as described above. In a preferred embodiment, the dressing 500 illustrated in FIG. 33A has a longitudinal length of approximately 250 mm, and a transverse width of approximately 200 mm. The longitudinal length of the absorbent layer 503 (and corresponding obscuring layer, if so provided) measures approximately 200 mm, with a transverse width of approximately 150 mm. The embodiment of the dressing 500 illustrated in FIG. 33B has a longitudinal length of approximately 200 mm, and a transverse width of approximately 150 mm. The longitudinal length of the absorbent layer 503 (and corresponding obscuring layer, if so provided) measures approximately 150 mm, with a transverse width of approximately 100 mm. Although no viewing windows 507 are illustrated, it will of course be understood that one or more such windows 507 may be provided on the dressing 500. The spacing between each arm of the cutout 501 may be 72°, although it will of course be recognized that other angles and configurations are possible. As illustrated, the orifice or port 504 (and cutout 501) are preferably centered on the transverse midline of the dressing 500, and situated approximately 52-55 mm from the top edge of the dressing 500.

Figure 34A:
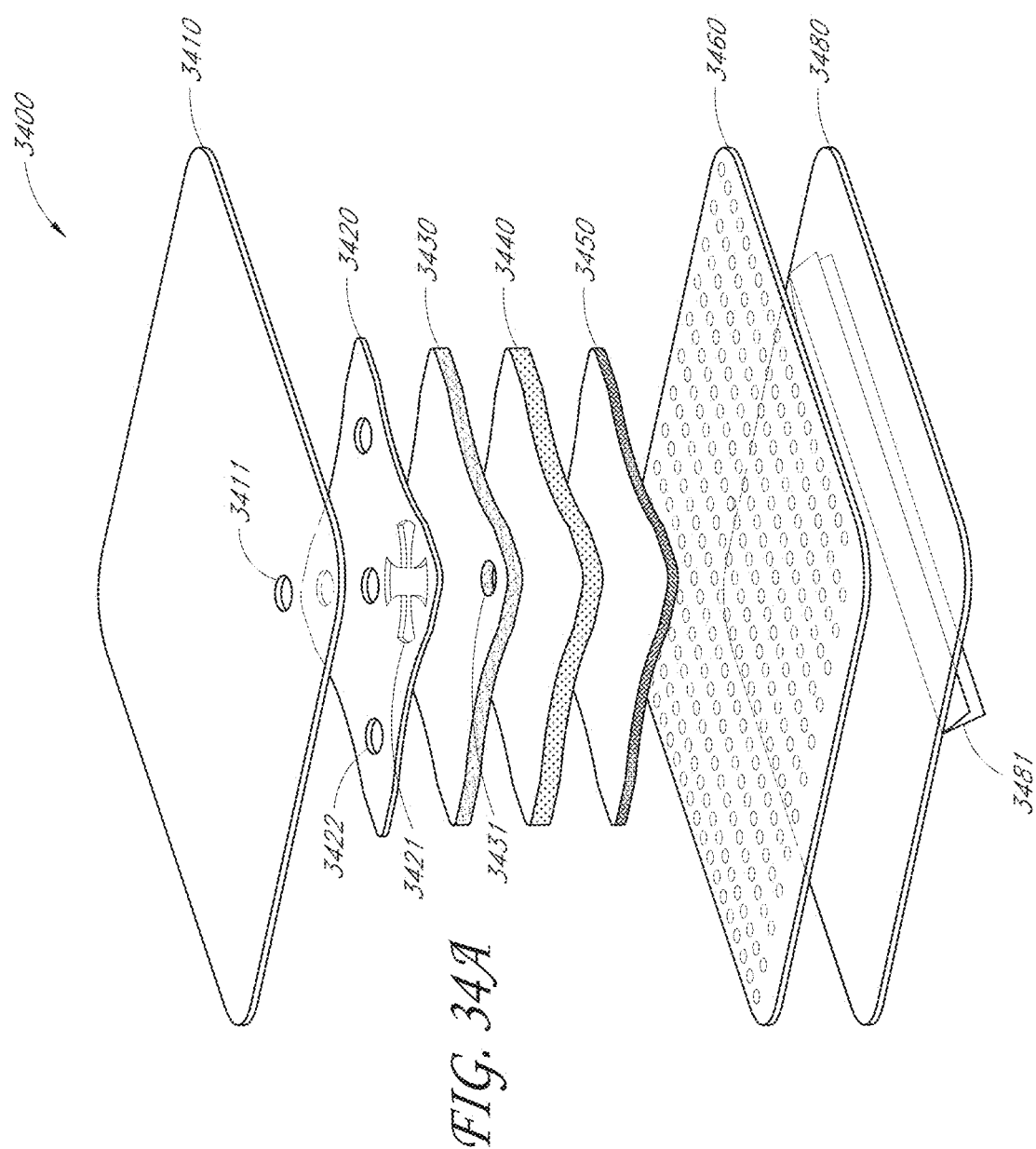
FIG. 34A illustrates an exploded view of an embodiment of a wound dressing.

FIG. 34A illustrates an exploded view of a dressing 3400 for use in negative pressure wound therapy. Although this figure illustrates a dressing having one particular shape, the construction of the layers can be applied to any of the embodiments identified above, including FIGS. 4A-14, 16-22, and 24A-33B. The dressing 3400 comprises a release layer 3480, wound contact layer 3460, a transmission layer 3450, an acquisition distribution layer (ADL) 3440, an absorbent layer 3430, an obscuring layer 3420, and a backing layer 3410. The dressing 3400 may be connected to a port, such as described below with respect to FIGS. 35 and 36. At least the wound contact layer 3460, transmission layer 3450, absorbent layer 3430, obscuring layer 3420, and backing layer 3410 may have properties as described with respect to particular embodiments above, such as the embodiments of FIGS. 3A-22, and 24A-33B, as well as or instead of the properties described below.

The dressing 3400 may optionally comprise a wound contact layer 3460 for sealing the dressing 3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing 3400, and the lower adhesive layer may be employed for sealing the dressing 3400 to the healthy skin of a patient around a wound site. As described above, in some embodiments with respect to FIGS. 3A-C, some embodiments of the polyurethane film layer may be perforated. Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer 3460 may not be provided with adhesive. In some embodiments, the wound contact layer 3460 may be transparent or translucent. The film layer of the wound contact layer 3460 may define a perimeter with a rectangular or a square shape. A release layer 3480 may be removably attached to the underside of the wound contact layer 3460, for example covering the lower adhesive layer, and may be peeled off using flaps 3481. Some embodiments of the release layer 3480 may have a plurality of flaps extending along the length of the layer 3480.

Some embodiments of the dressing 3400 may comprise an optional spacer or transmission layer 3450. The transmission layer 3450 may comprise a porous material or 3D fabric configured to allow for the passage of fluids therethrough away from the wound site and into the upper layers of the dressing 3400. In particular, the transmission layer 3450 can ensure that an open air channel can be maintained to communicate negative pressure over the wound area even when the absorbent layer 3430 has absorbed substantial amounts of exudates. The transmission layer 3450 should remain open under the typical pressures that will be applied during negative pressure wound therapy as described above, so that the whole wound site sees an equalized negative pressure. An outer perimeter of the transmission layer may be smaller than the outer perimeter of the dressing layer positioned above the transmission layer, for example the ADL 3440 and/or absorbent layer 3430. In some embodiments, the entire outer perimeter of the transmission layer may be spaced inward from the outer perimeter of the overlying layer by 5 mm, or approximately 5 mm, or 2 mm to 8 mm, or approximately 2 mm to approximately 8 mm.

Some embodiments of the transmission layer 3450 may be formed of a material having a three dimensional structure. For example, a knitted or woven spacer fabric (for example Baltex 7970 weft knitted polyester) or a non-woven fabric can be used. In some embodiments, the transmission layer 3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 3400 where the absorbent layer 3430 helps lock the liquid away or itself wicks the liquid onwards towards the cover layer 3410 where it can be transpired. Other materials can be utilized, and examples of such materials are described in U.S. Patent Pub. No. 2011/0282309, which are hereby incorporated by reference and made part of this disclosure. However, the transmission layer 3450 may be optional, and for example may be optional in embodiments of the dressing 3400 which comprise the acquisition distribution layer 3440, described below.

Some embodiments may comprise a wicking or acquisition distribution layer (ADL) 3440 to horizontally wick fluid such as wound exudate as it is absorbed upward through the layers of the dressing 3400. Lateral wicking of fluid may allow maximum distribution of the fluid through the absorbent layer 3430 and may enable the absorbent layer 3430 to reach its full holding capacity. This may advantageously increase moisture vapor permeation and efficient delivery of negative pressure to the wound site. Some embodiments of the ADL 3440 may comprise viscose, polyester, polypropylene, cellulose, or a combination of some or all of these, and the material may be needle-punched. Some embodiments of the ADL 3440 may comprise polyethylene in the range of 40-150 grams per square meter (gsm). In some embodiments, the ADL 3440 may have a thickness of 1.2 mm or about 1.2 mm, or may have a thickness in the range of 0.5 mm to 3.0 mm, or about 0.5 mm to about 3.0 mm.

The dressing 3400 may further comprise an absorbent or superabsorbent layer 3430. The absorbent layer can be manufactured from ALLEVYN™ foam, Freudenberg 114-224-4 and/or Chem-Positec™11C-450, or any other suitable material. In some embodiments, the absorbent layer 3430 can be a layer of non-woven cellulose fibers having superabsorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In some embodiments, the absorbent layer 3430 may have a thickness of 1.7 mm or about 1.7 mm, or may have a thickness in the range of 0.5 mm to 3.0 mm, or about 0.5 mm to about 3.0 mm.

For example, some embodiments of the absorbent layer 3430 may comprise a layered construction of an upper layer of non-woven cellulose fibers, superabsorbent particles (SAP), and a lower layer of cellulose fibers with 40-80% SAP. In some embodiments, the absorbent layer 3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™11C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer 3430 can have one or more through holes 3431 located so as to underlie the suction port.

Some embodiments of the present disclosure may employ a masking or obscuring layer 3420 to help reduce the unsightly appearance of a dressing 3400 during use due to the absorption of wound exudate. The obscuring layer 3420 may be a colored portion of the absorbent material, or may be a separate layer that covers the absorbent material. The obscuring layer 3420 may be one of a variety of colors such as blue, orange, yellow, green, or any color suitable for masking the presence of wound exudate in the dressing 3400. For example, a blue obscuring layer 3420 may be a shade of blue similar to the shade of blue commonly used for the material of medical gowns, scrubs, and drapes. Some embodiments of the obscuring layer 3420 may comprise polypropylene spunbond material. Further, some embodiments of the obscuring layer 3420 may comprise a hydrophobic additive or coating. Other embodiments may comprise a thin fibrous sheet of 60, 70, or 80 gsm. In some embodiments, the obscuring layer 3420 may have a thickness of 0.045 mm or about 0.045 mm, or may have a thickness in the range of 0.02 mm to 0.5 mm, or about 0.02 mm to about 0.5 mm.

The obscuring layer may comprise at least one viewing window 3422 configured to allow a visual determination of the saturation level of the absorbent layer. The at least one viewing window 3422 may comprise at least one aperture made through the obscuring layer. The at least one viewing window 3422 may comprise at least one uncolored region of the obscuring layer. Some embodiments of the obscuring layer may comprise a plurality of viewing windows or an array of viewing windows, as discussed above with respect to FIGS. 25-32.

The masking capabilities of the obscuring layer 3420 should preferably only be partial, to allow clinicians to access the information they require by observing the spread of exudate across the dressing surface. A obscuring layer 3420 may be partial due to material properties allowing wound exudate to slightly alter the appearance of the dressing or due to the presence of at least one viewing window 3422 in a completely obscuring material. The partial masking nature of the obscuring layer 3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

Tests performed upon various dressings with respect to the transmittance properties of the dressing indicate the ability of various samples to mask colour. The ability to mask colour may be calculated, for example, by measuring the reduction in absorption of light radiation at particular wavelengths. The tests utilized a UV-Vis spectrophotometer Jasco with integrating sphere, with a scanning range 340 to 800 nm, bandwidth 5 nm and 1000 nm/sec scanning speed. The data labelled black background represents the extreme of exudate colour (the most colour an exudate might have)—the highest level of radiation absorbed and the least amount of radiation reflected from the sample. The data for white background represents the upper limit for total masking—generally the lowest level of radiation absorbed and the highest level of reflection. Sample 1 was a tinted polymer film placed over a black background, which was judged not to sufficiently mask the black background (representing wound exudate) satisfactorily. Sample 2 was a sheet of 3-dimensional spacer fabric (Baltex 3D) placed over a black background, and was judged to provide adequate masking of the black background. Sample 3 was a sheet of non-woven material dyed green placed over a black background, and provided complete masking of the black background.

Wound exudate may have dark yellow, red and/or brown tones. Therefore, to appropriately mask these colours, an obscuring layer 3420 would preferably shield light wavelengths of below 600 nm.

Measuring the reduction in absorption of light radiation at particular wavelengths may be performed by calculating:

$$\% \text{ reduction} = (A_{background} - A_{sample\ placed\ on\ background}) / (A_{background}) \times 100$$

where A is the absorption of light radiation at the particular wavelength.

Using this formula, using light at a wavelength of 460 nm, the percentage of absorption reduction was calculated as shown in Table 3 below.

TABLE 3

| Sample | Absorption reduction at 460 nm | Appropriate masking observed |
|---|---|---|
| Sample 1 | 34% | No |
| Sample 2 | 77% | Yes - partial |
| Sample 3 | 69% | Yes - complete |

It has been found that materials that reduce light absorption by about 50% or more will provide enough partial or complete masking of wound exudate (as judged by the inventors). Of course a complete masking element would preferably require a means for a clinician to judge the spread of wound exudate in the dressing below the obscuring layer 3420, e.g. the masking element not completely covering the entire dressing. For example, as described above with respect to FIGS. 25-33, a plurality of viewing windows may be provided in the obscuring layer 3420 such that the spread of exudate in the dressing below may be adequately assessed. Alternatively a partial masking element may allow a clinician to judge the spread of exudate in the dressing below without additional means.

It will be understood that the wetting of a masking material (by exudate for example) will also affect the masking performance of the masking element, since hydrophilic materials will allow chromophore-carrying species to travel through them more easily. As such, the absorption reduction rate should also be tested on wet materials.

The above-mentioned Samples 1, 2 and 3 were also tested for their masking properties by measuring CIE L*a*b* values (a known 3-dimensional model for representing colour space). The analysis employed Jasco software using the range 380 to 780 nm, stard observed 2 (deg), lightsource D65, colour matching JIS Z8701-1999.

Table 4 below shows the L*a*b* values found when Samples 1, 2 and 3 were respectively placed over a black background. The results for the black background alone and a white background are also shown.

TABLE 4

| Sample | CIE L*a*b* values recorded | | | Appropriate masking observed? |
|---|---|---|---|---|
| | L* | a* | b* | |
| Black background | 0 | 0 | 0 | n/a |
| Sample 1 (on black) | 36.59 | 3.76 | −1.80 | No |
| Sample 2 (on black) | 71.76 | −0.20 | −1.08 | Yes - partial |
| Sample 3 (on black) | 70.64 | −0.25 | −1.23 | Yes - complete |
| White background | 100 | 0 | 0 | n/a |

Generally, samples which lead to an increase in L* value will provide a lighter colour tone than the reference surface, which is the main contributor to masking a dark colour. From the values above, apt partial masking materials will yield an L* value above 50, or more aptly above 70.

However, completely opaque masking layers, such as for example a tinted polymeric film, may cover the area to be masked with a darker tone altogether, in which case the measure of L* is not relevant. Once again these values should also be considered on wet material, for the reasons stated above.

Figure 38:
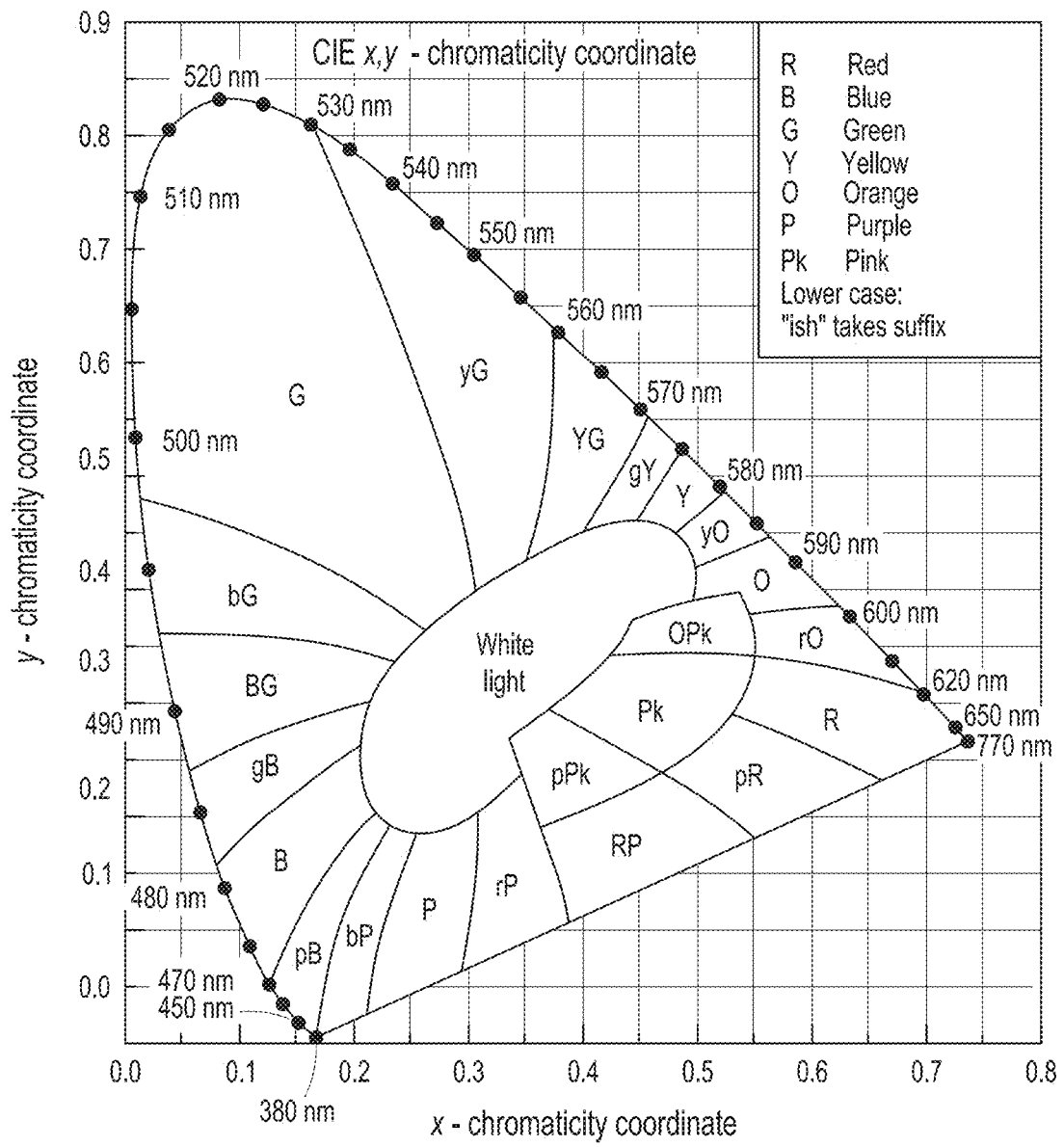
FIG. 38 illustrates a CIE chromaticity scale.

In addition to transmittance properties, the color of the obscuring layer 3420 may affect the masking ability of the layer. In liquid permeable embodiments of the obscuring layer, various colors are suitable for masking the usual colors of wound exudate, while other colors may not provide optimal masking of the exudate. For example, with reference to the CIE chromaticity diagram illustrated in FIG. 38, some embodiments of the obscuring layer, in a dry state, may be configured to yield a CIE y value of 0.4 or less and a CIE x value of 0.5 or less. Some embodiments of the obscuring layer, in a dry state, may have a color of Bg, gB, B, pB, bP, P, rP, pPk, RP, O, rO, or yO on the CIE x, y chromaticity diagram. It will be appreciated that liquid impermeable embodiments of the obscuring layer may be configured with any color.

The obscuring layer 3420 can have one or more through holes located so as to underlie the suction port. Some embodiments may have a maltese cross 3421 or other shaped cutout underlying the suction port, wherein the diameter of the maltese cross 3421 is greater than the diameter of the port. This may allow a clinician to easily asses the amount of wound exudate absorbed into the layers beneath the port. The obscuring layer 3420 may have an outer perimeter that is larger than the dressing layer or layers provided beneath it, for example the absorbent layer 3430, ADL 3440 and/or transmission layer 3450. In some embodiments the entire outer perimeter of the obscuring layer 3420 is spaced 1 mm, or approximately 1 mm, or 0.5 mm to 3 mm, or approximately 0.5 to approximately 3 mm, beyond the dressing layer or layers provided beneath it. The larger perimeter of the obscuring layer 3420 may ensure that the underlying layers are adequately covered for visual obscuring of wound exudate.

The dressing 3400 may also comprise a backing layer, or cover layer 3410 extending across the width of the wound dressing. The cover layer 3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film. The cover layer 3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer 3410 can have an orifice 3411 located so as to underlie the suction port. The orifice 3411 may allow transmission of negative pressure through the cover layer 3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

Figure 34B:
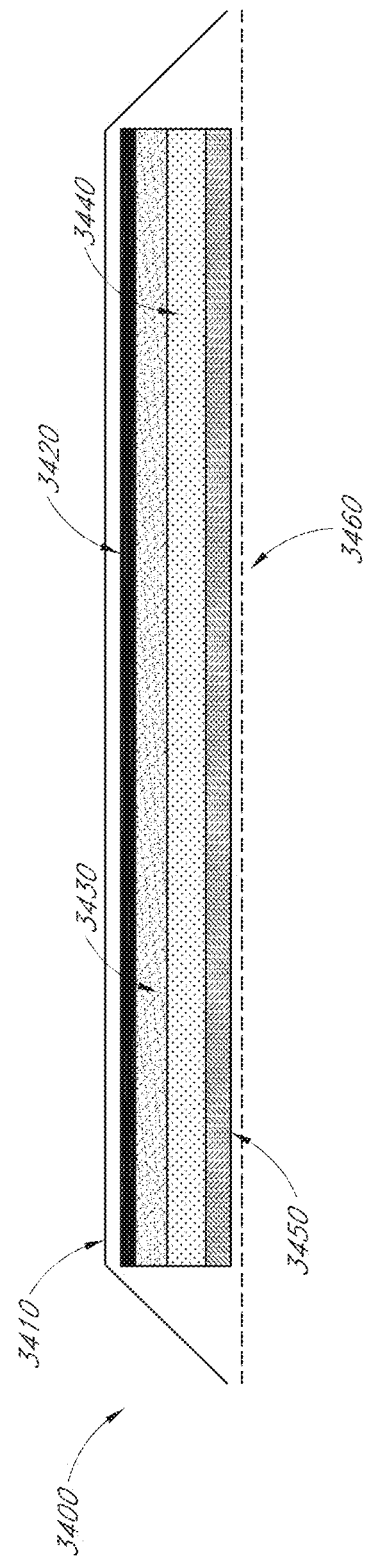
FIG. 34B illustrates a cross sectional view of an embodiment of a wound dressing.

FIG. 34B illustrates a cross sectional view of the wound dressing 3400, displaying an embodiment of the relative thicknesses of layers of the dressing 3400. In some embodiments, the wound contact layer 3460 may be flat and the top film layer 3410 may be contoured over the inner layers of the dressing 3400. The spacer layer 3450 may be half as thick as the acquisition distribution layer 3440 in some embodiments. In some embodiments, the absorbent layer 3430 may be about 1.5 times thicker than the spacer layer 3450. The obscuring layer 3420 may be about half the thickness of the spacer layer 3450.

Figure 35:
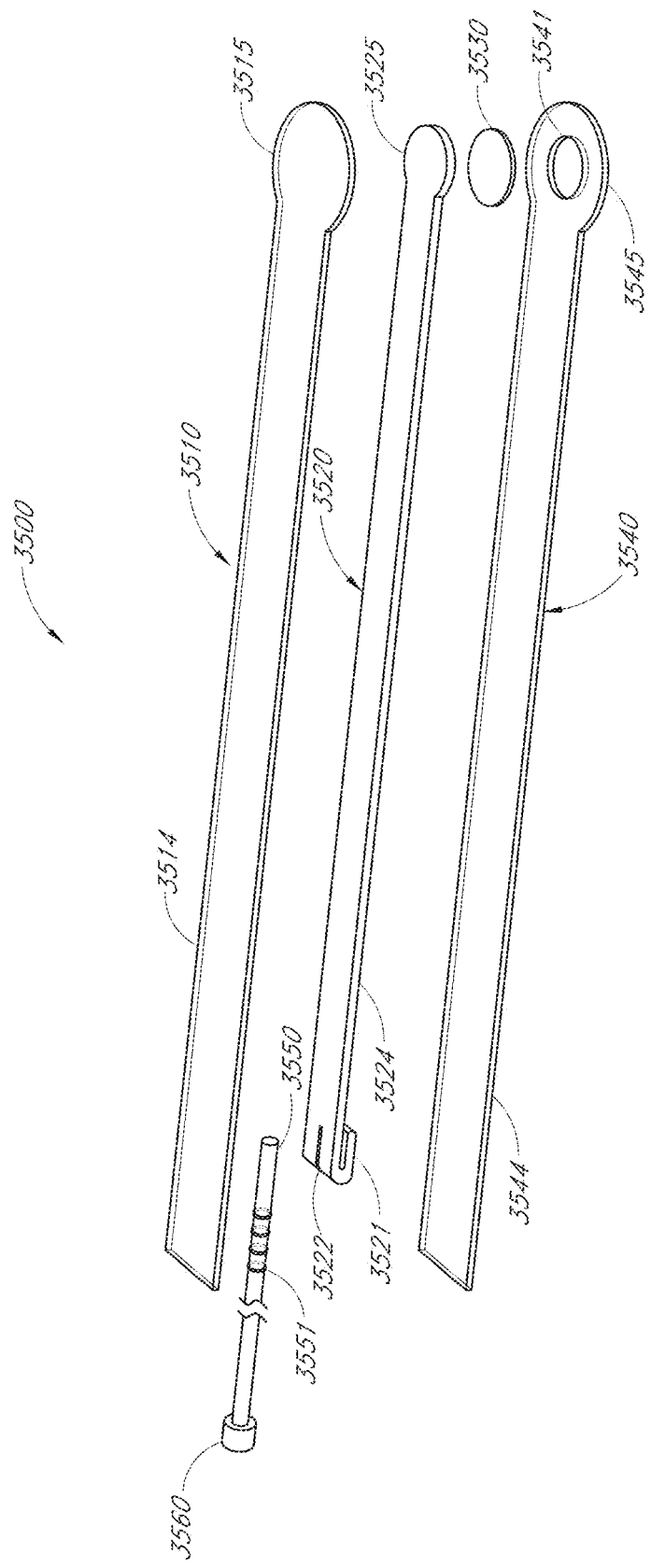
FIG. 35 illustrates an exploded view of an embodiment of a soft or flexible port for transmitting negative pressure to a wound dressing.

FIG. 35 illustrates a perspective exploded view of an embodiment of a flexible port or fluidic connector 3500 that may be used to connect any of the wound dressings described herein to a source of negative pressure. The port 3500 comprises a top layer 3510, a spacer layer 3520, a filter element 3530, a bottom layer 3540, and a conduit 3550. The conduit optionally comprises a connector 3560. The distal end of the port 3500 (the end connectable to the dressing 3400) is depicted as having an enlarged circular shape, although it will be appreciated that any suitable shape may be used and that the distal end need not be enlarged. For example, the distal end can have any of the shapes shown in FIGS. 23A and 23B above. The distal end can also have the shape shown in FIGS. 3A-3C of International Application No. PCT/IB2013/001469, filed May 22, 2013, incorporated by reference herein.

The bottom layer 3540 may comprise an elongate bridge portion 3544, an enlarged (e.g., rounded or circular) sealing portion 3545, and an orifice 3541. In some embodiments a plurality of orifices may be provided in the bottom layer. Some embodiments of the rounded sealing portion 3545 may comprise a layer of adhesive, for example a pressure sensitive adhesive, on the lower surface for use in sealing the port 3500 to a dressing. For example, the port may be sealed to the cover layer 3410 of the dressing in FIG. 34. The orifice 3541 in the bottom layer 3540 of the port 3500 may be aligned with the orifice 3411 in the cover layer 3410 of the dressing 3400 in order to transmit negative pressure through the dressing 3400 and into a wound site.

The top layer 3515 may be substantially the same shape as the bottom layer in that it comprises an elongate bridge 3514 and an enlarged (e.g., rounded or circular) portion 3515. The top layer 3515 and the bottom layer 3545 may be sealed together, for example by heat welding. In some embodiments, the bottom layer 3545 may be substantially flat and the top layer 3515 may be slightly larger than the bottom layer 3545 in order to accommodate the height of the spacer layer 3520 and seal to the bottom layer 3545. In other embodiments, the top layer 3515 and bottom layer 3145 may be substantially the same size, and the layers may be sealed together approximately at the middle of the height of the spacer layer 3520. In some embodiments, the elongate bridge portions 3544, 3514 may have a length of 10 cm (or about 10 cm) or more, more preferably a length of 20 cm (or about 20 cm) or more and in some embodiments, may be about 27 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions 3544, 3514 to their widths may in some embodiments exceed 6:1, and may more preferably exceed 8:1 or even 10:1. The diameter of the circular portion 3545, 3515 may be about 3.5 cm in some embodiments.

The bottom and top layers may comprise at least one layer of a flexible film, and in some embodiments may be transparent. Some embodiments of the bottom layer 3540 and top layer 3515 may be polyurethane, and may be liquid impermeable. The top layer may comprise a flexible film having a thickness of 90 gsm, or approximately 90 gsm, or any thickness suitable for making the top film difficult to puncture.

The port 3500 may comprise a spacer layer 3520, such as the 3D fabric discussed above, positioned between the lower layer 3540 and the top layer 3510. The spacer layer 3520 may be made of any suitable material, for example material resistant to collapsing in at least one direction, thereby enabling effective transmission of negative pressure therethrough. Instead of or in addition to the 3D fabric discussed above, some embodiments of the spacer layer 520 may comprise a fabric configured for lateral wicking of fluid, which may comprise viscose, polyester, polypropylene, cellulose, or a combination of some or all of these, and the material may be needle-punched. Some embodiments of the spacer layer 520 may comprise polyethylene in the range of 40-160 grams per square meter (gsm) (or about 40 to about 160 gsm), for example 80 (or about 80) gsm. Such materials may be constructed so as to resist compression under the levels of negative pressure commonly applied during negative pressure therapy.

The spacer layer 3520 may comprise an enlarged (e.g., rounded or circular) portion 3525, and may optionally include a fold 3521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion 3525 may be slightly smaller than the diameters of the enlarged ends 3545, 3515, and in one embodiment is about 2 cm. Some embodiments of the spacer layer 3520 may have adhesive on one or both of its proximal and distal ends (e.g., one or more dabs of adhesive) in order to secure the spacer layer 3520 to the top layer 3510 and/or the bottom layer 3540. Adhesive may also be provided along a portion or the entire length of the spacer layer. In other embodiments, the spacer layer 3520 may be freely movable within the sealed chamber of the top and bottom layers.

The fold 3521 of the spacer fabric may make the end of the port 3500 softer and therefore more comfortable for a patient, and may also help prevent the conduit 3550 from blockage. The fold 3521 may further protect the end of the conduit 3550 from being occluded by the top or bottom layers. The fold 3521 may, in some embodiments, be between 1 cm and 3 cm (or between about 1 cm and about 3 cm) long, and in one embodiment is 2 cm (or about 2 cm) long. The spacer fabric may be folded underneath itself, that is toward the bottom layer 3540, and in other embodiments may be folded upward toward the top layer 3510. Other embodiments of the spacer layer 3520 may contain no fold. A slot or channel 3522 may extend perpendicularly away from the proximal end of the fold 3521, and the conduit 3550 may rest in the slot or channel 3522. In some embodiments the slot 3522 may extend through one layer of the fold, and in others it may extend through both layers of the fold. The slot 3522 may, in some embodiments, be 1 cm (or about 1 cm) long. Some embodiments may instead employ a circular or elliptical hole in the fold 3521. The hole may face proximally so that the conduit 3550 may be inserted into the hole and rest between the folded layers of spacer fabric. In some embodiments, the conduit 3550 may be adhered to the material of the fold 3521, while in other embodiments it may not.

The port 3500 may have a filter element 3530 located adjacent the orifice 3541, and as illustrated is located between the lower layer 3540 and the spacer layer 3520. As illustrated, the filter element 3530 may have a round or disc shape. The filter element 3530 is impermeable to liquids, but permeable to gases. The filter element 3530 can act as a liquid barrier, to substantially prevent or inhibit liquids from escaping from the wound dressing, as well as an odor barrier. The filter element 3530 may also function as a bacterial barrier. In some embodiments, the pore size of the filter element 3530 can be approximately 0.2 µm. Suitable materials for the filter material of the filter element include 0.2 micron Gore™ expanded PTFE from the MMT range, PALL Versapore™ 200R, and Donaldson™ TX6628. The filter element 3530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element 3530 may be adhered to one or both of top surface of the bottom layer 3540 and the bottom surface of the spacer layer 3520 using an adhesive such as, but not limited to, a UV cured adhesive. In other embodiments, the filter 3530 may be welded to the inside of the spacer layer 3520 and to the top surface of the bottom layer 3540. The filter may also be provided adjacent the orifice on a lower surface of the bottom layer 3540. Other possible details regarding the filter are disclosed in U.S. Patent Pub. No. 2011/0282309 and incorporated by reference herein.

The proximal end of the port 3500 may be connected to the distal end of a conduit 3550. The conduit 3550 may comprise one or more circular ribs 3551. The ribs 3551 may be formed in the conduit 3550 by grooves in a mold during the manufacturing of the conduit. During heat welding of the upper and lower layers 3515, 3545 melted material from those layers may flow around the ribs 3551, advantageously providing a stronger connection between the conduit 3550 and the layers. As a result, it may be more difficult to dislodge the conduit 3550 out from between the layers during use of the port 3500.

The proximal end of the conduit 3550 may be optionally attached to a connector 3560. The connector 3560 may be used to connect the port 3500 to a source of negative pressure, or in some embodiments to an extension conduit which may in turn be connected to a source of negative pressure. The distal end of the conduit 3550, which is inserted into the spacer layer 3520, may be shaped in such a way to reduce the possibility of occlusion.

Figure 36:
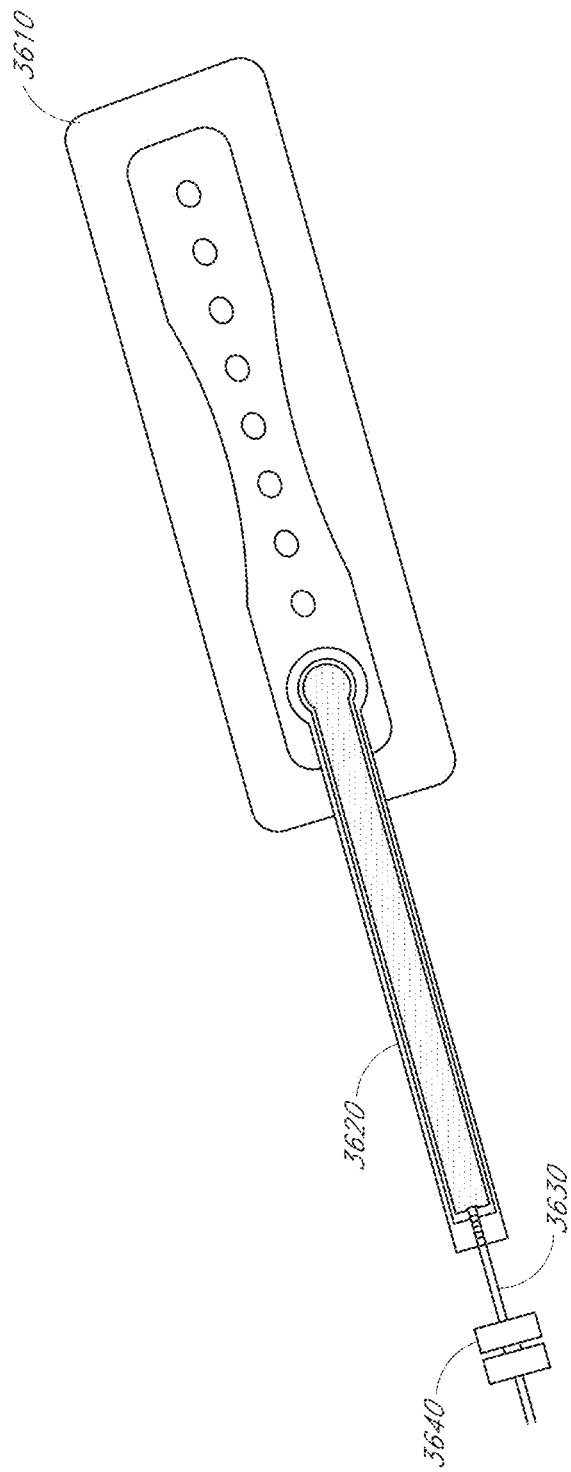
FIG. 36 illustrates an embodiment of a soft or flexible port attached to a wound dressing.

FIG. 36 illustrates an embodiment of a wound dressing 3610 with a flexible port 3620 such as described with respect to FIG. 35 attached. The port 3620 comprises a conduit 3630 and a connector 3640 for connecting the port to a source of negative pressure or to an extension conduit. The dressing 3610 comprises an obscuring layer with one row of eight holes in a linear arrangement, and is described above in more detail with respect to FIG. 25. Although in this depiction the port 3620 is connected over a circular window in the obscuring layer of the dressing 3610, in other embodiments the port 3620 may be connected over a maltese cross in the obscuring layer. In some embodiments, the maltese cross may be of a larger diameter than the port and may be at least partially viewable after the port is attached to the dressing.

Figure 37A:
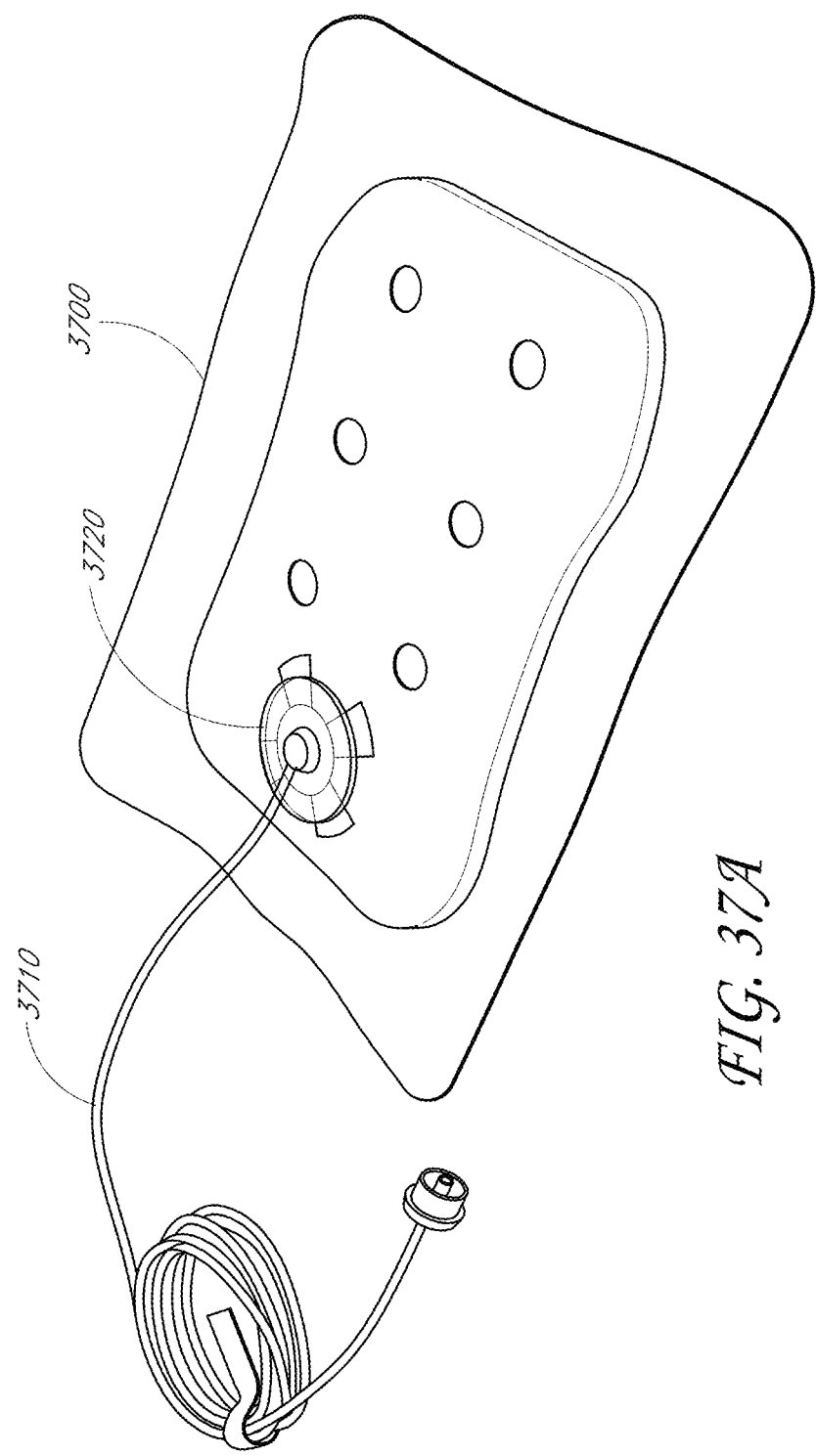
FIGS. 37A illustrates a perspective view of a wound dressing.

FIGS. 37A illustrates a line drawing perspective view of an embodiment of the dressing. Although the configuration as depicted is similar to the embodiment of FIG. 29B, the dressing can have any of the constructions of different layers previously described. Conduit 3710 is connected to the dressing 3700 via port 3720, however other embodiments of ports may be connected to the dressing, for example the flexible port of FIG. 35.

Figure 37B:
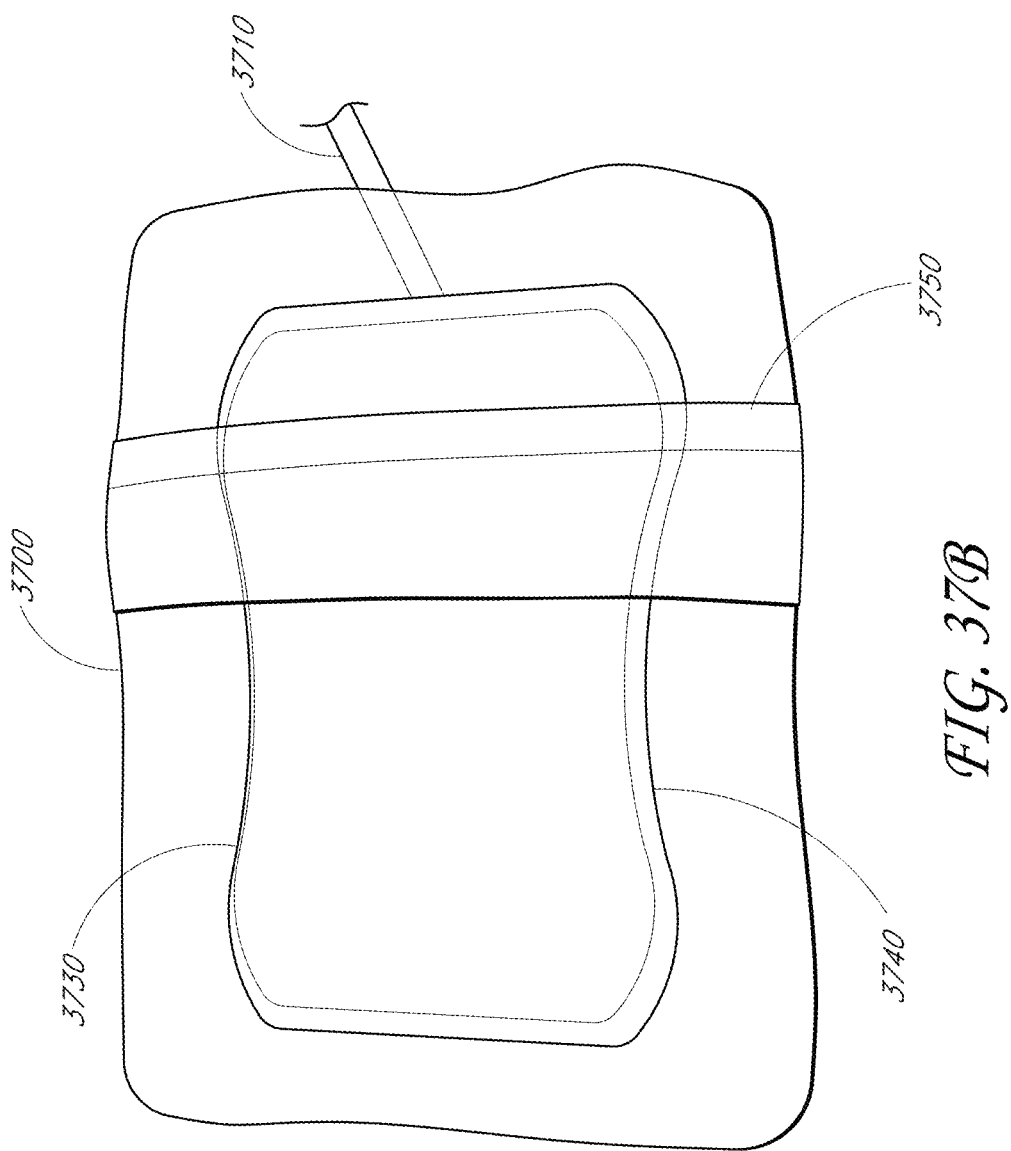
FIGS. 37B illustrates a bottom view of the wound dressing of FIGS. 37A.

FIGS. 37B illustrates a line drawing bottom view of the dressing 3700. The view illustrates a transmission layer 3730 and an acquisition distribution layer 3740, which may be similar to the transmission layer 3450 and acquisition distribution layer 3440 of FIGS. 34A and 34B. In some embodiments, the perimeter of the transmission layer 3730 may be slightly smaller than the perimeter of the acquisition distribution layer 3740. The view also illustrates one embodiment of a release layer 3750 similar to release layer 3480 previously described for use in protecting the adhesive side of the wound contact layer. The release layer 3750 as illustrated is made of two separate layers of material that can be removed from the adhesive side of the wound contact layer by pulling on flaps attached to the release layer.

Figure 37C:
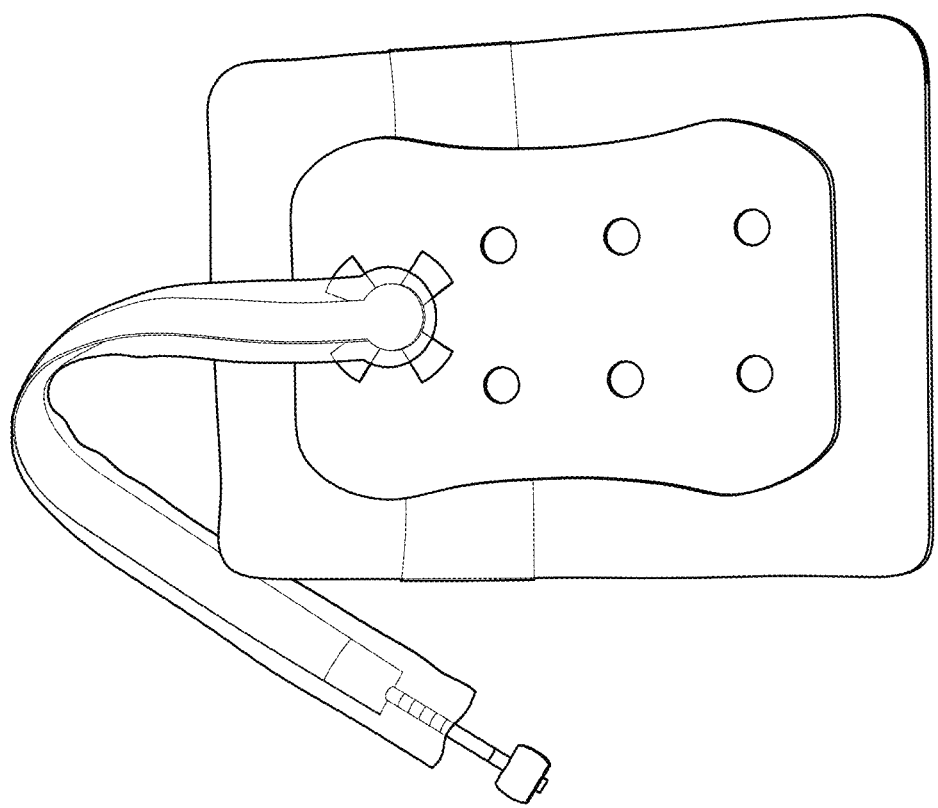
FIG. 37C illustrates an embodiment of a wound dressing having a soft or flexible port for transmitting negative pressure secured over a cross-shaped viewing window.

FIG. 37C illustrates an embodiment of a wound dressing having a soft or flexible port for transmitting negative pressure secured over a cross-shaped viewing window in an obscuring layer of the dressing. The port comprises a 3D fabric encased in transparent plastic film layers as described above. As illustrated in FIG. 35, the plastic film layers have a perimeter larger than the perimeter of the 3D fabric. An enlarged distal end of the port is positioned over the cross-shaped viewing window in the obscuring layer of the wound dressing, such that an end portion of each arm of the cross-shaped viewing window extends past the perimeter of the film layers of the enlarged distal end.

FIG. 39A illustrates another embodiment of a wound dressing 3900. The wound dressing may comprise a release layer 3980, wound contact layer 3960, a transmission layer 3950, an acquisition distribution layer 3940, an adhesive layer 3970, an absorbent layer 3930, an obscuring layer 3920, and a backing layer 3910. Although this figure illustrates a dressing having one particular shape, the construction of the layers can be applied to any of the embodiments identified above, including FIGS. 4A-14, 16-22, and 24A-33B. At least the wound contact layer 3960, transmission layer 3950, absorbent layer 3930, obscuring layer 3920, and backing layer 3910 may have properties as described with respect to particular embodiments above, such as the embodiments of FIGS. 3A-22, and 24A-33B, and these layers as well as the acquisition distribution layer 3940 may have properties similar to those described for the layers of the dressing embodiment of FIG. 34A, as well as or instead of the properties described below.

Figure 39B:
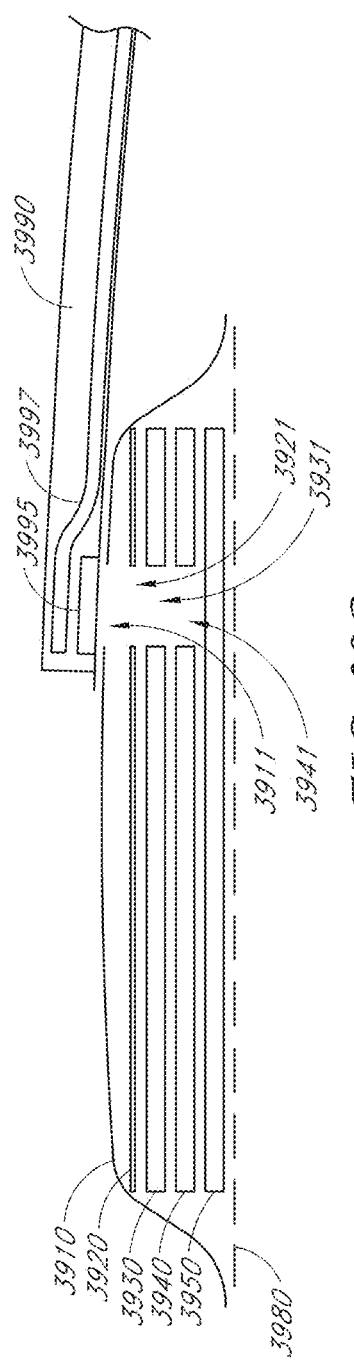
FIG. 39B illustrates a cross-sectional view of the wound dressing of FIG. 39A.

The dressing 3900 may be connected to a port 3990, such as described above with respect to FIGS. 35 and 36 and as illustrated in FIG. 39B (shown without the release layer 3980). At least the backing layer 3910, obscuring layer 3920, absorbent layer 3930, and acquisition distribution layer 3940 may have openings underlying the port 3990, and the port 3990 may comprise a three-dimensional fabric 3997 and a filter element 3995 overlying the openings. In some embodiments, the opening 3921 in the obscuring layer may be cross-shaped. As illustrated, the cross-shaped opening 3921 may comprise four arms of roughly equal length extending outward from a central point of intersection of the arms, wherein the sides of each arm are angled or arced such that the far end of each arm is wider than the end closest to the intersection. The far ends of the four arms may comprise arcs, for example four arcs from a single circle, giving the cross a rounded shape. The opening 3911 in the backing layer 3910, opening 3931 in the absorbent layer 3930, and opening 3941 in the acquisition distribution layer 3940 may be aligned with the central intersection point of the cross-shaped opening 3921. The openings 3911, 3931, and 3941 may be the same size or of varying sizes.

The backing layer 3910 (as well as the backing layer of previously described embodiments) may comprise, in some embodiments, EU33 film and may optionally have a pressure-sensitive adhesive provided on a lower surface thereof. For example, the adhesive may be a water dispersible acrylic adhesive, for example K5. The adhesive may be able to be pattern spread, and may be hydrophilic.

The obscuring layer 3920 may be provided to increase patient comfort by masking the presence of wound exudate absorbed by the inner layers of the dressing. The obscuring layer 3920 may have an outer perimeter that is spaced 1 mm, or approximately 1 mm, or 0.5 mm to 3 mm, or approximately 0.5 to approximately 3 mm, beyond the adjacent perimeter edge of the dressing layer or layers provided beneath it, for example the absorbent layer 3930, ADL 3940, and/or transmission layer 3950. The obscuring layer 3920 may be provided with a plurality of viewing windows 3922 which may be used to assess the spread of exudate across the dressing 3900. The cross-shaped opening 3921 may be used as a viewing window to ascertain the level of saturation of the layer or layers underlying an attached port. The width of the cross-shaped opening 3921 may be greater than the width of an attached port to enable such assessment. Some embodiments of the obscuring layer 3920 (including other embodiments of the obscuring layer previously described) may comprise polypropylene spunbond material of suitable colors such as described above, including medical blue. Further, some embodiments of the obscuring layer 3420 may comprise a hydrophobic additive or coating.

The absorbent layer 3930 may be configured to absorb and retain exudate from a patient's wound. The absorbent layer 3930 will preferably be constructed from a material which has good absorbent qualities under negative pressure. In some embodiments (including any of the earlier described embodiments), the absorbent layer may comprise cellulose fibers or air-laid materials. Some embodiments may comprise a cellulose fibers with 40-80% superabsorbent particles (SAP), for example 40%-60% (or about 40% to about 60%) SAP or 60%-80% (or about 60% to about 80%) SAP. Heat fusible fibers can optionally be used to assist in holding the structure of the absorbent pad together. Some embodiments may combine cellulose fibers and air-laid materials, for example as a hybrid bonded airlaid composite in the range of 400-500 gsm (or about 400 to about 500 gsm), for example 460 (or about 460) gsm. The absorbent layer 3930 may include polyacrylate superabsorber powder to increase the absorbent capabilities of the material. Some embodiments of the absorbent layer 3930 comprise a tissue dispersant layer. This may, in some embodiments, be provided along the lower surface of the layer, resulting in an asymmetric construction of the absorbent layer. The tissue dispersant layer may comprise a heat fusible binder to aid in holding the layer structure together. The tissue dispersant layer may provide the advantage of enabling fluid transport. In some embodiments, the tissue dispersant layer may comprise a hot melt adhesive such as ethylene vinyl acetate (EVA), for example applied as a solution to cellulose fibers of the absorbent layer.

The adhesive layer 3970 may bond an upper surface of the acquisition distribution layer 3940 to a lower surface of the absorbent layer 3930. As illustrated, in some embodiments the adhesive layer 3970 may comprise an adhesive web or net. In other embodiments, the adhesive layer 3970 may comprise adhesive tape. Yet other embodiments may employ a hot melt adhesive, such as EVA. For example, EVA powder may be sprinkled over the ADL 3940, which may then be heat bonded to the adhesive layer 3970. In some embodiments the acquisition distribution layer 3940 and the absorbent layer 3930 may be stitched or sewn together, and the adhesive layer 3970 may comprise suitable fibers, strands, or threads. Preferred embodiments of the adhesive layer 3970 are hydrophilic so as not to affect the transport of water and/or water-based solutions between the acquisition distribution layer 3940 and absorbent layer 3930. In some embodiments, the adhesive layer may comprise a fine sprinkle of adhesive powder such that the acquisition distribution layer 3940 and absorbent layer 3930 are not bonded together across the entire upper and lower surfaces, respectively, but may be merely tacked together in a number of locations. However, some embodiments of the dressing may be constructed without the use of an adhesive between the acquisition distribution layer 3940 and absorbent layer 3930.

The acquisition distribution layer (ADL) 3940 may be constructed so as to advantageously horizontally wick fluid, such as wound exudate, as it is absorbed upward through the layers of the dressing 3900. Such lateral wicking of fluid may allow maximum distribution of the fluid through the absorbent layer 3930, enabling the absorbent layer 3930 to reach its full holding capacity. Some embodiments of the ADL 3440 (including any embodiments of the ADL previously described) may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy.

Some embodiments of the dressing 3900 may optionally comprise a spacer or transmission layer 3950. The transmission layer 3950 may comprise a porous material or 3D fabric configured to allow for the passage of fluids therethrough away from the wound site and into the upper layers of the dressing 3400. In particular, the transmission layer 3450 should remain open under the typical pressures that will be applied during negative pressure wound therapy as described above, so that the whole wound site sees an equalized negative pressure. In some embodiments, the acquisition distribution layer 3940 may be sufficient to maintain even transmission of negative pressure throughout the dressing 3900 and the transmission layer 3950 may be excluded. An outer perimeter of the transmission layer may be spaced 5 mm, or approximately 5 mm, or 2 mm to 8 mm, or approximately 2 mm to approximately 8 mm, inward of the adjacent perimeter edge of the dressing layer positioned above the transmission layer, for example the ADL 3940 or absorbent layer 3930.

The dressing 3900 may optionally comprise a wound contact layer 3960 for sealing the dressing 3900 to the healthy skin of a patient surrounding a wound area. As discussed above with respect to FIG. 34A, the wound contact layer 3960 may comprise flexible polyurethane film, and may be provided with a silicone adhesive on a lower surface thereof. The wound contact layer 3960 may be perforated to allow for the transmission of fluids such as wound exudate therethrough, so that the fluids may be passed through or retained by the inner layers of the dressing 3900. Prior to use, the wound contact layer 3960 may be protected by a protective release layer 3980, which may be provided with at least one set of flaps 3981 for removing or peeling off the release layer 3980.

Figure 40A:
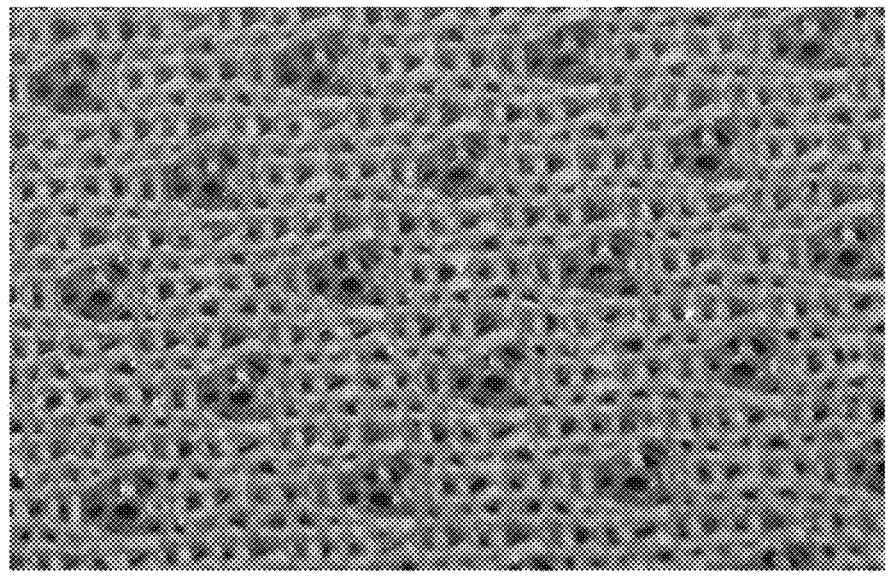
FIGS. 40A and 40B illustrate one embodiment of spacer layer material.
Figure 40B:
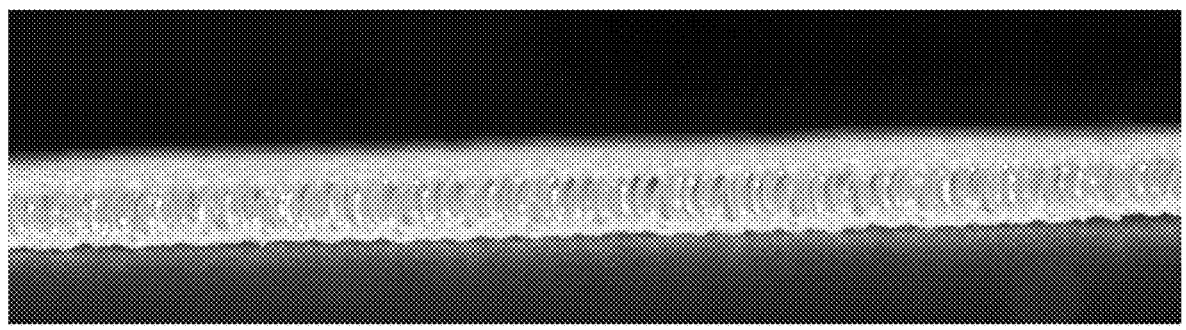

FIGS. 40A and 40B illustrate one embodiment of spacer layer, or transmission layer, material which may be used in any of the dressing embodiments described above, and which may also be used in any of the port or fluidic connector embodiments described above. The spacer or transmission material is preferably formed of a material having a three dimensional structure, and may have a top layer and a bottom layer comprising a knit pattern. For example, a knitted or woven spacer fabric (for example Baltex 7970 weft knitted polyester) or a non-woven fabric could be used. The top and bottom fabric layers may comprise polyester, such as 84/144 textured polyester or a flat denier polyester. Other materials and other linear mass densities of fiber could of course be used. In some embodiments, the top and bottom fabric layers may be the same pattern and the same material, and in other embodiments they may be different patterns and/or different materials. The top fabric layer may have more filaments in a yarn used to form it than the number of filaments making up the yarn used to form the bottom fabric layer, in order to control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. FIG. 40A illustrates one possible knit pattern for a top or bottom fabric layer.

As illustrated in the side view of FIG. 40B, between the top and bottom fabric layers may be a plurality of filaments. The filaments may comprise a monofilament fiber or a multistrand fiber, and may be knitted polyester viscose or cellulose. In some embodiments, a majority of the filaments, by volume, may extend vertically (that is, perpendicular to the plane of the top and bottom layers), or substantially or generally vertically. In another embodiment, 80%-90% (or approximately 80% to approximately 90%) of the filaments or more, by volume, may extend vertically, or substantially or generally vertically. In another embodiment, all or substantially all of the filaments, by volume, may extend vertically, or substantially or generally vertically. In some embodiments, a majority, 80%-90% (or approximately 80% to approximately 90%) of the filaments or more, or even all or substantially all of the filaments, extend upward from the bottom fabric layer and/or downward from the top fabric layer, and in some embodiments, such filaments extend over a length more than half the distance between the top and bottom fabric layers. In some embodiments, a majority, 80%-90% (or approximately 80% to approximately 90%) of the filaments or more, or even all or substantially all of the filaments, span a distance that is greater in a direction perpendicular to the top and bottom fabric layers (a vertical direction) than in a direction parallel to the top and bottom fabric layers (a horizontal direction). The orientation of such filaments may promote vertical wicking of fluid through the spacer layer. In some embodiments, the ratio of the amount of fluid wicked vertically through the spacer material to the amount of fluid wicked laterally across the spacer material when under negative pressure may be 2:1 or more, or approximately 2:1 or more, or may be up to 10:1 or more, or approximately 10:1 or more, in some embodiments. Such filaments may also keep the top and bottom layers spaced apart when exposed to compressive forces or negative pressure.

FIGS. 41A-D illustrate one embodiment of acquisition distribution layer (ADL) material which may be used in any of the dressing embodiments described above, and which may also be used in any of the port or fluidic connector embodiments described above. The ADL material, in an uncompressed state, may be 0.5 mm to 3 mm thick, or approximately 0.5 mm to approximately 3 mm thick, and in some embodiments may be 1.2 mm thick, or approximately 1.2 mm thick, in an uncompressed state. The ADL material may comprise a plurality of loosely packed fibers, which may be arranged in a substantially horizontal fibrous network.

In some embodiments, the ADL material may consist of a mix of two fiber types. One may be a flat fiber which may be 20 µm to 50 µm in width, or approximately 20 µm to approximately 50 µm in width, and may comprise a cellulosic based material. The other fiber may be a two component fiber that has an inner core that is 8 µm to 10 µm in diameter, or approximately is 8 µm to approximately 10 µm in diameter, and an outer layer with a thickness of 1 µm to 2 µm, or approximately 1 µm to approximately 2 µm. The two component fiber may be a mix of a polyethylene (PE) type material, and polyethylene terephthalate (PET). In some embodiments the inner core of the two component fiber may be PET and the outer layer may be PE. The PE/PET fibers may have a smooth surface morphology, while the cellulosic fibers may have a relatively rougher surface morphology. In some embodiments the ADL material may comprise about 60% to about 90% cellulosic fibers, for example approximately 75% cellulosic fibers, and may comprise about 10% to about 40% PE/PET fibers, for example approximately 25% PE/PET fibers.

Figure 41A:
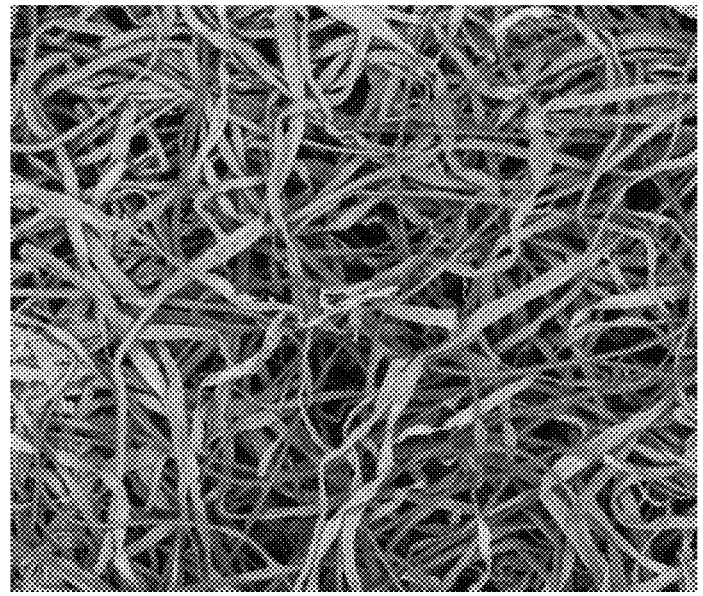
FIGS. 41A-D illustrate one embodiment of acquisition distribution layer material.
Figure 41B:
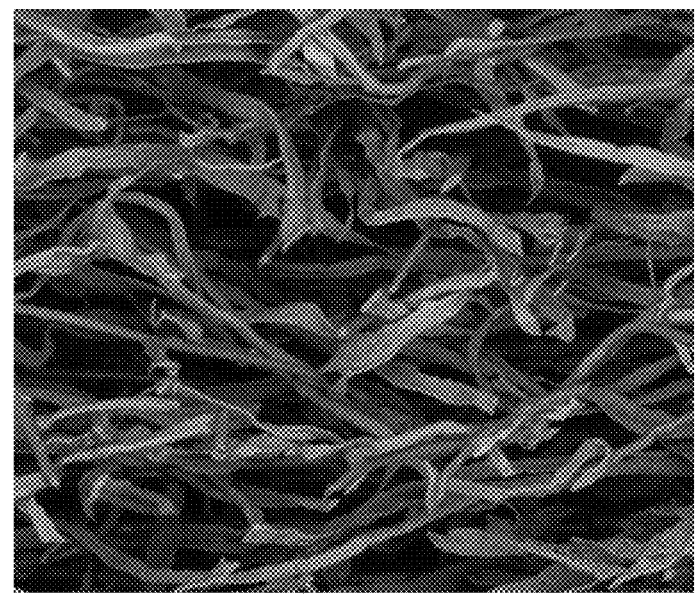

FIG. 41A illustrates a backscatter scanning electron microscope (SEM) plan view of a sample portion of acquisition distribution layer material at 140× magnification. FIG. 41B illustrates an SEM cross sectional view at 250× magnification. As illustrated in FIG. 41B, a majority of the fiber volume may extend horizontally (that is, parallel to the plane of the top and bottom surfaces of the material), or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

Figure 41C:
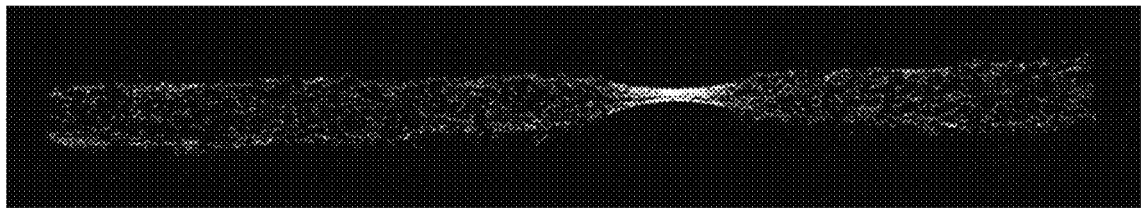
Figure 41D:
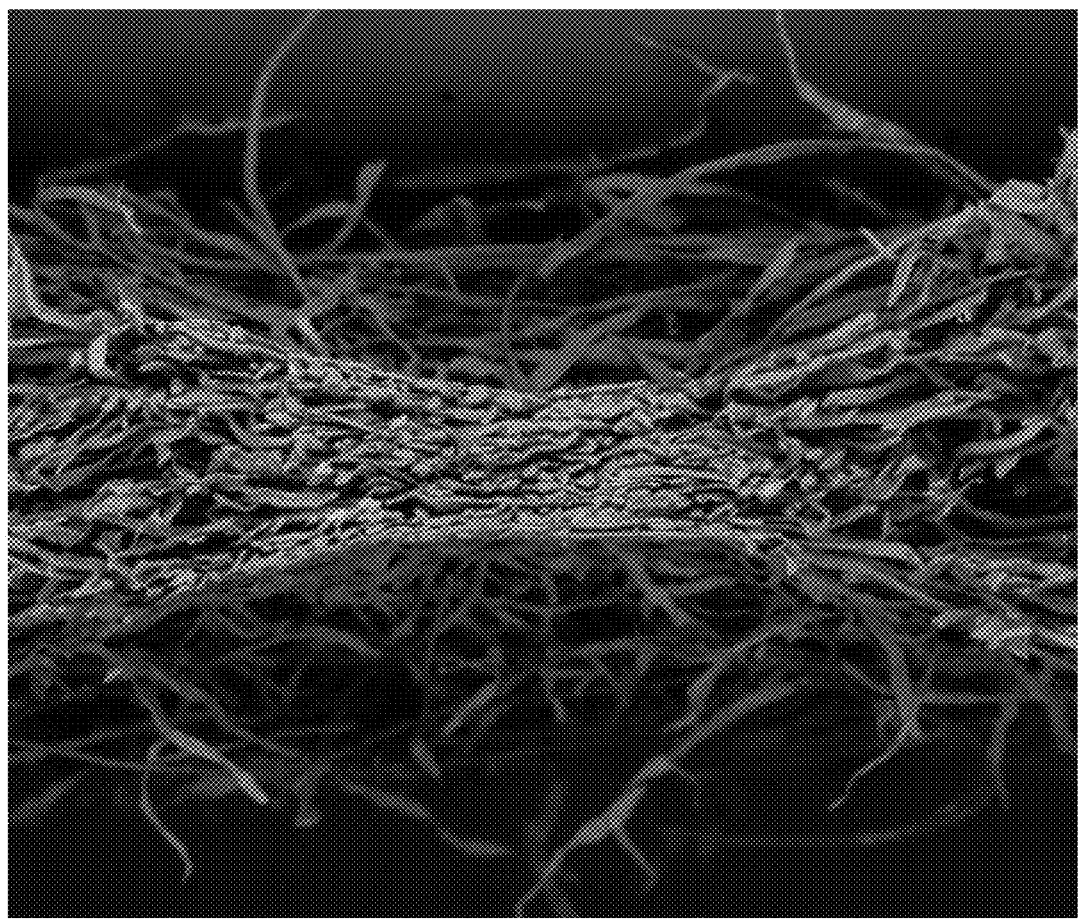

FIG. 41C is a two dimensional microtomographic cross sectional view of a compressed portion of a sample of ADL material which is approximately 9.2 mm long. FIG. 41D is an SEM cross sectional view at 130× magnification of the compressed portion illustrated in FIG. 41C. Such compressed portions may occur in the ADL material may occur due to the application of pressure to the material. FIGS. 41C and 41D further illustrate the horizontal network of ADL fibers.

Figure 42A:
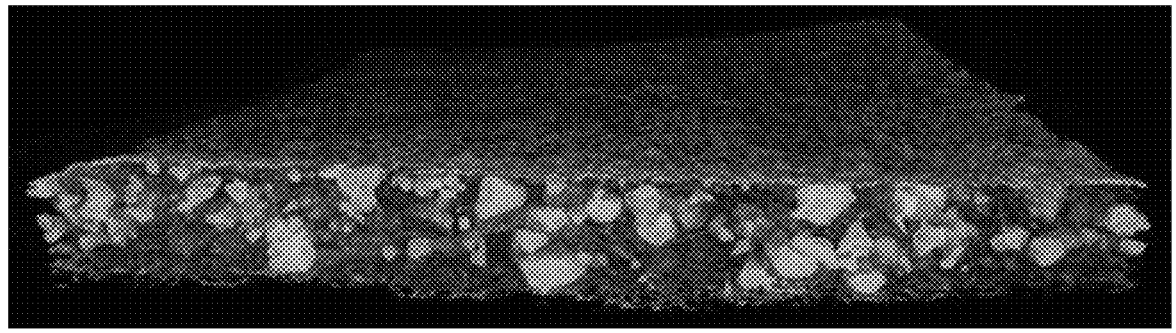
FIGS. 42A and 42B illustrate one embodiment of absorbent layer material.
Figure 42B:
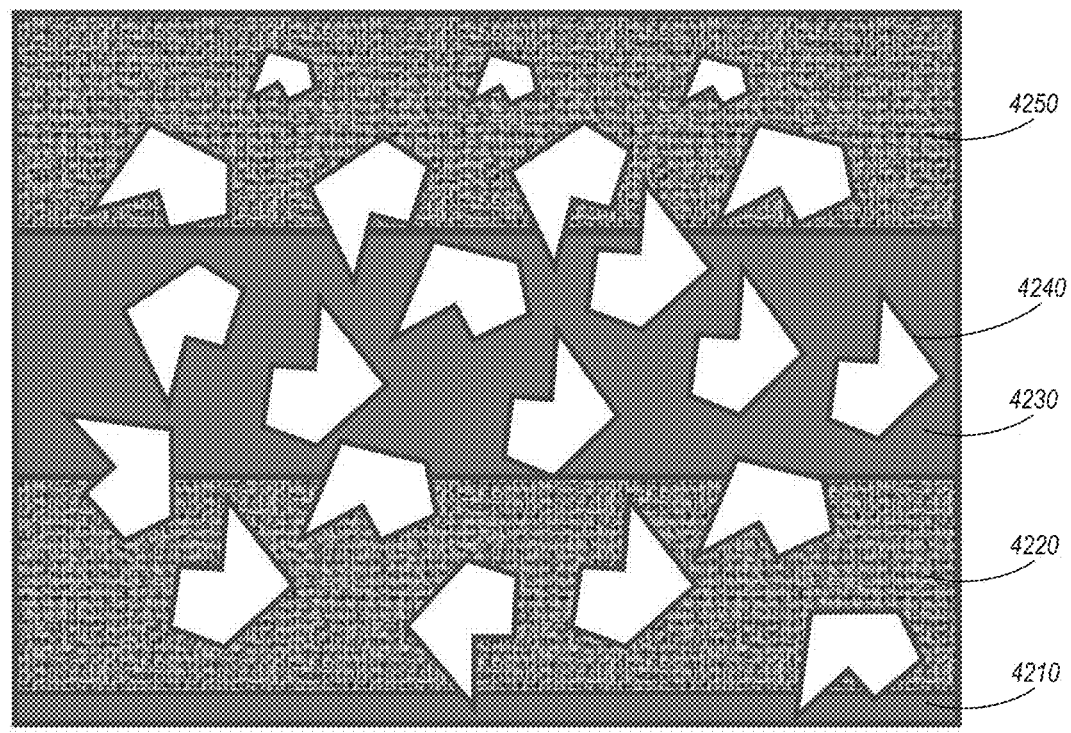

FIGS. 42A and 42B illustrate one embodiment of absorbent material which may be used in any of the dressing embodiments described above. FIG. 42A illustrates a three dimensional microtomographic cross sectional view of a sample of absorbent material, depicting a fibrous composition interspersed with superabsorbent particles. The absorbent material may, for example, be any of the materials described in U.S. Patent Pub. No. 2012/308780, titled "Absorbent Structure," filed May 25, 2012, the contents of which are hereby incorporated by reference in their entirety.

FIG. 42B is a cross sectional schematic diagram of an embodiment of the absorbent material illustrating a plurality of layers within the absorbent material. The absorbent material may have a textured layer 4210 on one side of a fibrous network, the fibrous network defining the bulk of the absorbent material and comprising layers 4220, 4240, and 4250. Superabsorbent particles 4230 may be dispersed throughout layers 4220, 4240, and 4250. The textured layer 4210, also referred to as the "tissue dispersant layer" in above portions of this specification, may be configured to laterally transmit fluid. Though depicted as the lowermost layer of the absorbent material, the textured layer 4210 may in some embodiments be positioned as the uppermost layer of the absorbent material, and in some embodiments may be positioned as both the lowermost and uppermost layers of the absorbent material. The textured layer 4210 may comprise flat fibers 20 µm to 50 µm in width, or approximately 20 µm to approximately 50 µm in width. The textured layer 4210 may comprise 1 to 2 or approximately 1 to approximately 2 layers of the flat fibers, and the textured layer 4210 may have an overall thickness of 0.04 mm, or approximately 0.04 mm.

The bulk of the absorbent material, comprising layers 4220, 4240, and 4250, may have a thickness of 1.7 mm, or approximately 1.7 mm, or may have a thickness in the range of 0.5 mm to 3.0 mm, or about 0.5 mm to about 3.0 mm. The bulk of the absorbent material may comprise a mix of two fiber types arranged in a fibrous network, for example the cellulosic fiber having a width of 20 µm to 50 µm, or approximately 20 µm to approximately 50 µm, and the PE/PET composite fiber, described above with respect to the ADL material. The superabsorbent particles 4230 may be irregularly shaped and varied in size, and may have a diameter of up to 1 mm, or approximately 1 mm. The superabsorbent particles 4230 may comprise a sodium acrylate type material. There may be relatively fewer superabsorbent particles in a portion of the uppermost surface of the bulk of the absorbent material (the surface of layer 4250 opposite the textured layer 4210), for example in an uppermost surface having a thickness of approximately 0.1 mm.

Layer 4220 may be a liquid absorption layer configured to draw liquid upward through the material towards layers 4240 and 4250. Layer 4240 may be a storage layer configured to hold absorbed liquid. Layer 4220 may be a liquid distribution layer configured to apply a "reverse suction" effect to the liquid storage layer 4240 in order to inhibit (or substantially inhibit) absorbed liquid from leaking back down through the lower layers of the absorbent material, a phenomenon which is commonly known as "backwetting." Superabsorbent particles 4230 may be distributed primarily within the storage layer 4240, may extend partially into the absorption layer 4220 and liquid distribution layer 4250, or may be distributed evenly (or substantially evenly) throughout the layers. The layers 4220, 4240, and 4250 may overlap with a portion of adjacent layers, and may or may not be separable.

Figure 43A:
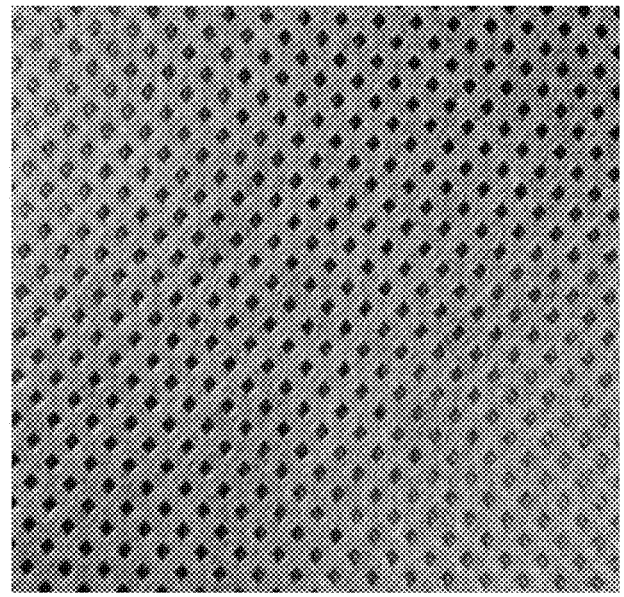
FIGS. 43A and 43B illustrate one embodiment of obscuring layer material.
Figure 43B:
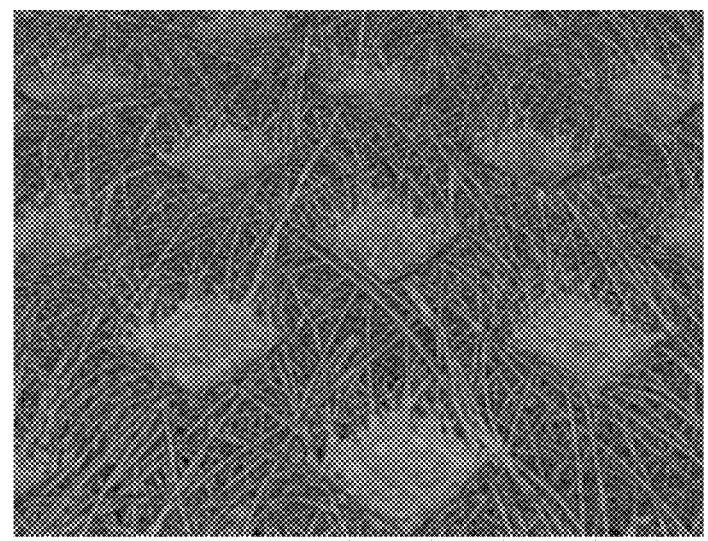

FIGS. 43A and 43B illustrate one embodiment of obscuring layer material which may be used in any of the dressing embodiments described above. FIG. 43A illustrates a photographic plan view of obscuring material, depicting a material comprising a fibrous network having a reoccurring regularly spaced criss-cross diamond pattern. The diamond shaped pattern may, in one embodiment, be 1.2 mm long by 1.0 mm wide, and may have a thickness of approximately 0.04 mm thick, consisting of fibers that are more densely packed relative to the surrounding area of the material. The diamond shaped pattern may increase structural stability of the fibrous network of the material, for example serving as "tacking" points. FIG. 43B illustrates a three dimensional microtomographic perspective view of the compressed diamond pattern and the surrounding uncompressed fibers.

Some embodiments of the obscuring material may comprise polypropylene spunbond material. Further, some embodiments of the obscuring material may comprise a hydrophobic additive or coating, for example a hydrophobic wash designed to permeate the fibers of the obscuring material to make the material substantially waterproof while permitting vapor permeability. Other embodiments may comprise a thin fibrous sheet of 60, 70, or 80 gsm. The fibers of the obscuring material may, in one embodiment, comprise layers of polypropylene (PP) fibers having a smooth surface morphology, and the PP fibers may have a thickness of approximately 25 μm. In some embodiments, the obscuring material may have a thickness of 0.045 mm or about 0.045 mm, or may have a thickness in the range of 0.02 mm to 0.5 mm, or about 0.02 mm to about 0.5 mm.

Figure 44:
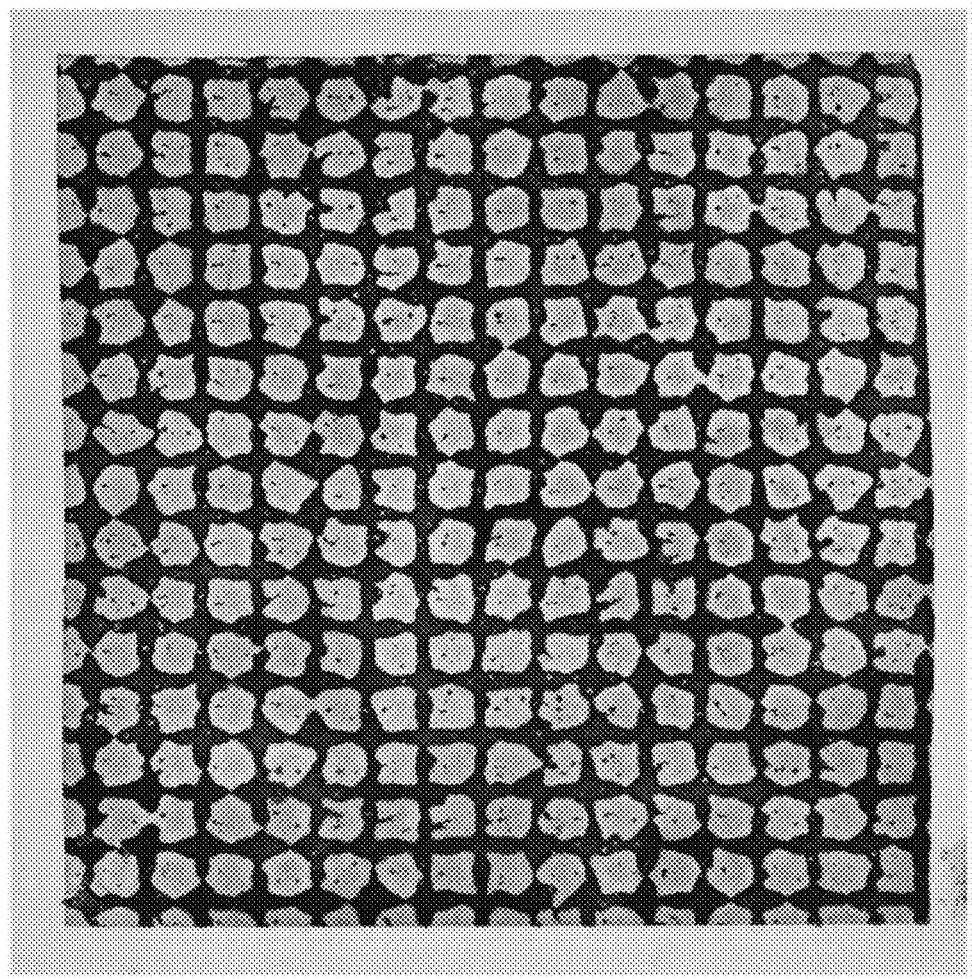
FIG. 44 illustrates one embodiment of an adhesive spread on cover layer material.

FIG. 44 illustrates one embodiment of an adhesive spread on approximately one square centimeter of a film material, which may be used as the cover or backing layer in any of the dressing embodiments or fluidic connector embodiments described above. The adhesive on the film has been covered with carbon powder for ease of illustrating the spread of the adhesive. The adhesive may comprise, for example, an acrylate type adhesive, for example K5 adhesive, and may be laid down in a criss cross pattern. In some embodiments, the adhesive material may cover approximately 45.5%± approximately 1.3% of the film surface. The pattern and coverage of the adhesive may vary so long as the configuration is suitable for desired vapor permeability.

FIGS. 45A-D illustrate one embodiment of a sealing strip assembly 4501 which may be used with a wound dressing and/or fluidic connector to provide additional sealing against the skin of the patient surrounding the wound dressing or fluidic connector. Sealing strips may also be used to reseal a cut or punctured wound dressing or fluidic connector. The sealing strips of FIGS. 45A-D may be used, for example, like the fixation strips 210 of FIG. 2D.

As illustrated in FIG. 45A (top view), a plurality of sealing strips 4501 (labeled 4501*a*-4501*f*) may be provided together on one sheet 4500 with a plurality of perforations or weakened lines 4515, separating the individual sealing strips on the sheet. In some embodiments anywhere from 2 to 10 or more sealing strips may be provided on one sheet. As illustrated, 6 sealing strips 4501*a*, 4501*b*, 4501*c*, 4501*d*, 4501*e* and 4501*f* are provided on one sheet 4500 in FIG. 45A. In other embodiments each sealing strip may be provided separately, or a plurality of separate sealing strips may be provided, for example in a kit. A kit may be provided in the form of a tray, for example a sealed tray, which may include one or more sheets containing a plurality of sealing strips 4501 separated by the plurality of perforations or weakened lines 4515, or other embodiments of sealing strips as described. The kit may also contain a wound dressing with a fluidic connector that may be pre-connected to the wound dressing or separately provided. The wound dressing may have any of the shapes and layer configurations described above, and the fluidic connector may be any of the soft or hard ports described above. In some embodiments, the kit may further comprise a pump configured to connect to the fluidic connector and transmit negative pressure to the wound dressing.

An example perforation pattern of a perforated cut 4515 is illustrated in FIG. 45B, which an enlarged view of the portion of FIG. 45A labeled with the reference number 45B. In some embodiments, a repeating perforation gap 4525 may extend across the perforation, each gap separated by a connected or intact portion 4590. These perforation gaps 4525 may extend through some or all of the layers of the sealing strip assembly described further below. In some embodiments, a perforation gap 4525 may be 10 mm, or approximately 10 mm, in length, wherein length is the dimension measured along the perforation line. The perforation gap length may be also in the range of 2 mm to 20 mm, or approximately 2 mm to approximately 20 mm, in some embodiments. The intact portion 4590 separating perforation gaps may be in the range of 0.25 mm to 3 mm, or approximately 0.25 mm to approximately 3 mm, in length, for example 0.5 mm, or approximately 0.5 mm, in length.

As shown in FIGS. 45C and 45D (which are side or cross-sectional views of FIG. 45A), the sheet 4500 of sealing strips 4501, or an individual sealing strip 4501, may comprise an adhesive film 4545, which may be a flexible film material provided with a pressure-sensitive adhesive on a lower surface thereof. The adhesive film 4545 may, in some embodiments, be thin and prone to sticking to itself when folded or handled. Therefore, the adhesive film 4545 may be provided with a carrier layer 4535 on an upper, non-adhesive surface having the same length and width as the adhesive film 4545, and may also be provided with a one or protective layers 4570, 4580 on its lower, adhesive surface. The protective layers 4570, 4580 may be configured to protect the adhesive surface of the adhesive film 4545. First and second outer protective layers 4570 may be provided at opposite ends of the sheet 4500 or an individual sealing strip assembly 4501 (on the right and left sides of FIGS. 45A and 45C, with only the right side shown in FIG. 45D), thereby covering the opposite ends of the individual sealing strips 4501. A central protective layer 4580 may be provided over a central portion of the sheet 4500 or an individual sealing strip assembly 4501 and therefore over a central portion of adhesive film 4545, between the opposite ends of the adhesive film 4545 and partially overlapping with and underlying the outer protective layers 4570. As illustrated, the protective layers 4570 may have an outer edge (shown on the right in FIG. 45D) that is positioned beyond the outer edge of the adhesive film 4545, and may also include a folded handle 4575 that is covered by the central protective layer 4580. The folded handles 4575 of protective layer 4570 are therefore not in direct contact with the adhesive surface of the adhesive film 4545 to facilitate removal of the outer protective layers 4570. Similarly, the portions 4585 of the central protective layer 4580 overlapping the outer protective layers 4570 are not in direct contact with the adhesive surface of the adhesive film 4545, and are not adhered to the outer protective layers 4570, thereby forming handles to facilitate removal of the central protective layer 4580.

The carrier layer 4535 that may be provided on the upper surface of the adhesive film may be configured to releasably attach to the non-adhesive surface of the adhesive film 4545, and may comprise a sheet of paper or film with relatively more rigidity than the adhesive film. Release tabs 4595 may be provided on one or both opposite ends of the carrier layer 4535 for ease of removing the carrier layer 4535 from the adhesive film 4545. As illustrated in FIG. 45D, the release tabs 4595 may extend outwardly from the adhesive film 4545 and carrier layer 4535 to an outer edge aligned with an outer edge of the outer protective layer 4570. In some embodiments, graphical and/or numbered instructions for removal of the protective layer and carrier layer may be provided on one or both of the protective layer and carrier layer.

To utilize the sealing strips as described above, one or more sealing strips 4501 may be removed from the sheet 4500 by cutting or tearing along the perforations 4515. The central protective layer 4580 may be removed using the non-adhered portions 4585 of the central protective layer 4580, which serve as handles, for the exposing a central adhesive surface of the adhesive film 4545. The adhesive surface may then be applied to skin and/or a dressing or any desired location, or the adhesive surface may be applied after one or both of the outer protective layers 4570 is removed. The folded handle 4575 of outer protective layers 4570 may be grasped to remove the outer protective layers 4570, exposing the entirety of the lower adhesive surface of the adhesive film 4545. The outer edges of the adhesive surface of the adhesive film 4545 may be placed in a desired location. After sealing the adhesive film 4545, the release tab or tabs 4595 may be used to remove the carrier layer 4535 from the adhesive film 4545. This may be repeated with as many adhesive strips as are needed.

FIG. 45A illustrates a top view of assembly sheet 4500 of sealing strip assemblies 4501, in which the release tabs 4595 and carrier layer 4535 on adhesive film 4545 would be seen. The dashed lines in FIG. 45A illustrate edges or fold locations of the adhesive film 4545, central protective layer 4580, outer protective layers 4570, and carrier layer 4535. In some embodiments, each sealing strip 4501 may have a width 4530 of 40 mm, or approximately 40 mm, or a width in the range of 20 mm to 80 mm, or approximately 20 mm to 80 mm. The overall length 4510 of each sealing strip assembly (or the sheet 4500, including release tabs 4595 and outer protective layers 4570) may be 250 mm or 300 mm in some embodiments, or approximately 250 mm or approximately 300 mm, or in the range of 100 mm to 400 mm, or approximately 100 to approximately 400 mm. The length 4520 of the adhesive film 4545 and carrier layer 4535 may be 280 mm or 330 mm in some embodiments, or approximately 280 mm or approximately 330 mm, or in the range of 90 mm to 380 mm, or approximately 90 to approximately 380 mm. The length 4505 of central protective layer 4580 may be 210 mm or 260 mm in some embodiments, or approximately 210 mm or approximately 260 mm, or may be in the range of 100 mm to 300 mm, or approximately 100 mm to approximately 300 mm.

The length 4565 of outer protective layers 4570 (not including the folded portion) may be 85 mm or 110 mm in some embodiments, or approximately 85 mm or approximately 110 mm, or may be in the range of 50 mm to 200 mm, or approximately 500 mm to approximately 200 mm. The length 4555 of the folded portion or handle 4575 of outer protective layer 4570 may be 20 mm plus or minus 5 mm, in some embodiments, or approximately 20 mm plus or minus approximately 5 mm. The distance 4550 from the outer edge of the folded tab 4575 to the outer edge of the central protective layer 4580 may be 20 mm plus or minus 5 mm, in some embodiments, or approximately 20 mm plus or minus approximately 5 mm.

It will be of course appreciated that other dressing configurations are possible other than a narrow central portion configuration, a three-lobed configuration, a four-lobed configuration, including, for example, hexagonal or circular shaped backing layers for use in dressings. As illustrated in FIGS. 15A-B, these embodiments may also comprise various configurations of slits, described previously, so as to enhance conformability of the dressing in non-planar wounds. Also, as described previously, the absorbent layers of these embodiments may be colored or obscured with an obscuring layer, and optionally provided with one or more viewing windows. Further, the domed ports of these embodiments may also be replaced with one or more fluidic connectors of the type described below in FIGS. 23A-B, and vice versa. Additionally, all features and structures described for wound dressings with the waisted portion configuration can be incorporated into any shape or dressing configuration as described herein.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy kit comprising:
   a wound dressing; and
   a sheet separate from the wound dressing, the sheet comprising:
   a film having a length between first and second opposing edges of the film and a width between third and fourth opposing edges of the film, the film comprising an adhesive surface and a non-adhesive surface;
   a plurality of fixation strips formed in the film, wherein each fixation strip of the plurality of fixation strips has a length equal to the length of the film, and wherein the plurality of fixation strips are configured to secure the wound dressing during use;
   a carrier layer provided on the non-adhesive surface of the film;
   a central protective layer provided on the adhesive surface of the film;
   a first outer protective layer and a second outer protective layer provided on the adhesive surface of the film, the first outer protective layer provided at or near the first opposing edge and the second outer protective layer provided at or near the second opposing edge, each of the first and second outer protective layers comprising a folded handle extending along the width of film; and
   a plurality of perforation lines each extending the length of the film and configured to facilitate separation of the fixation strips from the sheet.

2. The negative pressure wound therapy kit of claim 1, wherein the perforation lines extend through the carrier layer, the central protective layer and the first and second outer protective layers.

3. The negative pressure wound therapy kit of claim 1, wherein all of the perforation lines are parallel to each other.

4. The negative pressure wound therapy kit of claim 1, wherein the carrier layer further comprises a tab that extends beyond the length of the film.

5. The negative pressure wound therapy kit of claim 1, wherein each perforation line comprises a repeating perforation gap, each gap separated by a connected or intact portion that connects adjacent fixation strips.

6. The negative pressure wound therapy kit of claim 1, wherein an edge extending the length of each fixation strip is adjacent to an edge extending the length of at least one other fixation strip.

7. The negative pressure wound therapy kit of claim 1, wherein the carrier layer comprises a material with more rigidity than the film.

8. The negative pressure wound therapy kit of claim 1, wherein a first end of the central protective layer overlaps with a portion of the first outer protective layer and a second end of the central protective layer overlaps with a portion of the second outer protective layer such that a portion of the first end of the central protective layer does not contact the adhesive surface and a portion of the second end of the central protective layer does not contact the adhesive surface.

9. The negative pressure wound therapy kit of claim 1, wherein the wound dressing comprises:
   a backing layer;
   an absorbent layer positioned below the backing layer;
   a spacer layer positioned below the absorbent layer; and
   a wound contact layer positioned below the spacer layer.

10. The negative pressure wound therapy kit of claim 9, wherein the backing layer has a perimeter that is larger than that of the absorbent layer to form a border region that extends beyond a periphery of the absorbent layer.

11. The negative pressure wound therapy kit of claim 9, further comprising an acquisition distribution layer between the absorbent layer and the spacer layer.

12. The negative pressure wound therapy kit of claim 9, wherein the wound contact layer comprises a silicone adhesive on a lower surface thereof.

13. The negative pressure wound therapy kit of claim 9, further comprising a release layer on a lower surface of the wound contact layer.

14. The negative pressure wound therapy kit of claim 1, further comprising a fluidic connector attached to the wound dressing, the fluidic connector comprising an exudate channel and an air leak channel.

15. A negative pressure wound therapy system, comprising the negative pressure wound therapy kit of claim 1, and further comprising a negative pressure pump.

16. A negative pressure wound therapy kit comprising:
    a wound dressing; and
    a sheet separate from the wound dressing, the sheet having a length between first and second opposing edges of the sheet and a width between third and fourth opposing edges of the sheet, the sheet comprising a plurality of fixation strips connected to one another, the plurality of fixation strips configured to secure the wound dressing during use, wherein each fixation strip comprises:
    a film comprising an adhesive surface and a non-adhesive surface;
    a central protective layer provided on the adhesive surface of the film;
    a first outer protective layer provided on the adhesive surface of the film at or near the first opposing edge and a second outer protective layer provided on the adhesive surface of the film at or near the second opposing edge, each of the first and second outer protective layers comprising a folded handle extending along a width of the fixation strip; and
    wherein adjacent fixation strips are separated from one another by a perforation line, and wherein each perforation line comprises a repeating perforation gap, each gap separated by a connected or intact portion that connects the adjacent fixation strips.

17. The negative pressure wound therapy kit of claim 16, wherein all of the perforation lines are parallel to each other.

18. The negative pressure wound therapy kit of claim 16, wherein the perforation lines extend through adjacent central protective layers and adjacent first and second outer protective layers.

19. The negative pressure wound therapy kit of claim 16, wherein an edge extending a length of each fixation strip is adjacent to an edge extending the length of at least one other fixation strip.

20. The negative pressure wound therapy kit of claim 16, wherein a first end of the central protective layer overlaps with a portion of the first outer protective layer and a second end of the central protective layer overlaps with a portion of the second outer protective layer such that a portion of the first end of the central protective layer does not contact the adhesive surface and a portion of the second end of the central protective layer does not contact the adhesive surface.

21. The negative pressure wound therapy kit of claim 16, wherein each fixation strip further comprises a carrier layer provided on the non-adhesive surface of the film, the perforation lines extending through adjacent carrier layers.

22. The negative pressure wound therapy kit of claim 16, wherein the wound dressing comprises:
- a backing layer;
- an absorbent layer positioned below the backing layer;
- a spacer layer positioned below the absorbent layer;
- an acquisition distribution layer between the absorbent layer and the spacer layer; and
- a wound contact layer positioned below the spacer layer, wherein the wound contact layer comprises a silicone adhesive on a lower surface thereof;
- wherein the backing layer has a perimeter that is larger than that of the absorbent layer to form a border region that extends beyond a periphery of the absorbent layer.

23. The negative pressure wound therapy kit of claim 22, further comprising a fluidic connector attached to the backing layer of the wound dressing, the fluidic connector comprising an exudate channel and an air leak channel.

24. A negative pressure wound therapy system, comprising the negative pressure wound therapy kit of claim 16, and further comprising a negative pressure pump.

\* \* \* \* \*